(12) United States Patent
Maki et al.

(10) Patent No.: US 8,741,607 B2
(45) Date of Patent: Jun. 3, 2014

(54) HCV/GBV-B CHIMERIC VIRUS

(75) Inventors: Noboru Maki, Wako (JP); Kenichi Mori, Wako (JP); Hiromi Fukai, Wako (JP)

(73) Assignee: Advanced Life Science Institute, Inc., Wako-Shi (JP)

( * ) Notice: Subject to any disclaimer, the term of this patent is extended or adjusted under 35 U.S.C. 154(b) by 86 days.

(21) Appl. No.: 13/054,356

(22) PCT Filed: Jul. 15, 2009

(86) PCT No.: PCT/JP2009/062786
§ 371 (c)(1),
(2), (4) Date: Mar. 11, 2011

(87) PCT Pub. No.: WO2010/008010
PCT Pub. Date: Jan. 21, 2010

(65) Prior Publication Data
US 2011/0289610 A1    Nov. 24, 2011

(30) Foreign Application Priority Data
Jul. 15, 2008 (JP) ................................. 2008-184179

(51) Int. Cl.
*C12N 15/09* (2006.01)
*C12N 5/10* (2006.01)
*C12N 7/00* (2006.01)
*C07K 14/18* (2006.01)

(52) U.S. Cl.
USPC ............ 435/91.51; 424/93.2; 424/93.21; 435/320.1; 435/91.4

(58) Field of Classification Search
CPC ............ C12N 2770/24221; C12N 15/86; C12N 2770/24243; C12N 2770/24262; G01N 33/56983; A61K 39/29
USPC ............ 435/5, 320.1, 69.1, 325, 91.4; 424/228.1
See application file for complete search history.

(56) References Cited

U.S. PATENT DOCUMENTS

2010/0173298 A1    7/2010    Mori et al.

FOREIGN PATENT DOCUMENTS

| JP | 2005528885 T | 9/2005 |
| WO | WO 03/059944 A2 | 7/2003 |
| WO | WO 03059944 A2 | 7/2003 |
| WO | WO 2004/005498 A1 | 1/2004 |
| WO | WO 2006/036879 A2 | 4/2006 |
| WO | WO 2006/036879 A2 * | 6/2006 |
| WO | WO 2008/136470 A1 | 11/2008 |

OTHER PUBLICATIONS

Brass et al, J Virol, 2010, 84:11580-11584.*
Lindstrom et al, Virus Research, 2006, 121:169-178.*
Buckwold et al, Antiviral Research, 2005, 66:165-168.*
Landford and Bigger, Virology, 2002, 293:1-9.*
Rijnbrand et al, Hepatology, 2005, 41:986-994.*
Takikawa et al, PNAS, 2006, 103:3345-3350.*
Warter et al, PLoS ONE, 2009, 4:e4419:1-14.*
Weatherford et al, J Virol, 2009, 83:8062-8075.*
Bukh et al., "Toward a Surrogate Model for Hepatitis C: An Infectious Molecular Clone of the GB Virus-B Hepatitis Agent," Virology, vol. 262, No. 2, pp. 470-478, Sep. 30, 1999.
Haqshenas et al., "A chimeric GB virus B encoding the hepatitis C virus hypervariable region 1 is infectious in vivo," Journal of General Virology, vol. 88, pp. 895-902, 2007.
International Search Report issued Aug. 25, 2009, in PCT International Application No. PCT/JP2009/062786.
Lemm et al., "Replication-Competent Chimeric Hepatitis C Virus Subgenomic Replicons," Intervirology, vol. 48, pp. 183-191, 2005.
Lindstrom et al., "Mutations of the Hepatitis C virus protein NS4B on either side of the ER membrane affect the efficiency of subgenomic replicons," Virus Research, vol. 121, pp. 169-178, 2006.
Lohmann et al., "Viral and Cellular Determinants of Hepatitis C Virus RNA Replication in Cell Culture," Journal of Virology, vol. 77, No. 5, pp. 3007-3019, Mar. 2003.
Muerhoff et al., "Genomic Organization of GB Viruses A and B: Two New Members of the Flaviviridae Associated with GB Agent Hepatitis," Journal of Virology, vol. 69, No. 9, pp. 5621-5630, Sep. 1995.
Rijnbrand et al., "A Chimeric GB Virus B with 5' Nontranslated RNA Sequence from Hepatitis C Virus Causes Hepatitis in Tamarins," Hepatology, vol. 41, pp. 986-994, 2005.
European Search Report issued Jan. 1, 2013, in EP Application No. 09797935.5.

* cited by examiner

*Primary Examiner* — Chi-Feng Hsu
(74) *Attorney, Agent, or Firm* — Birch, Stewart, Kolasch & Birch, LLP

(57) ABSTRACT

An HCV/GBV-B chimeric virus which maintains the replication function of HCV and is capable of infecting tamarin is disclosed in order to construct an HCV animal model which can be used as a development or evaluation system for therapeutic agents for HCV. The HCV/GBV-B chimeric RNA comprises an RNA of hepatitis C virus and an RNA of GB virus-B, wherein the RNA of hepatitis C virus comprises an RNA encoding leucine at the 1804th position and lysine at the 1966th position in the amino acid sequence of the polyprotein of hepatitis C virus.

16 Claims, 3 Drawing Sheets

```
                          SEQUENCE LISTING

<160> NUMBER OF SEQ ID NOS: 108

<210> SEQ ID NO 1
<211> LENGTH: 60
<212> TYPE: DNA
<213> ORGANISM: Hepatitis GB virus B

<400> SEQUENCE: 1
cgtacgcttg ctggaggatg gagtcaactg ggctactggt tggttcggtg tccaccttt        60

<210> SEQ ID NO 2
<211> LENGTH: 60
<212> TYPE: DNA
<213> ORGANISM: Hepatitis GB virus B

<400> SEQUENCE: 2
tgtggtatgt ctgctatctt tggcctgtcc ctgtagtggg gcgcgggtca ctgacccaga        60

<210> SEQ ID NO 3
<211> LENGTH: 60
<212> TYPE: DNA
<213> ORGANISM: Hepatitis GB virus B

<400> SEQUENCE: 3
cacaaatacc acaatcctga ccaattgctg ccagcgtaat caggttatct attgttctcc        60

<210> SEQ ID NO 4
<211> LENGTH: 60
<212> TYPE: DNA
<213> ORGANISM: Hepatitis GB virus B

<400> SEQUENCE: 4
ttccacttgc ctacacgagc ctggttgtgt gatctgtgcg gacgagtgct gggttcccgc        60

<210> SEQ ID NO 5
<211> LENGTH: 60
<212> TYPE: DNA
<213> ORGANISM: Hepatitis GB virus B

<400> SEQUENCE: 5
caatccgtac atctcacacc cttccaattg gactggcacg gactccttct tggctgacca        60

<210> SEQ ID NO 6
<211> LENGTH: 60
<212> TYPE: DNA
<213> ORGANISM: Hepatitis GB virus B

<400> SEQUENCE: 6
cattgatttt gttatgggcg ctcttgtgac ctgtgacgcc cttgacattg gtgagttgtg        60

<210> SEQ ID NO 7
<211> LENGTH: 60
<212> TYPE: DNA
<213> ORGANISM: Hepatitis GB virus B

<400> SEQUENCE: 7
tggtgcgtgt gtattagtcg gtgactggct tgtcaggcac tggcttattc acatagacct        60
```

```
<210> SEQ ID NO 8
<211> LENGTH: 60
<212> TYPE: DNA
<213> ORGANISM: Hepatitis GB virus B

<400> SEQUENCE: 8
caatgaaact ggtacttgtt acctggaagt gcccactgga atagatcctg ggttcctagg    60

<210> SEQ ID NO 9
<211> LENGTH: 60
<212> TYPE: DNA
<213> ORGANISM: Hepatitis GB virus B

<400> SEQUENCE: 9
gtttatcggg tggatggccg gcaaggtcga ggctgtcatc ttcttgacca aactggcttc    60

<210> SEQ ID NO 10
<211> LENGTH: 60
<212> TYPE: DNA
<213> ORGANISM: Hepatitis GB virus B

<400> SEQUENCE: 10
acaagtacca tacgctattg cgactatgtt tagcagtgta cactacctgg cggttggcgc    60

<210> SEQ ID NO 11
<211> LENGTH: 60
<212> TYPE: DNA
<213> ORGANISM: Hepatitis GB virus B

<400> SEQUENCE: 11
tctgatctac tatgcctctc ggggcaagtg gtatcagttg ctcctagcgc ttatgcttta    60

<210> SEQ ID NO 12
<211> LENGTH: 60
<212> TYPE: DNA
<213> ORGANISM: Hepatitis GB virus B

<400> SEQUENCE: 12
catagaagcg acctctggaa accccatcag ggtgcccact ggatgctcaa tagctgagtt    60

<210> SEQ ID NO 13
<211> LENGTH: 60
<212> TYPE: DNA
<213> ORGANISM: Hepatitis GB virus B

<400> SEQUENCE: 13
ttgctcgcct ttgatgatac catgtccttg ccactcttat ttgagtgaga atgtgtcaga    60

<210> SEQ ID NO 14
<211> LENGTH: 60
<212> TYPE: DNA
<213> ORGANISM: Hepatitis GB virus B

<400> SEQUENCE: 14
agtcatttgt tacagtccaa agtggaccag gcctatcact ctagagtata acaactccat    60

<210> SEQ ID NO 15
<211> LENGTH: 60
<212> TYPE: DNA
<213> ORGANISM: Hepatitis GB virus B

<400> SEQUENCE: 15
atcttggtac ccctatacaa tccctggtgc gaggggatgt atggttaaat tcaaaaataa    60
```

```
<210> SEQ ID NO 16
<211> LENGTH: 60
<212> TYPE: DNA
<213> ORGANISM: Hepatitis GB virus B

<400> SEQUENCE: 16
cacatggggt tgctgccgta ttcgcaatgt gccatcgtac tgcactatgg gcactgatgc     60

<210> SEQ ID NO 17
<211> LENGTH: 60
<212> TYPE: DNA
<213> ORGANISM: Hepatitis GB virus B

<400> SEQUENCE: 17
agtgtggaac gacactcgca acacttacga agcatgcggt gtaacaccat ggctaacaac     60

<210> SEQ ID NO 18
<211> LENGTH: 60
<212> TYPE: DNA
<213> ORGANISM: Hepatitis GB virus B

<400> SEQUENCE: 18
cgcatggcac aacggctcag ccctgaaatt ggctatatta caatacccctg gtctaaaga    60

<210> SEQ ID NO 19
<211> LENGTH: 60
<212> TYPE: DNA
<213> ORGANISM: Hepatitis GB virus B

<400> SEQUENCE: 19 aatgttaaa cctcataatt ggatgtcagg ccatttgtat tttgagggat cagataccccc    60

<210> SEQ ID NO 20
<211> LENGTH: 60
<212> TYPE: DNA
<213> ORGANISM: Hepatitis GB virus B

<400> SEQUENCE: 20
tatagtttac ttttatgacc ctgtgaattc cactctccta ccaccggaga ggtgggctag     60

<210> SEQ ID NO 21
<211> LENGTH: 60
<212> TYPE: DNA
<213> ORGANISM: Hepatitis GB virus B

<400> SEQUENCE: 21
gttgcccggt accccacctg tggtacgtgg ttcttggtta caggttccgc aagggtttta     60

<210> SEQ ID NO 22
<211> LENGTH: 60
<212> TYPE: DNA
<213> ORGANISM: Hepatitis GB virus B

<400> SEQUENCE: 22
cagtgatgtg aaagacctag ccacaggatt gatcaccaaa gacaaagcct ggaaaaatta     60

<210> SEQ ID NO 23
<211> LENGTH: 60
<212> TYPE: DNA
<213> ORGANISM: Hepatitis GB virus B

<400> SEQUENCE: 23
tcaggtctta tattccgcca cgggtgcttt gtctcttacg ggagttacca ccaaggccgt     60
```

```
<210> SEQ ID NO 24
<211> LENGTH: 60
<212> TYPE: DNA
<213> ORGANISM: Hepatitis GB virus B

<400> SEQUENCE: 24
ggtgctaatt ctgttggggt tgtgtggcag caagtatctt attttagcct acctctgtta    60

<210> SEQ ID NO 25
<211> LENGTH: 60
<212> TYPE: DNA
<213> ORGANISM: Hepatitis GB virus B

<400> SEQUENCE: 25
cttgtccctt tgttttgggc gcgcttctgg ttacccttgg cgtcctgtgc tcccatccca    60

<210> SEQ ID NO 26
<211> LENGTH: 60
<212> TYPE: DNA
<213> ORGANISM: Hepatitis GB virus B

<400> SEQUENCE: 26
gtcgtatctc caagctggct gggatgtttt gtctaaagct caagtagctc cttttgcttt    60

<210> SEQ ID NO 27
<211> LENGTH: 60
<212> TYPE: DNA
<213> ORGANISM: Hepatitis GB virus B

<400> SEQUENCE: 27
gattttcttc atctgttgct atctccgctg caggctacgt tatgctgccc ttttagggtt    60

<210> SEQ ID NO 28
<211> LENGTH: 49
<212> TYPE: DNA
<213> ORGANISM: Hepatitis GB virus B

<400> SEQUENCE: 28
gcccgcagcc atgggcacaa accctaaaag ggcagcataa cgtagcctg               49

<210> SEQ ID NO 29
<211> LENGTH: 60
<212> TYPE: DNA
<213> ORGANISM: Hepatitis GB virus B

<400> SEQUENCE: 29
cagcggagat agcaacagat gaagaaaatc aaagcaaaag gagctacttg agctttagac    60

<210> SEQ ID NO 30
<211> LENGTH: 60
<212> TYPE: DNA
<213> ORGANISM: Hepatitis GB virus B

<400> SEQUENCE: 30
aaaacatccc agccagcttg gagatacgac tgggatggga gcacaggacg caaagggtaa    60

<210> SEQ ID NO 31
<211> LENGTH: 60
<212> TYPE: DNA
<213> ORGANISM: Hepatitis GB virus B

<400> SEQUENCE: 31
ccagaagcgc gcccaaaaca aagggacaag taacagaggt aggctaaaat aagatacttg    60
```

```
<210> SEQ ID NO 32
<211> LENGTH: 60
<212> TYPE: DNA
<213> ORGANISM: Hepatitis GB virus B

<400> SEQUENCE: 32
ctgccacaca accccaacag aattagcacc acggccttgg tggtaactcc cgtaagagac      60

<210> SEQ ID NO 33
<211> LENGTH: 60
<212> TYPE: DNA
<213> ORGANISM: Hepatitis GB virus B

<400> SEQUENCE: 33
aaagcacccg tggcggaata aagacctga taatttttcc aggctttgtc tttggtgatc      60

<210> SEQ ID NO 34
<211> LENGTH: 60
<212> TYPE: DNA
<213> ORGANISM: Hepatitis GB virus B

<400> SEQUENCE: 34
aatcctgtgg ctaggtcttt cacatcactg taaaaccctt gcggaacctg taaccaagaa      60

<210> SEQ ID NO 35
<211> LENGTH: 60
<212> TYPE: DNA
<213> ORGANISM: Hepatitis GB virus B

<400> SEQUENCE: 35
ccacgtacca caggtggggt accgggcaac ctagcccacc tctccggtgg taggagagtg      60

<210> SEQ ID NO 36
<211> LENGTH: 60
<212> TYPE: DNA
<213> ORGANISM: Hepatitis GB virus B

<400> SEQUENCE: 36
gaattcacag ggtcataaaa gtaaactata ggggtatctg atccctcaaa atacaaatgg      60

<210> SEQ ID NO 37
<211> LENGTH: 60
<212> TYPE: DNA
<213> ORGANISM: Hepatitis GB virus B

<400> SEQUENCE: 37
cctgacatcc aattatgagg tttaaacatt tctttagacc cagggtattg taatatagcc      60

<210> SEQ ID NO 38
<211> LENGTH: 60
<212> TYPE: DNA
<213> ORGANISM: Hepatitis GB virus B

<400> SEQUENCE: 38
aatttcaggg ctgagccgtt gtgccatgcg gttgttagcc atggtgttac accgcatgct      60

<210> SEQ ID NO 39
<211> LENGTH: 60
<212> TYPE: DNA
<213> ORGANISM: Hepatitis GB virus B

<400> SEQUENCE: 39
tcgtaagtgt tgcgagtgtc gttccacact gcatcagtgc ccatagtgca gtacgatggc      60
```

```
<210> SEQ ID NO 40
<211> LENGTH: 60
<212> TYPE: DNA
<213> ORGANISM: Hepatitis GB virus B

<400> SEQUENCE: 40
acattgcgaa tacggcagca accccatgtg ttattttga atttaaccat acatcccctc    60

<210> SEQ ID NO 41
<211> LENGTH: 60
<212> TYPE: DNA
<213> ORGANISM: Hepatitis GB virus B

<400> SEQUENCE: 41
gcaccaggga ttgtataggg gtaccaagat atggagttgt tatactctag agtgataggc    60

<210> SEQ ID NO 42
<211> LENGTH: 60
<212> TYPE: DNA
<213> ORGANISM: Hepatitis GB virus B

<400> SEQUENCE: 42
ctggtccact ttggactgta acaaatgact tctgacacat tctcactcaa ataagagtgg    60

<210> SEQ ID NO 43
<211> LENGTH: 60
<212> TYPE: DNA
<213> ORGANISM: Hepatitis GB virus B

<400> SEQUENCE: 43
caaggacatg gtatcatcaa aggcgagcaa aactcagcta ttgagcatcc agtgggcacc    60

<210> SEQ ID NO 44
<211> LENGTH: 60
<212> TYPE: DNA
<213> ORGANISM: Hepatitis GB virus B

<400> SEQUENCE: 44
ctgatggggt ttccagaggt cgcttctatg taaagcataa gcgctaggag caactgatac    60

<210> SEQ ID NO 45
<211> LENGTH: 60
<212> TYPE: DNA
<213> ORGANISM: Hepatitis GB virus B

<400> SEQUENCE: 45
cacttgcccc gagaggcata gtagatcaga gcgccaaccg ccaggtagtg tacactgcta    60

<210> SEQ ID NO 46
<211> LENGTH: 60
<212> TYPE: DNA
<213> ORGANISM: Hepatitis GB virus B

<400> SEQUENCE: 46
aacatagtcg caatagcgta tggtacttgt gaagccagtt tggtcaagaa gatgacagcc    60

<210> SEQ ID NO 47
<211> LENGTH: 60
<212> TYPE: DNA
<213> ORGANISM: Hepatitis GB virus B

<400> SEQUENCE: 47
tcgaccttgc cggccatcca cccgataaac cctaggaacc caggatctat tccagtgggc    60
```

```
<210> SEQ ID NO 48
<211> LENGTH: 60
<212> TYPE: DNA
<213> ORGANISM: Hepatitis GB virus B

<400> SEQUENCE: 48
acttccaggt aacaagtacc agtttcattg aggtctatgt gaataagcca gtgcctgaca       60

<210> SEQ ID NO 49
<211> LENGTH: 60
<212> TYPE: DNA
<213> ORGANISM: Hepatitis GB virus B

<400> SEQUENCE: 49
agccagtcac cgactaatac acacgcacca cacaactcac caatgtcaag ggcgtcacag       60

<210> SEQ ID NO 50
<211> LENGTH: 60
<212> TYPE: DNA
<213> ORGANISM: Hepatitis GB virus B

<400> SEQUENCE: 50
gtcacaagag cgcccataac aaaatcaatg tggtcagcca agaaggagtc cgtgccagtc       60

<210> SEQ ID NO 51
<211> LENGTH: 60
<212> TYPE: DNA
<213> ORGANISM: Hepatitis GB virus B

<400> SEQUENCE: 51
caattggaag ggtgtgagat gtacggattg gcgggaaccc agcactcgtc cgcacagatc       60

<210> SEQ ID NO 52
<211> LENGTH: 60
<212> TYPE: DNA
<213> ORGANISM: Hepatitis GB virus B

<400> SEQUENCE: 52
acacaaccag gctcgtgtag gcaagtggaa ggagaacaat agataacctg attacgctgg       60

<210> SEQ ID NO 53
<211> LENGTH: 60
<212> TYPE: DNA
<213> ORGANISM: Hepatitis GB virus B

<400> SEQUENCE: 53
cagcaattgg tcaggattgt ggtatttgtg tctgggtcag tgacccgcgc cccactacag       60

<210> SEQ ID NO 54
<211> LENGTH: 62
<212> TYPE: DNA
<213> ORGANISM: Hepatitis GB virus B

<400> SEQUENCE: 54
ggacaggcca agatagcag acataccaca aaaggtgga caccgaacca accagtagcc         60
ca                                                                     62

<210> SEQ ID NO 55
<211> LENGTH: 9456
<212> TYPE: RNA
<213> ORGANISM: Artificial Sequence
<220> FEATURE:
<223> OTHER INFORMATION: Chimeric virus of Hepatitis C virus and GBV-B
<220> FEATURE:
<221> NAME/KEY: CDS
```

<222> LOCATION: (342)..(9233)

<400> SEQUENCE: 55

```
gccagccccc ugaugggggc gacacuccac cauagaucac uccccuguga ggaacuacug    60
ucuucacgca gaaagcgucu agccauggcg uuaguaugag ugucgugcag ccuccaggac   120
ccccccuccc gggagagcca uaguggucug cggaaccggu gaguacaccg gaauugccag   180
gacgaccggg uccuuucuug gaucaacccg cucaaugccu ggagauuugg gcgugccccc   240
gcgagacugc uagccaguau guguugggu cgcgaaaggcc uuguguacu gccugauagg    300 gugcuugcga gugccccggg aggucucgua daccgugcau c aug agc aca aau ccu  356
                                             Met Ser Thr Asn Pro
                                              1               5
```

| | | | | | | | | | | | | | | | | |
|---|---|---|---|---|---|---|---|---|---|---|---|---|---|---|---|---|
| aaa | ccu | caa | aga | aaa | acc | aaa | cgu | aac | acc | aac | cgc | cgc | cca | cag | gac | 404 |
| Lys | Pro | Gln | Arg | Lys | Thr | Lys | Arg | Asn | Thr | Asn | Arg | Arg | Pro | Gln | Asp | |
| | | | 10 | | | | 15 | | | | 20 | | | | | |

| guc | aag | uuc | ccg | ggc | ggu | ggc | cag | auc | guu | ggu | gga | guu | uac | cug | uug | 452 |
|---|---|---|---|---|---|---|---|---|---|---|---|---|---|---|---|---|
| Val | Lys | Phe | Pro | Gly | Gly | Gly | Gln | Ile | Val | Gly | Gly | Val | Tyr | Leu | Leu | |
| | | 25 | | | | | 30 | | | | 35 | | | | | |

| ccg | cgc | agg | ggc | ccc | agg | uug | ggu | gug | cgc | gcg | acu | agg | aag | acu | ucc | 500 |
|---|---|---|---|---|---|---|---|---|---|---|---|---|---|---|---|---|
| Pro | Arg | Arg | Gly | Pro | Arg | Leu | Gly | Val | Arg | Ala | Thr | Arg | Lys | Thr | Ser | |
| | 40 | | | | 45 | | | | | 50 | | | | | | |

| gag | cgg | ucg | caa | ccu | cgu | gga | agg | cga | caa | ccu | auc | ccc | aag | gcu | cgc | 548 |
|---|---|---|---|---|---|---|---|---|---|---|---|---|---|---|---|---|
| Glu | Arg | Ser | Gln | Pro | Arg | Gly | Arg | Arg | Gln | Pro | Ile | Pro | Lys | Ala | Arg | |
| 55 | | | | | 60 | | | | 65 | | | | | | | |

| cag | ccc | gag | ggc | agg | gcc | ugg | gcu | cag | ccc | ggg | uau | ccu | ugg | ccc | cuc | 596 |
|---|---|---|---|---|---|---|---|---|---|---|---|---|---|---|---|---|
| Gln | Pro | Glu | Gly | Arg | Ala | Trp | Ala | Gln | Pro | Gly | Tyr | Pro | Trp | Pro | Leu | |
| 70 | | | | 75 | | | | 80 | | | | 85 | | | | |

| uau | ggc | aac | gag | ggu | cug | ggg | ugg | gca | gga | ugg | cuc | cug | uca | ccc | cgu | 644 |
|---|---|---|---|---|---|---|---|---|---|---|---|---|---|---|---|---|
| Tyr | Gly | Asn | Glu | Gly | Leu | Gly | Trp | Ala | Gly | Trp | Leu | Leu | Ser | Pro | Arg | |
| | | | 90 | | | | 95 | | | | 100 | | | | | |

| ggc | ucu | cgg | ccu | agu | ugg | ggc | ccc | acg | gac | ccc | cgg | cgu | agg | ucg | cgu | 692 |
|---|---|---|---|---|---|---|---|---|---|---|---|---|---|---|---|---|
| Gly | Ser | Arg | Pro | Ser | Trp | Gly | Pro | Thr | Asp | Pro | Arg | Arg | Arg | Ser | Arg | |
| | | 105 | | | | | 110 | | | | 115 | | | | | |

| aau | uug | ggu | aag | guc | auc | gau | acc | cuc | aca | ugc | ggc | uuc | gcc | gac | cuc | 740 |
|---|---|---|---|---|---|---|---|---|---|---|---|---|---|---|---|---|
| Asn | Leu | Gly | Lys | Val | Ile | Asp | Thr | Leu | Thr | Cys | Gly | Phe | Ala | Asp | Leu | |
| | 120 | | | | 125 | | | | | 130 | | | | | | |

| aug | ggg | uac | auu | ccg | cuc | guc | ggc | gcc | ccc | cua | gga | ggc | gcu | gcc | agg | 788 |
|---|---|---|---|---|---|---|---|---|---|---|---|---|---|---|---|---|
| Met | Gly | Tyr | Ile | Pro | Leu | Val | Gly | Ala | Pro | Leu | Gly | Gly | Ala | Ala | Arg | |
| 135 | | | | | 140 | | | | 145 | | | | | | | |

| gcc | cug | gcg | cau | ggc | gua | cgc | uug | cug | gag | gau | gga | guc | aac | ugg | gcu | 836 |
|---|---|---|---|---|---|---|---|---|---|---|---|---|---|---|---|---|
| Ala | Leu | Ala | His | Gly | Val | Arg | Leu | Leu | Glu | Asp | Gly | Val | Asn | Trp | Ala | |
| 150 | | | | 155 | | | | 160 | | | | 165 | | | | |

| acu | ggu | ugg | uuc | ggu | guc | cac | cuu | uuu | gug | gua | ugu | cug | cua | ucu | uug | 884 |
|---|---|---|---|---|---|---|---|---|---|---|---|---|---|---|---|---|
| Thr | Gly | Trp | Phe | Gly | Val | His | Leu | Phe | Val | Val | Cys | Leu | Leu | Ser | Leu | |
| | | | 170 | | | | 175 | | | | 180 | | | | | |

| gcc | ugu | ccc | ugu | agu | ggg | gcg | cgg | guc | acu | gac | cca | gac | aca | aau | acc | 932 |
|---|---|---|---|---|---|---|---|---|---|---|---|---|---|---|---|---|
| Ala | Cys | Pro | Cys | Ser | Gly | Ala | Arg | Val | Thr | Asp | Pro | Asp | Thr | Asn | Thr | |
| | | 185 | | | | | 190 | | | | 195 | | | | | |

| aca | auc | cug | acc | aau | ugc | ugc | cag | cgu | aau | cag | guu | auc | uau | ugu | ucu | 980 |
|---|---|---|---|---|---|---|---|---|---|---|---|---|---|---|---|---|
| Thr | Ile | Leu | Thr | Asn | Cys | Cys | Gln | Arg | Asn | Gln | Val | Ile | Tyr | Cys | Ser | |
| | | 200 | | | | 205 | | | | | 210 | | | | | |

| ccu | ucc | acu | ugc | cua | cac | gag | ccu | ggu | ugu | gug | auc | ugu | gcg | gac | gag | 1028 |
|---|---|---|---|---|---|---|---|---|---|---|---|---|---|---|---|---|
| Pro | Ser | Thr | Cys | Leu | His | Glu | Pro | Gly | Cys | Val | Ile | Cys | Ala | Asp | Glu | |
| | 215 | | | | 220 | | | | 225 | | | | | | | |

| ugc | ugg | guu | ccc | gcc | aau | ccg | uac | auc | uca | cac | ccu | ucc | aau | ugg | acu | 1076 |
|---|---|---|---|---|---|---|---|---|---|---|---|---|---|---|---|---|
| Cys | Trp | Val | Pro | Ala | Asn | Pro | Tyr | Ile | Ser | His | Pro | Ser | Asn | Trp | Thr | |
| 230 | | | | 235 | | | | 240 | | | | 245 | | | | |

| ggc | acg | gac | ucc | uuc | uug | gcu | gac | cac | auu | gau | uuu | guu | aug | ggc | gcu | 1124 |
|---|---|---|---|---|---|---|---|---|---|---|---|---|---|---|---|---|
| Gly | Thr | Asp | Ser | Phe | Leu | Ala | Asp | His | Ile | Asp | Phe | Val | Met | Gly | Ala | |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     | 250 |     |     |     | 255 |     |     |     | 260 |     |     |     |     |     |      |
| cuu | gug | acc | ugu | gac | gcc | cuu | gac | auu | ggu | gag | uug | ugu | ggu | gcg | ugu | 1172 |
| Leu | Val | Thr | Cys | Asp | Ala | Leu | Asp | Ile | Gly | Glu | Leu | Cys | Gly | Ala | Cys |      |
|     |     | 265 |     |     |     | 270 |     |     |     | 275 |     |     |     |     |     |      |
| gua | uua | guc | ggu | gac | ugg | cuu | guc | agg | cac | ugg | cuu | auu | cac | aua | gac | 1220 |
| Val | Leu | Val | Gly | Asp | Trp | Leu | Val | Arg | His | Trp | Leu | Ile | His | Ile | Asp |      |
|     |     | 280 |     |     |     | 285 |     |     |     | 290 |     |     |     |     |     |      |
| cuc | aau | gaa | acu | ggu | acu | ugu | uac | cug | gaa | gug | ccc | acu | gga | aua | gau | 1268 |
| Leu | Asn | Glu | Thr | Gly | Thr | Cys | Tyr | Leu | Glu | Val | Pro | Thr | Gly | Ile | Asp |      |
|     |     | 295 |     |     |     | 300 |     |     |     | 305 |     |     |     |     |     |      |
| ccu | ggg | uuc | cua | ggg | uuu | auc | ggg | ugg | aug | gcc | ggc | aag | guc | gag | gcu | 1316 |
| Pro | Gly | Phe | Leu | Gly | Phe | Ile | Gly | Trp | Met | Ala | Gly | Lys | Val | Glu | Ala |      |
| 310 |     |     |     | 315 |     |     |     | 320 |     |     |     | 325 |     |     |     |      |
| guc | auc | uuc | uug | acc | aaa | cug | gcu | uca | caa | gua | cca | uac | gcu | auu | gcg | 1364 |
| Val | Ile | Phe | Leu | Thr | Lys | Leu | Ala | Ser | Gln | Val | Pro | Tyr | Ala | Ile | Ala |      |
|     |     |     |     | 330 |     |     |     | 335 |     |     |     | 340 |     |     |     |      |
| acu | aug | uuu | agc | agu | gua | cac | uac | cug | gcg | guu | ggc | gcu | cug | auc | uac | 1412 |
| Thr | Met | Phe | Ser | Ser | Val | His | Tyr | Leu | Ala | Val | Gly | Ala | Leu | Ile | Tyr |      |
|     |     |     | 345 |     |     |     | 350 |     |     |     | 355 |     |     |     |     |      |
| uau | gcc | ucu | cgg | ggc | aag | ugg | uau | cag | uug | cuc | cua | gcg | cuu | aug | cuu | 1460 |
| Tyr | Ala | Ser | Arg | Gly | Lys | Trp | Tyr | Gln | Leu | Leu | Leu | Ala | Leu | Met | Leu |      |
|     |     | 360 |     |     |     | 365 |     |     |     | 370 |     |     |     |     |     |      |
| uac | aua | gaa | gcg | acc | ucu | gga | aac | ccc | auc | agg | gug | ccc | acu | gga | ugc | 1508 |
| Tyr | Ile | Glu | Ala | Thr | Ser | Gly | Asn | Pro | Ile | Arg | Val | Pro | Thr | Gly | Cys |      |
|     | 375 |     |     |     | 380 |     |     |     | 385 |     |     |     |     |     |     |      |
| uca | aua | gcu | gag | uuu | ugc | ucg | ccu | uug | aug | aua | cca | ugu | ccu | ugc | cac | 1556 |
| Ser | Ile | Ala | Glu | Phe | Cys | Ser | Pro | Leu | Met | Ile | Pro | Cys | Pro | Cys | His |      |
| 390 |     |     |     | 395 |     |     |     | 400 |     |     |     | 405 |     |     |     |      |
| ucu | uau | uug | agu | gag | aau | gug | uca | gaa | guc | auu | ugu | uac | agu | cca | aag | 1604 |
| Ser | Tyr | Leu | Ser | Glu | Asn | Val | Ser | Glu | Val | Ile | Cys | Tyr | Ser | Pro | Lys |      |
|     |     |     | 410 |     |     |     | 415 |     |     |     | 420 |     |     |     |     |      |
| ugg | acc | agg | ccu | auc | acu | cua | gag | uau | aac | aac | uca | aua | ucu | ugg | uac | 1652 |
| Trp | Thr | Arg | Pro | Ile | Thr | Leu | Glu | Tyr | Asn | Asn | Ser | Ile | Ser | Trp | Tyr |      |
|     |     | 425 |     |     |     | 430 |     |     |     | 435 |     |     |     |     |     |      |
| ccc | uau | aca | auc | ccu | ggu | gcg | agg | gga | ugu | aug | guu | aaa | uuc | aaa | aau | 1700 |
| Pro | Tyr | Thr | Ile | Pro | Gly | Ala | Arg | Gly | Cys | Met | Val | Lys | Phe | Lys | Asn |      |
|     |     | 440 |     |     |     | 445 |     |     |     | 450 |     |     |     |     |     |      |
| aac | aca | ugg | ggu | ugc | ugc | cgu | auu | cgc | aau | gug | cca | ucg | uac | ugc | acu | 1748 |
| Asn | Thr | Trp | Gly | Cys | Cys | Arg | Ile | Arg | Asn | Val | Pro | Ser | Tyr | Cys | Thr |      |
|     | 455 |     |     |     | 460 |     |     |     | 465 |     |     |     |     |     |     |      |
| aug | ggc | acu | gau | gca | gug | ugg | aac | gac | acu | cgc | aac | acu | uac | gaa | gca | 1796 |
| Met | Gly | Thr | Asp | Ala | Val | Trp | Asn | Asp | Thr | Arg | Asn | Thr | Tyr | Glu | Ala |      |
| 470 |     |     |     | 475 |     |     |     | 480 |     |     |     | 485 |     |     |     |      |
| ugc | ggu | gua | aca | cca | ugg | cua | aca | acc | gca | ugg | cac | aac | ggc | uca | gcc | 1844 |
| Cys | Gly | Val | Thr | Pro | Trp | Leu | Thr | Thr | Ala | Trp | His | Asn | Gly | Ser | Ala |      |
|     |     |     |     | 490 |     |     |     | 495 |     |     |     | 500 |     |     |     |      |
| cug | aaa | uug | gcu | aua | uua | caa | uac | ccu | ggg | ucu | aaa | gaa | aug | uuu | aaa | 1892 |
| Leu | Lys | Leu | Ala | Ile | Leu | Gln | Tyr | Pro | Gly | Ser | Lys | Glu | Met | Phe | Lys |      |
|     |     |     | 505 |     |     |     | 510 |     |     |     | 515 |     |     |     |     |      |
| ccu | cau | aau | ugg | aug | uca | ggc | cau | uug | uau | uuu | gag | gga | uca | gau | acc | 1940 |
| Pro | His | Asn | Trp | Met | Ser | Gly | His | Leu | Tyr | Phe | Glu | Gly | Ser | Asp | Thr |      |
|     |     | 520 |     |     |     | 525 |     |     |     | 530 |     |     |     |     |     |      |
| ccu | aua | guu | uac | uuu | uau | gac | ccu | gug | aau | ucc | acu | cuc | cua | cca | ccg | 1988 |
| Pro | Ile | Val | Tyr | Phe | Tyr | Asp | Pro | Val | Asn | Ser | Thr | Leu | Leu | Pro | Pro |      |
|     | 535 |     |     |     | 540 |     |     |     | 545 |     |     |     |     |     |     |      |
| gag | agg | ugg | gcu | agg | uug | ccc | ggu | acc | cca | ccu | gug | gua | cgu | ggu | ucu | 2036 |
| Glu | Arg | Trp | Ala | Arg | Leu | Pro | Gly | Thr | Pro | Pro | Val | Val | Arg | Gly | Ser |      |
| 550 |     |     |     | 555 |     |     |     | 560 |     |     |     | 565 |     |     |     |      |
| ugg | uua | cag | guu | ccg | caa | ggg | uuu | uac | agu | gau | gug | aaa | gac | cua | gcc | 2084 |
| Trp | Leu | Gln | Val | Pro | Gln | Gly | Phe | Tyr | Ser | Asp | Val | Lys | Asp | Leu | Ala |      |

-continued

|     |     |     |     |     | 570 |     |     |     |     | 575 |     |     |     |     | 580 |     |      |
|-----|-----|-----|-----|-----|-----|-----|-----|-----|-----|-----|-----|-----|-----|-----|-----|-----|------|
| aca | gga | uug | auc | acc | aaa | gac | aaa | gcc | ugg | aaa | aau | uau | cag | guc | uua |     | 2132 |
| Thr | Gly | Leu | Ile | Thr | Lys | Asp | Lys | Ala | Trp | Lys | Asn | Tyr | Gln | Val | Leu |     |      |
|     |     |     |     | 585 |     |     |     |     | 590 |     |     |     |     | 595 |     |     |      |

```
                                 570                 575                 580
aca gga uug auc acc aaa gac aaa gcc ugg aaa aau uau cag guc uua              2132
Thr Gly Leu Ile Thr Lys Asp Lys Ala Trp Lys Asn Tyr Gln Val Leu
                585                 590                 595 uau ucc gcc acg ggu gcu uug ucu cuu acg gga guu acc acc aag gcc              2180
Tyr Ser Ala Thr Gly Ala Leu Ser Leu Thr Gly Val Thr Thr Lys Ala
            600                 605                 610 gug gug cua auu cug uug ggg uug ugu ggc agc aag uau cuu auu uua              2228
Val Val Leu Ile Leu Leu Gly Leu Cys Gly Ser Lys Tyr Leu Ile Leu
        615                 620                 625 gcc uac cuc ugu uac uug ucc cuu ugu uuu ggg cgc gcu ucu ggu uac              2276
Ala Tyr Leu Cys Tyr Leu Ser Leu Cys Phe Gly Arg Ala Ser Gly Tyr
630                 635                 640                 645 ccu uug cgu ccu gug cuc cca ucc cag ucg uau cuc caa gcu ggc ugg              2324
Pro Leu Arg Pro Val Leu Pro Ser Gln Ser Tyr Leu Gln Ala Gly Trp
                650                 655                 660 gau guu uug ucu aaa gcu caa gua gcu ccu uuu gcu uug auu uuc uuc              2372
Asp Val Leu Ser Lys Ala Gln Val Ala Pro Phe Ala Leu Ile Phe Phe
            665                 670                 675 auc ugu ugc uau cuc cgc ugc agg cua cgu uau gcu gcc cuu uua ggg              2420
Ile Cys Cys Tyr Leu Arg Cys Arg Leu Arg Tyr Ala Ala Leu Leu Gly
        680                 685                 690 uuu gug ccc aug gcu gag gcc gcc uua gag aac cug gug auc cuc aau              2468
Phe Val Pro Met Ala Glu Ala Ala Leu Glu Asn Leu Val Ile Leu Asn
695                 700                 705 gcg gcg ucu gug gcc gga gcg cau ggc guu cuc ucu uuc cuu gug uuc              2516
Ala Ala Ser Val Ala Gly Ala His Gly Val Leu Ser Phe Leu Val Phe
                710                 715                 720                 725 uuc ugc gcu gcc ugg uac auc aag ggc aag cug guc ccc ggg gcg gca              2564
Phe Cys Ala Ala Trp Tyr Ile Lys Gly Lys Leu Val Pro Gly Ala Ala
                    730                 735                 740 uau gcc uuc uau ggu gua ugg ccg cug cuc cug cuu cug cug uca uua              2612
Tyr Ala Phe Tyr Gly Val Trp Pro Leu Leu Leu Leu Leu Leu Ser Leu
                745                 750                 755 cca cca cga gca uac gcc uug gac cgg gag aug gcu gca ucg ugc gga              2660
Pro Pro Arg Ala Tyr Ala Leu Asp Arg Glu Met Ala Ala Ser Cys Gly
            760                 765                 770 ggc gcg guu uuc gua ggu cug aug cuc cug acc uug uca cca cac uac              2708
Gly Ala Val Phe Val Gly Leu Met Leu Leu Thr Leu Ser Pro His Tyr
775                 780                 785 aag gug uuu cuc gcu agg cuc aua ugg ugg uua cag uau uuu auc acc              2756
Lys Val Phe Leu Ala Arg Leu Ile Trp Trp Leu Gln Tyr Phe Ile Thr
                790                 795                 800                 805 agg gcc gag gcg cac uug cag gug ugg guc ccc ccc cuc aac guu cgg              2804
Arg Ala Glu Ala His Leu Gln Val Trp Val Pro Pro Leu Asn Val Arg
                    810                 815                 820 ggg ggc cgc gau gcc auc auc cuc cuc acg ugu gug guc cac cca gag              2852
Gly Gly Arg Asp Ala Ile Ile Leu Leu Thr Cys Val Val His Pro Glu
            825                 830                 835 cua auu uuu gac auc acc aaa auc uug cuc gcc aug cuc ggu ccg cuc              2900
Leu Ile Phe Asp Ile Thr Lys Ile Leu Leu Ala Met Leu Gly Pro Leu
        840                 845                 850 aug gug cuc cag gcu ggc cua acu aga gug ccg uac uuc gua cgc gcu              2948
Met Val Leu Gln Ala Gly Leu Thr Arg Val Pro Tyr Phe Val Arg Ala
855                 860                 865 caa ggg cuc auc cgu gca ugc aug uua gug cgg aaa guc gcu ggg ggc              2996
Gln Gly Leu Ile Arg Ala Cys Met Leu Val Arg Lys Val Ala Gly Gly
                870                 875                 880                 885 cac uau guc caa aug gcc cuc aug aaa cug gcc gca cug acg ggu acg              3044
His Tyr Val Gln Met Ala Leu Met Lys Leu Ala Ala Leu Thr Gly Thr
```

-continued

```
             890                 895                 900
uac guu uau gac cau cuu acu ccg cug cag gac ugg gcc cac gcg ggc      3092
Tyr Val Tyr Asp His Leu Thr Pro Leu Gln Asp Trp Ala His Ala Gly
            905                 910                 915 uug cga gac cuu gca gug gca guu gag ccc guc guc uuc ucu gac aug      3140
Leu Arg Asp Leu Ala Val Ala Val Glu Pro Val Val Phe Ser Asp Met
            920                 925                 930 gag acu aag guc auc acc ugg ggg gca gac acc gca gcg ugu ggg gac      3188
Glu Thr Lys Val Ile Thr Trp Gly Ala Asp Thr Ala Ala Cys Gly Asp
            935                 940                 945 auc auc ucg ggc cua ccc guc ucc gcc cga agg ggg agg gag aua cuu      3236
Ile Ile Ser Gly Leu Pro Val Ser Ala Arg Arg Gly Arg Glu Ile Leu
950                 955                 960                 965 cug ggc ccc gcc gac agg uuu gga gag cag ggg ugg cga cuc cuc gcg      3284
Leu Gly Pro Ala Asp Arg Phe Gly Glu Gln Gly Trp Arg Leu Leu Ala
            970                 975                 980 ccu auc acg gcu uac gcu caa cag acg cgg ggc cua cuu ggc ugu auc      3332
Pro Ile Thr Ala Tyr Ala Gln Gln Thr Arg Gly Leu Leu Gly Cys Ile
            985                 990                 995 auc acc agc  cuc aca ggc cgg gac  aag aac cag guc gag ggg gag        3377
Ile Thr Ser Leu Thr Gly Arg Asp Lys Asn Gln Val Glu Gly Glu
            1000                1005                1010 guu cag gug guu ucc acc gca acg caa ucu uuc cug gcg acc ugc          3422
Val Gln Val Val Ser Thr Ala Thr Gln Ser Phe Leu Ala Thr Cys
            1015                1020                1025 guc aac ggc gug ugu ugg acu guc uac cau ggu gcc ggc ucg aag          3467
Val Asn Gly Val Cys Trp Thr Val Tyr His Gly Ala Gly Ser Lys
            1030                1035                1040 acc cug gcc ggc ccg aag ggc cca auc acc caa aug uac acc aau          3512
Thr Leu Ala Gly Pro Lys Gly Pro Ile Thr Gln Met Tyr Thr Asn
            1045                1050                1055 gug gac caa gac cuc guc ggc ugg ccg gcg ccc ccc ggg gcg cgc          3557
Val Asp Gln Asp Leu Val Gly Trp Pro Ala Pro Pro Gly Ala Arg
            1060                1065                1070 ucc cug aca ccg ugc acc ugc ggc agc ucg gac cuc uac cug guc          3602
Ser Leu Thr Pro Cys Thr Cys Gly Ser Ser Asp Leu Tyr Leu Val
            1075                1080                1085 acg agg cau gcu gau guc auu ccg gug cgc cgg cgg ggc gac agc          3647
Thr Arg His Ala Asp Val Ile Pro Val Arg Arg Arg Gly Asp Ser
            1090                1095                1100 agg ggg agu cua cuc ucu ccc agg ccc auc ucc uac uua aag ggc          3692
Arg Gly Ser Leu Leu Ser Pro Arg Pro Ile Ser Tyr Leu Lys Gly
            1105                1110                1115 ucc uca ggu ggu cca cug cuu ugc ccc cug ggg cac gcu gug ggc          3737
Ser Ser Gly Gly Pro Leu Leu Cys Pro Leu Gly His Ala Val Gly
            1120                1125                1130 auc uuc cgg gcc gcu gug ugc acc cgg ggg guu gca aag gcg gug          3782
Ile Phe Arg Ala Ala Val Cys Thr Arg Gly Val Ala Lys Ala Val
            1135                1140                1145 gau uuu gua ccu guu gag ucu aug gaa acc acc aug cgg ucu ccg          3827
Asp Phe Val Pro Val Glu Ser Met Glu Thr Thr Met Arg Ser Pro
            1150                1155                1160 guc uuu acg gau aau uca ucu ccc ccg gcc gua ccg cag aca uuc          3872
Val Phe Thr Asp Asn Ser Ser Pro Pro Ala Val Pro Gln Thr Phe
            1165                1170                1175 caa gug gcc cau cua cac gcu ccc acu ggc agu ggc aag agc acu          3917
Gln Val Ala His Leu His Ala Pro Thr Gly Ser Gly Lys Ser Thr
            1180                1185                1190 aag gug ccg gcu gcg uac gca gcc caa ggg uac aag gua cuc guc          3962
Lys Val Pro Ala Ala Tyr Ala Ala Gln Gly Tyr Lys Val Leu Val
```

```
               1195                1200                1205
uug aac cca ucc guu gcc gcu acc uua ggg uuu ggg gcg uac aug      4007
Leu Asn Pro Ser Val Ala Ala Thr Leu Gly Phe Gly Ala Tyr Met
            1210                1215                1220 ucu aaa gca cau ggu guu gag ccu aac auc aga acu ggg gua agg      4052
Ser Lys Ala His Gly Val Glu Pro Asn Ile Arg Thr Gly Val Arg
            1225                1230                1235 acc auc acc acg ggc gcu ucc auc acg uau ucc acc uac ggu aag      4097
Thr Ile Thr Thr Gly Ala Ser Ile Thr Tyr Ser Thr Tyr Gly Lys
            1240                1245                1250 uuc cuu gcc gac ggu ggu ugc ucu ggg ggc gcc uau gac auc aua      4142
Phe Leu Ala Asp Gly Gly Cys Ser Gly Gly Ala Tyr Asp Ile Ile
            1255                1260                1265 aua ugu gau gag ugc cac uca acu gac ucg acu ucc auc uug ggc      4187
Ile Cys Asp Glu Cys His Ser Thr Asp Ser Thr Ser Ile Leu Gly
            1270                1275                1280 auu ggc aca guc cug gac caa gcg gag acg gcu gga gcg cgg cuc      4232
Ile Gly Thr Val Leu Asp Gln Ala Glu Thr Ala Gly Ala Arg Leu
            1285                1290                1295 guc gug cuc gcc acc gcu acg ccu ccg gga ucg guc acc gug cca      4277
Val Val Leu Ala Thr Ala Thr Pro Pro Gly Ser Val Thr Val Pro
            1300                1305                1310 cau ccc aau auc gag gag gug gcc uug ccc agc acc gga gaa auu      4322
His Pro Asn Ile Glu Glu Val Ala Leu Pro Ser Thr Gly Glu Ile
            1315                1320                1325 ccc uuc uac ggc aaa gcc auc ccc auu gag acc auc aag ggg ggg      4367
Pro Phe Tyr Gly Lys Ala Ile Pro Ile Glu Thr Ile Lys Gly Gly
            1330                1335                1340 agg cac cuc auc uuc ugc cac ucc aag aag aaa ugu gac gag cuc      4412
Arg His Leu Ile Phe Cys His Ser Lys Lys Lys Cys Asp Glu Leu
            1345                1350                1355 gcu gca aag cug gug ggc cuc gga guu aac gcu guu gcg uac uac      4457
Ala Ala Lys Leu Val Gly Leu Gly Val Asn Ala Val Ala Tyr Tyr
            1360                1365                1370 cgg ggu cuu gau gug ucc guc aua cca aca agc gga gau guc guu      4502
Arg Gly Leu Asp Val Ser Val Ile Pro Thr Ser Gly Asp Val Val
            1375                1380                1385 guc gug gca aca gac gcu cua aug acg ggc uuc acc ggc gac uuu      4547
Val Val Ala Thr Asp Ala Leu Met Thr Gly Phe Thr Gly Asp Phe
            1390                1395                1400 gac uca gug auc gac ugu aau acu ugu guc acc cag aca guu gau      4592
Asp Ser Val Ile Asp Cys Asn Thr Cys Val Thr Gln Thr Val Asp
            1405                1410                1415 uuc agc uug gac ccu acc uuc acc auu gag acg aca acc gug ccc      4637
Phe Ser Leu Asp Pro Thr Phe Thr Ile Glu Thr Thr Thr Val Pro
            1420                1425                1430 caa gac gcg gug ucg cgu ucg cag cga cga ggc agg acu ggc agg      4682
Gln Asp Ala Val Ser Arg Ser Gln Arg Arg Gly Arg Thr Gly Arg
            1435                1440                1445 ggc agg aug ggc aua uac agg uuu gug gcu cca ggg gaa cgg ccc      4727
Gly Arg Met Gly Ile Tyr Arg Phe Val Ala Pro Gly Glu Arg Pro
            1450                1455                1460 ucg ggc aug uuc gau ucu ucg guc cug ugu gag ugc uau gac gcg      4772
Ser Gly Met Phe Asp Ser Ser Val Leu Cys Glu Cys Tyr Asp Ala
            1465                1470                1475 ggc ugu gcu ugg uau gag cuc acg ccc gcc gag acc uca guc agg      4817
Gly Cys Ala Trp Tyr Glu Leu Thr Pro Ala Glu Thr Ser Val Arg
            1480                1485                1490 uug cgg gcu uac cua aau aca cca ggg cug ccc guc ugc cag gac      4862
Leu Arg Ala Tyr Leu Asn Thr Pro Gly Leu Pro Val Cys Gln Asp
```

-continued

|  |  |  |  |  |  |  |  |  |  |  |
|---|---|---|---|---|---|---|---|---|---|---|
|  | 1495 |  |  | 1500 |  |  | 1505 |  |  |  |
| cac | cug | gag | uuu | ugg | gag | ggg | guc | uuc | aca | ggc | cuc | acc | cac | aua | 4907 |
| His | Leu | Glu | Phe | Trp | Glu | Gly | Val | Phe | Thr | Gly | Leu | Thr | His | Ile |  |
|  | 1510 |  |  |  | 1515 |  |  |  | 1520 |  |  |  |  |  |
| gau | gcc | cau | uuc | uug | ucc | cag | acu | aag | cag | gca | gga | gau | aac | uuc | 4952 |
| Asp | Ala | His | Phe | Leu | Ser | Gln | Thr | Lys | Gln | Ala | Gly | Asp | Asn | Phe |  |
|  | 1525 |  |  |  | 1530 |  |  |  | 1535 |  |  |  |  |  |
| ccc | uac | cug | gua | gca | uac | cag | gcu | acg | gug | ugc | gcc | agg | gcc | cag | 4997 |
| Pro | Tyr | Leu | Val | Ala | Tyr | Gln | Ala | Thr | Val | Cys | Ala | Arg | Ala | Gln |  |
|  | 1540 |  |  |  | 1545 |  |  |  | 1550 |  |  |  |  |  |
| gcu | ccc | ccu | cca | ucg | ugg | gau | caa | aug | ugg | aag | ugu | cuc | aua | cgg | 5042 |
| Ala | Pro | Pro | Pro | Ser | Trp | Asp | Gln | Met | Trp | Lys | Cys | Leu | Ile | Arg |  |
|  | 1555 |  |  |  | 1560 |  |  |  | 1565 |  |  |  |  |  |
| cug | aag | ccu | aca | cua | cac | ggg | cca | acg | ccc | cug | uug | uau | agg | cua | 5087 |
| Leu | Lys | Pro | Thr | Leu | His | Gly | Pro | Thr | Pro | Leu | Leu | Tyr | Arg | Leu |  |
|  | 1570 |  |  |  | 1575 |  |  |  | 1580 |  |  |  |  |  |
| gga | gcc | guc | cag | aau | gag | guc | auc | cuc | aca | cau | ccc | aua | acc | aaa | 5132 |
| Gly | Ala | Val | Gln | Asn | Glu | Val | Ile | Leu | Thr | His | Pro | Ile | Thr | Lys |  |
|  | 1585 |  |  |  | 1590 |  |  |  | 1595 |  |  |  |  |  |
| uac | auc | aug | gca | ugc | aug | ucg | gcu | gac | cua | gag | guc | guc | acu | agc | 5177 |
| Tyr | Ile | Met | Ala | Cys | Met | Ser | Ala | Asp | Leu | Glu | Val | Val | Thr | Ser |  |
|  | 1600 |  |  |  | 1605 |  |  |  | 1610 |  |  |  |  |  |
| acc | ugg | gug | cug | guc | ggc | ggg | guc | cuu | gca | gcu | cug | gcc | gcg | uac | 5222 |
| Thr | Trp | Val | Leu | Val | Gly | Gly | Val | Leu | Ala | Ala | Leu | Ala | Ala | Tyr |  |
|  | 1615 |  |  |  | 1620 |  |  |  | 1625 |  |  |  |  |  |
| ugc | cug | acg | acg | ggc | agc | gug | guc | auu | gug | ggc | agg | auc | auc | uug | 5267 |
| Cys | Leu | Thr | Thr | Gly | Ser | Val | Val | Ile | Val | Gly | Arg | Ile | Ile | Leu |  |
|  | 1630 |  |  |  | 1635 |  |  |  | 1640 |  |  |  |  |  |
| ucc | ggg | aag | ccg | gcu | auc | auu | ccu | gac | agg | gaa | guc | cuc | uac | cgg | 5312 |
| Ser | Gly | Lys | Pro | Ala | Ile | Ile | Pro | Asp | Arg | Glu | Val | Leu | Tyr | Arg |  |
|  | 1645 |  |  |  | 1650 |  |  |  | 1655 |  |  |  |  |  |
| gag | uuc | gau | gaa | aug | gaa | gag | ugu | gcc | uca | cac | cuc | ccc | uac | auc | 5357 |
| Glu | Phe | Asp | Glu | Met | Glu | Glu | Cys | Ala | Ser | His | Leu | Pro | Tyr | Ile |  |
|  | 1660 |  |  |  | 1665 |  |  |  | 1670 |  |  |  |  |  |
| gaa | cag | gga | aug | cag | cuc | gcc | gaa | caa | uuc | aag | cag | aag | gcg | cuc | 5402 |
| Glu | Gln | Gly | Met | Gln | Leu | Ala | Glu | Gln | Phe | Lys | Gln | Lys | Ala | Leu |  |
|  | 1675 |  |  |  | 1680 |  |  |  | 1685 |  |  |  |  |  |
| ggg | uug | cug | cag | aca | gcc | acc | aag | caa | gcg | gaa | gcc | gcu | gcu | ccu | 5447 |
| Gly | Leu | Leu | Gln | Thr | Ala | Thr | Lys | Gln | Ala | Glu | Ala | Ala | Ala | Pro |  |
|  | 1690 |  |  |  | 1695 |  |  |  | 1700 |  |  |  |  |  |
| gug | gug | gag | ucc | aag | ugg | cga | gcc | cuu | gag | gcc | uuc | ugg | gcg | aag | 5492 |
| Val | Val | Glu | Ser | Lys | Trp | Arg | Ala | Leu | Glu | Ala | Phe | Trp | Ala | Lys |  |
|  | 1705 |  |  |  | 1710 |  |  |  | 1715 |  |  |  |  |  |
| cac | aug | ugg | aau | uuc | auc | agc | ggg | aua | cag | uac | uua | gca | ggc | uug | 5537 |
| His | Met | Trp | Asn | Phe | Ile | Ser | Gly | Ile | Gln | Tyr | Leu | Ala | Gly | Leu |  |
|  | 1720 |  |  |  | 1725 |  |  |  | 1730 |  |  |  |  |  |
| ucc | acu | cug | ccu | ggg | aac | ccc | gcg | aua | gca | uca | cug | aug | gca | uuc | 5582 |
| Ser | Thr | Leu | Pro | Gly | Asn | Pro | Ala | Ile | Ala | Ser | Leu | Met | Ala | Phe |  |
|  | 1735 |  |  |  | 1740 |  |  |  | 1745 |  |  |  |  |  |
| aca | gcc | ucu | auc | acc | agc | ccg | cuu | acc | acc | cua | cac | acc | cuc | cug | 5627 |
| Thr | Ala | Ser | Ile | Thr | Ser | Pro | Leu | Thr | Thr | Leu | His | Thr | Leu | Leu |  |
|  | 1750 |  |  |  | 1755 |  |  |  | 1760 |  |  |  |  |  |
| uuu | aac | auc | uug | gga | gga | ugg | gug | gcc | gcc | caa | cuu | gcc | ccc | ccc | 5672 |
| Phe | Asn | Ile | Leu | Gly | Gly | Trp | Val | Ala | Ala | Gln | Leu | Ala | Pro | Pro |  |
|  | 1765 |  |  |  | 1770 |  |  |  | 1775 |  |  |  |  |  |
| ggu | gcu | gcc | ucg | gcu | uuc | gug | ggc | gcc | ggc | auu | gcu | ggc | gca | gcu | 5717 |
| Gly | Ala | Ala | Ser | Ala | Phe | Val | Gly | Ala | Gly | Ile | Ala | Gly | Ala | Ala |  |
|  | 1780 |  |  |  | 1785 |  |  |  | 1790 |  |  |  |  |  |
| guu | ggc | agc | aua | ggc | cuu | ggg | aag | gug | cuu | gug | gac | auc | cug | gcg | 5762 |
| Val | Gly | Ser | Ile | Gly | Leu | Gly | Lys | Val | Leu | Val | Asp | Ile | Leu | Ala |  |

-continued

|  |  |  |  |  |  |  |  |  |  |  |  |  |  |  |
|---|---|---|---|---|---|---|---|---|---|---|---|---|---|---|
|  |  |  |  | 1795 |  |  |  | 1800 |  |  |  | 1805 |  |  |
| ggu | uau | gga | gca | ggg | gug | gca | ggc | gcg | cuc | gug | gcc | uuc | aag | guc | 5807 |
| Gly | Tyr | Gly | Ala | Gly | Val | Ala | Gly | Ala | Leu | Val | Ala | Phe | Lys | Val |  |
|  |  |  |  | 1810 |  |  |  | 1815 |  |  |  | 1820 |  |  |
| aug | agc | ggc | gag | aug | ccc | ucc | acc | gag | gac | cug | guc | aac | uua | cuc | 5852 |
| Met | Ser | Gly | Glu | Met | Pro | Ser | Thr | Glu | Asp | Leu | Val | Asn | Leu | Leu |  |
|  |  |  |  | 1825 |  |  |  | 1830 |  |  |  | 1835 |  |  |
| ccu | gcc | auc | cuc | ucu | ccu | ggu | gcc | cuu | guc | guc | ggg | guc | gug | ugc | 5897 |
| Pro | Ala | Ile | Leu | Ser | Pro | Gly | Ala | Leu | Val | Val | Gly | Val | Val | Cys |  |
|  |  |  |  | 1840 |  |  |  | 1845 |  |  |  | 1850 |  |  |
| gca | gca | aua | cug | cgu | cgg | cau | gug | ggc | ccg | ggg | gag | ggg | gcu | gug | 5942 |
| Ala | Ala | Ile | Leu | Arg | Arg | His | Val | Gly | Pro | Gly | Glu | Gly | Ala | Val |  |
|  |  |  |  | 1855 |  |  |  | 1860 |  |  |  | 1865 |  |  |
| caa | ugg | aug | aac | cgg | cug | aua | gcg | uuc | gcc | ucg | cgg | ggu | aac | cac | 5987 |
| Gln | Trp | Met | Asn | Arg | Leu | Ile | Ala | Phe | Ala | Ser | Arg | Gly | Asn | His |  |
|  |  |  |  | 1870 |  |  |  | 1875 |  |  |  | 1880 |  |  |
| guc | ucc | ccc | acg | cac | uau | gug | ccu | gag | agc | gac | gcu | gca | gcg | cgu | 6032 |
| Val | Ser | Pro | Thr | His | Tyr | Val | Pro | Glu | Ser | Asp | Ala | Ala | Ala | Arg |  |
|  |  |  |  | 1885 |  |  |  | 1890 |  |  |  | 1895 |  |  |
| guc | aca | cag | auc | cuc | ucu | agc | cuc | acc | auc | acu | cag | cua | cug | aag | 6077 |
| Val | Thr | Gln | Ile | Leu | Ser | Ser | Leu | Thr | Ile | Thr | Gln | Leu | Leu | Lys |  |
|  |  |  |  | 1900 |  |  |  | 1905 |  |  |  | 1910 |  |  |
| agg | cuc | cac | cag | ugg | auu | aau | aag | gac | ugc | ucc | aca | cca | ugc | ucc | 6122 |
| Arg | Leu | His | Gln | Trp | Ile | Asn | Lys | Asp | Cys | Ser | Thr | Pro | Cys | Ser |  |
|  |  |  |  | 1915 |  |  |  | 1920 |  |  |  | 1925 |  |  |
| ggc | ucg | ugg | cuu | agg | gac | guu | ugg | gac | ugg | aua | ugc | acg | guu | uug | 6167 |
| Gly | Ser | Trp | Leu | Arg | Asp | Val | Trp | Asp | Trp | Ile | Cys | Thr | Val | Leu |  |
|  |  |  |  | 1930 |  |  |  | 1935 |  |  |  | 1940 |  |  |
| agu | gac | uuc | aag | acc | ugg | cuc | cag | ucc | aag | cuc | cug | cca | cgg | uua | 6212 |
| Ser | Asp | Phe | Lys | Thr | Trp | Leu | Gln | Ser | Lys | Leu | Leu | Pro | Arg | Leu |  |
|  |  |  |  | 1945 |  |  |  | 1950 |  |  |  | 1955 |  |  |
| ccg | gga | guu | cca | uuc | cuu | uca | ugc | caa | cgu | ggg | uau | aag | ggg | guc | 6257 |
| Pro | Gly | Val | Pro | Phe | Leu | Ser | Cys | Gln | Arg | Gly | Tyr | Lys | Gly | Val |  |
|  |  |  |  | 1960 |  |  |  | 1965 |  |  |  | 1970 |  |  |
| ugg | cgg | gga | gau | ggc | auc | aug | cag | acc | ucc | ugc | cca | ugu | gga | gca | 6302 |
| Trp | Arg | Gly | Asp | Gly | Ile | Met | Gln | Thr | Ser | Cys | Pro | Cys | Gly | Ala |  |
|  |  |  |  | 1975 |  |  |  | 1980 |  |  |  | 1985 |  |  |
| caa | auc | gcc | gga | cau | guc | aag | aac | ggu | ucc | aug | agg | auc | guu | ggg | 6347 |
| Gln | Ile | Ala | Gly | His | Val | Lys | Asn | Gly | Ser | Met | Arg | Ile | Val | Gly |  |
|  |  |  |  | 1990 |  |  |  | 1995 |  |  |  | 2000 |  |  |
| ccu | aaa | acc | ugu | agc | aac | acg | ugg | cac | gga | aca | uuc | ccc | auu | aac | 6392 |
| Pro | Lys | Thr | Cys | Ser | Asn | Thr | Trp | His | Gly | Thr | Phe | Pro | Ile | Asn |  |
|  |  |  |  | 2005 |  |  |  | 2010 |  |  |  | 2015 |  |  |
| gcg | cac | acc | acg | ggc | ccc | ugc | aca | ccc | ucc | cca | gcg | ccg | aac | uac | 6437 |
| Ala | His | Thr | Thr | Gly | Pro | Cys | Thr | Pro | Ser | Pro | Ala | Pro | Asn | Tyr |  |
|  |  |  |  | 2020 |  |  |  | 2025 |  |  |  | 2030 |  |  |
| ucu | aag | gcg | uug | ugg | cgg | gug | gcu | gcu | gag | gag | uac | gug | gaa | guc | 6482 |
| Ser | Lys | Ala | Leu | Trp | Arg | Val | Ala | Ala | Glu | Glu | Tyr | Val | Glu | Val |  |
|  |  |  |  | 2035 |  |  |  | 2040 |  |  |  | 2045 |  |  |
| acg | cgg | gug | ggg | gau | uuc | cau | uac | gug | acg | ggc | aug | acc | acu | gac | 6527 |
| Thr | Arg | Val | Gly | Asp | Phe | His | Tyr | Val | Thr | Gly | Met | Thr | Thr | Asp |  |
|  |  |  |  | 2050 |  |  |  | 2055 |  |  |  | 2060 |  |  |
| aac | gua | aaa | ugc | cca | ugc | cag | guu | ccg | gcc | ccc | gaa | uuc | uuc | aca | 6572 |
| Asn | Val | Lys | Cys | Pro | Cys | Gln | Val | Pro | Ala | Pro | Glu | Phe | Phe | Thr |  |
|  |  |  |  | 2065 |  |  |  | 2070 |  |  |  | 2075 |  |  |
| gag | gug | gau | ggg | gua | cgg | cug | cac | agg | uac | gcu | ccg | gcg | ugc | aaa | 6617 |
| Glu | Val | Asp | Gly | Val | Arg | Leu | His | Arg | Tyr | Ala | Pro | Ala | Cys | Lys |  |
|  |  |  |  | 2080 |  |  |  | 2085 |  |  |  | 2090 |  |  |
| ccu | cuc | cua | cgg | gau | gag | guc | aca | uuc | cag | guc | ggg | cuc | aac | cag | 6662 |
| Pro | Leu | Leu | Arg | Asp | Glu | Val | Thr | Phe | Gln | Val | Gly | Leu | Asn | Gln |  |

```
                   2095              2100             2105
uuc ccg guu ggg uca cag cuc cca ugc gag ccc gaa ccg gau gua    6707
Phe Pro Val Gly Ser Gln Leu Pro Cys Glu Pro Glu Pro Asp Val
        2110             2115             2120 uca gug cuc acu ucc aug cuu acc gac ccu ucc cac auc aca gca    6752
Ser Val Leu Thr Ser Met Leu Thr Asp Pro Ser His Ile Thr Ala
        2125             2130             2135 gag acg gcu aag cgu agg cug gcc aga ggg ucu ucc ccc ucu uug    6797
Glu Thr Ala Lys Arg Arg Leu Ala Arg Gly Ser Ser Pro Ser Leu
        2140             2145             2150 gcc agc ucu uca gcu agu cag uug ucu gcg ccc uca uug aag gcg    6842
Ala Ser Ser Ser Ala Ser Gln Leu Ser Ala Pro Ser Leu Lys Ala
        2155             2160             2165 aca ugc acc acc cau cau gac ucc cca gac gcu gac cuc auu gag    6887
Thr Cys Thr Thr His His Asp Ser Pro Asp Ala Asp Leu Ile Glu
        2170             2175             2180 gcc aac cuc cug ugg cgg cag gag aug gga ggg aac auc acc cgu    6932
Ala Asn Leu Leu Trp Arg Gln Glu Met Gly Gly Asn Ile Thr Arg
        2185             2190             2195 gug gag uca gag aac aag gug gua auc cug gac ucu uuu gac ccg    6977
Val Glu Ser Glu Asn Lys Val Val Ile Leu Asp Ser Phe Asp Pro
        2200             2205             2210 cuu cga gcg gag gag gac gag agg gag gug ucu guu gcg gcg gag    7022
Leu Arg Ala Glu Glu Asp Glu Arg Glu Val Ser Val Ala Ala Glu
        2215             2220             2225 auc cug cgg aaa acc agg aag uuc ccc cca gcg aug ccc aua ugg    7067
Ile Leu Arg Lys Thr Arg Lys Phe Pro Pro Ala Met Pro Ile Trp
        2230             2235             2240 gca cgc ccg gac uac aac cca ccg cug cua gag acu ugg aag gac    7112
Ala Arg Pro Asp Tyr Asn Pro Pro Leu Leu Glu Thr Trp Lys Asp
        2245             2250             2255 ccg gac uac guc ccu cca gug gug cac ggg ugc cca uug cca ccu    7157
Pro Asp Tyr Val Pro Pro Val Val His Gly Cys Pro Leu Pro Pro
        2260             2265             2270 acc aag acc ccu cca aua cca ccu ccg cgg agg aaa aag aca guu    7202
Thr Lys Thr Pro Pro Ile Pro Pro Pro Arg Arg Lys Lys Thr Val
        2275             2280             2285 guc cug aca gag ucc acc gug ucu ucu gcc cug gcg gag cuu gcc    7247
Val Leu Thr Glu Ser Thr Val Ser Ser Ala Leu Ala Glu Leu Ala
        2290             2295             2300 aca aag acc uuu ggc agc ucc gga ucg ucg gcc guc gac agc ggc    7292
Thr Lys Thr Phe Gly Ser Ser Gly Ser Ser Ala Val Asp Ser Gly
        2305             2310             2315 aca gcg acc gcc ccc ccu aac cag cuc ucc gac gaa gug gau aca    7337
Thr Ala Thr Ala Pro Pro Asn Gln Leu Ser Asp Glu Val Asp Thr
        2320             2325             2330 gga ucc gac guu gag ucg uac ucc ucc aug ccc ccc cuu gag gga    7382
Gly Ser Asp Val Glu Ser Tyr Ser Ser Met Pro Pro Leu Glu Gly
        2335             2340             2345 gag ccg ggg gac ccc gau cuc agc gac ggg ucu ugg ucu acu gua    7427
Glu Pro Gly Asp Pro Asp Leu Ser Asp Gly Ser Trp Ser Thr Val
        2350             2355             2360 agu gag gag gcu ggu gag gac guc guc ugc ugc ucg aug ucc uac    7472
Ser Glu Glu Ala Gly Glu Asp Val Val Cys Cys Ser Met Ser Tyr
        2365             2370             2375 aca ugg aca ggc gcc uug auc acg ccg ugc gcc gcg gag gag agc    7517
Thr Trp Thr Gly Ala Leu Ile Thr Pro Cys Ala Ala Glu Glu Ser
        2380             2385             2390 aag cug ccc auc aau gcg cug agc aac ucu uug cug cgc cac cac    7562
Lys Leu Pro Ile Asn Ala Leu Ser Asn Ser Leu Leu Arg His His
```

```
                       2395                2400                 2405 aac aug guc uau gcc aca aca ucc cgc agc gca agc caa cgg cag        7607
Asn Met Val Tyr Ala Thr Thr Ser Arg Ser Ala Ser Gln Arg Gln
            2410                2415                2420 aaa aag guc acc uuu gac aga cug caa guc cug gac gac cau uac        7652
Lys Lys Val Thr Phe Asp Arg Leu Gln Val Leu Asp Asp His Tyr
            2425                2430                2435 cgg gac gug cuc aag gag aug aag gcg aag gcu ucc aca guu aag        7697
Arg Asp Val Leu Lys Glu Met Lys Ala Lys Ala Ser Thr Val Lys
            2440                2445                2450 gcu aaa cuu cua ucc gua gaa gag gcc ugc aag cug acg ccc cca        7742
Ala Lys Leu Leu Ser Val Glu Glu Ala Cys Lys Leu Thr Pro Pro
            2455                2460                2465 cac uca gcc agg ucc aaa uuu ggc uau ggg gcg aag gac guc cgg        7787
His Ser Ala Arg Ser Lys Phe Gly Tyr Gly Ala Lys Asp Val Arg
            2470                2475                2480 aac cua ucc agc aag gcc guu aac cac auc aac ucc gug ugg aag        7832
Asn Leu Ser Ser Lys Ala Val Asn His Ile Asn Ser Val Trp Lys
            2485                2490                2495 gac uug cug gaa gac acu gag aca cca auu gac acc acc auc aug        7877
Asp Leu Leu Glu Asp Thr Glu Thr Pro Ile Asp Thr Thr Ile Met
            2500                2505                2510 gca aaa aau gag guc uuc ugu guu caa cca gag aag gga ggc cgc        7922
Ala Lys Asn Glu Val Phe Cys Val Gln Pro Glu Lys Gly Gly Arg
            2515                2520                2525 aag cca gcu cgc cuu auc gua uac cca gac uug ggg gug cgu gug        7967
Lys Pro Ala Arg Leu Ile Val Tyr Pro Asp Leu Gly Val Arg Val
            2530                2535                2540 ugc gag aaa aug gcc cuu uac gac gug guc ucc acu cuu ccu cag        8012
Cys Glu Lys Met Ala Leu Tyr Asp Val Val Ser Thr Leu Pro Gln
            2545                2550                2555 gcc gug aug ggc ucc uca uac gga uuc cag uac ucu ccu ggg cag        8057
Ala Val Met Gly Ser Ser Tyr Gly Phe Gln Tyr Ser Pro Gly Gln
            2560                2565                2570 cgg guc gag uuc cug gug aau gcc ugg aaa uca aag aag aac ccu        8102
Arg Val Glu Phe Leu Val Asn Ala Trp Lys Ser Lys Lys Asn Pro
            2575                2580                2585 aug ggc uuc gca uau gac acc cgc ugu uuu gac uca acg guc acc        8147
Met Gly Phe Ala Tyr Asp Thr Arg Cys Phe Asp Ser Thr Val Thr
            2590                2595                2600 gag aac gac auc cgu guu gag gag uca auu uac caa ugu ugu gac        8192
Glu Asn Asp Ile Arg Val Glu Glu Ser Ile Tyr Gln Cys Cys Asp
            2605                2610                2615 uug gcc ccc gag gcc aga cag gug aua agg ucg cuc aca gag cgg        8237
Leu Ala Pro Glu Ala Arg Gln Val Ile Arg Ser Leu Thr Glu Arg
            2620                2625                2630 cuu uau guc ggg ggc ccc cug acu aau uca aaa ggg cag aac ugc        8282
Leu Tyr Val Gly Gly Pro Leu Thr Asn Ser Lys Gly Gln Asn Cys
            2635                2640                2645 ggu uau cgc cgg ugc cgc gcc agc ggc gug cug acg acu agc ugc        8327
Gly Tyr Arg Arg Cys Arg Ala Ser Gly Val Leu Thr Thr Ser Cys
            2650                2655                2660 ggu aau acc cuc aca ugu uac uug aag gcc ucu gca gcc ugu cga        8372
Gly Asn Thr Leu Thr Cys Tyr Leu Lys Ala Ser Ala Ala Cys Arg
            2665                2670                2675 gcu gca aag cuc cag gac ugc acg aug cuc gug ugc ggg gac gac        8417
Ala Ala Lys Leu Gln Asp Cys Thr Met Leu Val Cys Gly Asp Asp
            2680                2685                2690 cuu guc guu auc ugu gaa agc gcg ggg acc cag gag gac gcg gcg        8462
Leu Val Val Ile Cys Glu Ser Ala Gly Thr Gln Glu Asp Ala Ala
```

-continued

```
                 2695              2700              2705
agc cua cga guc uuc acg gag gcu aug acu agg uac ucc gcc ccc        8507
Ser Leu Arg Val Phe Thr Glu Ala Met Thr Arg Tyr Ser Ala Pro
         2710              2715              2720 ccc ggg gac ccg ccc cga ccg gaa uac gac uug gag uug aua aca        8552
Pro Gly Asp Pro Pro Arg Pro Glu Tyr Asp Leu Glu Leu Ile Thr
         2725              2730              2735 uca ugc ucc ucc aac gug ucg guc gcg cac gau gca ucu ggc aaa        8597
Ser Cys Ser Ser Asn Val Ser Val Ala His Asp Ala Ser Gly Lys
         2740              2745              2750 cgg gug uau uac cuc acc cgu gac ccc acc acc ccc cuu gcg cgg        8642
Arg Val Tyr Tyr Leu Thr Arg Asp Pro Thr Thr Pro Leu Ala Arg
         2755              2760              2765 gcu gcg ugg gag aca gcu aaa cac acu cca guc aac ucc ugg cua        8687
Ala Ala Trp Glu Thr Ala Lys His Thr Pro Val Asn Ser Trp Leu
         2770              2775              2780 ggc aac auc auc aug uau gcg ccc acc cuc ugg gca agg aug auu        8732
Gly Asn Ile Ile Met Tyr Ala Pro Thr Leu Trp Ala Arg Met Ile
         2785              2790              2795 cug aug acu cac uuc uuc ucc auc cuu cua gcu cag gag cag cuu        8777
Leu Met Thr His Phe Phe Ser Ile Leu Leu Ala Gln Glu Gln Leu
         2800              2805              2810 gaa aaa gcc cug gau ugu cag auc uac ggg gcc acu uac ucc auu        8822
Glu Lys Ala Leu Asp Cys Gln Ile Tyr Gly Ala Thr Tyr Ser Ile
         2815              2820              2825 gaa cca cuu gac cua ccu cag auc auu caa cga cuc cau ggu cuu        8867
Glu Pro Leu Asp Leu Pro Gln Ile Ile Gln Arg Leu His Gly Leu
         2830              2835              2840 agc gca uuc uca cuc cau agu uac ucu cca ggu gaa auc aau agg        8912
Ser Ala Phe Ser Leu His Ser Tyr Ser Pro Gly Glu Ile Asn Arg
         2845              2850              2855 gug gcu uca ugc cuc agg aaa cuu ggg gua ccg ccc uug cga guc        8957
Val Ala Ser Cys Leu Arg Lys Leu Gly Val Pro Pro Leu Arg Val
         2860              2865              2870 ugg aga cau cgg gcc aga agu guc cgc gcu aag cua cug ucc cag        9002
Trp Arg His Arg Ala Arg Ser Val Arg Ala Lys Leu Leu Ser Gln
         2875              2880              2885 ggg ggg agg gcu gcc acu ugu ggc aag uac cuc uuc aac ugg gca        9047
Gly Gly Arg Ala Ala Thr Cys Gly Lys Tyr Leu Phe Asn Trp Ala
         2890              2895              2900 gua agg acc aag cuc aaa cuc acu cca auc ccg gcu gcg ucc cag        9092
Val Arg Thr Lys Leu Lys Leu Thr Pro Ile Pro Ala Ala Ser Gln
         2905              2910              2915 uug gac uug ucc ggc ugg uuc auu gcu ggu uac agc ggg gga gac        9137
Leu Asp Leu Ser Gly Trp Phe Ile Ala Gly Tyr Ser Gly Gly Asp
         2920              2925              2930 aua uau cac agc cug ucu cgu gcc cga ccc cgc ugg uuu aug uug        9182
Ile Tyr His Ser Leu Ser Arg Ala Arg Pro Arg Trp Phe Met Leu
         2935              2940              2945 ugc cua cuc cua cuu ucu gug ggg gua ggc auc uac cug cuc ccc        9227
Cys Leu Leu Leu Leu Ser Val Gly Val Gly Ile Tyr Leu Leu Pro
         2950              2955              2960 aau cga ugaacggggg gcuaaacacu ccaggccaau aggccauucu guuuuuuuu      9283
Asn Arg uuuuuuuuuu uuuuuuuuuu uuuuuuuuuu uuuuuuuuuu uuuuuccuuu uuuuuuuuuu  9343
uuuucccuuu cuuuuggugg cuccaucuua gcccuaguca cggcuagcug ugaaaggucc  9403
gugagccgca ugacugcaga gagugcugau acuggcccucu cugcagauca ugc        9456
```

<210> SEQ ID NO 56
<211> LENGTH: 2964
<212> TYPE: PRT
<213> ORGANISM: Artificial Sequence
<220> FEATURE:
<223> OTHER INFORMATION: Chimeric virus of Hepatitis C virus and GBV-B

<400> SEQUENCE: 56

```
Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Gln Pro Glu Gly Arg Ala Trp Ala Gln Pro Gly
65                  70                  75                  80

Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Leu Leu Glu Asp
145                 150                 155                 160

Gly Val Asn Trp Ala Thr Gly Trp Phe Gly Val His Leu Phe Val Val
                165                 170                 175

Cys Leu Leu Ser Leu Ala Cys Pro Cys Ser Gly Ala Arg Val Thr Asp
            180                 185                 190

Pro Asp Thr Asn Thr Thr Ile Leu Thr Asn Cys Cys Gln Arg Asn Gln
        195                 200                 205

Val Ile Tyr Cys Ser Pro Ser Thr Cys Leu His Glu Pro Gly Cys Val
    210                 215                 220

Ile Cys Ala Asp Glu Cys Trp Val Pro Ala Asn Pro Tyr Ile Ser His
225                 230                 235                 240

Pro Ser Asn Trp Thr Gly Thr Asp Ser Phe Leu Ala Asp His Ile Asp
                245                 250                 255

Phe Val Met Gly Ala Leu Val Thr Cys Asp Ala Leu Asp Ile Gly Glu
            260                 265                 270

Leu Cys Gly Ala Cys Val Leu Val Gly Asp Trp Leu Val Arg His Trp
        275                 280                 285

Leu Ile His Ile Asp Leu Asn Glu Thr Gly Thr Cys Tyr Leu Glu Val
    290                 295                 300

Pro Thr Gly Ile Asp Pro Gly Phe Leu Gly Phe Ile Gly Trp Met Ala
305                 310                 315                 320

Gly Lys Val Glu Ala Val Ile Phe Leu Thr Lys Leu Ala Ser Gln Val
                325                 330                 335

Pro Tyr Ala Ile Ala Thr Met Phe Ser Ser Val His Tyr Leu Ala Val
            340                 345                 350

Gly Ala Leu Ile Tyr Tyr Ala Ser Arg Gly Lys Trp Tyr Gln Leu Leu
        355                 360                 365

Leu Ala Leu Met Leu Tyr Ile Glu Ala Thr Ser Gly Asn Pro Ile Arg
    370                 375                 380
```

-continued

```
Val Pro Thr Gly Cys Ser Ile Ala Glu Phe Cys Ser Pro Leu Met Ile
385                 390                 395                 400

Pro Cys Pro Cys His Ser Tyr Leu Ser Glu Asn Val Ser Glu Val Ile
            405                 410                 415

Cys Tyr Ser Pro Lys Trp Thr Arg Pro Ile Thr Leu Glu Tyr Asn Asn
        420                 425                 430

Ser Ile Ser Trp Tyr Pro Tyr Thr Ile Pro Gly Ala Arg Gly Cys Met
    435                 440                 445

Val Lys Phe Lys Asn Asn Thr Trp Gly Cys Cys Arg Ile Arg Asn Val
    450                 455                 460

Pro Ser Tyr Cys Thr Met Gly Thr Asp Ala Val Trp Asn Asp Thr Arg
465                 470                 475                 480

Asn Thr Tyr Glu Ala Cys Gly Val Thr Pro Trp Leu Thr Thr Ala Trp
                485                 490                 495

His Asn Gly Ser Ala Leu Lys Leu Ala Ile Leu Gln Tyr Pro Gly Ser
            500                 505                 510

Lys Glu Met Phe Lys Pro His Asn Trp Met Ser Gly His Leu Tyr Phe
        515                 520                 525

Glu Gly Ser Asp Thr Pro Ile Val Tyr Phe Tyr Asp Pro Val Asn Ser
    530                 535                 540

Thr Leu Leu Pro Pro Glu Arg Trp Ala Arg Leu Pro Gly Thr Pro Pro
545                 550                 555                 560

Val Val Arg Gly Ser Trp Leu Gln Val Pro Gln Gly Phe Tyr Ser Asp
                565                 570                 575

Val Lys Asp Leu Ala Thr Gly Leu Ile Thr Lys Asp Lys Ala Trp Lys
    580                 585                 590

Asn Tyr Gln Val Leu Tyr Ser Ala Thr Gly Ala Leu Ser Leu Thr Gly
        595                 600                 605

Val Thr Thr Lys Ala Val Val Leu Ile Leu Leu Gly Leu Cys Gly Ser
    610                 615                 620

Lys Tyr Leu Ile Leu Ala Tyr Leu Cys Tyr Leu Ser Leu Cys Phe Gly
625                 630                 635                 640

Arg Ala Ser Gly Tyr Pro Leu Arg Pro Val Leu Pro Ser Gln Ser Tyr
                645                 650                 655

Leu Gln Ala Gly Trp Asp Val Leu Ser Lys Ala Gln Val Ala Pro Phe
        660                 665                 670

Ala Leu Ile Phe Phe Ile Cys Cys Tyr Leu Arg Cys Arg Leu Arg Tyr
    675                 680                 685

Ala Ala Leu Leu Gly Phe Val Pro Met Ala Glu Ala Ala Leu Glu Asn
690                 695                 700

Leu Val Ile Leu Asn Ala Ser Val Ala Gly Ala His Gly Val Leu
705                 710                 715                 720

Ser Phe Leu Val Phe Cys Ala Ala Trp Tyr Ile Lys Gly Lys Leu
                725                 730                 735

Val Pro Gly Ala Ala Tyr Ala Phe Tyr Gly Val Trp Pro Leu Leu Leu
        740                 745                 750

Leu Leu Leu Ser Leu Pro Pro Arg Ala Tyr Ala Leu Asp Arg Glu Met
    755                 760                 765

Ala Ala Ser Cys Gly Gly Ala Val Phe Val Gly Leu Met Leu Leu Thr
    770                 775                 780

Leu Ser Pro His Tyr Lys Val Phe Leu Ala Arg Leu Ile Trp Trp Leu
785                 790                 795                 800

Gln Tyr Phe Ile Thr Arg Ala Glu Ala His Leu Gln Val Trp Val Pro
```

```
                    805                 810                 815
Pro Leu Asn Val Arg Gly Gly Arg Asp Ala Ile Ile Leu Leu Thr Cys
                820                 825                 830
Val Val His Pro Glu Leu Ile Phe Asp Ile Thr Lys Ile Leu Leu Ala
                835                 840                 845
Met Leu Gly Pro Leu Met Val Leu Gln Ala Gly Leu Thr Arg Val Pro
850                 855                 860
Tyr Phe Val Arg Ala Gln Gly Leu Ile Arg Ala Cys Met Leu Val Arg
865                 870                 875                 880
Lys Val Ala Gly Gly His Tyr Val Gln Met Ala Leu Met Lys Leu Ala
                885                 890                 895
Ala Leu Thr Gly Thr Tyr Val Tyr Asp His Leu Thr Pro Leu Gln Asp
                900                 905                 910
Trp Ala His Ala Gly Leu Arg Asp Leu Ala Val Ala Val Glu Pro Val
                915                 920                 925
Val Phe Ser Asp Met Glu Thr Lys Val Ile Thr Trp Gly Ala Asp Thr
                930                 935                 940
Ala Ala Cys Gly Asp Ile Ile Ser Gly Leu Pro Val Ser Ala Arg Arg
945                 950                 955                 960
Gly Arg Glu Ile Leu Leu Gly Pro Ala Asp Arg Phe Gly Gln Gly
                965                 970                 975
Trp Arg Leu Leu Ala Pro Ile Thr Ala Tyr Ala Gln Gln Thr Arg Gly
                980                 985                 990
Leu Leu Gly Cys Ile Ile Thr Ser Leu Thr Gly Arg Asp Lys Asn Gln
                995                 1000                1005
Val Glu Gly Glu Val Gln Val Val Ser Thr Ala Thr Gln Ser Phe
        1010                1015                1020
Leu Ala Thr Cys Val Asn Gly Val Cys Trp Thr Val Tyr His Gly
        1025                1030                1035
Ala Gly Ser Lys Thr Leu Ala Gly Pro Lys Gly Pro Ile Thr Gln
        1040                1045                1050
Met Tyr Thr Asn Val Asp Gln Asp Leu Val Gly Trp Pro Ala Pro
        1055                1060                1065
Pro Gly Ala Arg Ser Leu Thr Pro Cys Thr Cys Gly Ser Ser Asp
        1070                1075                1080
Leu Tyr Leu Val Thr Arg His Ala Asp Val Ile Pro Val Arg Arg
        1085                1090                1095
Arg Gly Asp Ser Arg Gly Ser Leu Leu Ser Pro Arg Pro Ile Ser
        1100                1105                1110
Tyr Leu Lys Gly Ser Ser Gly Gly Pro Leu Leu Cys Pro Leu Gly
        1115                1120                1125
His Ala Val Gly Ile Phe Arg Ala Ala Val Cys Thr Arg Gly Val
        1130                1135                1140
Ala Lys Ala Val Asp Phe Val Pro Val Glu Ser Met Glu Thr Thr
        1145                1150                1155
Met Arg Ser Pro Val Phe Thr Asp Asn Ser Ser Pro Pro Ala Val
        1160                1165                1170
Pro Gln Thr Phe Gln Val Ala His Leu His Ala Pro Thr Gly Ser
        1175                1180                1185
Gly Lys Ser Thr Lys Val Pro Ala Ala Tyr Ala Ala Gln Gly Tyr
        1190                1195                1200
Lys Val Leu Val Leu Asn Pro Ser Val Ala Ala Thr Leu Gly Phe
        1205                1210                1215
```

-continued

```
Gly Ala Tyr Met Ser Lys Ala His Gly Val Glu Pro Asn Ile Arg
1220                1225                1230

Thr Gly Val Arg Thr Ile Thr Thr Gly Ala Ser Ile Thr Tyr Ser
1235                1240                1245

Thr Tyr Gly Lys Phe Leu Ala Asp Gly Gly Cys Ser Gly Gly Ala
1250                1255                1260

Tyr Asp Ile Ile Ile Cys Asp Glu Cys His Ser Thr Asp Ser Thr
1265                1270                1275

Ser Ile Leu Gly Ile Gly Thr Val Leu Asp Gln Ala Glu Thr Ala
1280                1285                1290

Gly Ala Arg Leu Val Val Leu Ala Thr Ala Thr Pro Pro Gly Ser
1295                1300                1305

Val Thr Val Pro His Pro Asn Ile Glu Glu Val Ala Leu Pro Ser
1310                1315                1320

Thr Gly Glu Ile Pro Phe Tyr Gly Lys Ala Ile Pro Ile Glu Thr
1325                1330                1335

Ile Lys Gly Gly Arg His Leu Ile Phe Cys His Ser Lys Lys Lys
1340                1345                1350

Cys Asp Glu Leu Ala Ala Lys Leu Val Gly Leu Gly Val Asn Ala
1355                1360                1365

Val Ala Tyr Tyr Arg Gly Leu Asp Val Ser Val Ile Pro Thr Ser
1370                1375                1380

Gly Asp Val Val Val Ala Thr Asp Ala Leu Met Thr Gly Phe
1385                1390                1395

Thr Gly Asp Phe Asp Ser Val Ile Asp Cys Asn Thr Cys Val Thr
1400                1405                1410

Gln Thr Val Asp Phe Ser Leu Asp Pro Thr Phe Thr Ile Glu Thr
1415                1420                1425

Thr Thr Val Pro Gln Asp Ala Val Ser Arg Ser Gln Arg Arg Gly
1430                1435                1440

Arg Thr Gly Arg Gly Arg Met Gly Ile Tyr Arg Phe Val Ala Pro
1445                1450                1455

Gly Glu Arg Pro Ser Gly Met Phe Asp Ser Ser Val Leu Cys Glu
1460                1465                1470

Cys Tyr Asp Ala Gly Cys Ala Trp Tyr Glu Leu Thr Pro Ala Glu
1475                1480                1485

Thr Ser Val Arg Leu Arg Ala Tyr Leu Asn Thr Pro Gly Leu Pro
1490                1495                1500

Val Cys Gln Asp His Leu Glu Phe Trp Glu Gly Val Phe Thr Gly
1505                1510                1515

Leu Thr His Ile Asp Ala His Phe Leu Ser Gln Thr Lys Gln Ala
1520                1525                1530

Gly Asp Asn Phe Pro Tyr Leu Val Ala Tyr Gln Ala Thr Val Cys
1535                1540                1545

Ala Arg Ala Gln Ala Pro Pro Pro Ser Trp Asp Gln Met Trp Lys
1550                1555                1560

Cys Leu Ile Arg Leu Lys Pro Thr Leu His Gly Pro Thr Pro Leu
1565                1570                1575

Leu Tyr Arg Leu Gly Ala Val Gln Asn Glu Val Ile Leu Thr His
1580                1585                1590

Pro Ile Thr Lys Tyr Ile Met Ala Cys Met Ser Ala Asp Leu Glu
1595                1600                1605

Val Val Thr Ser Thr Trp Val Leu Val Gly Gly Val Leu Ala Ala
1610                1615                1620
```

-continued

```
Leu Ala Ala Tyr Cys Leu Thr Thr Gly Ser Val Ile Val Gly
    1625                1630                1635

Arg Ile Ile Leu Ser Gly Lys Pro Ala Ile Ile Pro Asp Arg Glu
    1640                1645                1650

Val Leu Tyr Arg Glu Phe Asp Glu Met Glu Glu Cys Ala Ser His
    1655                1660                1665

Leu Pro Tyr Ile Glu Gln Gly Met Gln Leu Ala Glu Gln Phe Lys
    1670                1675                1680

Gln Lys Ala Leu Gly Leu Leu Gln Thr Ala Thr Lys Gln Ala Glu
    1685                1690                1695

Ala Ala Ala Pro Val Val Glu Ser Lys Trp Arg Ala Leu Glu Ala
    1700                1705                1710

Phe Trp Ala Lys His Met Trp Asn Phe Ile Ser Gly Ile Gln Tyr
    1715                1720                1725

Leu Ala Gly Leu Ser Thr Leu Pro Gly Asn Pro Ala Ile Ala Ser
    1730                1735                1740

Leu Met Ala Phe Thr Ala Ser Ile Thr Ser Pro Leu Thr Thr Leu
    1745                1750                1755

His Thr Leu Leu Phe Asn Ile Leu Gly Gly Trp Val Ala Ala Gln
    1760                1765                1770

Leu Ala Pro Pro Gly Ala Ala Ser Ala Phe Val Gly Ala Gly Ile
    1775                1780                1785

Ala Gly Ala Ala Val Gly Ser Ile Gly Leu Gly Lys Val Leu Val
    1790                1795                1800

Asp Ile Leu Ala Gly Tyr Gly Ala Gly Val Ala Gly Ala Leu Val
    1805                1810                1815

Ala Phe Lys Val Met Ser Gly Glu Met Pro Ser Thr Glu Asp Leu
    1820                1825                1830

Val Asn Leu Leu Pro Ala Ile Leu Ser Pro Gly Ala Leu Val Val
    1835                1840                1845

Gly Val Val Cys Ala Ala Ile Leu Arg Arg His Val Gly Pro Gly
    1850                1855                1860

Glu Gly Ala Val Gln Trp Met Asn Arg Leu Ile Ala Phe Ala Ser
    1865                1870                1875

Arg Gly Asn His Val Ser Pro Thr His Tyr Val Pro Glu Ser Asp
    1880                1885                1890

Ala Ala Ala Arg Val Thr Gln Ile Leu Ser Ser Leu Thr Ile Thr
    1895                1900                1905

Gln Leu Leu Lys Arg Leu His Gln Trp Ile Asn Lys Asp Cys Ser
    1910                1915                1920

Thr Pro Cys Ser Gly Ser Trp Leu Arg Asp Val Trp Asp Trp Ile
    1925                1930                1935

Cys Thr Val Leu Ser Asp Phe Lys Thr Trp Leu Gln Ser Lys Leu
    1940                1945                1950

Leu Pro Arg Leu Pro Gly Val Pro Phe Leu Ser Cys Gln Arg Gly
    1955                1960                1965

Tyr Lys Gly Val Trp Arg Gly Asp Gly Ile Met Gln Thr Ser Cys
    1970                1975                1980

Pro Cys Gly Ala Gln Ile Ala Gly His Val Lys Asn Gly Ser Met
    1985                1990                1995

Arg Ile Val Gly Pro Lys Thr Cys Ser Asn Thr Trp His Gly Thr
    2000                2005                2010

Phe Pro Ile Asn Ala His Thr Thr Gly Pro Cys Thr Pro Ser Pro
```

-continued

```
            2015                2020                2025

Ala Pro Asn Tyr Ser Lys Ala Leu Trp Arg Val Ala Ala Glu Glu
    2030                2035                2040

Tyr Val Glu Val Thr Arg Val Gly Asp Phe His Tyr Val Thr Gly
    2045                2050                2055

Met Thr Thr Asp Asn Val Lys Cys Pro Cys Gln Val Pro Ala Pro
    2060                2065                2070

Glu Phe Phe Thr Glu Val Asp Gly Val Arg Leu His Arg Tyr Ala
    2075                2080                2085

Pro Ala Cys Lys Pro Leu Leu Arg Asp Glu Val Thr Phe Gln Val
    2090                2095                2100

Gly Leu Asn Gln Phe Pro Val Gly Ser Gln Leu Pro Cys Glu Pro
    2105                2110                2115

Glu Pro Asp Val Ser Val Leu Thr Ser Met Leu Thr Asp Pro Ser
    2120                2125                2130

His Ile Thr Ala Glu Thr Ala Lys Arg Arg Leu Ala Arg Gly Ser
    2135                2140                2145

Ser Pro Ser Leu Ala Ser Ser Ser Ala Ser Gln Leu Ser Ala Pro
    2150                2155                2160

Ser Leu Lys Ala Thr Cys Thr Thr His His Asp Ser Pro Asp Ala
    2165                2170                2175

Asp Leu Ile Glu Ala Asn Leu Leu Trp Arg Gln Glu Met Gly Gly
    2180                2185                2190

Asn Ile Thr Arg Val Glu Ser Glu Asn Lys Val Val Ile Leu Asp
    2195                2200                2205

Ser Phe Asp Pro Leu Arg Ala Glu Glu Asp Glu Arg Glu Val Ser
    2210                2215                2220

Val Ala Ala Glu Ile Leu Arg Lys Thr Arg Lys Phe Pro Pro Ala
    2225                2230                2235

Met Pro Ile Trp Ala Arg Pro Asp Tyr Asn Pro Pro Leu Leu Glu
    2240                2245                2250

Thr Trp Lys Asp Pro Asp Tyr Val Pro Pro Val Val His Gly Cys
    2255                2260                2265

Pro Leu Pro Pro Thr Lys Thr Pro Pro Ile Pro Pro Pro Arg Arg
    2270                2275                2280

Lys Lys Thr Val Val Leu Thr Glu Ser Thr Val Ser Ser Ala Leu
    2285                2290                2295

Ala Glu Leu Ala Thr Lys Thr Phe Gly Ser Ser Gly Ser Ser Ala
    2300                2305                2310

Val Asp Ser Gly Thr Ala Thr Ala Pro Pro Asn Gln Leu Ser Asp
    2315                2320                2325

Glu Val Asp Thr Gly Ser Asp Val Glu Ser Tyr Ser Ser Met Pro
    2330                2335                2340

Pro Leu Glu Gly Glu Pro Gly Asp Pro Asp Leu Ser Asp Gly Ser
    2345                2350                2355

Trp Ser Thr Val Ser Glu Glu Ala Gly Glu Asp Val Val Cys Cys
    2360                2365                2370

Ser Met Ser Tyr Thr Trp Thr Gly Ala Leu Ile Thr Pro Cys Ala
    2375                2380                2385

Ala Glu Glu Ser Lys Leu Pro Ile Asn Ala Leu Ser Asn Ser Leu
    2390                2395                2400

Leu Arg His His Asn Met Val Tyr Ala Thr Thr Ser Arg Ser Ala
    2405                2410                2415
```

```
Ser Gln Arg Gln Lys Lys Val Thr Phe Asp Arg Leu Gln Val Leu
2420                2425                2430

Asp Asp His Tyr Arg Asp Val Leu Lys Glu Met Lys Ala Lys Ala
2435                2440                2445

Ser Thr Val Lys Ala Lys Leu Leu Ser Val Glu Glu Ala Cys Lys
2450                2455                2460

Leu Thr Pro Pro His Ser Ala Arg Ser Lys Phe Gly Tyr Gly Ala
2465                2470                2475

Lys Asp Val Arg Asn Leu Ser Ser Lys Ala Val Asn His Ile Asn
2480                2485                2490

Ser Val Trp Lys Asp Leu Leu Glu Asp Thr Glu Thr Pro Ile Asp
2495                2500                2505

Thr Thr Ile Met Ala Lys Asn Glu Val Phe Cys Val Gln Pro Glu
2510                2515                2520

Lys Gly Gly Arg Lys Pro Ala Arg Leu Ile Val Tyr Pro Asp Leu
2525                2530                2535

Gly Val Arg Val Cys Glu Lys Met Ala Leu Tyr Asp Val Val Ser
2540                2545                2550

Thr Leu Pro Gln Ala Val Met Gly Ser Ser Tyr Gly Phe Gln Tyr
2555                2560                2565

Ser Pro Gly Gln Arg Val Glu Phe Leu Val Asn Ala Trp Lys Ser
2570                2575                2580

Lys Lys Asn Pro Met Gly Phe Ala Tyr Asp Thr Arg Cys Phe Asp
2585                2590                2595

Ser Thr Val Thr Glu Asn Asp Ile Arg Val Glu Glu Ser Ile Tyr
2600                2605                2610

Gln Cys Cys Asp Leu Ala Pro Glu Ala Arg Gln Val Ile Arg Ser
2615                2620                2625

Leu Thr Glu Arg Leu Tyr Val Gly Gly Pro Leu Thr Asn Ser Lys
2630                2635                2640

Gly Gln Asn Cys Gly Tyr Arg Arg Cys Arg Ala Ser Gly Val Leu
2645                2650                2655

Thr Thr Ser Cys Gly Asn Thr Leu Thr Cys Tyr Leu Lys Ala Ser
2660                2665                2670

Ala Ala Cys Arg Ala Ala Lys Leu Gln Asp Cys Thr Met Leu Val
2675                2680                2685

Cys Gly Asp Asp Leu Val Val Ile Cys Glu Ser Ala Gly Thr Gln
2690                2695                2700

Glu Asp Ala Ala Ser Leu Arg Val Phe Thr Glu Ala Met Thr Arg
2705                2710                2715

Tyr Ser Ala Pro Pro Gly Asp Pro Pro Arg Pro Glu Tyr Asp Leu
2720                2725                2730

Glu Leu Ile Thr Ser Cys Ser Ser Asn Val Ser Val Ala His Asp
2735                2740                2745

Ala Ser Gly Lys Arg Val Tyr Tyr Leu Thr Arg Asp Pro Thr Thr
2750                2755                2760

Pro Leu Ala Arg Ala Ala Trp Glu Thr Ala Lys His Thr Pro Val
2765                2770                2775

Asn Ser Trp Leu Gly Asn Ile Ile Met Tyr Ala Pro Thr Leu Trp
2780                2785                2790

Ala Arg Met Ile Leu Met Thr His Phe Phe Ser Ile Leu Leu Ala
2795                2800                2805

Gln Glu Gln Leu Glu Lys Ala Leu Asp Cys Gln Ile Tyr Gly Ala
2810                2815                2820
```

```
Thr Tyr Ser Ile Glu Pro Leu Asp Leu Pro Gln Ile Ile Gln Arg
    2825            2830            2835

Leu His Gly Leu Ser Ala Phe Ser Leu His Ser Tyr Ser Pro Gly
    2840            2845            2850

Glu Ile Asn Arg Val Ala Ser Cys Leu Arg Lys Leu Gly Val Pro
    2855            2860            2865

Pro Leu Arg Val Trp Arg His Arg Ala Arg Ser Val Arg Ala Lys
    2870            2875            2880

Leu Leu Ser Gln Gly Gly Arg Ala Ala Thr Cys Gly Lys Tyr Leu
    2885            2890            2895

Phe Asn Trp Ala Val Arg Thr Lys Leu Lys Leu Thr Pro Ile Pro
    2900            2905            2910

Ala Ala Ser Gln Leu Asp Leu Ser Gly Trp Phe Ile Ala Gly Tyr
    2915            2920            2925

Ser Gly Gly Asp Ile Tyr His Ser Leu Ser Arg Ala Arg Pro Arg
    2930            2935            2940

Trp Phe Met Leu Cys Leu Leu Leu Leu Ser Val Gly Val Gly Ile
    2945            2950            2955

Tyr Leu Leu Pro Asn Arg
    2960

<210> SEQ ID NO 57
<211> LENGTH: 9594
<212> TYPE: RNA
<213> ORGANISM: Hepatitis C virus
<220> FEATURE:
<221> NAME/KEY: CDS
<222> LOCATION: (342)..(9371)

<400> SEQUENCE: 57
gccagccccc ugaugggggc gacacuccac cauagaucac uccccuguga ggaacuacug    60
ucuucacgca gaaagcgucu agccauggcg uuaguaugag ugucgugcag ccuccaggac   120
ccccccuccc gggagagcca uaguggucug cggaaccggu gaguacaccg gaauugccag   180
gacgaccggg uccuuucuug gaucaacccg cucaaugccu ggagauuugg gcgugccccc   240
gcgagacugc uagccgagua guguggguc gcgaaaggcc uugugguacu gccugauagg   300
gugcuugcga gugccccggg aggucucgua gaccgugcau c aug agc aca aau ccu   356
                                             Met Ser Thr Asn Pro
                                               1               5 aaa ccu caa aga aaa acc aaa cgu aac acc aac cgc cgc cca cag gac    404
Lys Pro Gln Arg Lys Thr Lys Arg Asn Thr Asn Arg Arg Pro Gln Asp
             10                  15                  20 guc aag uuc ccg ggc ggu ggc cag auc guu ggu gga guu uac cug uug    452
Val Lys Phe Pro Gly Gly Gly Gln Ile Val Gly Gly Val Tyr Leu Leu
         25                  30                  35 ccg cgc agg ggc ccc agg uug ggu gug cgc gcg acu agg aag acu ucc    500
Pro Arg Arg Gly Pro Arg Leu Gly Val Arg Ala Thr Arg Lys Thr Ser
     40                  45                  50 gag cgg ucg caa ccu cgu gga agg cga caa ccu auc ccc aag gcu cgc    548
Glu Arg Ser Gln Pro Arg Gly Arg Arg Gln Pro Ile Pro Lys Ala Arg
 55                  60                  65 cag ccc gag ggc agg gcc ugg gcu cag ccc ggg uau ccu ugg ccc cuc    596
Gln Pro Glu Gly Arg Ala Trp Ala Gln Pro Gly Tyr Pro Trp Pro Leu
 70                  75                  80                  85 uau ggc aac gag ggu cug ggg ugg gca gga ugg cuc cug uca ccc cgu    644
Tyr Gly Asn Glu Gly Leu Gly Trp Ala Gly Trp Leu Leu Ser Pro Arg
                 90                  95                 100
```

| | | |
|---|---|---|
| ggc ucu cgg ccu agu ugg ggc ccc acg gac ccc cgg cgu agg ucg cgu<br>Gly Ser Arg Pro Ser Trp Gly Pro Thr Asp Pro Arg Arg Ser Arg<br>105                         110                   115 | | 692 |
| aau uug ggu aag guc auc gau acc cuc aca ugc ggc uuc gcc gac cuc<br>Asn Leu Gly Lys Val Ile Asp Thr Leu Thr Cys Gly Phe Ala Asp Leu<br>    120                         125                    130 | | 740 |
| aug ggg uac auu ccg cuc guc ggc gcc cca cua gga ggc gcu gcc agg<br>Met Gly Tyr Ile Pro Leu Val Gly Ala Pro Leu Gly Ala Ala Arg<br>135                       140                   145 | | 788 |
| gcc cug gcg cau ggc guc cgg guu cug gag gac ggc gug aac uau gca<br>Ala Leu Ala His Gly Val Arg Val Leu Glu Asp Gly Val Asn Tyr Ala<br>150                   155                160               165 | | 836 |
| aca ggg aau cug ccc ggu ugc ccu uuc ucu auc uuc cuc uua gcu uug<br>Thr Gly Asn Leu Pro Gly Cys Pro Phe Ser Ile Phe Leu Leu Ala Leu<br>              170                   175                 180 | | 884 |
| cug ucc ugu uug acc auc cca gcu ucc gcu cac gaa gug cgc aac gua<br>Leu Ser Cys Leu Thr Ile Pro Ala Ser Ala His Glu Val Arg Asn Val<br>185                       190                   195 | | 932 |
| ucc ggg cug uac cau guc acg aac gac ugc ucc aac uca agc auu gug<br>Ser Gly Leu Tyr His Val Thr Asn Asp Cys Ser Asn Ser Ser Ile Val<br>    200                       205                   210 | | 980 |
| uau gag gca gcg gac aug auc aug cac acc ccc ggg ugc gug ccc ugc<br>Tyr Glu Ala Ala Asp Met Ile Met His Thr Pro Gly Cys Val Pro Cys<br>215                       220                  225 | | 1028 |
| guc cgg gag ggu aac ucc ucc cgc ugc ugg gua gcg cuc acu ccc acg<br>Val Arg Glu Gly Asn Ser Ser Arg Cys Trp Val Ala Leu Thr Pro Thr<br>230                     235                  240               245 | | 1076 |
| cuc gcg gcc agg aau agc agc guc ccc acu gcg aca aua cga cgc cau<br>Leu Ala Ala Arg Asn Ser Ser Val Pro Thr Ala Thr Ile Arg Arg His<br>               250                   255                 260 | | 1124 |
| guc gau uug cuc guc ggg gcg gcu gcc uuc ugu ucc gcu aug uac gug<br>Val Asp Leu Leu Val Gly Ala Ala Ala Phe Cys Ser Ala Met Tyr Val<br>265                       270                  275 | | 1172 |
| ggg gau cuu ugc gga ucu guu uuc cuc guc ucc cag cug uuc acc uuu<br>Gly Asp Leu Cys Gly Ser Val Phe Leu Val Ser Gln Leu Phe Thr Phe<br>    280                       285                   290 | | 1220 |
| uca ccu cgc cgg uac gag acg gua cag gac ugc aau ugc uca cuc uau<br>Ser Pro Arg Arg Tyr Glu Thr Val Gln Asp Cys Asn Cys Ser Leu Tyr<br>295                       300                  305 | | 1268 |
| ccc ggc cac gua uca ggc cau cgc aug gcu ugg gau aug aug aug aac<br>Pro Gly His Val Ser Gly His Arg Met Ala Trp Asp Met Met Met Asn<br>310                       315                  320               325 | | 1316 |
| ugg uca ccu aca aca gcc uua gug gua ucg cag uua cuc cgg auc cca<br>Trp Ser Pro Thr Thr Ala Leu Val Val Ser Gln Leu Leu Arg Ile Pro<br>              330                   335                 340 | | 1364 |
| caa gcc guc gug gau aug gug gua ggg gcc cac ugg gga guc cug gcg<br>Gln Ala Val Val Asp Met Val Val Gly Ala His Trp Gly Val Leu Ala<br>345                       350                  355 | | 1412 |
| ggc cuu gcc uac uau ucc aug gug ggg aac ugg gcu aag guc uug auu<br>Gly Leu Ala Tyr Tyr Ser Met Val Gly Asn Trp Ala Lys Val Leu Ile<br>    360                       365                   370 | | 1460 |
| gug aug cua cuc uuu gcc ggc guc gac ggg aag acc uac gug aca ggg<br>Val Met Leu Leu Phe Ala Gly Val Asp Gly Lys Thr Tyr Val Thr Gly<br>375                       380                  385 | | 1508 |
| ggg gcg cag agc cga gcc acu caa ggc uuu gcg ucc cuc uuu aca cgg<br>Gly Ala Gln Ser Arg Ala Thr Gln Gly Phe Ala Ser Leu Phe Thr Arg<br>390                       395                  400               405 | | 1556 |
| ggg ccg ucu cag aaa cuc cag cuu gua aau ucc aac ggc agc ugg cac<br>Gly Pro Ser Gln Lys Leu Gln Leu Val Asn Ser Asn Gly Ser Trp His<br>              410                   415                 420 | | 1604 |

| | | |
|---|---|---|
| auu aac agg acu gcc uug aac ugc aau gac ucc uuc cag acu ggg uuc<br>Ile Asn Arg Thr Ala Leu Asn Cys Asn Asp Ser Phe Gln Thr Gly Phe<br>              425                        430                          435 | 1652 |
| cuu gcc gcg cug uuu uac gca cac cgu uuc aac ucg ucc gga ugc cca<br>Leu Ala Ala Leu Phe Tyr Ala His Arg Phe Asn Ser Ser Gly Cys Pro<br>         440                        445                          450 | 1700 |
| gag cgc aug gcc agc ugc cgc ccc auc gac acg uuc gau cag ggg ugg<br>Glu Arg Met Ala Ser Cys Arg Pro Ile Asp Thr Phe Asp Gln Gly Trp<br>              455                        460                          465 | 1748 |
| ggc ccc auc acu cau guc gcg cgu cgc aca ucg gac cag agg ccu uau<br>Gly Pro Ile Thr His Val Ala Arg Arg Thr Ser Asp Gln Arg Pro Tyr<br>470                        475                          480                        485 | 1796 |
| ugc ugg cac uac gca ccu caa ccg ugu ggu auu gua ccc gcg uug cag<br>Cys Trp His Tyr Ala Pro Gln Pro Cys Gly Ile Val Pro Ala Leu Gln<br>                        490                          495                        500 | 1844 |
| gua ugu ggu cca gug uau ugc uuc acc cca agc ccc guc gug gug ggg<br>Val Cys Gly Pro Val Tyr Cys Phe Thr Pro Ser Pro Val Val Val Gly<br>         505                        510                          515 | 1892 |
| acg acc gau cgc uuc ggc gcc ccc acg uac aac ugg ggg gag aau gag<br>Thr Thr Asp Arg Phe Gly Ala Pro Thr Tyr Asn Trp Gly Glu Asn Glu<br>              520                        525                          530 | 1940 |
| acg gac gug cua cuc cuc aac aau acg cgg ccg cac ggc aac ugg<br>Thr Asp Val Leu Leu Leu Asn Asn Thr Arg Pro Pro His Gly Asn Trp<br>535                        540                          545 | 1988 |
| uuc ggc ugu aca ugg aug aau agu acc ggg uuc acc aag acg ugu ggg<br>Phe Gly Cys Thr Trp Met Asn Ser Thr Gly Phe Thr Lys Thr Cys Gly<br>550                        555                          560                        565 | 2036 |
| ggc ccc ccc ugc aac auc ggg ggg uuu ggc aac aac acc uug acc ugc<br>Gly Pro Pro Cys Asn Ile Gly Gly Phe Gly Asn Asn Thr Leu Thr Cys<br>                        570                          575                        580 | 2084 |
| ccu acg gau ugc uuc cgg aag cac ccc gag gcc acu uac acc aaa ugc<br>Pro Thr Asp Cys Phe Arg Lys His Pro Glu Ala Thr Tyr Thr Lys Cys<br>         585                        590                          595 | 2132 |
| ggc ucg ggg ccc ugg uug acg ccu agg ugc aug guu gau uac cca uac<br>Gly Ser Gly Pro Trp Leu Thr Pro Arg Cys Met Val Asp Tyr Pro Tyr<br>              600                        605                          610 | 2180 |
| aga cuu ugg cac uac ccc ugc acu guu aac uuu ucc auc uuc aag guc<br>Arg Leu Trp His Tyr Pro Cys Thr Val Asn Phe Ser Ile Phe Lys Val<br>615                        620                          625 | 2228 |
| agg aug uau gug ggg ggu gug gag cac agg cuc acc gcc gcg ugc aau<br>Arg Met Tyr Val Gly Gly Val Glu His Arg Leu Thr Ala Ala Cys Asn<br>630                        635                          640                        645 | 2276 |
| ugg acu cgg gga gag cgc ugc aac uug gag gau agg gac aga ucg gag<br>Trp Thr Arg Gly Glu Arg Cys Asn Leu Glu Asp Arg Asp Arg Ser Glu<br>                  650                        655                          660 | 2324 |
| cuc agc ccg cug cua cug ucu acc aca gag ugg cag gua cug ccc ugu<br>Leu Ser Pro Leu Leu Leu Ser Thr Thr Glu Trp Gln Val Leu Pro Cys<br>              665                        670                        675 | 2372 |
| ucu uuc acc acc uua ccg gcc cug ucc acu ggu uug auc cac cuc cac<br>Ser Phe Thr Thr Leu Pro Ala Leu Ser Thr Gly Leu Ile His Leu His<br>         680                        685                          690 | 2420 |
| cag aac auc gug gac gug caa uac cug uac ggu gug ggg uca ucg guu<br>Gln Asn Ile Val Asp Val Gln Tyr Leu Tyr Gly Val Gly Ser Ser Val<br>695                        700                          705 | 2468 |
| guc ucc auu gca auc agg ugg gag uau guc gug cug cuc uuc cuc cuc<br>Val Ser Ile Ala Ile Arg Trp Glu Tyr Val Val Leu Leu Phe Leu Leu<br>710                      715                        720                        725 | 2516 |
| cug gcg gac gcg cgy guu ugc gcc ugc uug ugg aug aug cug cug aua<br>Leu Ala Asp Ala Arg Val Cys Ala Cys Leu Trp Met Met Leu Leu Ile<br>                        730                          735                        740 | 2564 |

```
gcc caa gcu gag gcc gcc uua gag aac cug gug auc cuc aau gcg gcg    2612
Ala Gln Ala Glu Ala Ala Leu Glu Asn Leu Val Ile Leu Asn Ala Ala
        745                 750                 755 ucu gug gcc gga gcg cau ggc guu cuc ucu uuc cuu gug uuc uuc ugc    2660
Ser Val Ala Gly Ala His Gly Val Leu Ser Phe Leu Val Phe Phe Cys
            760                 765                 770 gcu gcc ugg uac auc aag ggc aag cug guc ccc ggg gcg gca uau gcc    2708
Ala Ala Trp Tyr Ile Lys Gly Lys Leu Val Pro Gly Ala Ala Tyr Ala
                775                 780                 785 uuc uau ggu gua ugg ccg cug cuc cug cuu cug cug uca uua cca cca    2756
Phe Tyr Gly Val Trp Pro Leu Leu Leu Leu Leu Leu Ser Leu Pro Pro
790                 795                 800                 805 cga gca uac gcc uug gac cgg gag aug gcu gca ucg ugc gga ggc gcg    2804
Arg Ala Tyr Ala Leu Asp Arg Glu Met Ala Ala Ser Cys Gly Gly Ala
            810                 815                 820 guu uuc gua ggu cug aug cuc cug acc uug uca cca cac uac aag gug    2852
Val Phe Val Gly Leu Met Leu Leu Thr Leu Ser Pro His Tyr Lys Val
                825                 830                 835 uuu cuc gcu agg cuc aua ugg ugg uua cag uau uuu auc acc agg gcc    2900
Phe Leu Ala Arg Leu Ile Trp Trp Leu Gln Tyr Phe Ile Thr Arg Ala
        840                 845                 850 gag gcg cac uug cag gug ugg guc ccc ccc cuc aac guu cgg ggg ggc    2948
Glu Ala His Leu Gln Val Trp Val Pro Pro Leu Asn Val Arg Gly Gly
    855                 860                 865 cgc gau gcc auc auc cuc cuc acg ugu gug guc cac cca gag cua auu    2996
Arg Asp Ala Ile Ile Leu Leu Thr Cys Val Val His Pro Glu Leu Ile
870                 875                 880                 885 uuu gac auc acc aaa auc uug cuc gcc aug cuc ggu ccg cuc aug gug    3044
Phe Asp Ile Thr Lys Ile Leu Leu Ala Met Leu Gly Pro Leu Met Val
            890                 895                 900 cuc cag gcu ggc cua acu aga gug ccg uac uuc gua cgc gcu caa ggg    3092
Leu Gln Ala Gly Leu Thr Arg Val Pro Tyr Phe Val Arg Ala Gln Gly
                905                 910                 915 cuc auc cgu gca ugc aug uua gug cgg aaa guc gcu ggg ggc cac uau    3140
Leu Ile Arg Ala Cys Met Leu Val Arg Lys Val Ala Gly Gly His Tyr
            920                 925                 930 guc caa aug gcc cuc aug aaa cug gcc gca cug acg ggu acg uac guu    3188
Val Gln Met Ala Leu Met Lys Leu Ala Ala Leu Thr Gly Thr Tyr Val
935                 940                 945 uau gac cau cuu acu ccg cug cag gac ugg gcc cac gcg ggc uug cga    3236
Tyr Asp His Leu Thr Pro Leu Gln Asp Trp Ala His Ala Gly Leu Arg
950                 955                 960                 965 gac cuu gca gug gca guu gag ccc guc guc uuc ucu gac aug gag acu    3284
Asp Leu Ala Val Ala Val Glu Pro Val Val Phe Ser Asp Met Glu Thr
            970                 975                 980 aag guc auc acc ugg ggg gca gac acc gca gcg ugu gga gac auc auc    3332
Lys Val Ile Thr Trp Gly Ala Asp Thr Ala Ala Cys Gly Asp Ile Ile
                985                 990                 995 ucg ggc cua ccc guc ucc gcc cga agg ggg agg gag aua cuu cug        3377
Ser Gly Leu Pro Val Ser Ala Arg Arg Gly Arg Glu Ile Leu Leu
            1000                1005                1010 ggc ccc gcc gac agg uuu gga gag cag ggg ugg cga cuc cuc gcg        3422
Gly Pro Ala Asp Arg Phe Gly Glu Gln Gly Trp Arg Leu Leu Ala
    1015                1020                1025 ccu auc acg gcu uac gcu caa cag acg cgg ggc cua cuu ggc ugu        3467
Pro Ile Thr Ala Tyr Ala Gln Gln Thr Arg Gly Leu Leu Gly Cys
        1030                1035                1040 auc auc acc agc cuc aca ggc cgg gac aag aac cag guc gag ggg        3512
Ile Ile Thr Ser Leu Thr Gly Arg Asp Lys Asn Gln Val Glu Gly
    1045                1050                1055
```

-continued

| | | | | | | | | | | | | |
|---|---|---|---|---|---|---|---|---|---|---|---|---|
| gag | guu | cag | gug | guu | ucc | acc | gca | acg | caa | ucu | uuc | cug | gcg | acc | 3557 |
| Glu | Val | Gln | Val | Val | Ser | Thr | Ala | Thr | Gln | Ser | Phe | Leu | Ala | Thr | |
| | | 1060 | | | | 1065 | | | | 1070 | | | | | |
| ugc | guc | aac | ggc | gug | ugu | ugg | acu | guc | uac | cau | ggu | gcc | ggc | ucg | 3602 |
| Cys | Val | Asn | Gly | Val | Cys | Trp | Thr | Val | Tyr | His | Gly | Ala | Gly | Ser | |
| | 1075 | | | | | 1080 | | | | | 1085 | | | | |
| aag | acc | cug | gcc | ggc | ccg | aag | ggc | cca | auc | acc | caa | aug | uac | acc | 3647 |
| Lys | Thr | Leu | Ala | Gly | Pro | Lys | Gly | Pro | Ile | Thr | Gln | Met | Tyr | Thr | |
| | | 1090 | | | | 1095 | | | | 1100 | | | | | |
| aau | gug | gac | caa | gac | cuc | guc | ggc | ugg | ccg | gcg | ccc | ccc | ggg | gcg | 3692 |
| Asn | Val | Asp | Gln | Asp | Leu | Val | Gly | Trp | Pro | Ala | Pro | Pro | Gly | Ala | |
| | 1105 | | | | | 1110 | | | | | 1115 | | | | |
| cgc | ucc | cug | aca | ccg | ugc | acc | ugc | ggc | agc | ucg | gac | cuc | uac | cug | 3737 |
| Arg | Ser | Leu | Thr | Pro | Cys | Thr | Cys | Gly | Ser | Ser | Asp | Leu | Tyr | Leu | |
| | | 1120 | | | | 1125 | | | | 1130 | | | | | |
| guc | acg | agg | cau | gcu | gau | guc | auu | ccg | gug | cgc | cgg | cgg | ggc | gac | 3782 |
| Val | Thr | Arg | His | Ala | Asp | Val | Ile | Pro | Val | Arg | Arg | Arg | Gly | Asp | |
| | 1135 | | | | | 1140 | | | | | 1145 | | | | |
| agc | agg | ggg | agu | cua | cuc | ucu | ccc | agg | ccc | auc | ucc | uac | uua | aag | 3827 |
| Ser | Arg | Gly | Ser | Leu | Leu | Ser | Pro | Arg | Pro | Ile | Ser | Tyr | Leu | Lys | |
| | | 1150 | | | | 1155 | | | | 1160 | | | | | |
| ggc | ucc | uca | ggu | ggu | cca | cug | cuu | ugc | ccc | cug | ggg | cac | gcu | gug | 3872 |
| Gly | Ser | Ser | Gly | Gly | Pro | Leu | Leu | Cys | Pro | Leu | Gly | His | Ala | Val | |
| | 1165 | | | | | 1170 | | | | | 1175 | | | | |
| ggc | auc | uuc | cgg | gcc | gcu | gug | ugc | acc | cgg | ggg | guu | gca | aag | gcg | 3917 |
| Gly | Ile | Phe | Arg | Ala | Ala | Val | Cys | Thr | Arg | Gly | Val | Ala | Lys | Ala | |
| | | 1180 | | | | 1185 | | | | 1190 | | | | | |
| gug | gau | uuu | gua | ccu | guu | gag | ucu | aug | gaa | acc | acc | aug | cgg | ucu | 3962 |
| Val | Asp | Phe | Val | Pro | Val | Glu | Ser | Met | Glu | Thr | Thr | Met | Arg | Ser | |
| | 1195 | | | | | 1200 | | | | | 1205 | | | | |
| ccg | guc | uuu | acg | gau | aau | uca | ucu | ccc | ccg | gcc | gua | ccg | cag | aca | 4007 |
| Pro | Val | Phe | Thr | Asp | Asn | Ser | Ser | Pro | Pro | Ala | Val | Pro | Gln | Thr | |
| | | 1210 | | | | 1215 | | | | 1220 | | | | | |
| uuc | caa | gug | gcc | cau | cua | cac | gcu | ccc | acu | ggc | agu | ggc | aag | agc | 4052 |
| Phe | Gln | Val | Ala | His | Leu | His | Ala | Pro | Thr | Gly | Ser | Gly | Lys | Ser | |
| | 1225 | | | | | 1230 | | | | | 1235 | | | | |
| acu | aag | gug | ccg | gcu | gcg | uac | gca | gcc | caa | ggg | uac | aag | gua | cuc | 4097 |
| Thr | Lys | Val | Pro | Ala | Ala | Tyr | Ala | Ala | Gln | Gly | Tyr | Lys | Val | Leu | |
| | | 1240 | | | | 1245 | | | | 1250 | | | | | |
| guc | uug | aac | cca | ucc | guu | gcc | gcu | acc | uua | ggg | uuu | ggg | gcg | uac | 4142 |
| Val | Leu | Asn | Pro | Ser | Val | Ala | Ala | Thr | Leu | Gly | Phe | Gly | Ala | Tyr | |
| | 1255 | | | | | 1260 | | | | | 1265 | | | | |
| aug | ucu | aaa | gca | cau | ggu | guu | gag | ccu | aac | auc | aga | acu | ggg | gua | 4187 |
| Met | Ser | Lys | Ala | His | Gly | Val | Glu | Pro | Asn | Ile | Arg | Thr | Gly | Val | |
| | | 1270 | | | | 1275 | | | | 1280 | | | | | |
| agg | acc | auc | acc | acg | ggc | gcu | ucc | auc | acg | uau | ucc | acc | uac | ggu | 4232 |
| Arg | Thr | Ile | Thr | Thr | Gly | Ala | Ser | Ile | Thr | Tyr | Ser | Thr | Tyr | Gly | |
| | 1285 | | | | | 1290 | | | | | 1295 | | | | |
| aag | uuc | cuu | gcc | gac | ggu | ggu | ugc | ucu | ggg | ggc | gcc | uau | gac | auc | 4277 |
| Lys | Phe | Leu | Ala | Asp | Gly | Gly | Cys | Ser | Gly | Gly | Ala | Tyr | Asp | Ile | |
| | | 1300 | | | | 1305 | | | | 1310 | | | | | |
| aua | aua | ugu | gau | gag | ugc | cac | uca | acu | gac | ucg | acu | ucc | auc | uug | 4322 |
| Ile | Ile | Cys | Asp | Glu | Cys | His | Ser | Thr | Asp | Ser | Thr | Ser | Ile | Leu | |
| | 1315 | | | | | 1320 | | | | | 1325 | | | | |
| ggc | auu | ggc | aca | guc | cug | gac | caa | gcg | gag | acg | gcu | gga | gcg | cgg | 4367 |
| Gly | Ile | Gly | Thr | Val | Leu | Asp | Gln | Ala | Glu | Thr | Ala | Gly | Ala | Arg | |
| | | 1330 | | | | 1335 | | | | 1340 | | | | | |
| cuc | guc | gug | cuc | gcc | acc | gcu | acg | ccu | ccg | gga | ucg | guc | acc | gug | 4412 |
| Leu | Val | Val | Leu | Ala | Thr | Ala | Thr | Pro | Pro | Gly | Ser | Val | Thr | Val | |
| | 1345 | | | | | 1350 | | | | | 1355 | | | | |

```
cca cau ccc aau auc gag gag gug gcc uug ccc agc acc gga gaa       4457
Pro His Pro Asn Ile Glu Glu Val Ala Leu Pro Ser Thr Gly Glu
        1360            1365                1370 auu ccc uuc uac ggc aaa gcc auc ccc auu gag acc auc aag ggg       4502
Ile Pro Phe Tyr Gly Lys Ala Ile Pro Ile Glu Thr Ile Lys Gly
        1375            1380                1385 ggg agg cac cuc auc uuc ugc cac ucc aag aag aaa ugu gac gag       4547
Gly Arg His Leu Ile Phe Cys His Ser Lys Lys Lys Cys Asp Glu
        1390            1395                1400 cuc gcu gca aag cug gug ggc cuc gga guu aac gcu guu gcg uac       4592
Leu Ala Ala Lys Leu Val Gly Leu Gly Val Asn Ala Val Ala Tyr
        1405            1410                1415 uac cgg ggu cuu gau gug ucc guc aua cca aca agc gga gau guc       4637
Tyr Arg Gly Leu Asp Val Ser Val Ile Pro Thr Ser Gly Asp Val
        1420            1425                1430 guu guc gug gca aca gac gcu cua aug acg ggc uuc acc ggc gac       4682
Val Val Val Ala Thr Asp Ala Leu Met Thr Gly Phe Thr Gly Asp
        1435            1440                1445 uuu gac uca gug auc gac ugu aau acu ugu guc acc cag aca guu       4727
Phe Asp Ser Val Ile Asp Cys Asn Thr Cys Val Thr Gln Thr Val
        1450            1455                1460 gau uuc agc uug gac ccu acc uuc acc auu gag acg aca acc gug       4772
Asp Phe Ser Leu Asp Pro Thr Phe Thr Ile Glu Thr Thr Thr Val
        1465            1470                1475 ccc caa gac gcg gug ucg cgu ucg cag cga cga ggc agg acu ggc       4817
Pro Gln Asp Ala Val Ser Arg Ser Gln Arg Arg Gly Arg Thr Gly
        1480            1485                1490 agg ggc agg aug ggc aua uac agg uuu gug gcu cca ggg gaa cgg       4862
Arg Gly Arg Met Gly Ile Tyr Arg Phe Val Ala Pro Gly Glu Arg
        1495            1500                1505 ccc ucg ggc aug uuc gau ucu ucg guc cug ugu gag ugc uau gac       4907
Pro Ser Gly Met Phe Asp Ser Ser Val Leu Cys Glu Cys Tyr Asp
        1510            1515                1520 gcg ggc ugu gcu ugg uau gag cuc acg ccc gcc gag acc uca guc       4952
Ala Gly Cys Ala Trp Tyr Glu Leu Thr Pro Ala Glu Thr Ser Val
        1525            1530                1535 agg uug cgg gcu uac cua aau aca cca ggg cug ccc guc ugc cag       4997
Arg Leu Arg Ala Tyr Leu Asn Thr Pro Gly Leu Pro Val Cys Gln
        1540            1545                1550 gac cac cug gag uuu ugg gag ggg guc uuc aca ggc cuc acc cac       5042
Asp His Leu Glu Phe Trp Glu Gly Val Phe Thr Gly Leu Thr His
        1555            1560                1565 aua gau gcc cau uuc uug ucc cag acu aag cag gca gga gau aac       5087
Ile Asp Ala His Phe Leu Ser Gln Thr Lys Gln Ala Gly Asp Asn
        1570            1575                1580 uuc ccc uac cug gua gca uac cag gcu acg gug ugc gcc agg gcc       5132
Phe Pro Tyr Leu Val Ala Tyr Gln Ala Thr Val Cys Ala Arg Ala
        1585            1590                1595 cag gcu ccc cct cca ucg ugg gau caa aug ugg aag ugu cuc aua       5177
Gln Ala Pro Pro Pro Ser Trp Asp Gln Met Trp Lys Cys Leu Ile
        1600            1605                1610 cgg cug aag ccu aca cua cac ggg cca acg ccc cug uug uau agg       5222
Arg Leu Lys Pro Thr Leu His Gly Pro Thr Pro Leu Leu Tyr Arg
        1615            1620                1625 cua gga gcc guc cag aau gag guc auc cuc aca cau ccc aua acc       5267
Leu Gly Ala Val Gln Asn Glu Val Ile Leu Thr His Pro Ile Thr
        1630            1635                1640 aaa uac auc aug gca ugc aug ucg gcu gac cua gag guc guc acu       5312
Lys Tyr Ile Met Ala Cys Met Ser Ala Asp Leu Glu Val Val Thr
        1645            1650                1655
```

```
agc acc ugg gug cug guc ggc ggg guc cuu gca gcu cug gcc gcg     5357
Ser Thr Trp Val Leu Val Gly Gly Val Leu Ala Ala Leu Ala Ala
        1660                1665                1670 uac ugc cug acg acg ggc agc gug guc auu gug ggc agg auc auc     5402
Tyr Cys Leu Thr Thr Gly Ser Val Val Ile Val Gly Arg Ile Ile
        1675                1680                1685 uug ucc ggg aag ccg gcu auc auu ccu gac agg gaa guc cuc uac     5447
Leu Ser Gly Lys Pro Ala Ile Ile Pro Asp Arg Glu Val Leu Tyr
        1690                1695                1700 cgg gag uuc gau gaa aug gaa gag ugu gcc uca cac cuc ccc uac     5492
Arg Glu Phe Asp Glu Met Glu Glu Cys Ala Ser His Leu Pro Tyr
        1705                1710                1715 auc gaa cag gga aug cag cuc gcc gaa caa uuc aag cag aag gcg     5537
Ile Glu Gln Gly Met Gln Leu Ala Glu Gln Phe Lys Gln Lys Ala
        1720                1725                1730 cuc ggg uug cug cag aca gcc acc aag caa gcg gaa gcc gcu gcu     5582
Leu Gly Leu Leu Gln Thr Ala Thr Lys Gln Ala Glu Ala Ala Ala
        1735                1740                1745 ccu gug gug gag ucc aag ugg cga gcc cuu gag gcc uuc ugg gcg     5627
Pro Val Val Glu Ser Lys Trp Arg Ala Leu Glu Ala Phe Trp Ala
        1750                1755                1760 aag cac aug ugg aau uuc auc agc ggg aua cag uac uua gca ggc     5672
Lys His Met Trp Asn Phe Ile Ser Gly Ile Gln Tyr Leu Ala Gly
        1765                1770                1775 uug ucc acu cug ccu ggg aac ccc gcg aua gca uca cug aug gca     5717
Leu Ser Thr Leu Pro Gly Asn Pro Ala Ile Ala Ser Leu Met Ala
        1780                1785                1790 uuc aca gcc ucu auc acc agc ccg cuu acc acc cua cac acc cuc     5762
Phe Thr Ala Ser Ile Thr Ser Pro Leu Thr Thr Leu His Thr Leu
        1795                1800                1805 cug uuu aac auc uug gga gga ugg gug gcc gcc caa cuu gcc ccc     5807
Leu Phe Asn Ile Leu Gly Gly Trp Val Ala Ala Gln Leu Ala Pro
        1810                1815                1820 ccc ggu gcu gcc ucg gcu uuc gug ggc gcc ggc auu gca ggc gca     5852
Pro Gly Ala Ala Ser Ala Phe Val Gly Ala Gly Ile Ala Gly Ala
        1825                1830                1835 gcu guu ggc agc aua ggc cuu ggg aag gug cuu gug gac auc cug     5897
Ala Val Gly Ser Ile Gly Leu Gly Lys Val Leu Val Asp Ile Leu
        1840                1845                1850 gcg ggu uau gga gca ggg gug gca ggc gcg cuc gug gcc uuc aag     5942
Ala Gly Tyr Gly Ala Gly Val Ala Gly Ala Leu Val Ala Phe Lys
        1855                1860                1865 guc aug agc ggc gag aug ccc ucc acc gag gac cug guc aac uua     5987
Val Met Ser Gly Glu Met Pro Ser Thr Glu Asp Leu Val Asn Leu
        1870                1875                1880 cuc ccu gcc auc cuc ucu ccu ggu gcc cuu guc guc ggg guc gug     6032
Leu Pro Ala Ile Leu Ser Pro Gly Ala Leu Val Val Gly Val Val
        1885                1890                1895 ugc gca gca aua cug cgu cgg cau gug ggc ccg ggg gag ggg gcu     6077
Cys Ala Ala Ile Leu Arg Arg His Val Gly Pro Gly Glu Gly Ala
        1900                1905                1910 gug caa ugg aug aac cgg cug aua gcg uuc gcc ucg cgg ggu aac     6122
Val Gln Trp Met Asn Arg Leu Ile Ala Phe Ala Ser Arg Gly Asn
        1915                1920                1925 cac guc ucc ccc acg cac uau gug ccu gag agc gac gcu gca gcg     6167
His Val Ser Pro Thr His Tyr Val Pro Glu Ser Asp Ala Ala Ala
        1930                1935                1940 cgu guc aca cag auc cuc ucu agc cuc acc auc acu cag cua cug     6212
Arg Val Thr Gln Ile Leu Ser Ser Leu Thr Ile Thr Gln Leu Leu
        1945                1950                1955
```

-continued

| | | | | | | | | | | | | |
|---|---|---|---|---|---|---|---|---|---|---|---|---|
| aag<br>Lys | agg<br>Arg<br>1960 | cuc<br>Leu | cac<br>His | cag<br>Gln | ugg<br>Trp | auu<br>Ile | aau<br>Asn<br>1965 | aag<br>Lys | gac<br>Asp | ugc<br>Cys | ucc<br>Ser | aca<br>Thr<br>1970 | cca<br>Pro | ugc<br>Cys | 6257 |
| ucc<br>Ser | ggc<br>Gly<br>1975 | ucg<br>Ser | ugg<br>Trp | cuu<br>Leu | agg<br>Arg | gac<br>Asp | guu<br>Val<br>1980 | ugg<br>Trp | gac<br>Asp | ugg<br>Trp | aua<br>Ile | ugc<br>Cys<br>1985 | acg<br>Thr | guu<br>Val | 6302 |
| uug<br>Leu | agu<br>Ser | gac<br>Asp<br>1990 | uuc<br>Phe | aag<br>Lys | acc<br>Thr | ugg<br>Trp | cuc<br>Leu<br>1995 | cag<br>Gln | ucc<br>Ser | aag<br>Lys | cuc<br>Leu | cug<br>Leu<br>2000 | cca<br>Pro | cgg<br>Arg | 6347 |
| uua<br>Leu | ccg<br>Pro | gga<br>Gly<br>2005 | guu<br>Val | cca<br>Pro | uuc<br>Phe | cuu<br>Leu | uca<br>Ser<br>2010 | ugc<br>Cys | caa<br>Gln | cgu<br>Arg | ggg<br>Gly | uau<br>Tyr<br>2015 | aag<br>Lys | ggg<br>Gly | 6392 |
| guc<br>Val | ugg<br>Trp | cgg<br>Arg<br>2020 | gga<br>Gly | gau<br>Asp | ggc<br>Gly | auc<br>Ile | aug<br>Met<br>2025 | cag<br>Gln | acc<br>Thr | ucc<br>Ser | ugc<br>Cys | cca<br>Pro<br>2030 | ugu<br>Cys | gga<br>Gly | 6437 |
| gca<br>Ala | caa<br>Gln | auc<br>Ile<br>2035 | gcc<br>Ala | gga<br>Gly | cau<br>His | guc<br>Val | aag<br>Lys<br>2040 | aac<br>Asn | ggu<br>Gly | ucc<br>Ser | aug<br>Met | agg<br>Arg<br>2045 | auc<br>Ile | guu<br>Val | 6482 |
| ggg<br>Gly | ccu<br>Pro | aaa<br>Lys<br>2050 | acc<br>Thr | ugu<br>Cys | agc<br>Ser | aac<br>Asn | acg<br>Thr<br>2055 | ugg<br>Trp | cac<br>His | gga<br>Gly | aca<br>Thr | uuc<br>Phe<br>2060 | ccc<br>Pro | auu<br>Ile | 6527 |
| aac<br>Asn | gcg<br>Ala | cac<br>His<br>2065 | acc<br>Thr | acg<br>Thr | ggc<br>Gly | ccc<br>Pro | ugc<br>Cys<br>2070 | aca<br>Thr | ccc<br>Pro | ucc<br>Ser | cca<br>Pro | gcg<br>Ala<br>2075 | ccg<br>Pro | aac<br>Asn | 6572 |
| uac<br>Tyr | ucu<br>Ser | aag<br>Lys<br>2080 | gcg<br>Ala | uug<br>Leu | ugg<br>Trp | cgg<br>Arg | gug<br>Val<br>2085 | gcu<br>Ala | gcu<br>Ala | gag<br>Glu | gag<br>Glu | uac<br>Tyr<br>2090 | gug<br>Val | gaa<br>Glu | 6617 |
| guc<br>Val | acg<br>Thr | cgg<br>Arg<br>2095 | gug<br>Val | ggg<br>Gly | gau<br>Asp | uuc<br>Phe | cau<br>His<br>2100 | uac<br>Tyr | gug<br>Val | acg<br>Thr | ggc<br>Gly | aug<br>Met<br>2105 | acc<br>Thr | acu<br>Thr | 6662 |
| gac<br>Asp | aac<br>Asn | gua<br>Val<br>2110 | aaa<br>Lys | ugc<br>Cys | cca<br>Pro | ugc<br>Cys | cag<br>Gln<br>2115 | guu<br>Val | ccg<br>Pro | gcc<br>Ala | ccc<br>Pro | gag<br>Glu<br>2120 | uuc<br>Phe | uuc<br>Phe | 6707 |
| aca<br>Thr | gag<br>Glu | gug<br>Val<br>2125 | gau<br>Asp | ggg<br>Gly | gua<br>Val | cgg<br>Arg | cug<br>Leu<br>2130 | cac<br>His | agg<br>Arg | uac<br>Tyr | gcu<br>Ala | ccg<br>Pro<br>2135 | gcg<br>Ala | ugc<br>Cys | 6752 |
| aaa<br>Lys | ccu<br>Pro | cuc<br>Leu<br>2140 | cua<br>Leu | cgg<br>Arg | gau<br>Asp | gag<br>Glu | guc<br>Val<br>2145 | aca<br>Thr | uuc<br>Phe | cag<br>Gln | guc<br>Val | ggg<br>Gly<br>2150 | cuc<br>Leu | aac<br>Asn | 6797 |
| cag<br>Gln | uuc<br>Phe | ccg<br>Pro<br>2155 | guu<br>Val | ggg<br>Gly | uca<br>Ser | cag<br>Gln | cuc<br>Leu<br>2160 | cca<br>Pro | ugc<br>Cys | gag<br>Glu | ccc<br>Pro | gaa<br>Glu<br>2165 | ccg<br>Pro | gau<br>Asp | 6842 |
| gua<br>Val | uca<br>Ser | gug<br>Val<br>2170 | cuc<br>Leu | acu<br>Thr | ucc<br>Ser | aug<br>Met | cuu<br>Leu<br>2175 | acc<br>Thr | gac<br>Asp | ccu<br>Pro | ucc<br>Ser | cac<br>His<br>2180 | auc<br>Ile | aca<br>Thr | 6887 |
| gca<br>Ala | gag<br>Glu | acg<br>Thr<br>2185 | gcu<br>Ala | aag<br>Lys | cgu<br>Arg | agg<br>Arg | cug<br>Leu<br>2190 | gcc<br>Ala | aga<br>Arg | ggg<br>Gly | ucu<br>Ser | ucc<br>Ser<br>2195 | ccc<br>Pro | ucu<br>Ser | 6932 |
| uug<br>Leu | gcc<br>Ala | agc<br>Ser<br>2200 | ucu<br>Ser | uca<br>Ser | gcu<br>Ala | agu<br>Ser | cag<br>Gln<br>2205 | uug<br>Leu | ucu<br>Ser | gcg<br>Ala | ccc<br>Pro | uca<br>Ser<br>2210 | uug<br>Leu | aag<br>Lys | 6977 |
| gcg<br>Ala | aca<br>Thr | ugc<br>Cys<br>2215 | acc<br>Thr | acc<br>Thr | cau<br>His | cau<br>His | gac<br>Asp<br>2220 | ucc<br>Ser | cca<br>Pro | gac<br>Asp | gcu<br>Ala | gac<br>Asp<br>2225 | cuc<br>Leu | auu<br>Ile | 7022 |
| gag<br>Glu | gcc<br>Ala | aac<br>Asn<br>2230 | cuc<br>Leu | cug<br>Leu | ugg<br>Trp | cgg<br>Arg | cag<br>Gln<br>2235 | gag<br>Glu | aug<br>Met | gga<br>Gly | ggg<br>Gly | aac<br>Asn<br>2240 | auc<br>Ile | acc<br>Thr | 7067 |
| cgu<br>Arg | gug<br>Val | gag<br>Glu<br>2245 | uca<br>Ser | gag<br>Glu | aac<br>Asn | aag<br>Lys | gug<br>Val<br>2250 | gua<br>Val | auc<br>Ile | cug<br>Leu | gac<br>Asp | ucu<br>Ser<br>2255 | uuu<br>Phe | gac<br>Asp | 7112 |

| | | | | | | | | | | | | | |
|---|---|---|---|---|---|---|---|---|---|---|---|---|---|
| ccg | cuu | cga | gcg | gag | gag | gac | gag | agg | gag | gug | ucu | guu | gcg gcg | 7157 |
| Pro | Leu | Arg | Ala | Glu | Glu | Asp | Glu | Arg | Glu | Val | Ser | Val | Ala Ala |
| | | 2260 | | | 2265 | | | | 2270 | | | | |
| gag | auc | cug | cgg | aaa | acc | agg | aag | uuc | ccc | cca | gcg | aug | ccc aua | 7202 |
| Glu | Ile | Leu | Arg | Lys | Thr | Arg | Lys | Phe | Pro | Pro | Ala | Met | Pro Ile |
| | | 2275 | | | 2280 | | | | 2285 | | | | |
| ugg | gca | cgc | ccg | gac | uac | aac | cca | ccg | cug | cua | gag | acu | ugg aag | 7247 |
| Trp | Ala | Arg | Pro | Asp | Tyr | Asn | Pro | Pro | Leu | Leu | Glu | Thr | Trp Lys |
| | | 2290 | | | 2295 | | | | 2300 | | | | |
| gac | ccg | gac | uac | guc | ccu | cca | gug | gug | cac | ggg | ugc | cca | uug cca | 7292 |
| Asp | Pro | Asp | Tyr | Val | Pro | Pro | Val | Val | His | Gly | Cys | Pro | Leu Pro |
| | | 2305 | | | 2310 | | | | 2315 | | | | |
| ccu | acc | aag | acc | ccu | cca | aua | cca | ccu | ccg | cgg | agg | aaa | aag aca | 7337 |
| Pro | Thr | Lys | Thr | Pro | Pro | Ile | Pro | Pro | Pro | Arg | Arg | Lys | Lys Thr |
| | | 2320 | | | 2325 | | | | 2330 | | | | |
| guu | guc | cug | aca | gag | ucc | acc | gug | ucu | ucu | gcc | cug | gcg | gag cuu | 7382 |
| Val | Val | Leu | Thr | Glu | Ser | Thr | Val | Ser | Ser | Ala | Leu | Ala | Glu Leu |
| | | 2335 | | | 2340 | | | | 2345 | | | | |
| gcc | aca | aag | acc | uuu | ggc | agc | ucc | gga | ucg | ucg | gcc | guc | gac agc | 7427 |
| Ala | Thr | Lys | Thr | Phe | Gly | Ser | Ser | Gly | Ser | Ser | Ala | Val | Asp Ser |
| | | 2350 | | | 2355 | | | | 2360 | | | | |
| ggc | aca | gcg | acc | gcc | ccc | ccu | aac | cag | cuc | ucc | gac | gaa | gug gau | 7472 |
| Gly | Thr | Ala | Thr | Ala | Pro | Pro | Asn | Gln | Leu | Ser | Asp | Glu | Val Asp |
| | | 2365 | | | 2370 | | | | 2375 | | | | |
| aca | gga | ucc | gac | guu | gag | ucg | uac | ucc | ucc | aug | ccc | ccc | cuu gag | 7517 |
| Thr | Gly | Ser | Asp | Val | Glu | Ser | Tyr | Ser | Ser | Met | Pro | Pro | Leu Glu |
| | | 2380 | | | 2385 | | | | 2390 | | | | |
| gga | gag | ccg | ggg | gac | ccc | gau | cuc | agc | gac | ggg | ucu | ugg | ucu acu | 7562 |
| Gly | Glu | Pro | Gly | Asp | Pro | Asp | Leu | Ser | Asp | Gly | Ser | Trp | Ser Thr |
| | | 2395 | | | 2400 | | | | 2405 | | | | |
| gua | agu | gag | gag | gcu | ggu | gag | gac | guc | guc | ugc | ugc | ucg | aug ucc | 7607 |
| Val | Ser | Glu | Glu | Ala | Gly | Glu | Asp | Val | Val | Cys | Cys | Ser | Met Ser |
| | | 2410 | | | 2415 | | | | 2420 | | | | |
| uac | aca | ugg | aca | ggc | gcc | uug | auc | acg | ccg | ugc | gcc | gcg | gag gag | 7652 |
| Tyr | Thr | Trp | Thr | Gly | Ala | Leu | Ile | Thr | Pro | Cys | Ala | Ala | Glu Glu |
| | | 2425 | | | 2430 | | | | 2435 | | | | |
| agc | aag | cug | ccc | auc | aau | gcg | cug | agc | aac | ucu | uug | cug | cgc cac | 7697 |
| Ser | Lys | Leu | Pro | Ile | Asn | Ala | Leu | Ser | Asn | Ser | Leu | Leu | Arg His |
| | | 2440 | | | 2445 | | | | 2450 | | | | |
| cac | aac | aug | guc | uau | gcc | aca | aca | ucc | cgc | agc | gca | agc | caa cgg | 7742 |
| His | Asn | Met | Val | Tyr | Ala | Thr | Thr | Ser | Arg | Ser | Ala | Ser | Gln Arg |
| | | 2455 | | | 2460 | | | | 2465 | | | | |
| cag | aaa | aag | guc | acc | uuu | gac | aga | cug | caa | guc | cug | gac | gac cau | 7787 |
| Gln | Lys | Lys | Val | Thr | Phe | Asp | Arg | Leu | Gln | Val | Leu | Asp | Asp His |
| | | 2470 | | | 2475 | | | | 2480 | | | | |
| uac | cgg | gac | gug | cuc | aag | gag | aug | aag | gcg | aag | gcg | ucc | aca guu | 7832 |
| Tyr | Arg | Asp | Val | Leu | Lys | Glu | Met | Lys | Ala | Lys | Ala | Ser | Thr Val |
| | | 2485 | | | 2490 | | | | 2495 | | | | |
| aag | gcu | aaa | cuu | cua | ucc | gua | gaa | gag | gcc | ugc | aag | cug | acg ccc | 7877 |
| Lys | Ala | Lys | Leu | Leu | Ser | Val | Glu | Glu | Ala | Cys | Lys | Leu | Thr Pro |
| | | 2500 | | | 2505 | | | | 2510 | | | | |
| cca | cac | uca | gcc | agg | ucc | aaa | uuu | ggc | uau | ggg | gcg | aag | gac guc | 7922 |
| Pro | His | Ser | Ala | Arg | Ser | Lys | Phe | Gly | Tyr | Gly | Ala | Lys | Asp Val |
| | | 2515 | | | 2520 | | | | 2525 | | | | |
| cgg | aac | cua | ucc | agc | aag | gcc | guu | aac | cac | auc | aac | ucc | gug ugg | 7967 |
| Arg | Asn | Leu | Ser | Ser | Lys | Ala | Val | Asn | His | Ile | Asn | Ser | Val Trp |
| | | 2530 | | | 2535 | | | | 2540 | | | | |
| aag | gac | uug | cug | gaa | gac | acu | gag | aca | cca | auu | gac | acc | acc auc | 8012 |
| Lys | Asp | Leu | Leu | Glu | Asp | Thr | Glu | Thr | Pro | Ile | Asp | Thr | Thr Ile |
| | | 2545 | | | 2550 | | | | 2555 | | | | |

```
                                          -continued
aug gca aaa aau gag guc uuc ugu guu caa cca gag aag gga ggc      8057
Met Ala Lys Asn Glu Val Phe Cys Val Gln Pro Glu Lys Gly Gly
    2560             2565                 2570 cgc aag cca gcu cgc cuu auc gua uac cca gac uug ggg gug cgu      8102
Arg Lys Pro Ala Arg Leu Ile Val Tyr Pro Asp Leu Gly Val Arg
    2575             2580                 2585 gug ugc gag aaa aug gcc cuu uac gac gug guc ucc acu cuu ccu      8147
Val Cys Glu Lys Met Ala Leu Tyr Asp Val Val Ser Thr Leu Pro
    2590             2595                 2600 cag gcc gug aug ggc ucc uca uac gga uuc cag uac ucu ccu ggg      8192
Gln Ala Val Met Gly Ser Ser Tyr Gly Phe Gln Tyr Ser Pro Gly
    2605             2610                 2615 cag cgg guc gag uuc cug gug aau gcc ugg aaa uca aag aag aac      8237
Gln Arg Val Glu Phe Leu Val Asn Ala Trp Lys Ser Lys Lys Asn
    2620             2625                 2630 ccu aug ggc uuc gca uau gac acc cgc ugu uuu gac uca acg guc      8282
Pro Met Gly Phe Ala Tyr Asp Thr Arg Cys Phe Asp Ser Thr Val
    2635             2640                 2645 acc gag aac gac auc cgu guu gag gag uca auu uac caa ugu ugu      8327
Thr Glu Asn Asp Ile Arg Val Glu Glu Ser Ile Tyr Gln Cys Cys
    2650             2655                 2660 gac uug gcc ccc gag gcc aga cag gug aua agg ucg cuc aca gag      8372
Asp Leu Ala Pro Glu Ala Arg Gln Val Ile Arg Ser Leu Thr Glu
    2665             2670                 2675 cgg cuu uau guc ggg ggc ccc cug acu aau uca aaa ggg cag aac      8417
Arg Leu Tyr Val Gly Gly Pro Leu Thr Asn Ser Lys Gly Gln Asn
    2680             2685                 2690 ugc ggu uau cgc cgg ugc cgc gcc agc ggc gug cug acg acu agc      8462
Cys Gly Tyr Arg Arg Cys Arg Ala Ser Gly Val Leu Thr Thr Ser
    2695             2700                 2705 ugc ggu aau acc cuc aca ugu uac uug aag gcc ucu gca gcc ugu      8507
Cys Gly Asn Thr Leu Thr Cys Tyr Leu Lys Ala Ser Ala Ala Cys
    2710             2715                 2720 cga gcu gca aag cuc cag gac ugc acg aug cuc gug ugc ggg gac      8552
Arg Ala Ala Lys Leu Gln Asp Cys Thr Met Leu Val Cys Gly Asp
    2725             2730                 2735 gac cuu guc guu auc ugu gaa agc gcg ggg acc cag gag gac gcg      8597
Asp Leu Val Val Ile Cys Glu Ser Ala Gly Thr Gln Glu Asp Ala
    2740             2745                 2750 gcg agc cua cga guc uuc acg gag gcu aug acu agg uac ucc gcc      8642
Ala Ser Leu Arg Val Phe Thr Glu Ala Met Thr Arg Tyr Ser Ala
    2755             2760                 2765 ccc ccc ggg gac ccg ccc cga ccg gaa uac gac uug gag uug aua      8687
Pro Pro Gly Asp Pro Pro Arg Pro Glu Tyr Asp Leu Glu Leu Ile
    2770             2775                 2780 aca uca ugc ucc ucc aac gug ucg guc gcg cac gau gca ucu ggc      8732
Thr Ser Cys Ser Ser Asn Val Ser Val Ala His Asp Ala Ser Gly
    2785             2790                 2795 aaa cgg gug uau uac cuc acc cgu gac ccc acc acc ccc cuu gcg      8777
Lys Arg Val Tyr Tyr Leu Thr Arg Asp Pro Thr Thr Pro Leu Ala
    2800             2805                 2810 cgg gcu gcg ugg gag aca gcu aaa cac acu cca guc aac ucc ugg      8822
Arg Ala Ala Trp Glu Thr Ala Lys His Thr Pro Val Asn Ser Trp
    2815             2820                 2825 cua ggc aac auc auc aug uau gcg ccc acc cuc ugg gca agg aug      8867
Leu Gly Asn Ile Ile Met Tyr Ala Pro Thr Leu Trp Ala Arg Met
    2830             2835                 2840 auu cug aug acu cac uuc uuc ucc auc cuu cua gcu cag gag cag      8912
Ile Leu Met Thr His Phe Phe Ser Ile Leu Leu Ala Gln Glu Gln
    2845             2850                 2855
```

-continued

| | | | | | | | | | | | | | |
|---|---|---|---|---|---|---|---|---|---|---|---|---|---|
| cuu | gaa | aaa | gcc | cug | gau | ugu | cag | auc | uac | ggg | gcc | acu | uac ucc | 8957 |
| Leu | Glu | Lys | Ala | Leu | Asp | Cys | Gln | Ile | Tyr | Gly | Ala | Thr | Tyr Ser | |
| | 2860 | | | | 2865 | | | | 2870 | | | | | | auu gaa cca cuu gac cua ccu cag auc auu caa cga cuc cau ggu 9002
Ile Glu Pro Leu Asp Leu Pro Gln Ile Ile Gln Arg Leu His Gly
 2875 2880 2885 cuu agc gca uuc uca cuc cau agu uac ucu cca ggu gaa auc aau 9047
Leu Ser Ala Phe Ser Leu His Ser Tyr Ser Pro Gly Glu Ile Asn
 2890 2895 2900 agg gug gcu uca ugc cuc agg aaa cuu ggu gua ccg ccc uug cga 9092
Arg Val Ala Ser Cys Leu Arg Lys Leu Gly Val Pro Pro Leu Arg
 2905 2910 2915 guc ugg aga cau cgg gcc aga agu guc cgc gcu aag cua cug ucc 9137
Val Trp Arg His Arg Ala Arg Ser Val Arg Ala Lys Leu Leu Ser
 2920 2925 2930 cag ggg ggg agg gcu gcc acu ugu ggc aag uac cuc uuc aac ugg 9182
Gln Gly Gly Arg Ala Ala Thr Cys Gly Lys Tyr Leu Phe Asn Trp
 2935 2940 2945 gca gua agg acc aag cuc aaa cuc acu cca auc ccg gcu gcg ucc 9227
Ala Val Arg Thr Lys Leu Lys Leu Thr Pro Ile Pro Ala Ala Ser
 2950 2955 2960 cag uug gac uug ucc ggc ugg uuc auu gcu ggu uac agc ggg gga 9272
Gln Leu Asp Leu Ser Gly Trp Phe Ile Ala Gly Tyr Ser Gly Gly
 2965 2970 2975 gac aua uau cac agc cug ucu cgu gcc cga ccc cgc ugg uuu aug 9317
Asp Ile Tyr His Ser Leu Ser Arg Ala Arg Pro Arg Trp Phe Met
 2980 2985 2990 uug ugc cua cuc cua cuu ucu gug ggg gua ggc auc uac cug cuc 9362
Leu Cys Leu Leu Leu Leu Ser Val Gly Val Gly Ile Tyr Leu Leu
 2995 3000 3005 ccc aau cga ugaacggggg gcuaaacacu ccaggccaau aggccauucu 9411
Pro Asn Arg
 3010 guuuuuuuuu uuuuuuuuuu uuuuuuuuuu uuuuuuuuuu uuuuuuuuuu uuuuuccuuu 9471 uuuuuuuuuu uuuucccuuu cuuuuggugg cuccaucuua gcccuaguca cggcuagcug 9531 ugaaaggucc gugagccgca ugacugcaga gagugcugau acuggccucu cugcagauca 9591 ugu 9594

<210> SEQ ID NO 58
<211> LENGTH: 3010
<212> TYPE: PRT
<213> ORGANISM: Hepatitis C virus

<400> SEQUENCE: 58

Met Ser Thr Asn Pro Lys Pro Gln Arg Lys Thr Lys Arg Asn Thr Asn
1               5                  10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Gln Pro Glu Gly Arg Ala Trp Ala Gln Pro Gly
65                  70                  75                  80

Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Thr Asp Pro
            100                 105                 110

```
Arg Arg Arg Ser Arg Asn Leu Gly Lys Val Ile Asp Thr Leu Thr Cys
            115                 120                 125

Gly Phe Ala Asp Leu Met Gly Tyr Ile Pro Leu Val Gly Ala Pro Leu
        130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Pro Phe Ser Ile
                165                 170                 175

Phe Leu Leu Ala Leu Leu Ser Cys Leu Thr Ile Pro Ala Ser Ala His
            180                 185                 190

Glu Val Arg Asn Val Ser Gly Leu Tyr His Val Thr Asn Asp Cys Ser
        195                 200                 205

Asn Ser Ser Ile Val Tyr Glu Ala Ala Asp Met Ile Met His Thr Pro
210                 215                 220

Gly Cys Val Pro Cys Val Arg Glu Gly Asn Ser Ser Arg Cys Trp Val
225                 230                 235                 240

Ala Leu Thr Pro Thr Leu Ala Ala Arg Asn Ser Ser Val Pro Thr Ala
                245                 250                 255

Thr Ile Arg Arg His Val Asp Leu Leu Val Gly Ala Ala Phe Cys
            260                 265                 270

Ser Ala Met Tyr Val Gly Asp Leu Cys Gly Ser Val Phe Leu Val Ser
        275                 280                 285

Gln Leu Phe Thr Phe Ser Pro Arg Arg Tyr Glu Thr Val Gln Asp Cys
        290                 295                 300

Asn Cys Ser Leu Tyr Pro Gly His Val Ser Gly His Arg Met Ala Trp
305                 310                 315                 320

Asp Met Met Met Asn Trp Ser Pro Thr Thr Ala Leu Val Val Ser Gln
                325                 330                 335

Leu Leu Arg Ile Pro Gln Ala Val Val Asp Met Val Val Gly Ala His
            340                 345                 350

Trp Gly Val Leu Ala Gly Leu Ala Tyr Tyr Ser Met Val Gly Asn Trp
        355                 360                 365

Ala Lys Val Leu Ile Val Met Leu Leu Phe Ala Gly Val Asp Gly Lys
        370                 375                 380

Thr Tyr Val Thr Gly Gly Ala Gln Ser Arg Ala Thr Gln Gly Phe Ala
385                 390                 395                 400

Ser Leu Phe Thr Arg Gly Pro Ser Gln Lys Leu Gln Leu Val Asn Ser
            405                 410                 415

Asn Gly Ser Trp His Ile Asn Arg Thr Ala Leu Asn Cys Asn Asp Ser
            420                 425                 430

Phe Gln Thr Gly Phe Leu Ala Ala Leu Phe Tyr Ala His Arg Phe Asn
        435                 440                 445

Ser Ser Gly Cys Pro Glu Arg Met Ala Ser Cys Arg Pro Ile Asp Thr
450                 455                 460

Phe Asp Gln Gly Trp Gly Pro Ile Thr His Val Ala Arg Arg Thr Ser
465                 470                 475                 480

Asp Gln Arg Pro Tyr Cys Trp His Tyr Ala Pro Gln Pro Cys Gly Ile
                485                 490                 495

Val Pro Ala Leu Gln Val Cys Gly Pro Val Tyr Cys Phe Thr Pro Ser
            500                 505                 510

Pro Val Val Val Gly Thr Thr Asp Arg Phe Gly Ala Pro Thr Tyr Asn
        515                 520                 525

Trp Gly Glu Asn Glu Thr Asp Val Leu Leu Leu Asn Asn Thr Arg Pro
```

-continued

```
                530                 535                 540
Pro His Gly Asn Trp Phe Gly Cys Thr Trp Met Asn Ser Thr Gly Phe
545                 550                 555                 560

Thr Lys Thr Cys Gly Gly Pro Pro Cys Asn Ile Gly Gly Phe Gly Asn
                565                 570                 575

Asn Thr Leu Thr Cys Pro Thr Asp Cys Phe Arg Lys His Pro Glu Ala
                580                 585                 590

Thr Tyr Thr Lys Cys Gly Ser Gly Pro Trp Leu Thr Pro Arg Cys Met
                595                 600                 605

Val Asp Tyr Pro Tyr Arg Leu Trp His Tyr Pro Cys Thr Val Asn Phe
610                 615                 620

Ser Ile Phe Lys Val Arg Met Tyr Val Gly Val Glu His Arg Leu
625                 630                 635                 640

Thr Ala Ala Cys Asn Trp Thr Arg Gly Glu Arg Cys Asn Leu Glu Asp
                645                 650                 655

Arg Asp Arg Ser Glu Leu Ser Pro Leu Leu Leu Ser Thr Thr Glu Trp
                660                 665                 670

Gln Val Leu Pro Cys Ser Phe Thr Thr Leu Pro Ala Leu Ser Thr Gly
                675                 680                 685

Leu Ile His Leu His Gln Asn Ile Val Asp Val Gln Tyr Leu Tyr Gly
690                 695                 700

Val Gly Ser Ser Val Val Ser Ile Ala Ile Arg Trp Glu Tyr Val Val
705                 710                 715                 720

Leu Leu Phe Leu Leu Leu Ala Asp Ala Arg Val Cys Ala Cys Leu Trp
                725                 730                 735

Met Met Leu Leu Ile Ala Gln Ala Glu Ala Ala Leu Glu Asn Leu Val
                740                 745                 750

Ile Leu Asn Ala Ala Ser Val Ala Gly Ala His Gly Val Leu Ser Phe
                755                 760                 765

Leu Val Phe Phe Cys Ala Ala Trp Tyr Ile Lys Gly Lys Leu Val Pro
770                 775                 780

Gly Ala Ala Tyr Ala Phe Tyr Gly Val Trp Pro Leu Leu Leu Leu
785                 790                 795                 800

Leu Ser Leu Pro Pro Arg Ala Tyr Ala Leu Asp Arg Glu Met Ala Ala
                805                 810                 815

Ser Cys Gly Gly Ala Val Phe Val Gly Leu Met Leu Leu Thr Leu Ser
                820                 825                 830

Pro His Tyr Lys Val Phe Leu Ala Arg Leu Ile Trp Trp Leu Gln Tyr
                835                 840                 845

Phe Ile Thr Arg Ala Glu Ala His Leu Gln Val Trp Val Pro Pro Leu
850                 855                 860

Asn Val Arg Gly Gly Arg Asp Ala Ile Ile Leu Leu Thr Cys Val Val
865                 870                 875                 880

His Pro Glu Leu Ile Phe Asp Ile Thr Lys Ile Leu Leu Ala Met Leu
                885                 890                 895

Gly Pro Leu Met Val Leu Gln Ala Gly Leu Thr Arg Val Pro Tyr Phe
                900                 905                 910

Val Arg Ala Gln Gly Leu Ile Arg Ala Cys Met Leu Val Arg Lys Val
                915                 920                 925

Ala Gly Gly His Tyr Val Gln Met Ala Leu Met Lys Leu Ala Ala Leu
                930                 935                 940

Thr Gly Thr Tyr Val Tyr Asp His Leu Thr Pro Leu Gln Asp Trp Ala
945                 950                 955                 960
```

-continued

```
His Ala Gly Leu Arg Asp Leu Ala Val Ala Val Glu Pro Val Val Phe
                965                 970                 975
Ser Asp Met Glu Thr Lys Val Ile Thr Trp Gly Ala Asp Thr Ala Ala
                980                 985                 990
Cys Gly Asp Ile Ile Ser Gly Leu Pro Val Ser Ala Arg Arg Gly Arg
            995                 1000                1005
Glu Ile Leu Leu Gly Pro Ala Asp Arg Phe Gly Glu Gln Gly Trp
        1010                1015                1020
Arg Leu Leu Ala Pro Ile Thr Ala Tyr Ala Gln Gln Thr Arg Gly
        1025                1030                1035
Leu Leu Gly Cys Ile Ile Thr Ser Leu Thr Gly Arg Asp Lys Asn
        1040                1045                1050
Gln Val Glu Gly Glu Val Gln Val Val Ser Thr Ala Thr Gln Ser
        1055                1060                1065
Phe Leu Ala Thr Cys Val Asn Gly Val Cys Trp Thr Val Tyr His
        1070                1075                1080
Gly Ala Gly Ser Lys Thr Leu Ala Gly Pro Lys Gly Pro Ile Thr
        1085                1090                1095
Gln Met Tyr Thr Asn Val Asp Gln Asp Leu Val Gly Trp Pro Ala
        1100                1105                1110
Pro Pro Gly Ala Arg Ser Leu Thr Pro Cys Thr Cys Gly Ser Ser
        1115                1120                1125
Asp Leu Tyr Leu Val Thr Arg His Ala Asp Val Ile Pro Val Arg
        1130                1135                1140
Arg Arg Gly Asp Ser Arg Gly Ser Leu Leu Ser Pro Arg Pro Ile
        1145                1150                1155
Ser Tyr Leu Lys Gly Ser Ser Gly Gly Pro Leu Leu Cys Pro Leu
        1160                1165                1170
Gly His Ala Val Gly Ile Phe Arg Ala Ala Val Cys Thr Arg Gly
        1175                1180                1185
Val Ala Lys Ala Val Asp Phe Val Pro Val Glu Ser Met Glu Thr
        1190                1195                1200
Thr Met Arg Ser Pro Val Phe Thr Asp Asn Ser Ser Pro Pro Ala
        1205                1210                1215
Val Pro Gln Thr Phe Gln Val Ala His Leu His Ala Pro Thr Gly
        1220                1225                1230
Ser Gly Lys Ser Thr Lys Val Pro Ala Ala Tyr Ala Ala Gln Gly
        1235                1240                1245
Tyr Lys Val Leu Val Leu Asn Pro Ser Val Ala Ala Thr Leu Gly
        1250                1255                1260
Phe Gly Ala Tyr Met Ser Lys Ala His Gly Val Glu Pro Asn Ile
        1265                1270                1275
Arg Thr Gly Val Arg Thr Ile Thr Thr Gly Ala Ser Ile Thr Tyr
        1280                1285                1290
Ser Thr Tyr Gly Lys Phe Leu Ala Asp Gly Gly Cys Ser Gly Gly
        1295                1300                1305
Ala Tyr Asp Ile Ile Ile Cys Asp Glu Cys His Ser Thr Asp Ser
        1310                1315                1320
Thr Ser Ile Leu Gly Ile Gly Thr Val Leu Asp Gln Ala Glu Thr
        1325                1330                1335
Ala Gly Ala Arg Leu Val Val Leu Ala Thr Ala Thr Pro Pro Gly
        1340                1345                1350
Ser Val Thr Val Pro His Pro Asn Ile Glu Glu Val Ala Leu Pro
        1355                1360                1365
```

```
Ser Thr Gly Glu Ile Pro Phe Tyr Gly Lys Ala Ile Pro Ile Glu
    1370            1375            1380

Thr Ile Lys Gly Gly Arg His Leu Ile Phe Cys His Ser Lys Lys
    1385            1390            1395

Lys Cys Asp Glu Leu Ala Ala Lys Leu Val Gly Leu Gly Val Asn
    1400            1405            1410

Ala Val Ala Tyr Tyr Arg Gly Leu Asp Val Ser Val Ile Pro Thr
    1415            1420            1425

Ser Gly Asp Val Val Val Ala Thr Asp Ala Leu Met Thr Gly
    1430            1435            1440

Phe Thr Gly Asp Phe Asp Ser Val Ile Asp Cys Asn Thr Cys Val
    1445            1450            1455

Thr Gln Thr Val Asp Phe Ser Leu Asp Pro Thr Phe Thr Ile Glu
    1460            1465            1470

Thr Thr Thr Val Pro Gln Asp Ala Val Ser Arg Ser Gln Arg Arg
    1475            1480            1485

Gly Arg Thr Gly Arg Gly Arg Met Gly Ile Tyr Arg Phe Val Ala
    1490            1495            1500

Pro Gly Glu Arg Pro Ser Gly Met Phe Asp Ser Ser Val Leu Cys
    1505            1510            1515

Glu Cys Tyr Asp Ala Gly Cys Ala Trp Tyr Glu Leu Thr Pro Ala
    1520            1525            1530

Glu Thr Ser Val Arg Leu Arg Ala Tyr Leu Asn Thr Pro Gly Leu
    1535            1540            1545

Pro Val Cys Gln Asp His Leu Glu Phe Trp Glu Gly Val Phe Thr
    1550            1555            1560

Gly Leu Thr His Ile Asp Ala His Phe Leu Ser Gln Thr Lys Gln
    1565            1570            1575

Ala Gly Asp Asn Phe Pro Tyr Leu Val Ala Tyr Gln Ala Thr Val
    1580            1585            1590

Cys Ala Arg Ala Gln Ala Pro Pro Pro Ser Trp Asp Gln Met Trp
    1595            1600            1605

Lys Cys Leu Ile Arg Leu Lys Pro Thr Leu His Gly Pro Thr Pro
    1610            1615            1620

Leu Leu Tyr Arg Leu Gly Ala Val Gln Asn Glu Val Ile Leu Thr
    1625            1630            1635

His Pro Ile Thr Lys Tyr Ile Met Ala Cys Met Ser Ala Asp Leu
    1640            1645            1650

Glu Val Val Thr Ser Thr Trp Val Leu Val Gly Gly Val Leu Ala
    1655            1660            1665

Ala Leu Ala Ala Tyr Cys Leu Thr Thr Gly Ser Val Val Ile Val
    1670            1675            1680

Gly Arg Ile Ile Leu Ser Gly Lys Pro Ala Ile Pro Asp Arg
    1685            1690            1695

Glu Val Leu Tyr Arg Glu Phe Asp Glu Met Glu Glu Cys Ala Ser
    1700            1705            1710

His Leu Pro Tyr Ile Glu Gln Gly Met Gln Leu Ala Glu Gln Phe
    1715            1720            1725

Lys Gln Lys Ala Leu Gly Leu Leu Gln Thr Ala Thr Lys Gln Ala
    1730            1735            1740

Glu Ala Ala Ala Pro Val Val Glu Ser Lys Trp Arg Ala Leu Glu
    1745            1750            1755

Ala Phe Trp Ala Lys His Met Trp Asn Phe Ile Ser Gly Ile Gln
```

```
                    1760                1765                1770

Tyr Leu Ala Gly Leu Ser Thr Leu Pro Gly Asn Pro Ala Ile Ala
    1775                1780                1785

Ser Leu Met Ala Phe Thr Ala Ser Ile Thr Ser Pro Leu Thr Thr
    1790                1795                1800

Leu His Thr Leu Leu Phe Asn Ile Leu Gly Gly Trp Val Ala Ala
    1805                1810                1815

Gln Leu Ala Pro Pro Gly Ala Ala Ser Ala Phe Val Gly Ala Gly
    1820                1825                1830

Ile Ala Gly Ala Ala Val Gly Ser Ile Gly Leu Gly Lys Val Leu
    1835                1840                1845

Val Asp Ile Leu Ala Gly Tyr Gly Ala Gly Val Ala Gly Ala Leu
    1850                1855                1860

Val Ala Phe Lys Val Met Ser Gly Glu Met Pro Ser Thr Glu Asp
    1865                1870                1875

Leu Val Asn Leu Leu Pro Ala Ile Leu Ser Pro Gly Ala Leu Val
    1880                1885                1890

Val Gly Val Val Cys Ala Ala Ile Leu Arg Arg His Val Gly Pro
    1895                1900                1905

Gly Glu Gly Ala Val Gln Trp Met Asn Arg Leu Ile Ala Phe Ala
    1910                1915                1920

Ser Arg Gly Asn His Val Ser Pro Thr His Tyr Val Pro Glu Ser
    1925                1930                1935

Asp Ala Ala Ala Arg Val Thr Gln Ile Leu Ser Ser Leu Thr Ile
    1940                1945                1950

Thr Gln Leu Leu Lys Arg Leu His Gln Trp Ile Asn Lys Asp Cys
    1955                1960                1965

Ser Thr Pro Cys Ser Gly Ser Trp Leu Arg Asp Val Trp Asp Trp
    1970                1975                1980

Ile Cys Thr Val Leu Ser Asp Phe Lys Thr Trp Leu Gln Ser Lys
    1985                1990                1995

Leu Leu Pro Arg Leu Pro Gly Val Pro Phe Leu Ser Cys Gln Arg
    2000                2005                2010

Gly Tyr Lys Gly Val Trp Arg Gly Asp Gly Ile Met Gln Thr Ser
    2015                2020                2025

Cys Pro Cys Gly Ala Gln Ile Ala Gly His Val Lys Asn Gly Ser
    2030                2035                2040

Met Arg Ile Val Gly Pro Lys Thr Cys Ser Asn Thr Trp His Gly
    2045                2050                2055

Thr Phe Pro Ile Asn Ala His Thr Thr Gly Pro Cys Thr Pro Ser
    2060                2065                2070

Pro Ala Pro Asn Tyr Ser Lys Ala Leu Trp Arg Val Ala Ala Glu
    2075                2080                2085

Glu Tyr Val Glu Val Thr Arg Val Gly Asp Phe His Tyr Val Thr
    2090                2095                2100

Gly Met Thr Thr Asp Asn Val Lys Cys Pro Cys Gln Val Pro Ala
    2105                2110                2115

Pro Glu Phe Phe Thr Glu Val Asp Gly Val Arg Leu His Arg Tyr
    2120                2125                2130

Ala Pro Ala Cys Lys Pro Leu Leu Arg Asp Glu Val Thr Phe Gln
    2135                2140                2145

Val Gly Leu Asn Gln Phe Pro Val Gly Ser Gln Leu Pro Cys Glu
    2150                2155                2160
```

```
Pro Glu Pro Asp Val Ser Val Leu Thr Ser Met Leu Thr Asp Pro
2165                 2170                2175

Ser His Ile Thr Ala Glu Thr Ala Lys Arg Arg Leu Ala Arg Gly
2180                 2185                2190

Ser Ser Pro Ser Leu Ala Ser Ser Ser Ala Ser Gln Leu Ser Ala
2195                 2200                2205

Pro Ser Leu Lys Ala Thr Cys Thr Thr His His Asp Ser Pro Asp
2210                 2215                2220

Ala Asp Leu Ile Glu Ala Asn Leu Leu Trp Arg Gln Glu Met Gly
2225                 2230                2235

Gly Asn Ile Thr Arg Val Glu Ser Glu Asn Lys Val Val Ile Leu
2240                 2245                2250

Asp Ser Phe Asp Pro Leu Arg Ala Glu Glu Asp Glu Arg Glu Val
2255                 2260                2265

Ser Val Ala Ala Glu Ile Leu Arg Lys Thr Arg Lys Phe Pro Pro
2270                 2275                2280

Ala Met Pro Ile Trp Ala Arg Pro Asp Tyr Asn Pro Pro Leu Leu
2285                 2290                2295

Glu Thr Trp Lys Asp Pro Asp Tyr Val Pro Pro Val Val His Gly
2300                 2305                2310

Cys Pro Leu Pro Pro Thr Lys Thr Pro Pro Ile Pro Pro Pro Arg
2315                 2320                2325

Arg Lys Lys Thr Val Val Leu Thr Glu Ser Thr Val Ser Ser Ala
2330                 2335                2340

Leu Ala Glu Leu Ala Thr Lys Thr Phe Gly Ser Ser Gly Ser Ser
2345                 2350                2355

Ala Val Asp Ser Gly Thr Ala Thr Ala Pro Pro Asn Gln Leu Ser
2360                 2365                2370

Asp Glu Val Asp Thr Gly Ser Asp Val Glu Ser Tyr Ser Ser Met
2375                 2380                2385

Pro Pro Leu Glu Gly Glu Pro Gly Asp Pro Asp Leu Ser Asp Gly
2390                 2395                2400

Ser Trp Ser Thr Val Ser Glu Glu Ala Gly Glu Asp Val Val Cys
2405                 2410                2415

Cys Ser Met Ser Tyr Thr Trp Thr Gly Ala Leu Ile Thr Pro Cys
2420                 2425                2430

Ala Ala Glu Glu Ser Lys Leu Pro Ile Asn Ala Leu Ser Asn Ser
2435                 2440                2445

Leu Leu Arg His His Asn Met Val Tyr Ala Thr Thr Ser Arg Ser
2450                 2455                2460

Ala Ser Gln Arg Gln Lys Lys Val Thr Phe Asp Arg Leu Gln Val
2465                 2470                2475

Leu Asp Asp His Tyr Arg Asp Val Leu Lys Glu Met Lys Ala Lys
2480                 2485                2490

Ala Ser Thr Val Lys Ala Lys Leu Leu Ser Val Glu Glu Ala Cys
2495                 2500                2505

Lys Leu Thr Pro Pro His Ser Ala Arg Ser Lys Phe Gly Tyr Gly
2510                 2515                2520

Ala Lys Asp Val Arg Asn Leu Ser Ser Lys Ala Val Asn His Ile
2525                 2530                2535

Asn Ser Val Trp Lys Asp Leu Leu Glu Asp Thr Glu Thr Pro Ile
2540                 2545                2550

Asp Thr Thr Ile Met Ala Lys Asn Glu Val Phe Cys Val Gln Pro
2555                 2560                2565
```

```
Glu Lys Gly Gly Arg Lys Pro Ala Arg Leu Ile Val Tyr Pro Asp
    2570            2575                2580

Leu Gly Val Arg Val Cys Glu Lys Met Ala Leu Tyr Asp Val Val
    2585            2590                2595

Ser Thr Leu Pro Gln Ala Val Met Gly Ser Ser Tyr Gly Phe Gln
    2600            2605                2610

Tyr Ser Pro Gly Gln Arg Val Glu Phe Leu Val Asn Ala Trp Lys
    2615            2620                2625

Ser Lys Lys Asn Pro Met Gly Phe Ala Tyr Asp Thr Arg Cys Phe
    2630            2635                2640

Asp Ser Thr Val Thr Glu Asn Asp Ile Arg Val Glu Glu Ser Ile
    2645            2650                2655

Tyr Gln Cys Cys Asp Leu Ala Pro Glu Ala Arg Gln Val Ile Arg
    2660            2665                2670

Ser Leu Thr Glu Arg Leu Tyr Val Gly Gly Pro Leu Thr Asn Ser
    2675            2680                2685

Lys Gly Gln Asn Cys Gly Tyr Arg Arg Cys Arg Ala Ser Gly Val
    2690            2695                2700

Leu Thr Thr Ser Cys Gly Asn Thr Leu Thr Cys Tyr Leu Lys Ala
    2705            2710                2715

Ser Ala Ala Cys Arg Ala Ala Lys Leu Gln Asp Cys Thr Met Leu
    2720            2725                2730

Val Cys Gly Asp Asp Leu Val Val Ile Cys Glu Ser Ala Gly Thr
    2735            2740                2745

Gln Glu Asp Ala Ala Ser Leu Arg Val Phe Thr Glu Ala Met Thr
    2750            2755                2760

Arg Tyr Ser Ala Pro Pro Gly Asp Pro Pro Arg Pro Glu Tyr Asp
    2765            2770                2775

Leu Glu Leu Ile Thr Ser Cys Ser Ser Asn Val Ser Val Ala His
    2780            2785                2790

Asp Ala Ser Gly Lys Arg Val Tyr Tyr Leu Thr Arg Asp Pro Thr
    2795            2800                2805

Thr Pro Leu Ala Arg Ala Ala Trp Glu Thr Ala Lys His Thr Pro
    2810            2815                2820

Val Asn Ser Trp Leu Gly Asn Ile Ile Met Tyr Ala Pro Thr Leu
    2825            2830                2835

Trp Ala Arg Met Ile Leu Met Thr His Phe Phe Ser Ile Leu Leu
    2840            2845                2850

Ala Gln Glu Gln Leu Glu Lys Ala Leu Asp Cys Gln Ile Tyr Gly
    2855            2860                2865

Ala Thr Tyr Ser Ile Glu Pro Leu Asp Leu Pro Gln Ile Ile Gln
    2870            2875                2880

Arg Leu His Gly Leu Ser Ala Phe Ser Leu His Ser Tyr Ser Pro
    2885            2890                2895

Gly Glu Ile Asn Arg Val Ala Ser Cys Leu Arg Lys Leu Gly Val
    2900            2905                2910

Pro Pro Leu Arg Val Trp Arg His Arg Ala Arg Ser Val Arg Ala
    2915            2920                2925

Lys Leu Leu Ser Gln Gly Gly Arg Ala Ala Thr Cys Gly Lys Tyr
    2930            2935                2940

Leu Phe Asn Trp Ala Val Arg Thr Lys Leu Lys Leu Thr Pro Ile
    2945            2950                2955

Pro Ala Ala Ser Gln Leu Asp Leu Ser Gly Trp Phe Ile Ala Gly
```

-continued

```
    2960                2965                2970

Tyr Ser  Gly Gly Asp Ile Tyr  His Ser Leu Ser Arg  Ala Arg Pro
    2975                2980                2985

Arg Trp  Phe Met Leu Cys Leu  Leu Leu Leu Ser Val  Gly Val Gly
    2990                2995                3000

Ile Tyr  Leu Leu Pro Asn Arg
    3005                3010
```

<210> SEQ ID NO 59
<211> LENGTH: 60
<212> TYPE: DNA
<213> ORGANISM: Hepatitis GB virus B

<400> SEQUENCE: 59
accggtgagt acaccggaat tgccaggacg accgggtcct ttcttggatc aacccgctca 60

<210> SEQ ID NO 60
<211> LENGTH: 60
<212> TYPE: DNA
<213> ORGANISM: Hepatitis GB virus B

<400> SEQUENCE: 60
atgcctggag atttgggcgt gcccccgcga gactgctagc cgagtagtgt tgggtcgcga 60

<210> SEQ ID NO 61
<211> LENGTH: 60
<212> TYPE: DNA
<213> ORGANISM: Hepatitis GB virus B

<400> SEQUENCE: 61
aaggccttgt ggtactgcct gatagggtgc ttgcgagtgc cccgggaggt ctcgtagacc 60

<210> SEQ ID NO 62
<211> LENGTH: 60
<212> TYPE: DNA
<213> ORGANISM: Hepatitis GB virus B

<400> SEQUENCE: 62
gtgcatcatg cctgttattt ctactcaaac aagtcctgta cctgcgccca gaacgcgcaa 60

<210> SEQ ID NO 63
<211> LENGTH: 60
<212> TYPE: DNA
<213> ORGANISM: Hepatitis GB virus B

<400> SEQUENCE: 63
gaacaagcag acgcaggctt catatcctgt gtccattaaa acatctgttg aaaggggaca 60

<210> SEQ ID NO 64
<211> LENGTH: 60
<212> TYPE: DNA
<213> ORGANISM: Hepatitis GB virus B

<400> SEQUENCE: 64
acgagcaaag cgcaaagtcc agcgcgatgc tcggcctcgt aattacaaaa ttgctggtat 60

<210> SEQ ID NO 65
<211> LENGTH: 60
<212> TYPE: DNA
<213> ORGANISM: Hepatitis GB virus B

<400> SEQUENCE: 65
ccatgatggc ttgcagacat tggctcaggc tgctttgcca gctcatggtt ggggacgcca 60

```
<210> SEQ ID NO 66
<211> LENGTH: 60
<212> TYPE: DNA
<213> ORGANISM: Hepatitis GB virus B

<400> SEQUENCE: 66
agaccctcgc cataagtctc gcaatcttgg aatccttctg gattacccttt tggggtggat      60

<210> SEQ ID NO 67
<211> LENGTH: 60
<212> TYPE: DNA
<213> ORGANISM: Hepatitis GB virus B

<400> SEQUENCE: 67
tggtgatgtt acaactcaca cacctctagt aggcccgctg gtggcaggag cggtcgttcg      60

<210> SEQ ID NO 68
<211> LENGTH: 60
<212> TYPE: DNA
<213> ORGANISM: Hepatitis GB virus B

<400> SEQUENCE: 68
accagtctgc cagatagtac gcttgctgga ggatggagtc aactgggcta ctggttggtt      60

<210> SEQ ID NO 69
<211> LENGTH: 60
<212> TYPE: DNA
<213> ORGANISM: Hepatitis GB virus B

<400> SEQUENCE: 69
cggtgtccac cttttttgtgg tatgtctgct atctttggcc tgtccctgta gtggggcgcg     60

<210> SEQ ID NO 70
<211> LENGTH: 60
<212> TYPE: DNA
<213> ORGANISM: Hepatitis GB virus B

<400> SEQUENCE: 70
ggtcactgac ccagacacaa ataccacaat cctgaccaat tgctgccagc gtaatcaggt      60

<210> SEQ ID NO 71
<211> LENGTH: 60
<212> TYPE: DNA
<213> ORGANISM: Hepatitis GB virus B

<400> SEQUENCE: 71
tatctattgt tctccttcca cttgcctaca cgagcctggt tgtgtgatct gtgcggacga      60

<210> SEQ ID NO 72
<211> LENGTH: 60
<212> TYPE: DNA
<213> ORGANISM: Hepatitis GB virus B

<400> SEQUENCE: 72
gtgctgggtt cccgccaatc cgtacatctc acacccttcc aattggactg gcacggactc      60

<210> SEQ ID NO 73
<211> LENGTH: 60
<212> TYPE: DNA
<213> ORGANISM: Hepatitis GB virus B

<400> SEQUENCE: 73
cttcttggct gaccacattg attttgttat gggcgctctt gtgacctgtg acgcccttga      60
```

<210> SEQ ID NO 74
<211> LENGTH: 60
<212> TYPE: DNA
<213> ORGANISM: Hepatitis GB virus B

<400> SEQUENCE: 74
cattggtgag ttgtgtggtg cgtgtgtatt agtcggtgac tggcttgtca ggcactggct    60

<210> SEQ ID NO 75
<211> LENGTH: 60
<212> TYPE: DNA
<213> ORGANISM: Hepatitis GB virus B

<400> SEQUENCE: 75
tattcacata gacctcaatg aaactggtac ttgttacctg gaagtgccca ctggaataga    60

<210> SEQ ID NO 76
<211> LENGTH: 60
<212> TYPE: DNA
<213> ORGANISM: Hepatitis GB virus B

<400> SEQUENCE: 76
cctaggaacc caggatctat tccagtgggc acttccaggt aacaagtacc agtttcattg    60

<210> SEQ ID NO 77
<211> LENGTH: 60
<212> TYPE: DNA
<213> ORGANISM: Hepatitis GB virus B

<400> SEQUENCE: 77
aggtctatgt gaataagcca gtgcctgaca agccagtcac cgactaatac acacgcacca    60

<210> SEQ ID NO 78
<211> LENGTH: 60
<212> TYPE: DNA
<213> ORGANISM: Hepatitis GB virus B

<400> SEQUENCE: 78
cacaactcac caatgtcaag ggcgtcacag gtcacaagag cgcccataac aaaatcaatg    60

<210> SEQ ID NO 79
<211> LENGTH: 60
<212> TYPE: DNA
<213> ORGANISM: Hepatitis GB virus B

<400> SEQUENCE: 79
tggtcagcca agaaggagtc cgtgccagtc caattggaag ggtgtgagat gtacggattg    60

<210> SEQ ID NO 80
<211> LENGTH: 60
<212> TYPE: DNA
<213> ORGANISM: Hepatitis GB virus B

<400> SEQUENCE: 80
gcgggaaccc agcactcgtc cgcacagatc acacaaccag gctcgtgtag gcaagtggaa    60

<210> SEQ ID NO 81
<211> LENGTH: 60
<212> TYPE: DNA
<213> ORGANISM: Hepatitis GB virus B

<400> SEQUENCE: 81
ggagaacaat agataacctg attacgctgg cagcaattgg tcaggattgt ggtatttgtg    60

<210> SEQ ID NO 82
<211> LENGTH: 60
<212> TYPE: DNA
<213> ORGANISM: Hepatitis GB virus B

<400> SEQUENCE: 82
tctgggtcag tgacccgcgc cccactacag ggacaggcca aagatagcag acataccaca 60

<210> SEQ ID NO 83
<211> LENGTH: 60
<212> TYPE: DNA
<213> ORGANISM: Hepatitis GB virus B

<400> SEQUENCE: 83
aaaaggtgga caccgaacca accagtagcc cagttgactc catcctccag caagcgtact 60

<210> SEQ ID NO 84
<211> LENGTH: 60
<212> TYPE: DNA
<213> ORGANISM: Hepatitis GB virus B

<400> SEQUENCE: 84
atctggcaga ctggtcgaac gaccgctcct gccaccagcg ggcctactag aggtgtgtga 60

<210> SEQ ID NO 85
<211> LENGTH: 60
<212> TYPE: DNA
<213> ORGANISM: Hepatitis GB virus B

<400> SEQUENCE: 85
gttgtaacat caccaatcca ccccaaaggg taatccagaa ggattccaag attgcgagac 60

<210> SEQ ID NO 86
<211> LENGTH: 60
<212> TYPE: DNA
<213> ORGANISM: Hepatitis GB virus B

<400> SEQUENCE: 86
ttatggcgag ggtcttggcg tccccaacca tgagctggca aagcagcctg agccaatgtc 60

<210> SEQ ID NO 87
<211> LENGTH: 60
<212> TYPE: DNA
<213> ORGANISM: Hepatitis GB virus B

<400> SEQUENCE: 87
tgcaagccat catggatacc agcaattttg taattacgag gccgagcatc gcgctggact 60

<210> SEQ ID NO 88
<211> LENGTH: 60
<212> TYPE: DNA
<213> ORGANISM: Hepatitis GB virus B

<400> SEQUENCE: 88
ttgcgctttg ctcgttgtcc cctttcaaca gatgttttaa tggacacagg atatgaagcc 60

<210> SEQ ID NO 89
<211> LENGTH: 60
<212> TYPE: DNA
<213> ORGANISM: Hepatitis GB virus B

<400> SEQUENCE: 89
tgcgtctgct tgttcttgcg cgttctgggc gcaggtacag gacttgtttg agtagaaata 60

<210> SEQ ID NO 90
<211> LENGTH: 60
<212> TYPE: DNA
<213> ORGANISM: Hepatitis GB virus B

<400> SEQUENCE: 90
acaggcatga tgcacggtct acgagacctc ccggggcact cgcaagcacc ctatcaggca 60

<210> SEQ ID NO 91
<211> LENGTH: 60
<212> TYPE: DNA
<213> ORGANISM: Hepatitis GB virus B

<400> SEQUENCE: 91
gtaccacaag gcctttcgcg acccaacact actcggctag cagtctcgcg ggggcacgcc 60

<210> SEQ ID NO 92
<211> LENGTH: 60
<212> TYPE: DNA
<213> ORGANISM: Hepatitis GB virus B

<400> SEQUENCE: 92
caaatctcca ggcattgagc gggttgatcc aagaaaggac ccggtcgtcc tggcaattcc 60

<210> SEQ ID NO 93
<211> LENGTH: 9495
<212> TYPE: RNA
<213> ORGANISM: Artificial Sequence
<220> FEATURE:
<223> OTHER INFORMATION: Chimeric virus of Hepatitis C virus and GBV-B
<220> FEATURE:
<221> NAME/KEY: CDS
<222> LOCATION: (342)..(9272)

<400> SEQUENCE: 93
gccagccccc ugaugggggc gacacuccac cauagaucac uccccuguga ggaacuacug 60
ucuucacgca gaaagcgucu agccauggcg uuaguaugag ugucgugcag ccuccaggac 120
ccccccuccc gggagagcca uaguggucug cggaaccggu gaguacaccg gaauugccag 180
gacgaccggg uccuuucuug gaucaacccg cucaaugccu ggagauuugg gcgugccccc 240
gcgagacugc uagccgagua guguuggguc gcgaaaggcc uugugguacu gccugauagg 300
gugcuugcga gugccccggg aggucucgua gaccgugcau c aug agc aca aau ccu 356
Met Ser Thr Asn Pro
1 5 aaa ccu caa aga aaa acc aaa cgu aac acc aac cgc cgc cca cag gac 404
Lys Pro Gln Arg Lys Thr Lys Arg Asn Thr Asn Arg Arg Pro Gln Asp
10 15 20 guc aag uuc ccg ggc ggu ggc cag auc guu ggu gga guu uac cug uug 452
Val Lys Phe Pro Gly Gly Gly Gln Ile Val Gly Gly Val Tyr Leu Leu
25 30 35 ccg cgc agg ggc ccc agg uug ggu gug cgc gcg acu agg aag acu ucc 500
Pro Arg Arg Gly Pro Arg Leu Gly Val Arg Ala Thr Arg Lys Thr Ser
40 45 50 gag cgg ucg caa ccu cgu gga agg cga caa ccu auc ccc aag gcu cgc 548
Glu Arg Ser Gln Pro Arg Gly Arg Arg Gln Pro Ile Pro Lys Ala Arg
55 60 65 cag ccc gag ggc agg gcc ugg gcu cag ccc ggg uau ccu ugg ccc cuc 596
Gln Pro Glu Gly Arg Ala Trp Ala Gln Pro Gly Tyr Pro Trp Pro Leu
70 75 80 85 uau ggc aac gag ggu cug ggg ugg gca gga ugg cuc cug uca ccc cgu 644
Tyr Gly Asn Glu Gly Leu Gly Trp Ala Gly Trp Leu Leu Ser Pro Arg -continued

```
                    90                  95                  100
ggc ucu cgg ccu agu ugg ggc ccc acg gac ccc cgg cgu agg ucg cgu       692
Gly Ser Arg Pro Ser Trp Gly Pro Thr Asp Pro Arg Arg Arg Ser Arg
            105                 110                 115 aau uug ggu aag guc auc gau acc cuc aca ugc ggc uuc gcc gac cuc       740
Asn Leu Gly Lys Val Ile Asp Thr Leu Thr Cys Gly Phe Ala Asp Leu
            120                 125                 130 aug ggg uac auu ccg cuc guc ggc gcc cca cua gga ggc gcu gcc agg       788
Met Gly Tyr Ile Pro Leu Val Gly Ala Pro Leu Gly Gly Ala Ala Arg
            135                 140                 145 gcc cug gcg cau ggc guc cgg guu cug gag gac ggc gug aac uau gca       836
Ala Leu Ala His Gly Val Arg Val Leu Glu Asp Gly Val Asn Tyr Ala
150                 155                 160                 165 aca ggg aau cug ccc ggu ugc ccu uuc ucu auc uuc cuc uua gcu uug       884
Thr Gly Asn Leu Pro Gly Cys Pro Phe Ser Ile Phe Leu Leu Ala Leu
            170                 175                 180 cug ucc ugu uug acc auc cca gcu ucc gcu cac gaa gug cgc aac gua       932
Leu Ser Cys Leu Thr Ile Pro Ala Ser Ala His Glu Val Arg Asn Val
            185                 190                 195 ucc ggg cug uac gau gua acu gac cca gac aca aau acc aca auc cug       980
Ser Gly Leu Tyr Asp Val Thr Asp Pro Asp Thr Asn Thr Thr Ile Leu
            200                 205                 210 acc aau ugc ugc cag cgu aau cag guu auc uau ugu ucu ccu ucc acu      1028
Thr Asn Cys Cys Gln Arg Asn Gln Val Ile Tyr Cys Ser Pro Ser Thr
            215                 220                 225 ugc cua cac gag ccu ggu ugu gug auc ugu gcg gac gag ugu ugg guu      1076
Cys Leu His Glu Pro Gly Cys Val Ile Cys Ala Asp Glu Cys Trp Val
230                 235                 240                 245 ccc gcc aau ccg uac auc uca cac ccu ucc aau ugg acu ggc acg gac      1124
Pro Ala Asn Pro Tyr Ile Ser His Pro Ser Asn Trp Thr Gly Thr Asp
            250                 255                 260 ucc uuc uug gcu gac cac auu gau uuu guu aug ggc gcu cuu gug acc      1172
Ser Phe Leu Ala Asp His Ile Asp Phe Val Met Gly Ala Leu Val Thr
            265                 270                 275 ugu gac gcc cuu gac auu ggu gag uug ugu ggu gcg ugu gua uua guc      1220
Cys Asp Ala Leu Asp Ile Gly Glu Leu Cys Gly Ala Cys Val Leu Val
            280                 285                 290 ggu gac ugg cuu guc agg cac ugg cuu auu cac aua gac cuc aau gaa      1268
Gly Asp Trp Leu Val Arg His Trp Leu Ile His Ile Asp Leu Asn Glu
            295                 300                 305 acu ggu acu ugu uac cug gaa gug ccc acu gga aua gau ccu ggg uuc      1316
Thr Gly Thr Cys Tyr Leu Glu Val Pro Thr Gly Ile Asp Pro Gly Phe
310                 315                 320                 325 cua ggg uuu auc ggg ugg aug gcc ggc aag guc gag gcu guc auc uuc      1364
Leu Gly Phe Ile Gly Trp Met Ala Gly Lys Val Glu Ala Val Ile Phe
            330                 335                 340 uug acc aaa cug gcu uca caa gua cca uac gcu auu gcg acu aug uuu      1412
Leu Thr Lys Leu Ala Ser Gln Val Pro Tyr Ala Ile Ala Thr Met Phe
            345                 350                 355 agc agu gua cac uac cug gcg guu ggc gcu cug auc uac uau gcc ucu      1460
Ser Ser Val His Tyr Leu Ala Val Gly Ala Leu Ile Tyr Tyr Ala Ser
            360                 365                 370 cgg ggc aag ugg uau cag uug cuc cua gcg cuu aug cuu uac aua gaa      1508
Arg Gly Lys Trp Tyr Gln Leu Leu Leu Ala Leu Met Leu Tyr Ile Glu
            375                 380                 385 gcg acc ucu gga aac ccc auc agg gug ccc acu gga ugc uca aua gcu      1556
Ala Thr Ser Gly Asn Pro Ile Arg Val Pro Thr Gly Cys Ser Ile Ala
390                 395                 400                 405 gag uuu ugc ucg ccu uug aug aua cca ugu ccu ugc cac ucu uau uug      1604
Glu Phe Cys Ser Pro Leu Met Ile Pro Cys Pro Cys His Ser Tyr Leu
```

```
                       410                 415                 420
agu gag aau gug uca gaa guc auu ugu uac agu cca aag ugg acc agg       1652
Ser Glu Asn Val Ser Glu Val Ile Cys Tyr Ser Pro Lys Trp Thr Arg
            425                 430                 435 ccu auc acu cua gag uau aac aac ucc aua ucu ugg uac ccc uau aca       1700
Pro Ile Thr Leu Glu Tyr Asn Asn Ser Ile Ser Trp Tyr Pro Tyr Thr
        440                 445                 450 auc ccu ggu gcg agg gga ugu aug guu aaa uuc aaa aau aac aca ugg       1748
Ile Pro Gly Ala Arg Gly Cys Met Val Lys Phe Lys Asn Asn Thr Trp
    455                 460                 465 ggu ugc ugc cgu auu cgc aau gug cca ucg uac ugc acu aug ggc acu       1796
Gly Cys Cys Arg Ile Arg Asn Val Pro Ser Tyr Cys Thr Met Gly Thr
470                 475                 480                 485 gau gca gug ugg aac gac acu cgc aac acu uac gaa gca ugc ggu gua       1844
Asp Ala Val Trp Asn Asp Thr Arg Asn Thr Tyr Glu Ala Cys Gly Val
                490                 495                 500 aca cca ugg cua aca acc gca ugg cac aac ggc uca gcc cug aaa uug       1892
Thr Pro Trp Leu Thr Thr Ala Trp His Asn Gly Ser Ala Leu Lys Leu
            505                 510                 515 gcu aua uua caa uac ccu ggg ucu aaa gaa aug uuu aaa ccu cau aau       1940
Ala Ile Leu Gln Tyr Pro Gly Ser Lys Glu Met Phe Lys Pro His Asn
        520                 525                 530 ugg aug uca ggc cau uug uau uuu gag gga uca gau acc ccu aua guu       1988
Trp Met Ser Gly His Leu Tyr Phe Glu Gly Ser Asp Thr Pro Ile Val
    535                 540                 545 uac uuu uau gac ccu gug aau ucc acu cuc cua cca ccg gag agg ugg       2036
Tyr Phe Tyr Asp Pro Val Asn Ser Thr Leu Leu Pro Pro Glu Arg Trp
550                 555                 560                 565 gcu agg uug ccc ggu acc cca ccu gug gua cgu ggu ucu ugg uua cag       2084
Ala Arg Leu Pro Gly Thr Pro Pro Val Val Arg Gly Ser Trp Leu Gln
                570                 575                 580 guu ccg caa ggg uuu uac agu gau gug aaa gac cua gcc aca gga uug       2132
Val Pro Gln Gly Phe Tyr Ser Asp Val Lys Asp Leu Ala Thr Gly Leu
            585                 590                 595 auc acc aaa gac aaa gcc ugg aaa aau uau cag guc uua uau ucc gcc       2180
Ile Thr Lys Asp Lys Ala Trp Lys Asn Tyr Gln Val Leu Tyr Ser Ala
        600                 605                 610 acg ggu gcu uug ucu cuu acg gga guu acc acc aag gcc gug gug cua       2228
Thr Gly Ala Leu Ser Leu Thr Gly Val Thr Thr Lys Ala Val Val Leu
    615                 620                 625 auu cug uug ggg uug ugu ggc agc aag uau cuu auu uua gcc uac cuc       2276
Ile Leu Leu Gly Leu Cys Gly Ser Lys Tyr Leu Ile Leu Ala Tyr Leu
630                 635                 640                 645 ugu uac uug ucc cuu ugu uuu ggg cgc gcu ucu ggu uac ccu uug cgu       2324
Cys Tyr Leu Ser Leu Cys Phe Gly Arg Ala Ser Gly Tyr Pro Leu Arg
                650                 655                 660 ccu gug cuc cca ucc cag ucg uau cuc caa gcu ggu ugg gau guu uug       2372
Pro Val Leu Pro Ser Gln Ser Tyr Leu Gln Ala Gly Trp Asp Val Leu
            665                 670                 675 ucu aaa gcu caa gua gcu ccu uuu gcu uug auu uuc uuc auc ugu ugc       2420
Ser Lys Ala Gln Val Ala Pro Phe Ala Leu Ile Phe Phe Ile Cys Cys
        680                 685                 690 uau cuc cgc ugc agg cua cgu uau gcu gcc cuu uua ggg uuu gug ccc       2468
Tyr Leu Arg Cys Arg Leu Arg Tyr Ala Ala Leu Leu Gly Phe Val Pro
    695                 700                 705 aug gcu gag gcc gcc uua gag aac cug gug auc cuc aau gcg gcg ucu       2516
Met Ala Glu Ala Ala Leu Glu Asn Leu Val Ile Leu Asn Ala Ala Ser
710                 715                 720                 725 gug gcc gga gcg cau ggc guu cuc ucu uuc cuu gug uuc uuc ugc gcu       2564
Val Ala Gly Ala His Gly Val Leu Ser Phe Leu Val Phe Phe Cys Ala
```

-continued

| | | | | | | | | | | | | |
|---|---|---|---|---|---|---|---|---|---|---|---|---|
| | | | | 730 | | | 735 | | | 740 | | |
| gcc | ugg | uac | auc | aag | ggc | aag | cug | guc | ccc | ggg | gcg | gca | uau | gcc | uuc | 2612 |
| Ala | Trp | Tyr | Ile | Lys | Gly | Lys | Leu | Val | Pro | Gly | Ala | Ala | Tyr | Ala | Phe | |
| | | | 745 | | | | 750 | | | | 755 | | | | | |
| uau | ggu | gua | ugg | ccg | cug | cuc | cug | cuu | cug | cug | uca | uua | cca | cca | cga | 2660 |
| Tyr | Gly | Val | Trp | Pro | Leu | Leu | Leu | Leu | Leu | Leu | Ser | Leu | Pro | Pro | Arg | |
| | | 760 | | | | | 765 | | | | | 770 | | | | |
| gca | uac | gcc | uug | gac | cgg | gag | aug | gcu | gca | ucg | ugc | gga | ggc | gcg | guu | 2708 |
| Ala | Tyr | Ala | Leu | Asp | Arg | Glu | Met | Ala | Ala | Ser | Cys | Gly | Gly | Ala | Val | |
| | | 775 | | | | | 780 | | | | | 785 | | | | |
| uuc | gua | ggu | cug | aug | cuc | cug | acc | uug | uca | cca | cac | uac | aag | gug | uuu | 2756 |
| Phe | Val | Gly | Leu | Met | Leu | Leu | Thr | Leu | Ser | Pro | His | Tyr | Lys | Val | Phe | |
| 790 | | | | | 795 | | | | | 800 | | | | | 805 | |
| cuc | gcu | agg | cuc | aua | ugg | ugg | uua | cag | uau | uuu | auc | acc | agg | gcc | gag | 2804 |
| Leu | Ala | Arg | Leu | Ile | Trp | Trp | Leu | Gln | Tyr | Phe | Ile | Thr | Arg | Ala | Glu | |
| | | | | 810 | | | | | 815 | | | | | 820 | | |
| gcg | cac | uug | cag | gug | ugg | guc | ccc | ccc | cuc | aac | guu | cgg | ggg | ggc | cgc | 2852 |
| Ala | His | Leu | Gln | Val | Trp | Val | Pro | Pro | Leu | Asn | Val | Arg | Gly | Gly | Arg | |
| | | | 825 | | | | | 830 | | | | | 835 | | | |
| gau | gcc | auc | auc | cuc | cuc | acg | ugu | gug | guc | cac | cca | gag | cua | auu | uuu | 2900 |
| Asp | Ala | Ile | Ile | Leu | Leu | Thr | Cys | Val | Val | His | Pro | Glu | Leu | Ile | Phe | |
| | | | 840 | | | | | 845 | | | | | 850 | | | |
| gac | auc | acc | aaa | auc | uug | cuc | gcc | aug | cuc | ggu | ccg | cuc | aug | gug | cuc | 2948 |
| Asp | Ile | Thr | Lys | Ile | Leu | Leu | Ala | Met | Leu | Gly | Pro | Leu | Met | Val | Leu | |
| | 855 | | | | | 860 | | | | | 865 | | | | | |
| cag | gcu | ggc | cua | acu | aga | gug | ccg | uac | uuc | gua | cgc | gcu | caa | ggg | cuc | 2996 |
| Gln | Ala | Gly | Leu | Thr | Arg | Val | Pro | Tyr | Phe | Val | Arg | Ala | Gln | Gly | Leu | |
| 870 | | | | | 875 | | | | | 880 | | | | | 885 | |
| auc | cgu | gca | ugc | aug | uua | gug | cgg | aaa | guc | gcu | ggg | ggc | cac | uau | guc | 3044 |
| Ile | Arg | Ala | Cys | Met | Leu | Val | Arg | Lys | Val | Ala | Gly | Gly | His | Tyr | Val | |
| | | | | 890 | | | | | 895 | | | | | 900 | | |
| caa | aug | gcc | cuc | aug | aaa | cug | gcc | gca | cug | acg | ggu | acg | uac | guu | uau | 3092 |
| Gln | Met | Ala | Leu | Met | Lys | Leu | Ala | Ala | Leu | Thr | Gly | Thr | Tyr | Val | Tyr | |
| | | | 905 | | | | | 910 | | | | | 915 | | | |
| gac | cau | cuu | acu | ccg | cug | cag | gac | ugg | gcc | cac | gcg | ggc | uug | cga | gac | 3140 |
| Asp | His | Leu | Thr | Pro | Leu | Gln | Asp | Trp | Ala | His | Ala | Gly | Leu | Arg | Asp | |
| | | 920 | | | | | 925 | | | | | 930 | | | | |
| cuu | gca | gug | gca | guu | gag | ccc | guc | guc | uuc | ucu | gac | aug | gag | acu | aag | 3188 |
| Leu | Ala | Val | Ala | Val | Glu | Pro | Val | Val | Phe | Ser | Asp | Met | Glu | Thr | Lys | |
| | 935 | | | | | 940 | | | | | 945 | | | | | |
| guc | auc | acc | ugg | ggg | gca | gac | acc | gca | gcg | ugu | ggg | gac | auc | auc | ucg | 3236 |
| Val | Ile | Thr | Trp | Gly | Ala | Asp | Thr | Ala | Ala | Cys | Gly | Asp | Ile | Ile | Ser | |
| 950 | | | | | 955 | | | | | 960 | | | | | 965 | |
| ggc | cua | ccc | guc | ucc | gcc | cga | agg | ggg | agg | gag | aua | cuu | cug | ggc | ccc | 3284 |
| Gly | Leu | Pro | Val | Ser | Ala | Arg | Arg | Gly | Arg | Glu | Ile | Leu | Leu | Gly | Pro | |
| | | | 970 | | | | | 975 | | | | | 980 | | | |
| gcc | gac | agg | uuu | gga | gag | cag | ggg | ugg | cga | cuc | cuc | gcg | ccu | auc | acg | 3332 |
| Ala | Asp | Arg | Phe | Gly | Glu | Gln | Gly | Trp | Arg | Leu | Leu | Ala | Pro | Ile | Thr | |
| | | | 985 | | | | | 990 | | | | | 995 | | | |
| gcu | uac | gcu | caa | cag | acg | cgg | ggc | cua | cuu | ggc | ugu | auc | auc | acc | | 3377 |
| Ala | Tyr | Ala | Gln | Gln | Thr | Arg | Gly | Leu | Leu | Gly | Cys | Ile | Ile | Thr | | |
| | | | 1000 | | | | 1005 | | | | | 1010 | | | | |
| agc | cuc | aca | ggc | cgg | gac | aag | aac | cag | guc | gag | ggg | gag | guu | cag | | 3422 |
| Ser | Leu | Thr | Gly | Arg | Asp | Lys | Asn | Gln | Val | Glu | Gly | Glu | Val | Gln | | |
| | | 1015 | | | | | 1020 | | | | | 1025 | | | | |
| gug | guu | ucc | acc | gca | acg | caa | ucu | uuc | cug | gcg | acc | ugc | guc | aac | | 3467 |
| Val | Val | Ser | Thr | Ala | Thr | Gln | Ser | Phe | Leu | Ala | Thr | Cys | Val | Asn | | |
| | | 1030 | | | | | 1035 | | | | | 1040 | | | | |
| ggc | gug | ugu | ugg | acu | guc | uac | cau | ggu | gcc | ggc | ucg | aag | acc | cug | | 3512 |
| Gly | Val | Cys | Trp | Thr | Val | Tyr | His | Gly | Ala | Gly | Ser | Lys | Thr | Leu | | |

-continued

```
        1045              1050              1055
gcc ggc ccg aag ggc cca auc acc caa aug uac acc aau gug gac    3557
Ala Gly Pro Lys Gly Pro Ile Thr Gln Met Tyr Thr Asn Val Asp
        1060              1065              1070 caa gac cuc guc ggu ugg ccg gcg ccc ccc ggg gcg cgc ucc cug    3602
Gln Asp Leu Val Gly Trp Pro Ala Pro Pro Gly Ala Arg Ser Leu
        1075              1080              1085 aca ccg ugc acc ugc ggc agc ucg gac cuc uac cug guc acg agg    3647
Thr Pro Cys Thr Cys Gly Ser Ser Asp Leu Tyr Leu Val Thr Arg
        1090              1095              1100 cau gcu gau guc auu ccg gug cgc cgg cgg ggc gac agc agg ggg    3692
His Ala Asp Val Ile Pro Val Arg Arg Arg Gly Asp Ser Arg Gly
        1105              1110              1115 agu cua cuc ucu ccc agg ccc auc ucc uac uua aag ggc ucc uca    3737
Ser Leu Leu Ser Pro Arg Pro Ile Ser Tyr Leu Lys Gly Ser Ser
        1120              1125              1130 ggu ggu cca cug cuu ugc ccc cug ggg cac gcu gug ggc auc uuc    3782
Gly Gly Pro Leu Leu Cys Pro Leu Gly His Ala Val Gly Ile Phe
        1135              1140              1145 cgg gcc gcu gug ugc acc cgg ggg guu gca aag gcg gug gau uuu    3827
Arg Ala Ala Val Cys Thr Arg Gly Val Ala Lys Ala Val Asp Phe
        1150              1155              1160 gua ccu guu gag ucu aug gaa acc acc aug cgg ucu ccg guc uuu    3872
Val Pro Val Glu Ser Met Glu Thr Thr Met Arg Ser Pro Val Phe
        1165              1170              1175 acg gau aau uca ucu ccc ccg gcc gua ccg cag aca uuc caa gug    3917
Thr Asp Asn Ser Ser Pro Pro Ala Val Pro Gln Thr Phe Gln Val
        1180              1185              1190 gcc cau cua cac gcu ccc acu ggc agu ggc aag agc acu aag gug    3962
Ala His Leu His Ala Pro Thr Gly Ser Gly Lys Ser Thr Lys Val
        1195              1200              1205 ccg gcu gcg uac gca gcc caa ggg uac aag gua cuc guc uug aac    4007
Pro Ala Ala Tyr Ala Ala Gln Gly Tyr Lys Val Leu Val Leu Asn
        1210              1215              1220 cca ucc guu gcc gcu acc uua ggg uuu ggg gcg uac aug ucu aaa    4052
Pro Ser Val Ala Ala Thr Leu Gly Phe Gly Ala Tyr Met Ser Lys
        1225              1230              1235 gca cau ggu guu gag ccu aac auc aga acu ggg gua agg acc auc    4097
Ala His Gly Val Glu Pro Asn Ile Arg Thr Gly Val Arg Thr Ile
        1240              1245              1250 acc acg ggc gcu ucc auc acg uau ucc acc uac ggu aag uuc cuu    4142
Thr Thr Gly Ala Ser Ile Thr Tyr Ser Thr Tyr Gly Lys Phe Leu
        1255              1260              1265 gcc gac ggu ggu ugc ucu ggg ggc gcc uau gac auc aua aua ugu    4187
Ala Asp Gly Gly Cys Ser Gly Gly Ala Tyr Asp Ile Ile Ile Cys
        1270              1275              1280 gau gag ugc cac uca acu gac ucg acu ucc auc uug ggc auu ggc    4232
Asp Glu Cys His Ser Thr Asp Ser Thr Ser Ile Leu Gly Ile Gly
        1285              1290              1295 aca guc cug gac caa gcg gag acg gcu gga gcg cgg cuc guc gug    4277
Thr Val Leu Asp Gln Ala Glu Thr Ala Gly Ala Arg Leu Val Val
        1300              1305              1310 cuc gcc acc gcu acg ccu ccg gga ucg guc acc gug cca cau ccc    4322
Leu Ala Thr Ala Thr Pro Pro Gly Ser Val Thr Val Pro His Pro
        1315              1320              1325 aau auc gag gag gug gcc uug ccc agc acc gga gaa auu ccc uuc    4367
Asn Ile Glu Glu Val Ala Leu Pro Ser Thr Gly Glu Ile Pro Phe
        1330              1335              1340 uac ggc aaa gcc auc ccc auu gag acc auc aag ggg ggg agg cac    4412
Tyr Gly Lys Ala Ile Pro Ile Glu Thr Ile Lys Gly Gly Arg His
```

-continued

```
              1345                1350                    1355
cuc  auc  uuc  ugc  cac  ucc  aag  aag  aaa  ugu  gac  gag  cuc  gcu  gca      4457
Leu  Ile  Phe  Cys  His  Ser  Lys  Lys  Lys  Cys  Asp  Glu  Leu  Ala  Ala
              1360                1365                    1370 aag  cug  gug  ggc  cuc  gga  guu  aac  gcu  guu  gcg  uac  uac  cgg  ggu      4502
Lys  Leu  Val  Gly  Leu  Gly  Val  Asn  Ala  Val  Ala  Tyr  Tyr  Arg  Gly
              1375                1380                    1385 cuu  gau  gug  ucc  guc  aua  cca  aca  agc  gga  gau  guc  guu  guc  gug      4547
Leu  Asp  Val  Ser  Val  Ile  Pro  Thr  Ser  Gly  Asp  Val  Val  Val  Val
              1390                1395                    1400 gca  aca  gac  gcu  cua  aug  acg  ggc  uuc  acc  ggc  gac  uuu  gac  uca      4592
Ala  Thr  Asp  Ala  Leu  Met  Thr  Gly  Phe  Thr  Gly  Asp  Phe  Asp  Ser
              1405                1410                    1415 gug  auc  gac  ugu  aau  acu  ugu  guc  acc  cag  aca  guu  gau  uuc  agc      4637
Val  Ile  Asp  Cys  Asn  Thr  Cys  Val  Thr  Gln  Thr  Val  Asp  Phe  Ser
              1420                1425                    1430 uug  gac  ccu  acc  uuc  acc  auu  gag  acg  aca  acc  gug  ccc  caa  gac      4682
Leu  Asp  Pro  Thr  Phe  Thr  Ile  Glu  Thr  Thr  Thr  Val  Pro  Gln  Asp
              1435                1440                    1445 gcg  gug  ucg  cgu  ucg  cag  cga  cga  ggc  agg  acu  ggc  agg  ggc  agg      4727
Ala  Val  Ser  Arg  Ser  Gln  Arg  Arg  Gly  Arg  Thr  Gly  Arg  Gly  Arg
              1450                1455                    1460 aug  ggc  aua  uac  agg  uuu  gug  gcu  cca  ggg  gaa  cgg  ccc  ucg  ggc      4772
Met  Gly  Ile  Tyr  Arg  Phe  Val  Ala  Pro  Gly  Glu  Arg  Pro  Ser  Gly
              1465                1470                    1475 aug  uuc  gau  ucu  ucg  guc  cug  ugu  gag  ugc  uau  gac  gcg  ggc  ugu      4817
Met  Phe  Asp  Ser  Ser  Val  Leu  Cys  Glu  Cys  Tyr  Asp  Ala  Gly  Cys
              1480                1485                    1490 gcu  ugg  uau  gag  cuc  acg  ccc  gcc  gag  acc  uca  guc  agg  uug  cgg      4862
Ala  Trp  Tyr  Glu  Leu  Thr  Pro  Ala  Glu  Thr  Ser  Val  Arg  Leu  Arg
              1495                1500                    1505 gcu  uac  cua  aau  aca  cca  ggg  cug  ccc  guc  ugc  cag  gac  cac  cug      4907
Ala  Tyr  Leu  Asn  Thr  Pro  Gly  Leu  Pro  Val  Cys  Gln  Asp  His  Leu
              1510                1515                    1520 gag  uuu  ugg  gag  ggg  guc  uuc  aca  ggc  cuc  acc  cac  aua  gau  gcc      4952
Glu  Phe  Trp  Glu  Gly  Val  Phe  Thr  Gly  Leu  Thr  His  Ile  Asp  Ala
              1525                1530                    1535 cau  uuc  uug  ucc  cag  acu  aag  cag  gca  gga  gau  aac  uuc  ccc  uac      4997
His  Phe  Leu  Ser  Gln  Thr  Lys  Gln  Ala  Gly  Asp  Asn  Phe  Pro  Tyr
              1540                1545                    1550 cug  gua  gca  uac  cag  gcu  acg  gug  ugc  gcc  agg  gcc  cag  gcu  ccc      5042
Leu  Val  Ala  Tyr  Gln  Ala  Thr  Val  Cys  Ala  Arg  Ala  Gln  Ala  Pro
              1555                1560                    1565 ccu  cca  ucg  ugg  gau  caa  aug  ugg  aag  ugu  cuc  aua  cgg  cug  aag      5087
Pro  Pro  Ser  Trp  Asp  Gln  Met  Trp  Lys  Cys  Leu  Ile  Arg  Leu  Lys
              1570                1575                    1580 ccu  aca  cua  cac  ggg  cca  acg  ccc  cug  uug  uau  agg  cua  gga  gcc      5132
Pro  Thr  Leu  His  Gly  Pro  Thr  Pro  Leu  Leu  Tyr  Arg  Leu  Gly  Ala
              1585                1590                    1595 guc  cag  aau  gag  guc  auc  cuc  aca  cau  ccc  aua  acc  aaa  uac  auc      5177
Val  Gln  Asn  Glu  Val  Ile  Leu  Thr  His  Pro  Ile  Thr  Lys  Tyr  Ile
              1600                1605                    1610 aug  gca  ugc  aug  ucg  gcu  gac  cua  gag  guc  guc  acu  agc  acc  ugg      5222
Met  Ala  Cys  Met  Ser  Ala  Asp  Leu  Glu  Val  Val  Thr  Ser  Thr  Trp
              1615                1620                    1625 gug  cug  guc  ggc  ggg  guc  cuu  gca  gcu  cug  gcc  gcg  uac  ugc  cug      5267
Val  Leu  Val  Gly  Gly  Val  Leu  Ala  Ala  Leu  Ala  Ala  Tyr  Cys  Leu
              1630                1635                    1640 acg  acg  ggc  agc  gug  guc  auu  gug  ggc  agg  auc  auc  uug  ucc  ggg      5312
Thr  Thr  Gly  Ser  Val  Val  Ile  Val  Gly  Arg  Ile  Ile  Leu  Ser  Gly
```

-continued

```
           1645                1650                 1655
aag ccg gcu auc auu ccu gac agg gaa guc cuc uac cgg gag uuc      5357
Lys Pro Ala Ile Ile Pro Asp Arg Glu Val Leu Tyr Arg Glu Phe
            1660                1665                1670
gau gaa aug gaa gag ugu gcc uca cac cuc ccc uac auc gaa cag      5402
Asp Glu Met Glu Glu Cys Ala Ser His Leu Pro Tyr Ile Glu Gln
            1675                1680                1685
gga aug cag cuc gcc gaa caa uuc aag cag aag gcg cuc ggg uug      5447
Gly Met Gln Leu Ala Glu Gln Phe Lys Gln Lys Ala Leu Gly Leu
            1690                1695                1700
cug cag aca gcc acc aag caa gcg gaa gcc gcu gcu ccu gug gug      5492
Leu Gln Thr Ala Thr Lys Gln Ala Glu Ala Ala Ala Pro Val Val
            1705                1710                1715
gag ucc aag ugg cga gcc cuu gag gcc uuc ugg gcg aag cac aug      5537
Glu Ser Lys Trp Arg Ala Leu Glu Ala Phe Trp Ala Lys His Met
            1720                1725                1730
ugg aau uuc auc agc ggg aua cag uac uua gca ggc uug ucc acu      5582
Trp Asn Phe Ile Ser Gly Ile Gln Tyr Leu Ala Gly Leu Ser Thr
            1735                1740                1745
cug ccu ggg aac ccc gcg aua gca uca cug aug gca uuc aca gcc      5627
Leu Pro Gly Asn Pro Ala Ile Ala Ser Leu Met Ala Phe Thr Ala
            1750                1755                1760
ucu auc acc agc ccg cuu acc acc cua cac acc cuc cug uuu aac      5672
Ser Ile Thr Ser Pro Leu Thr Thr Leu His Thr Leu Leu Phe Asn
            1765                1770                1775
auc uug gga gga ugg gug gcc gcc caa cuu gcc ccc ccc ggu gcu      5717
Ile Leu Gly Gly Trp Val Ala Ala Gln Leu Ala Pro Pro Gly Ala
            1780                1785                1790
gcc ucg gcu uuc gug ggc gcc ggc auu gcu ggc gca gcu guu ggc      5762
Ala Ser Ala Phe Val Gly Ala Gly Ile Ala Gly Ala Ala Val Gly
            1795                1800                1805
agc aua ggc cuu ggg aag gug cuu gug gac auc cug gcg ggu uau      5807
Ser Ile Gly Leu Gly Lys Val Leu Val Asp Ile Leu Ala Gly Tyr
            1810                1815                1820
gga gca ggg gug gca ggc gcg cuc gug gcc uuc aag guc aug agc      5852
Gly Ala Gly Val Ala Gly Ala Leu Val Ala Phe Lys Val Met Ser
            1825                1830                1835
ggc gag aug ccc ucc acc gag gac cug guc aac uua cuc ccu gcc      5897
Gly Glu Met Pro Ser Thr Glu Asp Leu Val Asn Leu Leu Pro Ala
            1840                1845                1850
auc cuc ucu ccu ggu gcc cuu guc guc ggg guc gug ugc gca gca      5942
Ile Leu Ser Pro Gly Ala Leu Val Val Gly Val Val Cys Ala Ala
            1855                1860                1865
aua cug cgu cgg cau gug ggc ccg ggg gag ggg gcu gug caa ugg      5987
Ile Leu Arg Arg His Val Gly Pro Gly Glu Gly Ala Val Gln Trp
            1870                1875                1880
aug aac cgg cug aua gcg uuc gcc ucg cgg ggu aac cac guc ucc      6032
Met Asn Arg Leu Ile Ala Phe Ala Ser Arg Gly Asn His Val Ser
            1885                1890                1895
ccc acg cac uau gug ccu gag agc gac gcu gca gcg cgu guc aca      6077
Pro Thr His Tyr Val Pro Glu Ser Asp Ala Ala Ala Arg Val Thr
            1900                1905                1910
cag auc cuc ucu agc cuc acc auc acu cag cua cug aag agg cuc      6122
Gln Ile Leu Ser Ser Leu Thr Ile Thr Gln Leu Leu Lys Arg Leu
            1915                1920                1925
cac cag ugg auu aau aag gac ugc ucc aca cca ugc ucc ggc ucg      6167
His Gln Trp Ile Asn Lys Asp Cys Ser Thr Pro Cys Ser Gly Ser
            1930                1935                1940
ugg cuu agg gac guu ugg gac ugg aua ugc acg guu uug agu gac      6212
Trp Leu Arg Asp Val Trp Asp Trp Ile Cys Thr Val Leu Ser Asp
```

|       |       |       | 1945  |       |       |       |       | 1950  |       |       |       |       | 1955  |       |      |
|-------|-------|-------|-------|-------|-------|-------|-------|-------|-------|-------|-------|-------|-------|-------|------| uuc aag acc ugg cuc cag ucc aag cuc cug cca cgg uua ccg gga    6257
Phe Lys Thr Trp Leu Gln Ser Lys Leu Leu Pro Arg Leu Pro Gly
        1960                1965                1970 guu cca uuc cuu uca ugc caa cgu ggg uau aag ggg guc ugg cgg    6302
Val Pro Phe Leu Ser Cys Gln Arg Gly Tyr Lys Gly Val Trp Arg
        1975                1980                1985 gga gau ggc auc aug cag acc ucc ugc cca ugu gga gca caa auc    6347
Gly Asp Gly Ile Met Gln Thr Ser Cys Pro Cys Gly Ala Gln Ile
        1990                1995                2000 gcc gga cau guc aag aac ggu ucc aug agg auc guu ggg ccu aaa    6392
Ala Gly His Val Lys Asn Gly Ser Met Arg Ile Val Gly Pro Lys
        2005                2010                2015 acc ugu agc aac acg ugg cac gga aca uuc ccc auu aac gcg cac    6437
Thr Cys Ser Asn Thr Trp His Gly Thr Phe Pro Ile Asn Ala His
        2020                2025                2030 acc acg ggc ccc ugc aca ccc ucc cca gcg ccg aac uac ucu aag    6482
Thr Thr Gly Pro Cys Thr Pro Ser Pro Ala Pro Asn Tyr Ser Lys
        2035                2040                2045 gcg uug ugg cgg gug gcu gcu gag gag uac gug gaa guc acg cgg    6527
Ala Leu Trp Arg Val Ala Ala Glu Glu Tyr Val Glu Val Thr Arg
        2050                2055                2060 gug ggg gau uuc cau uac gug acg ggc aug acc acu gac aac gua    6572
Val Gly Asp Phe His Tyr Val Thr Gly Met Thr Thr Asp Asn Val
        2065                2070                2075 aaa ugc cca ugc cag guu ccg gcc ccc gaa uuc uuc aca gag gug    6617
Lys Cys Pro Cys Gln Val Pro Ala Pro Glu Phe Phe Thr Glu Val
        2080                2085                2090 gau ggg gua cgg cug cac agg uac gcu ccg gcg ugc aaa ccu cuc    6662
Asp Gly Val Arg Leu His Arg Tyr Ala Pro Ala Cys Lys Pro Leu
        2095                2100                2105 cua cgg gau gag guc aca uuc cag guc ggg cuc aac cag uuc ccg    6707
Leu Arg Asp Glu Val Thr Phe Gln Val Gly Leu Asn Gln Phe Pro
        2110                2115                2120 guu ggg uca cag cuc cca ugc gag ccc gaa ccg gau gua uca gug    6752
Val Gly Ser Gln Leu Pro Cys Glu Pro Glu Pro Asp Val Ser Val
        2125                2130                2135 cuc acu ucc aug cuu acc gac ccu ucc cac auc aca gca gag acg    6797
Leu Thr Ser Met Leu Thr Asp Pro Ser His Ile Thr Ala Glu Thr
        2140                2145                2150 gcu aag cgu agg cug gcc aga ggg ucu ucc ccc ucu uug gcc agc    6842
Ala Lys Arg Arg Leu Ala Arg Gly Ser Ser Pro Ser Leu Ala Ser
        2155                2160                2165 ucu uca gcu agu cag uug ucu gcg ccc uca uug aag gcg aca ugc    6887
Ser Ser Ala Ser Gln Leu Ser Ala Pro Ser Leu Lys Ala Thr Cys
        2170                2175                2180 acc acc cau cau gac ucc cca gac gcu gac cuc auu gag gcc aac    6932
Thr Thr His His Asp Ser Pro Asp Ala Asp Leu Ile Glu Ala Asn
        2185                2190                2195 cuc cug ugg cgg cag gag aug gga ggg aac auc acc cgu gug gag    6977
Leu Leu Trp Arg Gln Glu Met Gly Gly Asn Ile Thr Arg Val Glu
        2200                2205                2210 uca gag aac aag gug gua auc cug gac ucu uuu gac ccg cuu cga    7022
Ser Glu Asn Lys Val Val Ile Leu Asp Ser Phe Asp Pro Leu Arg
        2215                2220                2225 gcg gag gag gac gag agg gag gug ucu guu gcg gcg gag auc cug    7067
Ala Glu Glu Asp Glu Arg Glu Val Ser Val Ala Ala Glu Ile Leu
        2230                2235                2240 cgg aaa acc agg aag uuc ccc cca gcg aug ccc aua ugg gca cgc    7112
Arg Lys Thr Arg Lys Phe Pro Pro Ala Met Pro Ile Trp Ala Arg -continued

| | | | | | | | | | | | | |
|---|---|---|---|---|---|---|---|---|---|---|---|---|
| | | | 2245 | | | 2250 | | | | 2255 | | |
| ccg | gac | uac | aac | cca | ccg | cug | cua | gag | acu | ugg | aag | gac | ccg | gac | 7157 |
| Pro | Asp | Tyr | Asn | Pro | Pro | Leu | Leu | Glu | Thr | Trp | Lys | Asp | Pro | Asp | |
| | | 2260 | | | | 2265 | | | | 2270 | | | | | |
| uac | guc | ccu | cca | gug | gug | cac | ggg | ugc | cca | uug | cca | ccu | acc | aag | 7202 |
| Tyr | Val | Pro | Pro | Val | Val | His | Gly | Cys | Pro | Leu | Pro | Pro | Thr | Lys | |
| | | 2275 | | | | 2280 | | | | 2285 | | | | | |
| acc | ccu | cca | aua | cca | ccu | ccg | cgg | agg | aaa | aag | aca | guu | guc | cug | 7247 |
| Thr | Pro | Pro | Ile | Pro | Pro | Pro | Arg | Arg | Lys | Lys | Thr | Val | Val | Leu | |
| | | 2290 | | | | 2295 | | | | 2300 | | | | | |
| aca | gag | ucc | acc | gug | ucu | ucu | gcc | cug | gcg | gag | cuu | gcc | aca | aag | 7292 |
| Thr | Glu | Ser | Thr | Val | Ser | Ser | Ala | Leu | Ala | Glu | Leu | Ala | Thr | Lys | |
| | | 2305 | | | | 2310 | | | | 2315 | | | | | |
| acc | uuu | ggc | agc | ucc | gga | ucg | ucg | gcc | guc | gac | agc | ggc | aca | gcg | 7337 |
| Thr | Phe | Gly | Ser | Ser | Gly | Ser | Ser | Ala | Val | Asp | Ser | Gly | Thr | Ala | |
| | | 2320 | | | | 2325 | | | | 2330 | | | | | |
| acc | gcc | ccc | ccu | aac | cag | cuc | ucc | gac | gaa | gug | gau | aca | gga | ucc | 7382 |
| Thr | Ala | Pro | Pro | Asn | Gln | Leu | Ser | Asp | Glu | Val | Asp | Thr | Gly | Ser | |
| | | 2335 | | | | 2340 | | | | 2345 | | | | | |
| gac | guu | gag | ucg | uac | ucc | ucc | aug | ccc | ccc | cuu | gag | gga | gag | ccg | 7427 |
| Asp | Val | Glu | Ser | Tyr | Ser | Ser | Met | Pro | Pro | Leu | Glu | Gly | Glu | Pro | |
| | | 2350 | | | | 2355 | | | | 2360 | | | | | |
| ggg | gac | ccc | gau | cuc | agc | gac | ggg | ucu | ugg | ucu | acu | gua | agu | gag | 7472 |
| Gly | Asp | Pro | Asp | Leu | Ser | Asp | Gly | Ser | Trp | Ser | Thr | Val | Ser | Glu | |
| | | 2365 | | | | 2370 | | | | 2375 | | | | | |
| gag | gcu | ggu | gag | gac | guc | guc | ugc | ugc | ucg | aug | ucc | uac | aca | ugg | 7517 |
| Glu | Ala | Gly | Glu | Asp | Val | Val | Cys | Cys | Ser | Met | Ser | Tyr | Thr | Trp | |
| | | 2380 | | | | 2385 | | | | 2390 | | | | | |
| aca | ggc | gcc | uug | auc | acg | ccg | ugc | gcc | gcg | gag | gag | agc | aag | cug | 7562 |
| Thr | Gly | Ala | Leu | Ile | Thr | Pro | Cys | Ala | Ala | Glu | Glu | Ser | Lys | Leu | |
| | | 2395 | | | | 2400 | | | | 2405 | | | | | |
| ccc | auc | aau | gcg | cug | agc | aac | ucu | uug | cug | cgc | cac | cac | aac | aug | 7607 |
| Pro | Ile | Asn | Ala | Leu | Ser | Asn | Ser | Leu | Leu | Arg | His | His | Asn | Met | |
| | | 2410 | | | | 2415 | | | | 2420 | | | | | |
| guc | uau | gcc | aca | aca | ucc | cgc | agc | gca | agc | caa | cgg | cag | aaa | aag | 7652 |
| Val | Tyr | Ala | Thr | Thr | Ser | Arg | Ser | Ala | Ser | Gln | Arg | Gln | Lys | Lys | |
| | | 2425 | | | | 2430 | | | | 2435 | | | | | |
| guc | acc | uuu | gac | aga | cug | caa | guc | cug | gac | gac | cau | uac | cgg | gac | 7697 |
| Val | Thr | Phe | Asp | Arg | Leu | Gln | Val | Leu | Asp | Asp | His | Tyr | Arg | Asp | |
| | | 2440 | | | | 2445 | | | | 2450 | | | | | |
| gug | cuc | aag | gag | aug | aag | gcg | aag | gcg | ucc | aca | guu | aag | gcu | aaa | 7742 |
| Val | Leu | Lys | Glu | Met | Lys | Ala | Lys | Ala | Ser | Thr | Val | Lys | Ala | Lys | |
| | | 2455 | | | | 2460 | | | | 2465 | | | | | |
| cuu | cua | ucc | gua | gaa | gag | gcc | ugc | aag | cug | acg | ccc | cca | cac | uca | 7787 |
| Leu | Leu | Ser | Val | Glu | Glu | Ala | Cys | Lys | Leu | Thr | Pro | Pro | His | Ser | |
| | | 2470 | | | | 2475 | | | | 2480 | | | | | |
| gcc | agg | ucc | aaa | uuu | ggc | uau | ggg | gcg | aag | gac | guc | cgg | aac | cua | 7832 |
| Ala | Arg | Ser | Lys | Phe | Gly | Tyr | Gly | Ala | Lys | Asp | Val | Arg | Asn | Leu | |
| | | 2485 | | | | 2490 | | | | 2495 | | | | | |
| ucc | agc | aag | gcc | guu | aac | cac | auc | aac | ucc | gug | ugg | aag | gac | uug | 7877 |
| Ser | Ser | Lys | Ala | Val | Asn | His | Ile | Asn | Ser | Val | Trp | Lys | Asp | Leu | |
| | | 2500 | | | | 2505 | | | | 2510 | | | | | |
| cug | gaa | gac | acu | gag | aca | cca | auu | gac | acc | acc | auc | aug | gca | aaa | 7922 |
| Leu | Glu | Asp | Thr | Glu | Thr | Pro | Ile | Asp | Thr | Thr | Ile | Met | Ala | Lys | |
| | | 2515 | | | | 2520 | | | | 2525 | | | | | |
| aau | gag | guc | uuc | ugu | guu | caa | cca | gag | aag | gga | ggc | cgc | aag | cca | 7967 |
| Asn | Glu | Val | Phe | Cys | Val | Gln | Pro | Glu | Lys | Gly | Gly | Arg | Lys | Pro | |
| | | 2530 | | | | 2535 | | | | 2540 | | | | | |
| gcu | cgc | cuu | auc | gua | uac | cca | gac | uug | ggg | gug | cgu | gug | ugc | gag | 8012 |
| Ala | Arg | Leu | Ile | Val | Tyr | Pro | Asp | Leu | Gly | Val | Arg | Val | Cys | Glu | |

```
                  2545                2550                2555
aaa  aug  gcc  cuu  uac  gac  gug  guc  ucc  acu  cuu  ccu  cag  gcc  gug      8057
Lys  Met  Ala  Leu  Tyr  Asp  Val  Val  Ser  Thr  Leu  Pro  Gln  Ala  Val
               2560                2565                2570 aug  ggc  ucc  uca  uac  gga  uuc  cag  uac  ucu  ccu  ggg  cag  cgg  guc      8102
Met  Gly  Ser  Ser  Tyr  Gly  Phe  Gln  Tyr  Ser  Pro  Gly  Gln  Arg  Val
               2575                2580                2585 gag  uuc  cug  gug  aau  gcc  ugg  aaa  uca  aag  aag  aac  ccu  aug  ggc      8147
Glu  Phe  Leu  Val  Asn  Ala  Trp  Lys  Ser  Lys  Lys  Asn  Pro  Met  Gly
               2590                2595                2600 uuc  gca  uau  gac  acc  cgu  ugu  uuu  gac  uca  acg  guc  acc  gag  aac      8192
Phe  Ala  Tyr  Asp  Thr  Arg  Cys  Phe  Asp  Ser  Thr  Val  Thr  Glu  Asn
               2605                2610                2615 gac  auc  cgu  guu  gag  gag  uca  auu  uac  caa  ugu  ugu  gac  uug  gcc      8237
Asp  Ile  Arg  Val  Glu  Glu  Ser  Ile  Tyr  Gln  Cys  Cys  Asp  Leu  Ala
               2620                2625                2630 ccc  gag  gcc  aga  cag  gug  aua  agg  ucg  cuc  aca  gag  cgg  cuu  uau      8282
Pro  Glu  Ala  Arg  Gln  Val  Ile  Arg  Ser  Leu  Thr  Glu  Arg  Leu  Tyr
               2635                2640                2645 guc  ggg  ggc  ccc  cug  acu  aau  uca  aaa  ggg  cag  aac  ugc  ggu  uau      8327
Val  Gly  Gly  Pro  Leu  Thr  Asn  Ser  Lys  Gly  Gln  Asn  Cys  Gly  Tyr
               2650                2655                2660 cgc  cgg  ugc  cgc  gcc  agc  ggc  gug  cug  acg  acu  agc  ugc  ggu  aau      8372
Arg  Arg  Cys  Arg  Ala  Ser  Gly  Val  Leu  Thr  Thr  Ser  Cys  Gly  Asn
               2665                2670                2675 acc  cuc  aca  ugu  uac  uug  aag  gcc  ucu  gca  gcc  ugu  cga  gcu  gca      8417
Thr  Leu  Thr  Cys  Tyr  Leu  Lys  Ala  Ser  Ala  Ala  Cys  Arg  Ala  Ala
               2680                2685                2690 aag  cuc  cag  gac  ugc  acg  aug  cuc  gug  ugc  ggg  gac  gac  cuu  guc      8462
Lys  Leu  Gln  Asp  Cys  Thr  Met  Leu  Val  Cys  Gly  Asp  Asp  Leu  Val
               2695                2700                2705 guu  auc  ugu  gaa  agc  gcg  ggg  acc  cag  gag  gac  gcg  gcg  agc  cua      8507
Val  Ile  Cys  Glu  Ser  Ala  Gly  Thr  Gln  Glu  Asp  Ala  Ala  Ser  Leu
               2710                2715                2720 cga  guc  uuc  acg  gag  gcu  aug  acu  agg  uac  ucc  gcc  ccc  ccc  ggg      8552
Arg  Val  Phe  Thr  Glu  Ala  Met  Thr  Arg  Tyr  Ser  Ala  Pro  Pro  Gly
               2725                2730                2735 gac  ccg  ccc  cga  ccg  gaa  uac  gac  uug  gag  uug  aua  aca  uca  ugc      8597
Asp  Pro  Pro  Arg  Pro  Glu  Tyr  Asp  Leu  Glu  Leu  Ile  Thr  Ser  Cys
               2740                2745                2750 ucc  ucc  aac  gug  ucg  guc  gcg  cac  gau  gca  ucu  ggc  aaa  cgg  gug      8642
Ser  Ser  Asn  Val  Ser  Val  Ala  His  Asp  Ala  Ser  Gly  Lys  Arg  Val
               2755                2760                2765 uau  uac  cuc  acc  cgu  gac  ccc  acc  acc  ccc  cuu  gcg  cgg  gcu  gcg      8687
Tyr  Tyr  Leu  Thr  Arg  Asp  Pro  Thr  Thr  Pro  Leu  Ala  Arg  Ala  Ala
               2770                2775                2780 ugg  gag  aca  gcu  aaa  cac  acu  cca  guc  aac  ucc  ugg  cua  ggc  aac      8732
Trp  Glu  Thr  Ala  Lys  His  Thr  Pro  Val  Asn  Ser  Trp  Leu  Gly  Asn
               2785                2790                2795 auc  auc  aug  uau  gcg  ccc  acc  cuc  ugg  gca  agg  aug  auu  cug  aug      8777
Ile  Ile  Met  Tyr  Ala  Pro  Thr  Leu  Trp  Ala  Arg  Met  Ile  Leu  Met
               2800                2805                2810 acu  cac  uuc  uuc  ucc  auc  cuu  cua  gcu  cag  gag  cag  cuu  gaa  aaa      8822
Thr  His  Phe  Phe  Ser  Ile  Leu  Leu  Ala  Gln  Glu  Gln  Leu  Glu  Lys
               2815                2820                2825 gcc  cug  gau  ugu  cag  auc  uac  ggg  gcc  acu  uac  ucc  auu  gaa  cca      8867
Ala  Leu  Asp  Cys  Gln  Ile  Tyr  Gly  Ala  Thr  Tyr  Ser  Ile  Glu  Pro
               2830                2835                2840 cuu  gac  cua  ccu  cag  auc  auu  caa  cga  cuc  cau  ggu  cuu  agc  gca      8912
Leu  Asp  Leu  Pro  Gln  Ile  Ile  Gln  Arg  Leu  His  Gly  Leu  Ser  Ala
```

```
                    2845                2850                2855
uuc  uca  cuc  cau  agu  uac  ucu  cca  ggu  gaa  auc  aau  agg  gug  gcu    8957
Phe  Ser  Leu  His  Ser  Tyr  Ser  Pro  Gly  Glu  Ile  Asn  Arg  Val  Ala
               2860                2865                2870 uca  ugc  cuc  agg  aaa  cuu  ggg  gua  ccg  ccc  uug  cga  guc  ugg  aga    9002
Ser  Cys  Leu  Arg  Lys  Leu  Gly  Val  Pro  Pro  Leu  Arg  Val  Trp  Arg
               2875                2880                2885 cau  cgg  gcc  aga  agu  guc  cgc  gcu  aag  cua  cug  ucc  cag  ggg  ggg    9047
His  Arg  Ala  Arg  Ser  Val  Arg  Ala  Lys  Leu  Leu  Ser  Gln  Gly  Gly
               2890                2895                2900 agg  gcu  gcc  acu  ugu  ggc  aag  uac  cuc  uuc  aac  ugg  gca  gua  agg    9092
Arg  Ala  Ala  Thr  Cys  Gly  Lys  Tyr  Leu  Phe  Asn  Trp  Ala  Val  Arg
               2905                2910                2915 acc  aag  cuc  aaa  cuc  acu  cca  auc  ccg  gcu  gcg  ucc  cag  uug  gac    9137
Thr  Lys  Leu  Lys  Leu  Thr  Pro  Ile  Pro  Ala  Ala  Ser  Gln  Leu  Asp
               2920                2925                2930 uug  ucc  ggc  ugg  uuc  auu  gcu  ggu  uac  agc  ggg  gga  gac  aua  uau    9182
Leu  Ser  Gly  Trp  Phe  Ile  Ala  Gly  Tyr  Ser  Gly  Gly  Asp  Ile  Tyr
               2935                2940                2945 cac  agc  cug  ucu  cgu  gcc  cga  ccc  cgc  ugg  uuu  aug  uug  ugc  cua    9227
His  Ser  Leu  Ser  Arg  Ala  Arg  Pro  Arg  Trp  Phe  Met  Leu  Cys  Leu
               2950                2955                2960 cuc  cua  cuu  ucu  gug  ggg  gua  ggc  auc  uac  cug  cuc  ccc  aau  cga    9272
Leu  Leu  Leu  Ser  Val  Gly  Val  Gly  Ile  Tyr  Leu  Leu  Pro  Asn  Arg
               2965                2970                2975 ugaacggggg gcuaaacacu ccaggccaau aggccauucu guuuuuuuu uuuuuuuuu            9332 uuuuuuuuuu uuuuuuuuuu uuuuuuuuuu uuuuccuuu uuuuuuuuu uuuccccuuu            9392 cuuuuggugg cuccaucuua gcccuaguca cggcuagcug ugaaaggucc gugagccgca          9452
ugacugcaga gagugcugau acuggccucu cugcagauca ugc                           9495

<210> SEQ ID NO 94
<211> LENGTH: 2977
<212> TYPE: PRT
<213> ORGANISM: Artificial Sequence
<220> FEATURE:
<223> OTHER INFORMATION: Chimeric virus of Hepatitis C virus and GBV-B

<400> SEQUENCE: 94

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
        50                  55                  60

Ile Pro Lys Ala Arg Gln Pro Glu Gly Arg Ala Trp Ala Gln Pro Gly
65                  70                  75                  80

Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Thr Asp Pro
                100                 105                 110

Arg Arg Arg Ser Arg Asn Leu Gly Lys Val Ile Asp Thr Leu Thr Cys
            115                 120                 125

Gly Phe Ala Asp Leu Met Gly Tyr Ile Pro Leu Val Gly Ala Pro Leu
        130                 135                 140

Gly Gly Ala Ala Arg Ala Leu Ala His Gly Val Arg Val Leu Glu Asp
```

```
            145                 150                 155                 160
        Gly Val Asn Tyr Ala Thr Gly Asn Leu Pro Gly Cys Pro Phe Ser Ile
                            165                 170                 175

Phe Leu Leu Ala Leu Leu Ser Cys Leu Thr Ile Pro Ala Ser Ala His
                        180                 185                 190

Glu Val Arg Asn Val Ser Gly Leu Tyr Asp Val Thr Asp Pro Asp Thr
                    195                 200                 205

Asn Thr Thr Ile Leu Thr Asn Cys Cys Gln Arg Asn Gln Val Ile Tyr
                210                 215                 220

Cys Ser Pro Ser Thr Cys Leu His Glu Pro Gly Cys Val Ile Cys Ala
        225                 230                 235                 240

Asp Glu Cys Trp Val Pro Ala Asn Pro Tyr Ile Ser His Pro Ser Asn
                            245                 250                 255

Trp Thr Gly Thr Asp Ser Phe Leu Ala Asp His Ile Asp Phe Val Met
                        260                 265                 270

Gly Ala Leu Val Thr Cys Asp Ala Leu Asp Ile Gly Glu Leu Cys Gly
                    275                 280                 285

Ala Cys Val Leu Val Gly Asp Trp Leu Val Arg His Trp Leu Ile His
                290                 295                 300

Ile Asp Leu Asn Glu Thr Gly Thr Cys Tyr Leu Glu Val Pro Thr Gly
        305                 310                 315                 320

Ile Asp Pro Gly Phe Leu Gly Phe Ile Gly Trp Met Ala Gly Lys Val
                            325                 330                 335

Glu Ala Val Ile Phe Leu Thr Lys Leu Ala Ser Gln Val Pro Tyr Ala
                        340                 345                 350

Ile Ala Thr Met Phe Ser Ser Val His Tyr Leu Ala Val Gly Ala Leu
                    355                 360                 365

Ile Tyr Tyr Ala Ser Arg Gly Lys Trp Tyr Gln Leu Leu Ala Leu
                370                 375                 380

Met Leu Tyr Ile Glu Ala Thr Ser Gly Asn Pro Ile Arg Val Pro Thr
        385                 390                 395                 400

Gly Cys Ser Ile Ala Glu Phe Cys Ser Pro Leu Met Ile Pro Cys Pro
                            405                 410                 415

Cys His Ser Tyr Leu Ser Glu Asn Val Ser Glu Val Ile Cys Tyr Ser
                        420                 425                 430

Pro Lys Trp Thr Arg Pro Ile Thr Leu Glu Tyr Asn Asn Ser Ile Ser
                    435                 440                 445

Trp Tyr Pro Tyr Thr Ile Pro Gly Ala Arg Gly Cys Met Val Lys Phe
                450                 455                 460

Lys Asn Asn Thr Trp Gly Cys Cys Arg Ile Arg Asn Val Pro Ser Tyr
        465                 470                 475                 480

Cys Thr Met Gly Thr Asp Ala Val Trp Asn Asp Thr Arg Asn Thr Tyr
                            485                 490                 495

Glu Ala Cys Gly Val Thr Pro Trp Leu Thr Thr Ala Trp His Asn Gly
                        500                 505                 510

Ser Ala Leu Lys Leu Ala Ile Leu Gln Tyr Pro Gly Ser Lys Glu Met
                    515                 520                 525

Phe Lys Pro His Asn Trp Met Ser Gly His Leu Tyr Phe Glu Gly Ser
                530                 535                 540

Asp Thr Pro Ile Val Tyr Phe Tyr Asp Pro Val Asn Ser Thr Leu Leu
        545                 550                 555                 560

Pro Pro Glu Arg Trp Ala Arg Leu Pro Gly Thr Pro Pro Val Val Arg
                            565                 570                 575
```

-continued

```
Gly Ser Trp Leu Gln Val Pro Gln Gly Phe Tyr Ser Asp Val Lys Asp
            580                 585                 590

Leu Ala Thr Gly Leu Ile Thr Lys Asp Lys Ala Trp Lys Asn Tyr Gln
            595                 600                 605

Val Leu Tyr Ser Ala Thr Gly Ala Leu Ser Leu Thr Gly Val Thr Thr
            610                 615                 620

Lys Ala Val Val Leu Ile Leu Leu Gly Leu Cys Gly Ser Lys Tyr Leu
625                 630                 635                 640

Ile Leu Ala Tyr Leu Cys Tyr Leu Ser Leu Cys Phe Gly Arg Ala Ser
                    645                 650                 655

Gly Tyr Pro Leu Arg Pro Val Leu Pro Ser Gln Ser Tyr Leu Gln Ala
                660                 665                 670

Gly Trp Asp Val Leu Ser Lys Ala Gln Val Ala Pro Phe Ala Leu Ile
            675                 680                 685

Phe Phe Ile Cys Cys Tyr Leu Arg Cys Arg Leu Arg Tyr Ala Ala Leu
            690                 695                 700

Leu Gly Phe Val Pro Met Ala Glu Ala Ala Leu Glu Asn Leu Val Ile
705                 710                 715                 720

Leu Asn Ala Ala Ser Val Ala Gly Ala His Gly Val Leu Ser Phe Leu
                    725                 730                 735

Val Phe Phe Cys Ala Ala Trp Tyr Ile Lys Gly Lys Leu Val Pro Gly
                740                 745                 750

Ala Ala Tyr Ala Phe Tyr Gly Val Trp Pro Leu Leu Leu Leu Leu Leu
            755                 760                 765

Ser Leu Pro Pro Arg Ala Tyr Ala Leu Asp Arg Glu Met Ala Ala Ser
770                 775                 780

Cys Gly Gly Ala Val Phe Val Gly Leu Met Leu Thr Leu Ser Pro
785                 790                 795                 800

His Tyr Lys Val Phe Leu Ala Arg Leu Ile Trp Trp Leu Gln Tyr Phe
                    805                 810                 815

Ile Thr Arg Ala Glu Ala His Leu Gln Val Trp Val Pro Pro Leu Asn
                820                 825                 830

Val Arg Gly Gly Arg Asp Ala Ile Ile Leu Leu Thr Cys Val Val His
            835                 840                 845

Pro Glu Leu Ile Phe Asp Ile Thr Lys Ile Leu Leu Ala Met Leu Gly
850                 855                 860

Pro Leu Met Val Leu Gln Ala Gly Leu Thr Arg Val Pro Tyr Phe Val
865                 870                 875                 880

Arg Ala Gln Gly Leu Ile Arg Ala Cys Met Leu Val Arg Lys Val Ala
                    885                 890                 895

Gly Gly His Tyr Val Gln Met Ala Leu Met Lys Leu Ala Ala Leu Thr
                900                 905                 910

Gly Thr Tyr Val Tyr Asp His Leu Thr Pro Leu Gln Asp Trp Ala His
            915                 920                 925

Ala Gly Leu Arg Asp Leu Ala Val Ala Val Glu Pro Val Phe Ser
            930                 935                 940

Asp Met Glu Thr Lys Val Ile Thr Trp Gly Ala Asp Thr Ala Ala Cys
945                 950                 955                 960

Gly Asp Ile Ile Ser Gly Leu Pro Val Ser Ala Arg Arg Gly Arg Glu
                    965                 970                 975

Ile Leu Leu Gly Pro Ala Asp Arg Phe Gly Glu Gln Gly Trp Arg Leu
                980                 985                 990

Leu Ala Pro Ile Thr Ala Tyr Ala Gln Gln Thr Arg Gly Leu Leu Gly
            995                 1000                1005
```

```
Cys Ile Ile Thr Ser Leu Thr Gly Arg Asp Lys Asn Gln Val Glu
    1010                1015                1020

Gly Glu Val Gln Val Val Ser Thr Ala Thr Gln Ser Phe Leu Ala
    1025                1030                1035

Thr Cys Val Asn Gly Val Cys Trp Thr Val Tyr His Gly Ala Gly
    1040                1045                1050

Ser Lys Thr Leu Ala Gly Pro Lys Gly Pro Ile Thr Gln Met Tyr
    1055                1060                1065

Thr Asn Val Asp Gln Asp Leu Val Gly Trp Pro Ala Pro Pro Gly
    1070                1075                1080

Ala Arg Ser Leu Thr Pro Cys Thr Cys Gly Ser Ser Asp Leu Tyr
    1085                1090                1095

Leu Val Thr Arg His Ala Asp Val Ile Pro Val Arg Arg Arg Gly
    1100                1105                1110

Asp Ser Arg Gly Ser Leu Leu Ser Pro Arg Pro Ile Ser Tyr Leu
    1115                1120                1125

Lys Gly Ser Ser Gly Gly Pro Leu Leu Cys Pro Leu Gly His Ala
    1130                1135                1140

Val Gly Ile Phe Arg Ala Ala Val Cys Thr Arg Gly Val Ala Lys
    1145                1150                1155

Ala Val Asp Phe Val Pro Val Glu Ser Met Glu Thr Thr Met Arg
    1160                1165                1170

Ser Pro Val Phe Thr Asp Asn Ser Ser Pro Pro Ala Val Pro Gln
    1175                1180                1185

Thr Phe Gln Val Ala His Leu His Ala Pro Thr Gly Ser Gly Lys
    1190                1195                1200

Ser Thr Lys Val Pro Ala Ala Tyr Ala Ala Gln Gly Tyr Lys Val
    1205                1210                1215

Leu Val Leu Asn Pro Ser Val Ala Ala Thr Leu Gly Phe Gly Ala
    1220                1225                1230

Tyr Met Ser Lys Ala His Gly Val Glu Pro Asn Ile Arg Thr Gly
    1235                1240                1245

Val Arg Thr Ile Thr Thr Gly Ala Ser Ile Thr Tyr Ser Thr Tyr
    1250                1255                1260

Gly Lys Phe Leu Ala Asp Gly Gly Cys Ser Gly Gly Ala Tyr Asp
    1265                1270                1275

Ile Ile Ile Cys Asp Glu Cys His Ser Thr Asp Ser Thr Ser Ile
    1280                1285                1290

Leu Gly Ile Gly Thr Val Leu Asp Gln Ala Glu Thr Ala Gly Ala
    1295                1300                1305

Arg Leu Val Val Leu Ala Thr Ala Thr Pro Pro Gly Ser Val Thr
    1310                1315                1320

Val Pro His Pro Asn Ile Glu Glu Val Ala Leu Pro Ser Thr Gly
    1325                1330                1335

Glu Ile Pro Phe Tyr Gly Lys Ala Ile Pro Ile Glu Thr Ile Lys
    1340                1345                1350

Gly Gly Arg His Leu Ile Phe Cys His Ser Lys Lys Lys Cys Asp
    1355                1360                1365

Glu Leu Ala Ala Lys Leu Val Gly Leu Gly Val Asn Ala Val Ala
    1370                1375                1380

Tyr Tyr Arg Gly Leu Asp Val Ser Val Ile Pro Thr Ser Gly Asp
    1385                1390                1395

Val Val Val Val Ala Thr Asp Ala Leu Met Thr Gly Phe Thr Gly
```

```
            1400                1405                1410

Asp Phe Asp Ser Val Ile Asp Cys Asn Thr Cys Val Thr Gln Thr
    1415                1420                1425

Val Asp Phe Ser Leu Asp Pro Thr Phe Thr Ile Glu Thr Thr Thr
    1430                1435                1440

Val Pro Gln Asp Ala Val Ser Arg Ser Gln Arg Arg Gly Arg Thr
    1445                1450                1455

Gly Arg Gly Arg Met Gly Ile Tyr Arg Phe Val Ala Pro Gly Glu
    1460                1465                1470

Arg Pro Ser Gly Met Phe Asp Ser Ser Val Leu Cys Glu Cys Tyr
    1475                1480                1485

Asp Ala Gly Cys Ala Trp Tyr Glu Leu Thr Pro Ala Glu Thr Ser
    1490                1495                1500

Val Arg Leu Arg Ala Tyr Leu Asn Thr Pro Gly Leu Pro Val Cys
    1505                1510                1515

Gln Asp His Leu Glu Phe Trp Glu Gly Val Phe Thr Gly Leu Thr
    1520                1525                1530

His Ile Asp Ala His Phe Leu Ser Gln Thr Lys Gln Ala Gly Asp
    1535                1540                1545

Asn Phe Pro Tyr Leu Val Ala Tyr Gln Ala Thr Val Cys Ala Arg
    1550                1555                1560

Ala Gln Ala Pro Pro Ser Trp Asp Gln Met Trp Lys Cys Leu
    1565                1570                1575

Ile Arg Leu Lys Pro Thr Leu His Gly Pro Thr Pro Leu Leu Tyr
    1580                1585                1590

Arg Leu Gly Ala Val Gln Asn Glu Val Ile Leu Thr His Pro Ile
    1595                1600                1605

Thr Lys Tyr Ile Met Ala Cys Met Ser Ala Asp Leu Glu Val Val
    1610                1615                1620

Thr Ser Thr Trp Val Leu Val Gly Gly Val Leu Ala Ala Leu Ala
    1625                1630                1635

Ala Tyr Cys Leu Thr Thr Gly Ser Val Val Ile Val Gly Arg Ile
    1640                1645                1650

Ile Leu Ser Gly Lys Pro Ala Ile Ile Pro Asp Arg Glu Val Leu
    1655                1660                1665

Tyr Arg Glu Phe Asp Glu Met Glu Glu Cys Ala Ser His Leu Pro
    1670                1675                1680

Tyr Ile Glu Gln Gly Met Gln Leu Ala Glu Gln Phe Lys Gln Lys
    1685                1690                1695

Ala Leu Gly Leu Leu Gln Thr Ala Thr Lys Gln Ala Glu Ala Ala
    1700                1705                1710

Ala Pro Val Val Glu Ser Lys Trp Arg Ala Leu Glu Ala Phe Trp
    1715                1720                1725

Ala Lys His Met Trp Asn Phe Ile Ser Gly Ile Gln Tyr Leu Ala
    1730                1735                1740

Gly Leu Ser Thr Leu Pro Gly Asn Pro Ala Ile Ala Ser Leu Met
    1745                1750                1755

Ala Phe Thr Ala Ser Ile Thr Ser Pro Leu Thr Thr Leu His Thr
    1760                1765                1770

Leu Leu Phe Asn Ile Leu Gly Gly Trp Val Ala Ala Gln Leu Ala
    1775                1780                1785

Pro Pro Gly Ala Ala Ser Ala Phe Val Gly Ala Gly Ile Ala Gly
    1790                1795                1800
```

-continued

Ala Ala Val Gly Ser Ile Gly Leu Gly Lys Val Leu Val Asp Ile
1805                1810                1815

Leu Ala Gly Tyr Gly Ala Gly Val Ala Gly Ala Leu Val Ala Phe
1820                1825                1830

Lys Val Met Ser Gly Glu Met Pro Ser Thr Glu Asp Leu Val Asn
1835                1840                1845

Leu Leu Pro Ala Ile Leu Ser Pro Gly Ala Leu Val Val Gly Val
1850                1855                1860

Val Cys Ala Ala Ile Leu Arg Arg His Val Gly Pro Gly Glu Gly
1865                1870                1875

Ala Val Gln Trp Met Asn Arg Leu Ile Ala Phe Ala Ser Arg Gly
1880                1885                1890

Asn His Val Ser Pro Thr His Tyr Val Pro Glu Ser Asp Ala Ala
1895                1900                1905

Ala Arg Val Thr Gln Ile Leu Ser Ser Leu Thr Ile Thr Gln Leu
1910                1915                1920

Leu Lys Arg Leu His Gln Trp Ile Asn Lys Asp Cys Ser Thr Pro
1925                1930                1935

Cys Ser Gly Ser Trp Leu Arg Asp Val Trp Asp Trp Ile Cys Thr
1940                1945                1950

Val Leu Ser Asp Phe Lys Thr Trp Leu Gln Ser Lys Leu Leu Pro
1955                1960                1965

Arg Leu Pro Gly Val Pro Phe Leu Ser Cys Gln Arg Gly Tyr Lys
1970                1975                1980

Gly Val Trp Arg Gly Asp Gly Ile Met Gln Thr Ser Cys Pro Cys
1985                1990                1995

Gly Ala Gln Ile Ala Gly His Val Lys Asn Gly Ser Met Arg Ile
2000                2005                2010

Val Gly Pro Lys Thr Cys Ser Asn Thr Trp His Gly Thr Phe Pro
2015                2020                2025

Ile Asn Ala His Thr Thr Gly Pro Cys Thr Pro Ser Pro Ala Pro
2030                2035                2040

Asn Tyr Ser Lys Ala Leu Trp Arg Val Ala Ala Glu Glu Tyr Val
2045                2050                2055

Glu Val Thr Arg Val Gly Asp Phe His Tyr Val Thr Gly Met Thr
2060                2065                2070

Thr Asp Asn Val Lys Cys Pro Cys Gln Val Pro Ala Pro Glu Phe
2075                2080                2085

Phe Thr Glu Val Asp Gly Val Arg Leu His Arg Tyr Ala Pro Ala
2090                2095                2100

Cys Lys Pro Leu Leu Arg Asp Glu Val Thr Phe Gln Val Gly Leu
2105                2110                2115

Asn Gln Phe Pro Val Gly Ser Gln Leu Pro Cys Glu Pro Glu Pro
2120                2125                2130

Asp Val Ser Val Leu Thr Ser Met Leu Thr Asp Pro Ser His Ile
2135                2140                2145

Thr Ala Glu Thr Ala Lys Arg Arg Leu Ala Arg Gly Ser Ser Pro
2150                2155                2160

Ser Leu Ala Ser Ser Ser Ala Ser Gln Leu Ser Ala Pro Ser Leu
2165                2170                2175

Lys Ala Thr Cys Thr Thr His His Asp Ser Pro Asp Ala Asp Leu
2180                2185                2190

Ile Glu Ala Asn Leu Leu Trp Arg Gln Glu Met Gly Gly Asn Ile
2195                2200                2205

-continued

```
Thr Arg Val Glu Ser Glu Asn Lys Val Val Ile Leu Asp Ser Phe
    2210            2215            2220

Asp Pro Leu Arg Ala Glu Glu Asp Glu Arg Glu Val Ser Val Ala
    2225            2230            2235

Ala Glu Ile Leu Arg Lys Thr Arg Lys Phe Pro Pro Ala Met Pro
    2240            2245            2250

Ile Trp Ala Arg Pro Asp Tyr Asn Pro Pro Leu Leu Glu Thr Trp
    2255            2260            2265

Lys Asp Pro Asp Tyr Val Pro Pro Val Val His Gly Cys Pro Leu
    2270            2275            2280

Pro Pro Thr Lys Thr Pro Pro Ile Pro Pro Pro Arg Arg Lys Lys
    2285            2290            2295

Thr Val Val Leu Thr Glu Ser Thr Val Ser Ser Ala Leu Ala Glu
    2300            2305            2310

Leu Ala Thr Lys Thr Phe Gly Ser Ser Gly Ser Ser Ala Val Asp
    2315            2320            2325

Ser Gly Thr Ala Thr Ala Pro Pro Asn Gln Leu Ser Asp Glu Val
    2330            2335            2340

Asp Thr Gly Ser Asp Val Glu Ser Tyr Ser Ser Met Pro Pro Leu
    2345            2350            2355

Glu Gly Glu Pro Gly Asp Pro Asp Leu Ser Asp Gly Ser Trp Ser
    2360            2365            2370

Thr Val Ser Glu Glu Ala Gly Glu Asp Val Val Cys Cys Ser Met
    2375            2380            2385

Ser Tyr Thr Trp Thr Gly Ala Leu Ile Thr Pro Cys Ala Ala Glu
    2390            2395            2400

Glu Ser Lys Leu Pro Ile Asn Ala Leu Ser Asn Ser Leu Leu Arg
    2405            2410            2415

His His Asn Met Val Tyr Ala Thr Thr Ser Arg Ser Ala Ser Gln
    2420            2425            2430

Arg Gln Lys Lys Val Thr Phe Asp Arg Leu Gln Val Leu Asp Asp
    2435            2440            2445

His Tyr Arg Asp Val Leu Lys Glu Met Lys Ala Lys Ala Ser Thr
    2450            2455            2460

Val Lys Ala Lys Leu Leu Ser Val Glu Glu Ala Cys Lys Leu Thr
    2465            2470            2475

Pro Pro His Ser Ala Arg Ser Lys Phe Gly Tyr Gly Ala Lys Asp
    2480            2485            2490

Val Arg Asn Leu Ser Ser Lys Ala Val Asn His Ile Asn Ser Val
    2495            2500            2505

Trp Lys Asp Leu Leu Glu Asp Thr Glu Thr Pro Ile Asp Thr Thr
    2510            2515            2520

Ile Met Ala Lys Asn Glu Val Phe Cys Val Gln Pro Glu Lys Gly
    2525            2530            2535

Gly Arg Lys Pro Ala Arg Leu Ile Val Tyr Pro Asp Leu Gly Val
    2540            2545            2550

Arg Val Cys Glu Lys Met Ala Leu Tyr Asp Val Val Ser Thr Leu
    2555            2560            2565

Pro Gln Ala Val Met Gly Ser Ser Tyr Gly Phe Gln Tyr Ser Pro
    2570            2575            2580

Gly Gln Arg Val Glu Phe Leu Val Asn Ala Trp Lys Ser Lys Lys
    2585            2590            2595

Asn Pro Met Gly Phe Ala Tyr Asp Thr Arg Cys Phe Asp Ser Thr
```

```
                    2600                2605                2610
Val Thr Glu Asn Asp Ile Arg Val Glu Glu Ser Ile Tyr Gln Cys
    2615                2620                2625

Cys Asp Leu Ala Pro Glu Ala Arg Gln Val Ile Arg Ser Leu Thr
    2630                2635                2640

Glu Arg Leu Tyr Val Gly Gly Pro Leu Thr Asn Ser Lys Gly Gln
    2645                2650                2655

Asn Cys Gly Tyr Arg Arg Cys Arg Ala Ser Gly Val Leu Thr Thr
    2660                2665                2670

Ser Cys Gly Asn Thr Leu Thr Cys Tyr Leu Lys Ala Ser Ala Ala
    2675                2680                2685

Cys Arg Ala Ala Lys Leu Gln Asp Cys Thr Met Leu Val Cys Gly
    2690                2695                2700

Asp Asp Leu Val Val Ile Cys Glu Ser Ala Gly Thr Gln Glu Asp
    2705                2710                2715

Ala Ala Ser Leu Arg Val Phe Thr Glu Ala Met Thr Arg Tyr Ser
    2720                2725                2730

Ala Pro Pro Gly Asp Pro Pro Arg Pro Glu Tyr Asp Leu Glu Leu
    2735                2740                2745

Ile Thr Ser Cys Ser Ser Asn Val Ser Val Ala His Asp Ala Ser
    2750                2755                2760

Gly Lys Arg Val Tyr Tyr Leu Thr Arg Asp Pro Thr Thr Pro Leu
    2765                2770                2775

Ala Arg Ala Ala Trp Glu Thr Ala Lys His Thr Pro Val Asn Ser
    2780                2785                2790

Trp Leu Gly Asn Ile Ile Met Tyr Ala Pro Thr Leu Trp Ala Arg
    2795                2800                2805

Met Ile Leu Met Thr His Phe Phe Ser Ile Leu Leu Ala Gln Glu
    2810                2815                2820

Gln Leu Glu Lys Ala Leu Asp Cys Gln Ile Tyr Gly Ala Thr Tyr
    2825                2830                2835

Ser Ile Glu Pro Leu Asp Leu Pro Gln Ile Ile Gln Arg Leu His
    2840                2845                2850

Gly Leu Ser Ala Phe Ser Leu His Ser Tyr Ser Pro Gly Glu Ile
    2855                2860                2865

Asn Arg Val Ala Ser Cys Leu Arg Lys Leu Gly Val Pro Pro Leu
    2870                2875                2880

Arg Val Trp Arg His Arg Ala Arg Ser Val Arg Ala Lys Leu Leu
    2885                2890                2895

Ser Gln Gly Gly Arg Ala Ala Thr Cys Gly Lys Tyr Leu Phe Asn
    2900                2905                2910

Trp Ala Val Arg Thr Lys Leu Lys Leu Thr Pro Ile Pro Ala Ala
    2915                2920                2925

Ser Gln Leu Asp Leu Ser Gly Trp Phe Ile Ala Gly Tyr Ser Gly
    2930                2935                2940

Gly Asp Ile Tyr His Ser Leu Ser Arg Ala Arg Pro Arg Trp Phe
    2945                2950                2955

Met Leu Cys Leu Leu Leu Leu Ser Val Gly Val Gly Ile Tyr Leu
    2960                2965                2970

Leu Pro Asn Arg
    2975

<210> SEQ ID NO 95
<211> LENGTH: 9543
```

-continued

```
<212> TYPE: RNA
<213> ORGANISM: Artificial Sequence
<220> FEATURE:
<223> OTHER INFORMATION: Chimeric virus of Hepatitis C virus and GBV-B
<220> FEATURE:
<221> NAME/KEY: CDS
<222> LOCATION: (342)..(9320)

<400> SEQUENCE: 95
gccagccccc ugauggggc gacacuccac cauagaucac uccccuguga ggaacuacug    60
ucuucacgca gaaagcgucu agccauggcg uuaguaugag ugucgugcag ccuccaggac   120 cccccucc   gggagagcca uaguggucug cggaaccggu gaguaaccg gaauugccag    180 gacgaccggg uccuuucuug gaucaacccg cucaaugccu ggagauuugg gcgugccccc   240
gcgagacugc uagccgagua uguugggguc gcgaaaggcc uuguggucacu gccugauagg   300 gugcuugcga gugccccggg aggucucgua gaccgugcau c aug agc aca aau ccu  356
                                              Met Ser Thr Asn Pro
                                              1               5 aaa ccu caa aga aaa acc aaa cgu aac acc aac cgc cga cca cag gac    404
Lys Pro Gln Arg Lys Thr Lys Arg Asn Thr Asn Arg Arg Pro Gln Asp
            10                  15                  20 guc aag uuc ccg ggu ggc cag auc guu ggu gga guu uac cug uug         452
Val Lys Phe Pro Gly Gly Gln Ile Val Gly Gly Val Tyr Leu Leu
        25                  30                  35 ccg cgc agg ggc ccc agg uug ggu gug cgc gcg acu agg aag acu ucc    500
Pro Arg Arg Gly Pro Arg Leu Gly Val Arg Ala Thr Arg Lys Thr Ser
    40                  45                  50 gag cgg ucg caa ccu cgu gga agg cga caa ccu auc ccc aag gcu cgc   548
Glu Arg Ser Gln Pro Arg Gly Arg Arg Gln Pro Ile Pro Lys Ala Arg
55                  60                  65 cag ccc gag ggc agg gcc ugg gcu cag ccc ggg uau ccu ugg ccc cuc    596
Gln Pro Glu Gly Arg Ala Trp Ala Gln Pro Gly Tyr Pro Trp Pro Leu
70                  75                  80                  85 uau ggc aac gag ggu cug ggg ugg gca gga ugg cuc cug uca ccc cgu   644
Tyr Gly Asn Glu Gly Leu Gly Trp Ala Gly Trp Leu Leu Ser Pro Arg
            90                  95                  100 ggc ucu cgg ccu agu ugg ggc ccc acg gac ccc cgg cgu agg ucg cgu   692
Gly Ser Arg Pro Ser Trp Gly Pro Thr Asp Pro Arg Arg Arg Ser Arg
        105                 110                 115 aau uug ggu aag guc auc gau acc cuc aca ugc ggc uuc gcc gac cuc   740
Asn Leu Gly Lys Val Ile Asp Thr Leu Thr Cys Gly Phe Ala Asp Leu
    120                 125                 130 aug ggg uac auu ccg cuc guc ggc gcc ccc cua gga ggc gcu gcc agg   788
Met Gly Tyr Ile Pro Leu Val Gly Ala Pro Leu Gly Gly Ala Ala Arg
135                 140                 145 gcc cug gcg cau ggc guc cgg guu cug gag gac ggc gug aac uau gca   836
Ala Leu Ala His Gly Val Arg Val Leu Glu Asp Gly Val Asn Tyr Ala
150                 155                 160                 165 aca ggg aau cug ccc ggu ugc ccu uuc ucu auc uuc cuc uua gcu uug   884
Thr Gly Asn Leu Pro Gly Cys Pro Phe Ser Ile Phe Leu Leu Ala Leu
            170                 175                 180 cug ucc ugu uug acc auc cca gcu ucc gcu cac gaa gug cgc aac gua   932
Leu Ser Cys Leu Thr Ile Pro Ala Ser Ala His Glu Val Arg Asn Val
        185                 190                 195 ucc ggg cug uac cau guc acg aac gac ugc ucc aac uca agc auu gug   980
Ser Gly Leu Tyr His Val Thr Asn Asp Cys Ser Asn Ser Ser Ile Val
    200                 205                 210 uau gag gca gcg gau gua acu gac cca gac aca aau acc aca auc cug  1028
Tyr Glu Ala Ala Asp Val Thr Asp Pro Asp Thr Asn Thr Thr Ile Leu
215                 220                 225
```

```
acc aau ugc ugc cag cgu aau cag guu auc uau ugu ucu ccu ucc acu    1076
Thr Asn Cys Cys Gln Arg Asn Gln Val Ile Tyr Cys Ser Pro Ser Thr
230             235                 240                 245 ugc cua cac gag ccu ggu ugu gug auc ugu gcg gac gag ugc ugg guu    1124
Cys Leu His Glu Pro Gly Cys Val Ile Cys Ala Asp Glu Cys Trp Val
            250                 255                 260 ccc gcc aau ccg uac auc uca cac ccu ucc aau ugg acu ggc acg gac    1172
Pro Ala Asn Pro Tyr Ile Ser His Pro Ser Asn Trp Thr Gly Thr Asp
                265                 270                 275 ucc uuc uug gcu gac cac auu gau uuu guu aug ggu gcu cuu gug acc    1220
Ser Phe Leu Ala Asp His Ile Asp Phe Val Met Gly Ala Leu Val Thr
        280                 285                 290 ugu gac gcc cuu gac auu ggu gag uug ugu ggu gcg ugu gua uua guc    1268
Cys Asp Ala Leu Asp Ile Gly Glu Leu Cys Gly Ala Cys Val Leu Val
    295                 300                 305 ggu gac ugg cuu guc agg cac ugg cuu auu cac aua gac cuc aau gaa    1316
Gly Asp Trp Leu Val Arg His Trp Leu Ile His Ile Asp Leu Asn Glu
310                 315                 320                 325 acu ggu acu ugu uac cug gaa gug ccc acu gga aua gau ccu ggg uuc    1364
Thr Gly Thr Cys Tyr Leu Glu Val Pro Thr Gly Ile Asp Pro Gly Phe
                330                 335                 340 cua ggg uuu auc ggg ugg aug gcc ggc aag guc gag gcu guc auc uuc    1412
Leu Gly Phe Ile Gly Trp Met Ala Gly Lys Val Glu Ala Val Ile Phe
            345                 350                 355 uug acc aaa cug gcu uca caa gua cca uac gcu auu gcg acu aug uuu    1460
Leu Thr Lys Leu Ala Ser Gln Val Pro Tyr Ala Ile Ala Thr Met Phe
        360                 365                 370 agc agu gua cac uac cug gcg guu ggc gcu cug auc uac uau gcc ucu    1508
Ser Ser Val His Tyr Leu Ala Val Gly Ala Leu Ile Tyr Tyr Ala Ser
    375                 380                 385 cgg ggc aag ugg uau cag uug cuc cua gcg cuu aug cuu uac aua gaa    1556
Arg Gly Lys Trp Tyr Gln Leu Leu Leu Ala Leu Met Leu Tyr Ile Glu
390                 395                 400                 405 gcg acc ucu gga aac ccc auc agg gug ccc acu gga ugc uca aua gcu    1604
Ala Thr Ser Gly Asn Pro Ile Arg Val Pro Thr Gly Cys Ser Ile Ala
                410                 415                 420 gag uuu ugc ucg ccu uug aug aua cca ugu ccu ugc cac ucu uau uug    1652
Glu Phe Cys Ser Pro Leu Met Ile Pro Cys Pro Cys His Ser Tyr Leu
            425                 430                 435 agu gag aau gug uca gaa guc auu ugu uac agu cca aag ugg acc agg    1700
Ser Glu Asn Val Ser Glu Val Ile Cys Tyr Ser Pro Lys Trp Thr Arg
        440                 445                 450 ccu auc acu cua gag uau aac aac ucc aua ucu ugg uac ccc uau aca    1748
Pro Ile Thr Leu Glu Tyr Asn Asn Ser Ile Ser Trp Tyr Pro Tyr Thr
    455                 460                 465 auc ccu ggu gcg agg gga ugu aug guu aaa uuc aaa aau aac aca ugg    1796
Ile Pro Gly Ala Arg Gly Cys Met Val Lys Phe Lys Asn Asn Thr Trp
470                 475                 480                 485 ggu ugc ugc cgu auu cgc aau gug cca ucg uac ugc acu aug ggc acu    1844
Gly Cys Cys Arg Ile Arg Asn Val Pro Ser Tyr Cys Thr Met Gly Thr
                490                 495                 500 gau gca gug ugg aac gac acu cgc aac acu uac gaa gca ugc ggu gua    1892
Asp Ala Val Trp Asn Asp Thr Arg Asn Thr Tyr Glu Ala Cys Gly Val
            505                 510                 515 aca cca ugg cua aca acc gca ugg cac aac ggc uca gcc cug aaa uug    1940
Thr Pro Trp Leu Thr Thr Ala Trp His Asn Gly Ser Ala Leu Lys Leu
        520                 525                 530 gcu aua uua caa uac ccu ggg ucu aaa gaa aug uuu aaa ccu cau aau    1988
Ala Ile Leu Gln Tyr Pro Gly Ser Lys Glu Met Phe Lys Pro His Asn
    535                 540                 545
```

-continued

| | |
|---|---|
| ugg aug uca ggc cau uug uau uuu gag gga uca gau acc ccu aua guu<br>Trp Met Ser Gly His Leu Tyr Phe Glu Gly Ser Asp Thr Pro Ile Val<br>550                  555                  560                  565 | 2036 |
| uac uuu uau gac ccu gug aau ucc acu cuc cua cca ccg gag agg ugg<br>Tyr Phe Tyr Asp Pro Val Asn Ser Thr Leu Leu Pro Pro Glu Arg Trp<br>570                  575                  580 | 2084 |
| gcu agg uug ccc ggu acc cca ccu gug gua cgu ggu ucu ugg uua cag<br>Ala Arg Leu Pro Gly Thr Pro Pro Val Val Arg Gly Ser Trp Leu Gln<br>585                  590                  595 | 2132 |
| guu ccg caa ggg uuu uac agu gau gug aaa gac cua gcc aca gga uug<br>Val Pro Gln Gly Phe Tyr Ser Asp Val Lys Asp Leu Ala Thr Gly Leu<br>600                  605                  610 | 2180 |
| auc acc aaa gac aaa gcc ugg aaa aau uau cag guc uua uau ucc gcc<br>Ile Thr Lys Asp Lys Ala Trp Lys Asn Tyr Gln Val Leu Tyr Ser Ala<br>615                  620                  625 | 2228 |
| acg ggu gcu uug ucu cuu acg gga guu acc acc aag gcc gug gug cua<br>Thr Gly Ala Leu Ser Leu Thr Gly Val Thr Thr Lys Ala Val Val Leu<br>630                  635                  640                  645 | 2276 |
| auu cug uug ggg uug ugu ggc agc aag uau cuu auu uua gcc uac cuc<br>Ile Leu Leu Gly Leu Cys Gly Ser Lys Tyr Leu Ile Leu Ala Tyr Leu<br>650                  655                  660 | 2324 |
| ugu uac uug ucc cuu ugu uuu ggg cgc gcu ucu ggu uac ccu uug cgu<br>Cys Tyr Leu Ser Leu Cys Phe Gly Arg Ala Ser Gly Tyr Pro Leu Arg<br>665                  670                  675 | 2372 |
| ccu gug cuc cca ucc cag ucg uau cuc caa gcu ggu ugg gau guu uug<br>Pro Val Leu Pro Ser Gln Ser Tyr Leu Gln Ala Gly Trp Asp Val Leu<br>680                  685                  690 | 2420 |
| ucu aaa gcu caa gua gcu ccu uuu gcu uug auu uuc auc ugu ugc<br>Ser Lys Ala Gln Val Ala Pro Phe Ala Leu Ile Phe Ile Cys Cys<br>695                  700                  705 | 2468 |
| uau cuc cgc ugc agg cua cgu uau gcu gcc cuu uua ggg uuu gug ccc<br>Tyr Leu Arg Cys Arg Leu Arg Tyr Ala Ala Leu Leu Gly Phe Val Pro<br>710                  715                  720                  725 | 2516 |
| aug gcu gag gcc gcc uua gag aac cug gug auc cuc aau gcg gcg ucu<br>Met Ala Glu Ala Ala Leu Glu Asn Leu Val Ile Leu Asn Ala Ala Ser<br>730                  735                  740 | 2564 |
| gug gcc gga gcg cau ggc guu cuc ucu uuc cuu gug uuc uuc ugc gcu<br>Val Ala Gly Ala His Gly Val Leu Ser Phe Leu Val Phe Phe Cys Ala<br>745                  750                  755 | 2612 |
| gcc ugg uac auc aag ggc aag cug guc ccc ggg gcg gca uau gcc uuc<br>Ala Trp Tyr Ile Lys Gly Lys Leu Val Pro Gly Ala Ala Tyr Ala Phe<br>760                  765                  770 | 2660 |
| uau ggu gua ugg ccg cug cuc cug cuu cug cug uca uua cca cca cga<br>Tyr Gly Val Trp Pro Leu Leu Leu Leu Leu Leu Ser Leu Pro Pro Arg<br>775                  780                  785 | 2708 |
| gca uac gcc uug gac cgg gag aug gca gca ucg ugc gga ggc gcg guu<br>Ala Tyr Ala Leu Asp Arg Glu Met Ala Ala Ser Cys Gly Gly Ala Val<br>790                  795                  800                  805 | 2756 |
| uuc gua ggu cug aug cuc cug acc uug uca cca cac uac aag gug uuu<br>Phe Val Gly Leu Met Leu Leu Thr Leu Ser Pro His Tyr Lys Val Phe<br>810                  815                  820 | 2804 |
| cuc gcu agg cuc aua ugg ugg uua cag uau uuu auc acc agg gcc gag<br>Leu Ala Arg Leu Ile Trp Trp Leu Gln Tyr Phe Ile Thr Arg Ala Glu<br>825                  830                  835 | 2852 |
| gcg cac uug cag gug ugg guc ccc ccc cuc aac guu cgg ggg ggc cgc<br>Ala His Leu Gln Val Trp Val Pro Pro Leu Asn Val Arg Gly Gly Arg<br>840                  845                  850 | 2900 |
| gau gcc auc auc cuc cuc acg ugu gug guc cac cca gag cua auu uuu<br>Asp Ala Ile Ile Leu Leu Thr Cys Val Val His Pro Glu Leu Ile Phe<br>855                  860                  865 | 2948 |

```
gac auc acc aaa auc uug cuc gcc aug cuc ggu ccg cuc aug gug cuc      2996
Asp Ile Thr Lys Ile Leu Leu Ala Met Leu Gly Pro Leu Met Val Leu
870             875                 880                 885 cag gcu ggc cua acu aga gug ccg uac uuc gua cgc gcu caa ggg cuc      3044
Gln Ala Gly Leu Thr Arg Val Pro Tyr Phe Val Arg Ala Gln Gly Leu
                890                 895                 900 auc cgu gca ugc aug uua gug cgg aaa guc gcu ggg ggc cac uau guc      3092
Ile Arg Ala Cys Met Leu Val Arg Lys Val Ala Gly Gly His Tyr Val
            905                 910                 915 caa aug gcc cuc aug aaa cug gcc gca cug acg ggu acg uac guu uau      3140
Gln Met Ala Leu Met Lys Leu Ala Ala Leu Thr Gly Thr Tyr Val Tyr
920             925                 930 gac cau cuu acu ccg cug cag gac ugg gcc cac gcg ggc uug cga gac      3188
Asp His Leu Thr Pro Leu Gln Asp Trp Ala His Ala Gly Leu Arg Asp
    935                 940                 945 cuu gca gug gca guu gag ccc guc guc uuc ucu gac aug gag acu aag      3236
Leu Ala Val Ala Val Glu Pro Val Val Phe Ser Asp Met Glu Thr Lys
950             955                 960                 965 guc auc acc ugg ggg gca gac acc gca gcg ugu ggg gac auc auc ucg      3284
Val Ile Thr Trp Gly Ala Asp Thr Ala Ala Cys Gly Asp Ile Ile Ser
                970                 975                 980 ggc cua ccc guc ucc gcc cga agg ggg agg gag aua cuu cug ggc ccc      3332
Gly Leu Pro Val Ser Ala Arg Arg Gly Arg Glu Ile Leu Leu Gly Pro
            985                 990                 995 gcc gac agg uuu gga gag cag ggg ugg cga cuc cuc gcg ccu auc          3377
Ala Asp Arg Phe Gly Glu Gln Gly Trp Arg Leu Leu Ala Pro Ile
        1000                1005                1010 acg gcu uac gcu caa cag acg cgg ggc cua cuu ggc ugu auc auc          3422
Thr Ala Tyr Ala Gln Gln Thr Arg Gly Leu Leu Gly Cys Ile Ile
            1015                1020                1025 acc agc cuc aca ggc cgg gac aag aac cag guc gag ggg gag guu          3467
Thr Ser Leu Thr Gly Arg Asp Lys Asn Gln Val Glu Gly Glu Val
        1030                1035                1040 cag gug guu ucc acc gca acg caa ucu uuc cug gcg acc ugc guc          3512
Gln Val Val Ser Thr Ala Thr Gln Ser Phe Leu Ala Thr Cys Val
            1045                1050                1055 aac ggc gug ugu ugg acu guc uac cau ggu gcc ggc ucg aag acc          3557
Asn Gly Val Cys Trp Thr Val Tyr His Gly Ala Gly Ser Lys Thr
        1060                1065                1070 cug gcc ggc ccg aag ggc cca auc acc caa aug uac acc aau gug          3602
Leu Ala Gly Pro Lys Gly Pro Ile Thr Gln Met Tyr Thr Asn Val
            1075                1080                1085 gac caa gac cuc guc ggc ugg ccg gcg ccc ccc ggg gcg cgc ucc          3647
Asp Gln Asp Leu Val Gly Trp Pro Ala Pro Pro Gly Ala Arg Ser
        1090                1095                1100 cug aca ccg ugc acc ugc ggc agc ucg gac cuc uac cug guc acg          3692
Leu Thr Pro Cys Thr Cys Gly Ser Ser Asp Leu Tyr Leu Val Thr
            1105                1110                1115 agg cau gcu gau guc auu ccg gug cgc cgg cgg ggc gac agc agg          3737
Arg His Ala Asp Val Ile Pro Val Arg Arg Arg Gly Asp Ser Arg
        1120                1125                1130 ggg agu cua cuc ucu ccc agg ccc auc ucc uac uua aag ggc ucc          3782
Gly Ser Leu Leu Ser Pro Arg Pro Ile Ser Tyr Leu Lys Gly Ser
            1135                1140                1145 uca ggu ggu cca cug cuu ugc ccc cug ggg cac gcu gug ggc auc          3827
Ser Gly Gly Pro Leu Leu Cys Pro Leu Gly His Ala Val Gly Ile
        1150                1155                1160 uuc cgg gcc gcu gug ugc acc cgg ggg guu gca aag gcg gug gau          3872
Phe Arg Ala Ala Val Cys Thr Arg Gly Val Ala Lys Ala Val Asp
            1165                1170                1175
```

```
uuu gua ccu guu gag ucu aug gaa acc acc aug cgg ucu ccg guc      3917
Phe Val Pro Val Glu Ser Met Glu Thr Thr Met Arg Ser Pro Val
        1180            1185            1190 uuu acg gau aau uca ucu ccc ccg gcc gua ccg cag aca uuc caa      3962
Phe Thr Asp Asn Ser Ser Pro Pro Ala Val Pro Gln Thr Phe Gln
        1195            1200            1205 gug gcc cau cua cac gcu ccc acu ggc agu ggc aag agc acu aag      4007
Val Ala His Leu His Ala Pro Thr Gly Ser Gly Lys Ser Thr Lys
        1210            1215            1220 gug ccg gcu gcg uac gca gcc caa ggg uac aag gua cuc guc uug      4052
Val Pro Ala Ala Tyr Ala Ala Gln Gly Tyr Lys Val Leu Val Leu
        1225            1230            1235 aac cca ucc guu gcc gcu acc uua ggg uuu ggg gcg uac aug ucu      4097
Asn Pro Ser Val Ala Ala Thr Leu Gly Phe Gly Ala Tyr Met Ser
        1240            1245            1250 aaa gca cau ggu guu gag ccu aac auc aga acu ggg gua agg acc      4142
Lys Ala His Gly Val Glu Pro Asn Ile Arg Thr Gly Val Arg Thr
        1255            1260            1265 auc acc acg ggc gcu ucc auc acg uau ucc acc uac ggu aag uuc      4187
Ile Thr Thr Gly Ala Ser Ile Thr Tyr Ser Thr Tyr Gly Lys Phe
        1270            1275            1280 cuu gcc gac ggu ggu ugc ucu ggg ggc gcc uau gac auc aua aua      4232
Leu Ala Asp Gly Gly Cys Ser Gly Gly Ala Tyr Asp Ile Ile Ile
        1285            1290            1295 ugu gau gag ugc cac uca acu gac ucg acu ucc auc uug ggc auu      4277
Cys Asp Glu Cys His Ser Thr Asp Ser Thr Ser Ile Leu Gly Ile
        1300            1305            1310 ggc aca guc cug gac caa gcg gag acg gcu gga gcg cgg cuc guc      4322
Gly Thr Val Leu Asp Gln Ala Glu Thr Ala Gly Ala Arg Leu Val
        1315            1320            1325 gug cuc gcc acc gcu acg ccu ccg gga ucg guc acc gug cca cau      4367
Val Leu Ala Thr Ala Thr Pro Pro Gly Ser Val Thr Val Pro His
        1330            1335            1340 ccc aau auc gag gag gug gcc uug ccc agc acc gga gaa auu ccc      4412
Pro Asn Ile Glu Glu Val Ala Leu Pro Ser Thr Gly Glu Ile Pro
        1345            1350            1355 uuc uac ggc aaa gcc auc ccc auu gag acc auc aag ggg ggg agg      4457
Phe Tyr Gly Lys Ala Ile Pro Ile Glu Thr Ile Lys Gly Gly Arg
        1360            1365            1370 cac cuc auc uuc ugc cac ucc aag aag aaa ugu gac gag cuc gcu      4502
His Leu Ile Phe Cys His Ser Lys Lys Lys Cys Asp Glu Leu Ala
        1375            1380            1385 gca aag cug gug ggc cuc gga guu aac gcu guu gcg uac uac cgg      4547
Ala Lys Leu Val Gly Leu Gly Val Asn Ala Val Ala Tyr Tyr Arg
        1390            1395            1400 ggu cuu gau gug ucc guc aua cca aca agc gga gau guc guu guc      4592
Gly Leu Asp Val Ser Val Ile Pro Thr Ser Gly Asp Val Val Val
        1405            1410            1415 gug gca aca gac gcu cua aug acg ggc uuc acc ggc gac uuu gac      4637
Val Ala Thr Asp Ala Leu Met Thr Gly Phe Thr Gly Asp Phe Asp
        1420            1425            1430 uca gug auc gac ugu aau acu ugu guc acc cag aca guu gau uuc      4682
Ser Val Ile Asp Cys Asn Thr Cys Val Thr Gln Thr Val Asp Phe
        1435            1440            1445 agc uug gac ccu acc uuc acc auu gag acg aca acc gug ccc caa      4727
Ser Leu Asp Pro Thr Phe Thr Ile Glu Thr Thr Thr Val Pro Gln
        1450            1455            1460 gac gcg gug ucg cgu ucg cag cga cga ggc agg acu ggc agg ggc      4772
Asp Ala Val Ser Arg Ser Gln Arg Arg Gly Arg Thr Gly Arg Gly
        1465            1470            1475
```

| | | | | | | | | | | | | |
|---|---|---|---|---|---|---|---|---|---|---|---|---|
| agg | aug | ggc | aua | uac | agg | uuu | gug | gcu | cca | ggg | gaa | cgg | ccc | ucg | 4817 |
| Arg | Met | Gly | Ile | Tyr | Arg | Phe | Val | Ala | Pro | Gly | Glu | Arg | Pro | Ser | |
| | | 1480 | | | | 1485 | | | | 1490 | | | | | | ggc aug uuc gau ucu ucg guc cug ugu gag ugc uau gac gcg ggc    4862
Gly Met Phe Asp Ser Ser Val Leu Cys Glu Cys Tyr Asp Ala Gly
        1495            1500                1505 ugu gcu ugg uau gag cuc acg ccc gcc gag acc uca guc agg uug    4907
Cys Ala Trp Tyr Glu Leu Thr Pro Ala Glu Thr Ser Val Arg Leu
        1510            1515                1520 cgg gcu uac cua aau aca cca ggg cug ccc guc ugc cag gac cac    4952
Arg Ala Tyr Leu Asn Thr Pro Gly Leu Pro Val Cys Gln Asp His
        1525            1530                1535 cug gag uuu ugg gag ggg guc uuc aca ggc cuc acc cac aua gau    4997
Leu Glu Phe Trp Glu Gly Val Phe Thr Gly Leu Thr His Ile Asp
        1540            1545                1550 gcc cau uuc uug ucc cag acu aag cag gca gga gau aac uuc ccc    5042
Ala His Phe Leu Ser Gln Thr Lys Gln Ala Gly Asp Asn Phe Pro
        1555            1560                1565 uac cug gua gca uac cag gcu acg gug ugc gcc agg gcc cag gcu    5087
Tyr Leu Val Ala Tyr Gln Ala Thr Val Cys Ala Arg Ala Gln Ala
        1570            1575                1580 ccc ccu cca ucg ugg gau caa aug ugg aag ugu cuc aua cgg cug    5132
Pro Pro Pro Ser Trp Asp Gln Met Trp Lys Cys Leu Ile Arg Leu
        1585            1590                1595 aag ccu aca cua cac ggg cca acg ccc cug uug uau agg cua gga    5177
Lys Pro Thr Leu His Gly Pro Thr Pro Leu Leu Tyr Arg Leu Gly
        1600            1605                1610 gcc guc cag aau gag guc auc cuc aca cau ccc aua acc aaa uac    5222
Ala Val Gln Asn Glu Val Ile Leu Thr His Pro Ile Thr Lys Tyr
        1615            1620                1625 auc aug gca ugc aug ucg gcu gac cua gag guc guc acu agc acc    5267
Ile Met Ala Cys Met Ser Ala Asp Leu Glu Val Val Thr Ser Thr
        1630            1635                1640 ugg gug cug guc ggc ggg guc cuu gca gcu cug gcc gcg uac ugc    5312
Trp Val Leu Val Gly Gly Val Leu Ala Ala Leu Ala Ala Tyr Cys
        1645            1650                1655 cug acg acg ggc agc gug guc auu gug ggc agg auc auc uug ucc    5357
Leu Thr Thr Gly Ser Val Val Ile Val Gly Arg Ile Ile Leu Ser
        1660            1665                1670 ggg aag ccg gcu auc auu ccu gac agg gaa guc cuc uac cgg gag    5402
Gly Lys Pro Ala Ile Ile Pro Asp Arg Glu Val Leu Tyr Arg Glu
        1675            1680                1685 uuc gau gaa aug gaa gag ugu gcc uca cac cuc ccc uac auc gaa    5447
Phe Asp Glu Met Glu Glu Cys Ala Ser His Leu Pro Tyr Ile Glu
        1690            1695                1700 cag gga aug cag cuc gcc gaa caa uuc aag cag aag gcg cuc ggg    5492
Gln Gly Met Gln Leu Ala Glu Gln Phe Lys Gln Lys Ala Leu Gly
        1705            1710                1715 uug cug cag aca gcc acc aag caa gcg gaa gcc gcu gcu ccu gug    5537
Leu Leu Gln Thr Ala Thr Lys Gln Ala Glu Ala Ala Ala Pro Val
        1720            1725                1730 gug gag ucc aag ugg cga gcc cuu gag gcc uuc ugg gcg aag cac    5582
Val Glu Ser Lys Trp Arg Ala Leu Glu Ala Phe Trp Ala Lys His
        1735            1740                1745 aug ugg aau uuc auc agc ggg aua cag uac uua gca ggc uug ucc    5627
Met Trp Asn Phe Ile Ser Gly Ile Gln Tyr Leu Ala Gly Leu Ser
        1750            1755                1760 acu cug ccu ggg aac ccc gcg aua gca uca cug aug gca uuc aca    5672
Thr Leu Pro Gly Asn Pro Ala Ile Ala Ser Leu Met Ala Phe Thr
        1765            1770                1775

| | | | | | | | | | | | | |
|---|---|---|---|---|---|---|---|---|---|---|---|---|
| gcc | ucu | auc | acc | agc | ccg | cuu | acc | acc | cua | cac | acc | cuc | cug | uuu | 5717 |
| Ala | Ser | Ile | Thr | Ser | Pro | Leu | Thr | Thr | Leu | His | Thr | Leu | Leu | Phe | |
| | | 1780 | | | | 1785 | | | | 1790 | | | | | |

```
gcc ucu auc acc agc ccg cuu acc acc cua cac acc cuc cug uuu     5717
Ala Ser Ile Thr Ser Pro Leu Thr Thr Leu His Thr Leu Leu Phe
        1780            1785            1790 aac auc uug gga gga ugg gug gcc gcc caa cuu gcc ccc ccc ggu     5762
Asn Ile Leu Gly Gly Trp Val Ala Ala Gln Leu Ala Pro Pro Gly
        1795            1800            1805 gcu gcc ucg gcu uuc gug ggc gcc ggc auu gcu ggc gca gcu guu     5807
Ala Ala Ser Ala Phe Val Gly Ala Gly Ile Ala Gly Ala Ala Val
        1810            1815            1820 ggc agc aua ggc cuu ggg aag gug cuu gug gac auc cug gcg ggu     5852
Gly Ser Ile Gly Leu Gly Lys Val Leu Val Asp Ile Leu Ala Gly
        1825            1830            1835 uau gga gca ggg gug gca ggc gcg cuc gug gcc uuc aag guc aug     5897
Tyr Gly Ala Gly Val Ala Gly Ala Leu Val Ala Phe Lys Val Met
        1840            1845            1850 agc ggc gag aug ccc ucc acc gag gac cug guc aac uua cuc ccu     5942
Ser Gly Glu Met Pro Ser Thr Glu Asp Leu Val Asn Leu Leu Pro
        1855            1860            1865 gcc auc cuc ucu ccu ggu gcc cuu guc guc ggg guc gug ugc gca     5987
Ala Ile Leu Ser Pro Gly Ala Leu Val Val Gly Val Val Cys Ala
        1870            1875            1880 gca aua cug cgu cgg cau gug ggc ccg ggg gag ggg gcu gug caa     6032
Ala Ile Leu Arg Arg His Val Gly Pro Gly Glu Gly Ala Val Gln
        1885            1890            1895 ugg aug aac cgg cug aua gcg uuc gcc ucg cgg ggu aac cac guc     6077
Trp Met Asn Arg Leu Ile Ala Phe Ala Ser Arg Gly Asn His Val
        1900            1905            1910 ucc ccc acg cac uau gug ccu gag agc gac gcu gca gcg cgu guc     6122
Ser Pro Thr His Tyr Val Pro Glu Ser Asp Ala Ala Ala Arg Val
        1915            1920            1925 aca cag auc cuc ucu agc cuc acc auc acu cag cua cug aag agg     6167
Thr Gln Ile Leu Ser Ser Leu Thr Ile Thr Gln Leu Leu Lys Arg
        1930            1935            1940 cuc cac cag ugg auu aau aag gac ugc ucc aca cca ugc ucc ggc     6212
Leu His Gln Trp Ile Asn Lys Asp Cys Ser Thr Pro Cys Ser Gly
        1945            1950            1955 ucg ugg cuu agg gac guu ugg gac ugg aua ugc acg guu uug agu     6257
Ser Trp Leu Arg Asp Val Trp Asp Trp Ile Cys Thr Val Leu Ser
        1960            1965            1970 gac uuc aag acc ugg cuc cag ucc aag cuc cug cca cgg uua ccg     6302
Asp Phe Lys Thr Trp Leu Gln Ser Lys Leu Leu Pro Arg Leu Pro
        1975            1980            1985 gga guu cca uuc cuu uca ugc caa cgu ggg uau aag ggg guc ugg     6347
Gly Val Pro Phe Leu Ser Cys Gln Arg Gly Tyr Lys Gly Val Trp
        1990            1995            2000 cgg gga gau ggc auc aug cag acc ucc ugc cca ugu gga gca caa     6392
Arg Gly Asp Gly Ile Met Gln Thr Ser Cys Pro Cys Gly Ala Gln
        2005            2010            2015 auc gcc gga cau guc aag aac ggu ucc aug agg auc guu ggg ccu     6437
Ile Ala Gly His Val Lys Asn Gly Ser Met Arg Ile Val Gly Pro
        2020            2025            2030 aaa acc ugu agc aac acg ugg cac gga aca uuc ccc auu aac gcg     6482
Lys Thr Cys Ser Asn Thr Trp His Gly Thr Phe Pro Ile Asn Ala
        2035            2040            2045 cac acc acg ggc ccc ugc aca ccc ucc cca gcg ccg aac uac ucu     6527
His Thr Thr Gly Pro Cys Thr Pro Ser Pro Ala Pro Asn Tyr Ser
        2050            2055            2060 aag gcg uug ugg cgg gug gcu gcu gag gag uac gug gaa guc acg     6572
Lys Ala Leu Trp Arg Val Ala Ala Glu Glu Tyr Val Glu Val Thr
        2065            2070            2075
```

-continued

| | | | | | | | | | | | | | | |
|---|---|---|---|---|---|---|---|---|---|---|---|---|---|---|
| cgg | gug | ggg | gau | uuc | cau | uac | gug | acg | ggc | aug | acc | acu | gac | aac | 6617 |
| Arg | Val | Gly | Asp | Phe | His | Tyr | Val | Thr | Gly | Met | Thr | Thr | Asp | Asn | |
| | | 2080 | | | | 2085 | | | | 2090 | | | | | |
| gua | aaa | ugc | cca | ugc | cag | guu | ccg | gcc | ccc | gaa | uuc | uuc | aca | gag | 6662 |
| Val | Lys | Cys | Pro | Cys | Gln | Val | Pro | Ala | Pro | Glu | Phe | Phe | Thr | Glu | |
| | | 2095 | | | | 2100 | | | | 2105 | | | | | |
| gug | gau | ggg | gua | cgg | cug | cac | agg | uac | gcu | ccg | gcg | ugc | aaa | ccu | 6707 |
| Val | Asp | Gly | Val | Arg | Leu | His | Arg | Tyr | Ala | Pro | Ala | Cys | Lys | Pro | |
| | | 2110 | | | | 2115 | | | | 2120 | | | | | |
| cuc | cua | cgg | gau | gag | guc | aca | uuc | cag | guc | ggg | cuc | aac | cag | uuc | 6752 |
| Leu | Leu | Arg | Asp | Glu | Val | Thr | Phe | Gln | Val | Gly | Leu | Asn | Gln | Phe | |
| | | 2125 | | | | 2130 | | | | 2135 | | | | | |
| ccg | guu | ggg | uca | cag | cuc | cca | ugc | gag | ccc | gaa | ccg | gau | gua | uca | 6797 |
| Pro | Val | Gly | Ser | Gln | Leu | Pro | Cys | Glu | Pro | Glu | Pro | Asp | Val | Ser | |
| | | 2140 | | | | 2145 | | | | 2150 | | | | | |
| gug | cuc | acu | ucc | aug | cuu | acc | gac | ccu | ucc | cac | auc | aca | gca | gag | 6842 |
| Val | Leu | Thr | Ser | Met | Leu | Thr | Asp | Pro | Ser | His | Ile | Thr | Ala | Glu | |
| | | 2155 | | | | 2160 | | | | 2165 | | | | | |
| acg | gcu | aag | cgu | agg | cug | gcc | aga | ggg | ucu | ucc | ccc | ucu | uug | gcc | 6887 |
| Thr | Ala | Lys | Arg | Arg | Leu | Ala | Arg | Gly | Ser | Ser | Pro | Ser | Leu | Ala | |
| | | 2170 | | | | 2175 | | | | 2180 | | | | | |
| agc | ucu | uca | gcu | agu | cag | uug | ucu | gcg | ccc | uca | uug | aag | gcg | aca | 6932 |
| Ser | Ser | Ser | Ala | Ser | Gln | Leu | Ser | Ala | Pro | Ser | Leu | Lys | Ala | Thr | |
| | | 2185 | | | | 2190 | | | | 2195 | | | | | |
| ugc | acc | acc | cau | cau | gac | ucc | cca | gac | gcu | gac | cuc | auu | gag | gcc | 6977 |
| Cys | Thr | Thr | His | His | Asp | Ser | Pro | Asp | Ala | Asp | Leu | Ile | Glu | Ala | |
| | | 2200 | | | | 2205 | | | | 2210 | | | | | |
| aac | cuc | cug | ugg | cgg | cag | gag | aug | gga | ggg | aac | auc | acc | cgu | gug | 7022 |
| Asn | Leu | Leu | Trp | Arg | Gln | Glu | Met | Gly | Gly | Asn | Ile | Thr | Arg | Val | |
| | | 2215 | | | | 2220 | | | | 2225 | | | | | |
| gag | uca | gag | aac | aag | gug | gua | auc | cug | gac | ucu | uuu | gac | ccg | cuu | 7067 |
| Glu | Ser | Glu | Asn | Lys | Val | Val | Ile | Leu | Asp | Ser | Phe | Asp | Pro | Leu | |
| | | 2230 | | | | 2235 | | | | 2240 | | | | | |
| cga | gcg | gag | gag | gac | gag | agg | gag | gug | ucu | guu | gcg | gcg | gag | auc | 7112 |
| Arg | Ala | Glu | Glu | Asp | Glu | Arg | Glu | Val | Ser | Val | Ala | Ala | Glu | Ile | |
| | | 2245 | | | | 2250 | | | | 2255 | | | | | |
| cug | cgg | aaa | acc | agg | aag | uuc | ccc | cca | gcg | aug | ccc | aua | ugg | gca | 7157 |
| Leu | Arg | Lys | Thr | Arg | Lys | Phe | Pro | Pro | Ala | Met | Pro | Ile | Trp | Ala | |
| | | 2260 | | | | 2265 | | | | 2270 | | | | | |
| cgc | ccg | gac | uac | aac | cca | ccg | cug | cua | gag | acu | ugg | aag | gac | ccg | 7202 |
| Arg | Pro | Asp | Tyr | Asn | Pro | Pro | Leu | Leu | Glu | Thr | Trp | Lys | Asp | Pro | |
| | | 2275 | | | | 2280 | | | | 2285 | | | | | |
| gac | uac | guc | ccu | cca | gug | gug | cac | ggg | ugc | cca | uug | cca | ccu | acc | 7247 |
| Asp | Tyr | Val | Pro | Pro | Val | Val | His | Gly | Cys | Pro | Leu | Pro | Pro | Thr | |
| | | 2290 | | | | 2295 | | | | 2300 | | | | | |
| aag | acc | ccu | cca | aua | cca | ccu | ccg | cgg | agg | aaa | aag | aca | guu | guc | 7292 |
| Lys | Thr | Pro | Pro | Ile | Pro | Pro | Pro | Arg | Arg | Lys | Lys | Thr | Val | Val | |
| | | 2305 | | | | 2310 | | | | 2315 | | | | | |
| cug | aca | gag | ucc | acc | gug | ucu | ucu | gcc | cug | gcg | gag | cuu | gcc | aca | 7337 |
| Leu | Thr | Glu | Ser | Thr | Val | Ser | Ser | Ala | Leu | Ala | Glu | Leu | Ala | Thr | |
| | | 2320 | | | | 2325 | | | | 2330 | | | | | |
| aag | acc | uuu | ggc | agc | ucc | gga | ucg | ucg | gcc | guc | gac | agc | ggc | aca | 7382 |
| Lys | Thr | Phe | Gly | Ser | Ser | Gly | Ser | Ser | Ala | Val | Asp | Ser | Gly | Thr | |
| | | 2335 | | | | 2340 | | | | 2345 | | | | | |
| gcg | acc | gcc | ccc | ccu | aac | cag | cuc | ucc | gac | gaa | gug | gau | aca | gga | 7427 |
| Ala | Thr | Ala | Pro | Pro | Asn | Gln | Leu | Ser | Asp | Glu | Val | Asp | Thr | Gly | |
| | | 2350 | | | | 2355 | | | | 2360 | | | | | |
| ucc | gac | guu | gag | ucg | uac | ucc | ucc | aug | ccc | ccc | cuu | gag | gga | gag | 7472 |
| Ser | Asp | Val | Glu | Ser | Tyr | Ser | Ser | Met | Pro | Pro | Leu | Glu | Gly | Glu | |
| | | 2365 | | | | 2370 | | | | 2375 | | | | | |

| | | | | | | | | | | | | |
|---|---|---|---|---|---|---|---|---|---|---|---|---|
| ccg | ggg | gac | ccc | gau | cuc | agc | gac | ggg | ucu | ugg | ucu | acu | gua | agu | 7517 |
| Pro | Gly | Asp | Pro | Asp | Leu | Ser | Asp | Gly | Ser | Trp | Ser | Thr | Val | Ser | |
| | | 2380 | | | | 2385 | | | | 2390 | | | | | |
| gag | gag | gcu | ggu | gag | gac | guc | guc | ugc | ugc | ucg | aug | ucc | uac | aca | 7562 |
| Glu | Glu | Ala | Gly | Glu | Asp | Val | Val | Cys | Cys | Ser | Met | Ser | Tyr | Thr | |
| | | 2395 | | | | 2400 | | | | 2405 | | | | | |
| ugg | aca | ggc | gcc | uug | auc | acg | ccg | ugc | gcc | gcg | gag | gag | agc | aag | 7607 |
| Trp | Thr | Gly | Ala | Leu | Ile | Thr | Pro | Cys | Ala | Ala | Glu | Glu | Ser | Lys | |
| | | 2410 | | | | 2415 | | | | 2420 | | | | | |
| cug | ccc | auc | aau | gcg | cug | agc | aac | ucu | uug | cug | cgc | cac | cac | aac | 7652 |
| Leu | Pro | Ile | Asn | Ala | Leu | Ser | Asn | Ser | Leu | Leu | Arg | His | His | Asn | |
| | | 2425 | | | | 2430 | | | | 2435 | | | | | |
| aug | guc | uau | gcc | aca | aca | ucc | cgc | agc | gca | agc | caa | cgg | cag | aaa | 7697 |
| Met | Val | Tyr | Ala | Thr | Thr | Ser | Arg | Ser | Ala | Ser | Gln | Arg | Gln | Lys | |
| | | 2440 | | | | 2445 | | | | 2450 | | | | | |
| aag | guc | acc | uuu | gac | aga | cug | caa | guc | cug | gac | gac | cau | uac | cgg | 7742 |
| Lys | Val | Thr | Phe | Asp | Arg | Leu | Gln | Val | Leu | Asp | Asp | His | Tyr | Arg | |
| | | 2455 | | | | 2460 | | | | 2465 | | | | | |
| gac | gug | cuc | aag | gag | aug | aag | gcg | aag | gcg | ucc | aca | guu | aag | gcu | 7787 |
| Asp | Val | Leu | Lys | Glu | Met | Lys | Ala | Lys | Ala | Ser | Thr | Val | Lys | Ala | |
| | | 2470 | | | | 2475 | | | | 2480 | | | | | |
| aaa | cuu | cua | ucc | gua | gaa | gag | gcc | ugc | aag | cug | acg | ccc | cca | cac | 7832 |
| Lys | Leu | Leu | Ser | Val | Glu | Glu | Ala | Cys | Lys | Leu | Thr | Pro | Pro | His | |
| | | 2485 | | | | 2490 | | | | 2495 | | | | | |
| uca | gcc | agg | ucc | aaa | uuu | ggc | uau | ggg | gcg | aag | gac | guc | cgg | aac | 7877 |
| Ser | Ala | Arg | Ser | Lys | Phe | Gly | Tyr | Gly | Ala | Lys | Asp | Val | Arg | Asn | |
| | | 2500 | | | | 2505 | | | | 2510 | | | | | |
| cua | ucc | agc | aag | gcc | guu | aac | cac | auc | aac | ucc | gug | ugg | aag | gac | 7922 |
| Leu | Ser | Ser | Lys | Ala | Val | Asn | His | Ile | Asn | Ser | Val | Trp | Lys | Asp | |
| | | 2515 | | | | 2520 | | | | 2525 | | | | | |
| uug | cug | gaa | gac | acu | gag | aca | cca | auu | gac | acc | acc | auc | aug | gca | 7967 |
| Leu | Leu | Glu | Asp | Thr | Glu | Thr | Pro | Ile | Asp | Thr | Thr | Ile | Met | Ala | |
| | | 2530 | | | | 2535 | | | | 2540 | | | | | |
| aaa | aau | gag | guc | uuc | ugu | guu | caa | cca | gag | aag | gga | ggc | cgc | aag | 8012 |
| Lys | Asn | Glu | Val | Phe | Cys | Val | Gln | Pro | Glu | Lys | Gly | Gly | Arg | Lys | |
| | | 2545 | | | | 2550 | | | | 2555 | | | | | |
| cca | gcu | cgc | cuu | auc | gua | uac | cca | gac | uug | ggg | gug | cgu | gug | ugc | 8057 |
| Pro | Ala | Arg | Leu | Ile | Val | Tyr | Pro | Asp | Leu | Gly | Val | Arg | Val | Cys | |
| | | 2560 | | | | 2565 | | | | 2570 | | | | | |
| gag | aaa | aug | gcc | cuu | uac | gac | gug | guc | ucc | acu | cuu | ccu | cag | gcc | 8102 |
| Glu | Lys | Met | Ala | Leu | Tyr | Asp | Val | Val | Ser | Thr | Leu | Pro | Gln | Ala | |
| | | 2575 | | | | 2580 | | | | 2585 | | | | | |
| gug | aug | ggc | ucc | uca | uac | gga | uuc | cag | uac | ucu | ccu | ggg | cag | cgg | 8147 |
| Val | Met | Gly | Ser | Ser | Tyr | Gly | Phe | Gln | Tyr | Ser | Pro | Gly | Gln | Arg | |
| | | 2590 | | | | 2595 | | | | 2600 | | | | | |
| guc | gag | uuc | cug | gug | aau | gcc | ugg | aaa | uca | aag | aag | aac | ccu | aug | 8192 |
| Val | Glu | Phe | Leu | Val | Asn | Ala | Trp | Lys | Ser | Lys | Lys | Asn | Pro | Met | |
| | | 2605 | | | | 2610 | | | | 2615 | | | | | |
| ggc | uuc | gca | uau | gac | acc | cgc | ugu | uuu | gac | uca | acg | guc | acc | gag | 8237 |
| Gly | Phe | Ala | Tyr | Asp | Thr | Arg | Cys | Phe | Asp | Ser | Thr | Val | Thr | Glu | |
| | | 2620 | | | | 2625 | | | | 2630 | | | | | |
| aac | gac | auc | cgu | guu | gag | gag | uca | auu | uac | caa | ugu | ugu | gac | uug | 8282 |
| Asn | Asp | Ile | Arg | Val | Glu | Glu | Ser | Ile | Tyr | Gln | Cys | Cys | Asp | Leu | |
| | | 2635 | | | | 2640 | | | | 2645 | | | | | |
| gcc | ccc | gag | gcc | aga | cag | gug | aua | agg | ucg | cuc | aca | gag | cgg | cuu | 8327 |
| Ala | Pro | Glu | Ala | Arg | Gln | Val | Ile | Arg | Ser | Leu | Thr | Glu | Arg | Leu | |
| | | 2650 | | | | 2655 | | | | 2660 | | | | | |
| uau | guc | ggg | ggc | ccc | cug | acu | aau | uca | aaa | ggg | cag | aac | ugc | ggu | 8372 |
| Tyr | Val | Gly | Gly | Pro | Leu | Thr | Asn | Ser | Lys | Gly | Gln | Asn | Cys | Gly | |
| | | 2665 | | | | 2670 | | | | 2675 | | | | | |

-continued

| | | | | | | | | | | | | | | |
|---|---|---|---|---|---|---|---|---|---|---|---|---|---|---|
| uau | cgc | cgg | ugc | cgc | gcc | agc | ggc | gug | cug | acg | acu | agc | ugc | ggu | 8417 |
| Tyr | Arg | Arg | Cys | Arg | Ala | Ser | Gly | Val | Leu | Thr | Thr | Ser | Cys | Gly | |
| | 2680 | | | | 2685 | | | | 2690 | | | | | | |

| aau | acc | cuc | aca | ugu | uac | uug | aag | gcc | ucu | gca | gcc | ugu | cga | gcu | 8462 |
| Asn | Thr | Leu | Thr | Cys | Tyr | Leu | Lys | Ala | Ser | Ala | Ala | Cys | Arg | Ala | |
| | | 2695 | | | | 2700 | | | | 2705 | | | | | |

| gca | aag | cuc | cag | gac | ugc | acg | aug | cuc | gug | ugc | ggg | gac | gac | cuu | 8507 |
| Ala | Lys | Leu | Gln | Asp | Cys | Thr | Met | Leu | Val | Cys | Gly | Asp | Asp | Leu | |
| 2710 | | | | | 2715 | | | | | 2720 | | | | | |

| guc | guu | auc | ugu | gaa | agc | gcg | ggg | acc | cag | gag | gac | gcg | gcg | agc | 8552 |
| Val | Val | Ile | Cys | Glu | Ser | Ala | Gly | Thr | Gln | Glu | Asp | Ala | Ala | Ser | |
| | 2725 | | | | 2730 | | | | 2735 | | | | | | |

| cua | cga | guc | uuc | acg | gag | gcu | aug | acu | agg | uac | ucc | gcc | ccc | ccc | 8597 |
| Leu | Arg | Val | Phe | Thr | Glu | Ala | Met | Thr | Arg | Tyr | Ser | Ala | Pro | Pro | |
| 2740 | | | | | 2745 | | | | | 2750 | | | | | |

| ggg | gac | ccg | ccc | cga | ccg | gaa | uac | gac | uug | gag | uug | aua | aca | uca | 8642 |
| Gly | Asp | Pro | Pro | Arg | Pro | Glu | Tyr | Asp | Leu | Glu | Leu | Ile | Thr | Ser | |
| | 2755 | | | | 2760 | | | | 2765 | | | | | | |

| ugc | ucc | ucc | aac | gug | ucg | guc | gcg | cac | gau | gca | ucu | ggc | aaa | cgg | 8687 |
| Cys | Ser | Ser | Asn | Val | Ser | Val | Ala | His | Asp | Ala | Ser | Gly | Lys | Arg | |
| | 2770 | | | | 2775 | | | | 2780 | | | | | | |

| gug | uau | uac | cuc | acc | cgu | gac | ccc | acc | acc | ccc | cuu | gcg | cgg | gcu | 8732 |
| Val | Tyr | Tyr | Leu | Thr | Arg | Asp | Pro | Thr | Thr | Pro | Leu | Ala | Arg | Ala | |
| 2785 | | | | | 2790 | | | | | 2795 | | | | | |

| gcg | ugg | gag | aca | gcu | aaa | cac | acu | cca | guc | aac | ucc | ugg | cua | ggc | 8777 |
| Ala | Trp | Glu | Thr | Ala | Lys | His | Thr | Pro | Val | Asn | Ser | Trp | Leu | Gly | |
| | | 2800 | | | | 2805 | | | | 2810 | | | | | |

| aac | auc | auc | aug | uau | gcg | ccc | acc | cuc | ugg | gca | agg | aug | auu | cug | 8822 |
| Asn | Ile | Ile | Met | Tyr | Ala | Pro | Thr | Leu | Trp | Ala | Arg | Met | Ile | Leu | |
| | 2815 | | | | 2820 | | | | 2825 | | | | | | |

| aug | acu | cac | uuc | uuc | ucc | auc | cuu | cua | gcu | cag | gag | cag | cuu | gaa | 8867 |
| Met | Thr | His | Phe | Phe | Ser | Ile | Leu | Leu | Ala | Gln | Glu | Gln | Leu | Glu | |
| 2830 | | | | | 2835 | | | | | 2840 | | | | | |

| aaa | gcc | cug | gau | ugu | cag | auc | uac | ggg | gcc | acu | uac | ucc | auu | gaa | 8912 |
| Lys | Ala | Leu | Asp | Cys | Gln | Ile | Tyr | Gly | Ala | Thr | Tyr | Ser | Ile | Glu | |
| | 2845 | | | | 2850 | | | | 2855 | | | | | | |

| cca | cuu | gac | cua | ccu | cag | auc | auu | caa | cga | cuc | cau | ggu | cuu | agc | 8957 |
| Pro | Leu | Asp | Leu | Pro | Gln | Ile | Ile | Gln | Arg | Leu | His | Gly | Leu | Ser | |
| 2860 | | | | | 2865 | | | | | 2870 | | | | | |

| gca | uuc | uca | cuc | cau | agu | uac | ucu | cca | ggu | gaa | auc | aau | agg | gug | 9002 |
| Ala | Phe | Ser | Leu | His | Ser | Tyr | Ser | Pro | Gly | Glu | Ile | Asn | Arg | Val | |
| | 2875 | | | | 2880 | | | | 2885 | | | | | | |

| gcu | uca | ugc | cuc | agg | aaa | cuu | ggg | gua | ccg | ccc | uug | cga | guc | ugg | 9047 |
| Ala | Ser | Cys | Leu | Arg | Lys | Leu | Gly | Val | Pro | Pro | Leu | Arg | Val | Trp | |
| | 2890 | | | | 2895 | | | | 2900 | | | | | | |

| aga | cau | cgg | gcc | aga | agu | guc | cgc | gcu | aag | cua | cug | ucc | cag | ggg | 9092 |
| Arg | His | Arg | Ala | Arg | Ser | Val | Arg | Ala | Lys | Leu | Leu | Ser | Gln | Gly | |
| | 2905 | | | | 2910 | | | | 2915 | | | | | | |

| ggg | agg | gcu | gcc | acu | ugu | ggc | aag | uac | cuc | uuc | aac | ugg | gca | gua | 9137 |
| Gly | Arg | Ala | Ala | Thr | Cys | Gly | Lys | Tyr | Leu | Phe | Asn | Trp | Ala | Val | |
| | 2920 | | | | 2925 | | | | 2930 | | | | | | |

| agg | acc | aag | cuc | aaa | cuc | acu | cca | auc | ccg | gcu | gcg | ucc | cag | uug | 9182 |
| Arg | Thr | Lys | Leu | Lys | Leu | Thr | Pro | Ile | Pro | Ala | Ala | Ser | Gln | Leu | |
| | 2935 | | | | 2940 | | | | 2945 | | | | | | |

| gac | uug | ucc | ggc | ugg | uuc | auu | gcu | ggu | uac | agc | ggg | gga | gac | aua | 9227 |
| Asp | Leu | Ser | Gly | Trp | Phe | Ile | Ala | Gly | Tyr | Ser | Gly | Gly | Asp | Ile | |
| | 2950 | | | | 2955 | | | | 2960 | | | | | | |

| uau | cac | agc | cug | ucu | cgu | gcc | cga | ccc | cgc | ugg | uuu | aug | uug | ugc | 9272 |
| Tyr | His | Ser | Leu | Ser | Arg | Ala | Arg | Pro | Arg | Trp | Phe | Met | Leu | Cys | |
| | 2965 | | | | 2970 | | | | 2975 | | | | | | |

-continued

```
cua cuc cua cuu ucu gug ggg gua  ggc auc uac cug cuc ccc aau      9317
Leu Leu Leu Leu Ser Val Gly Val  Gly Ile Tyr Leu Leu Pro Asn
            2980            2985            2990 cga ugaacggggg gcuaaacacu ccaggccaau aggccauucu guuuuuuuu          9370
Arg uuuuuuuuuu uuuuuuuuuu uuuuuuuuuu uuuuuuuuuu uuuuuccuuu uuuuuuuuuu  9430 uuuuccuuu cuuuuggugg cuccaucuua gcccuaguca cggcuagcug ugaaaggucc   9490
gugagccgca ugacugcaga gagugcugau acuggccucu cugcagauca ugc         9543

<210> SEQ ID NO 96
<211> LENGTH: 2993
<212> TYPE: PRT
<213> ORGANISM: Artificial Sequence
<220> FEATURE:
<223> OTHER INFORMATION: Chimeric virus of Hepatitis C virus and GBV-B

<400> SEQUENCE: 96

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Gln Pro Glu Gly Arg Ala Trp Ala Gln Pro Gly
65                  70                  75                  80

Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Pro Phe Ser Ile
                165                 170                 175

Phe Leu Leu Ala Leu Leu Ser Cys Leu Thr Ile Pro Ala Ser Ala His
            180                 185                 190

Glu Val Arg Asn Val Ser Gly Leu Tyr His Val Thr Asn Asp Cys Ser
        195                 200                 205

Asn Ser Ser Ile Val Tyr Glu Ala Ala Asp Val Thr Asp Pro Asp Thr
    210                 215                 220

Asn Thr Thr Ile Leu Thr Asn Cys Cys Gln Arg Asn Gln Val Ile Tyr
225                 230                 235                 240

Cys Ser Pro Ser Thr Cys Leu His Glu Pro Gly Cys Val Ile Cys Ala
                245                 250                 255

Asp Glu Cys Trp Val Pro Ala Asn Pro Tyr Ile Ser His Pro Ser Asn
            260                 265                 270

Trp Thr Gly Thr Asp Ser Phe Leu Ala Asp His Ile Asp Phe Val Met
        275                 280                 285

Gly Ala Leu Val Thr Cys Asp Ala Leu Asp Ile Gly Glu Leu Cys Gly
    290                 295                 300
```

-continued

```
Ala Cys Val Leu Val Gly Asp Trp Leu Val Arg His Trp Leu Ile His
305                 310                 315                 320

Ile Asp Leu Asn Glu Thr Gly Thr Cys Tyr Leu Glu Val Pro Thr Gly
                325                 330                 335

Ile Asp Pro Gly Phe Leu Gly Phe Ile Gly Trp Met Ala Gly Lys Val
            340                 345                 350

Glu Ala Val Ile Phe Leu Thr Lys Leu Ala Ser Gln Val Pro Tyr Ala
        355                 360                 365

Ile Ala Thr Met Phe Ser Ser Val His Tyr Leu Ala Val Gly Ala Leu
370                 375                 380

Ile Tyr Tyr Ala Ser Arg Gly Lys Trp Tyr Gln Leu Leu Ala Leu
385                 390                 395                 400

Met Leu Tyr Ile Glu Ala Thr Ser Gly Asn Pro Ile Arg Val Pro Thr
                405                 410                 415

Gly Cys Ser Ile Ala Glu Phe Cys Ser Pro Leu Met Ile Pro Cys Pro
            420                 425                 430

Cys His Ser Tyr Leu Ser Glu Asn Val Ser Glu Val Ile Cys Tyr Ser
        435                 440                 445

Pro Lys Trp Thr Arg Pro Ile Thr Leu Glu Tyr Asn Asn Ser Ile Ser
450                 455                 460

Trp Tyr Pro Tyr Thr Ile Pro Gly Ala Arg Gly Cys Met Val Lys Phe
465                 470                 475                 480

Lys Asn Asn Thr Trp Gly Cys Cys Arg Ile Arg Asn Val Pro Ser Tyr
                485                 490                 495

Cys Thr Met Gly Thr Asp Ala Val Trp Asn Asp Thr Arg Asn Thr Tyr
            500                 505                 510

Glu Ala Cys Gly Val Thr Pro Trp Leu Thr Thr Ala Trp His Asn Gly
        515                 520                 525

Ser Ala Leu Lys Leu Ala Ile Leu Gln Tyr Pro Gly Ser Lys Glu Met
530                 535                 540

Phe Lys Pro His Asn Trp Met Ser Gly His Leu Tyr Phe Glu Gly Ser
545                 550                 555                 560

Asp Thr Pro Ile Val Tyr Phe Tyr Asp Pro Val Asn Ser Thr Leu Leu
                565                 570                 575

Pro Pro Glu Arg Trp Ala Arg Leu Pro Gly Thr Pro Val Val Arg
            580                 585                 590

Gly Ser Trp Leu Gln Val Pro Gln Gly Phe Tyr Ser Asp Val Lys Asp
        595                 600                 605

Leu Ala Thr Gly Leu Ile Thr Lys Asp Lys Ala Trp Lys Asn Tyr Gln
610                 615                 620

Val Leu Tyr Ser Ala Thr Gly Ala Leu Ser Leu Thr Gly Val Thr Thr
625                 630                 635                 640

Lys Ala Val Val Leu Ile Leu Leu Gly Leu Cys Gly Ser Lys Tyr Leu
                645                 650                 655

Ile Leu Ala Tyr Leu Cys Tyr Leu Ser Leu Cys Phe Gly Arg Ala Ser
            660                 665                 670

Gly Tyr Pro Leu Arg Pro Val Leu Pro Ser Gln Ser Tyr Leu Gln Ala
        675                 680                 685

Gly Trp Asp Val Leu Ser Lys Ala Gln Val Ala Pro Phe Ala Leu Ile
690                 695                 700

Phe Phe Ile Cys Cys Tyr Leu Arg Cys Arg Leu Arg Tyr Ala Ala Leu
705                 710                 715                 720

Leu Gly Phe Val Pro Met Ala Glu Ala Ala Leu Glu Asn Leu Val Ile
                725                 730                 735
```

```
Leu Asn Ala Ala Ser Val Ala Gly Ala His Gly Val Leu Ser Phe Leu
            740                 745                 750

Val Phe Phe Cys Ala Ala Trp Tyr Ile Lys Gly Lys Leu Val Pro Gly
            755                 760                 765

Ala Ala Tyr Ala Phe Tyr Gly Val Trp Pro Leu Leu Leu Leu Leu Leu
            770                 775                 780

Ser Leu Pro Pro Arg Ala Tyr Ala Leu Asp Arg Glu Met Ala Ala Ser
785                 790                 795                 800

Cys Gly Gly Ala Val Phe Val Gly Leu Met Leu Thr Leu Ser Pro
                805                 810                 815

His Tyr Lys Val Phe Leu Ala Arg Leu Ile Trp Trp Leu Gln Tyr Phe
            820                 825                 830

Ile Thr Arg Ala Glu Ala His Leu Gln Val Trp Val Pro Pro Leu Asn
            835                 840                 845

Val Arg Gly Gly Arg Asp Ala Ile Ile Leu Leu Thr Cys Val Val His
850                 855                 860

Pro Glu Leu Ile Phe Asp Ile Thr Lys Ile Leu Leu Ala Met Leu Gly
865                 870                 875                 880

Pro Leu Met Val Leu Gln Ala Gly Leu Thr Arg Val Pro Tyr Phe Val
            885                 890                 895

Arg Ala Gln Gly Leu Ile Arg Ala Cys Met Leu Val Arg Lys Val Ala
            900                 905                 910

Gly Gly His Tyr Val Gln Met Ala Leu Met Lys Leu Ala Ala Leu Thr
            915                 920                 925

Gly Thr Tyr Val Tyr Asp His Leu Thr Pro Leu Gln Asp Trp Ala His
            930                 935                 940

Ala Gly Leu Arg Asp Leu Ala Val Ala Val Glu Pro Val Phe Ser
945                 950                 955                 960

Asp Met Glu Thr Lys Val Ile Thr Trp Gly Ala Asp Thr Ala Ala Cys
                965                 970                 975

Gly Asp Ile Ile Ser Gly Leu Pro Val Ser Ala Arg Arg Gly Arg Glu
            980                 985                 990

Ile Leu Leu Gly Pro Ala Asp Arg Phe Gly Glu Gln Gly Trp Arg Leu
            995                 1000                1005

Leu Ala Pro Ile Thr Ala Tyr Ala Gln Gln Thr Arg Gly Leu Leu
    1010                1015                1020

Gly Cys Ile Ile Thr Ser Leu Thr Gly Arg Asp Lys Asn Gln Val
    1025                1030                1035

Glu Gly Glu Val Gln Val Val Ser Thr Ala Thr Gln Ser Phe Leu
    1040                1045                1050

Ala Thr Cys Val Asn Gly Val Cys Trp Thr Val Tyr His Gly Ala
    1055                1060                1065

Gly Ser Lys Thr Leu Ala Gly Pro Lys Gly Pro Ile Thr Gln Met
    1070                1075                1080

Tyr Thr Asn Val Asp Gln Asp Leu Val Gly Trp Pro Ala Pro Pro
    1085                1090                1095

Gly Ala Arg Ser Leu Thr Pro Cys Thr Cys Gly Ser Ser Asp Leu
    1100                1105                1110

Tyr Leu Val Thr Arg His Ala Asp Val Ile Pro Val Arg Arg Arg
    1115                1120                1125

Gly Asp Ser Arg Gly Ser Leu Leu Ser Pro Arg Pro Ile Ser Tyr
    1130                1135                1140

Leu Lys Gly Ser Ser Gly Gly Pro Leu Leu Cys Pro Leu Gly His
```

```
                1145                1150                1155

Ala Val Gly Ile Phe Arg Ala Val Cys Thr Arg Gly Val Ala
    1160            1165                1170

Lys Ala Val Asp Phe Val Pro Val Glu Ser Met Glu Thr Thr Met
    1175            1180                1185

Arg Ser Pro Val Phe Thr Asp Asn Ser Ser Pro Ala Val Pro
    1190            1195                1200

Gln Thr Phe Gln Val Ala His Leu His Ala Pro Thr Gly Ser Gly
    1205            1210                1215

Lys Ser Thr Lys Val Pro Ala Ala Tyr Ala Ala Gln Gly Tyr Lys
    1220            1225                1230

Val Leu Val Leu Asn Pro Ser Val Ala Ala Thr Leu Gly Phe Gly
    1235            1240                1245

Ala Tyr Met Ser Lys Ala His Gly Val Glu Pro Asn Ile Arg Thr
    1250            1255                1260

Gly Val Arg Thr Ile Thr Thr Gly Ala Ser Ile Thr Tyr Ser Thr
    1265            1270                1275

Tyr Gly Lys Phe Leu Ala Asp Gly Gly Cys Ser Gly Gly Ala Tyr
    1280            1285                1290

Asp Ile Ile Ile Cys Asp Glu Cys His Ser Thr Asp Ser Thr Ser
    1295            1300                1305

Ile Leu Gly Ile Gly Thr Val Leu Asp Gln Ala Glu Thr Ala Gly
    1310            1315                1320

Ala Arg Leu Val Val Leu Ala Thr Ala Thr Pro Pro Gly Ser Val
    1325            1330                1335

Thr Val Pro His Pro Asn Ile Glu Glu Val Ala Leu Pro Ser Thr
    1340            1345                1350

Gly Glu Ile Pro Phe Tyr Gly Lys Ala Ile Pro Ile Glu Thr Ile
    1355            1360                1365

Lys Gly Gly Arg His Leu Ile Phe Cys His Ser Lys Lys Lys Cys
    1370            1375                1380

Asp Glu Leu Ala Ala Lys Leu Val Gly Leu Gly Val Asn Ala Val
    1385            1390                1395

Ala Tyr Tyr Arg Gly Leu Asp Val Ser Val Ile Pro Thr Ser Gly
    1400            1405                1410

Asp Val Val Val Ala Thr Asp Ala Leu Met Thr Gly Phe Thr
    1415            1420                1425

Gly Asp Phe Asp Ser Val Ile Asp Cys Asn Thr Cys Val Thr Gln
    1430            1435                1440

Thr Val Asp Phe Ser Leu Asp Pro Thr Phe Thr Ile Glu Thr Thr
    1445            1450                1455

Thr Val Pro Gln Asp Ala Val Ser Arg Ser Gln Arg Arg Gly Arg
    1460            1465                1470

Thr Gly Arg Gly Arg Met Gly Ile Tyr Arg Phe Val Ala Pro Gly
    1475            1480                1485

Glu Arg Pro Ser Gly Met Phe Asp Ser Ser Val Leu Cys Glu Cys
    1490            1495                1500

Tyr Asp Ala Gly Cys Ala Trp Tyr Glu Leu Thr Pro Ala Glu Thr
    1505            1510                1515

Ser Val Arg Leu Arg Ala Tyr Leu Asn Thr Pro Gly Leu Pro Val
    1520            1525                1530

Cys Gln Asp His Leu Glu Phe Trp Glu Gly Val Phe Thr Gly Leu
    1535            1540                1545
```

```
Thr His Ile Asp Ala His Phe Leu Ser Gln Thr Lys Gln Ala Gly
1550                1555                1560

Asp Asn Phe Pro Tyr Leu Val Ala Tyr Gln Ala Thr Val Cys Ala
1565                1570                1575

Arg Ala Gln Ala Pro Pro Ser Trp Asp Gln Met Trp Lys Cys
1580                1585                1590

Leu Ile Arg Leu Lys Pro Thr Leu His Gly Pro Thr Pro Leu Leu
1595                1600                1605

Tyr Arg Leu Gly Ala Val Gln Asn Glu Val Ile Leu Thr His Pro
1610                1615                1620

Ile Thr Lys Tyr Ile Met Ala Cys Met Ser Ala Asp Leu Glu Val
1625                1630                1635

Val Thr Ser Thr Trp Val Leu Val Gly Gly Val Leu Ala Ala Leu
1640                1645                1650

Ala Ala Tyr Cys Leu Thr Thr Gly Ser Val Val Ile Val Gly Arg
1655                1660                1665

Ile Ile Leu Ser Gly Lys Pro Ala Ile Ile Pro Asp Arg Glu Val
1670                1675                1680

Leu Tyr Arg Glu Phe Asp Glu Met Glu Glu Cys Ala Ser His Leu
1685                1690                1695

Pro Tyr Ile Glu Gln Gly Met Gln Leu Ala Glu Gln Phe Lys Gln
1700                1705                1710

Lys Ala Leu Gly Leu Leu Gln Thr Ala Thr Lys Gln Ala Glu Ala
1715                1720                1725

Ala Ala Pro Val Val Glu Ser Lys Trp Arg Ala Leu Glu Ala Phe
1730                1735                1740

Trp Ala Lys His Met Trp Asn Phe Ile Ser Gly Ile Gln Tyr Leu
1745                1750                1755

Ala Gly Leu Ser Thr Leu Pro Gly Asn Pro Ala Ile Ala Ser Leu
1760                1765                1770

Met Ala Phe Thr Ala Ser Ile Thr Ser Pro Leu Thr Thr Leu His
1775                1780                1785

Thr Leu Leu Phe Asn Ile Leu Gly Gly Trp Val Ala Ala Gln Leu
1790                1795                1800

Ala Pro Pro Gly Ala Ala Ser Ala Phe Val Gly Ala Gly Ile Ala
1805                1810                1815

Gly Ala Ala Val Gly Ser Ile Gly Leu Gly Lys Val Leu Val Asp
1820                1825                1830

Ile Leu Ala Gly Tyr Gly Ala Gly Val Ala Gly Ala Leu Val Ala
1835                1840                1845

Phe Lys Val Met Ser Gly Glu Met Pro Ser Thr Glu Asp Leu Val
1850                1855                1860

Asn Leu Leu Pro Ala Ile Leu Ser Pro Gly Ala Leu Val Val Gly
1865                1870                1875

Val Val Cys Ala Ala Ile Leu Arg Arg His Val Gly Pro Gly Glu
1880                1885                1890

Gly Ala Val Gln Trp Met Asn Arg Leu Ile Ala Phe Ala Ser Arg
1895                1900                1905

Gly Asn His Val Ser Pro Thr His Tyr Val Pro Glu Ser Asp Ala
1910                1915                1920

Ala Ala Arg Val Thr Gln Ile Leu Ser Ser Leu Thr Ile Thr Gln
1925                1930                1935

Leu Leu Lys Arg Leu His Gln Trp Ile Asn Lys Asp Cys Ser Thr
1940                1945                1950
```

-continued

```
Pro Cys Ser Gly Ser Trp Leu Arg Asp Val Trp Asp Trp Ile Cys
    1955                1960                1965
Thr Val Leu Ser Asp Phe Lys Thr Trp Leu Gln Ser Lys Leu Leu
    1970                1975                1980
Pro Arg Leu Pro Gly Val Pro Phe Leu Ser Cys Gln Arg Gly Tyr
    1985                1990                1995
Lys Gly Val Trp Arg Gly Asp Gly Ile Met Gln Thr Ser Cys Pro
    2000                2005                2010
Cys Gly Ala Gln Ile Ala Gly His Val Lys Asn Gly Ser Met Arg
    2015                2020                2025
Ile Val Gly Pro Lys Thr Cys Ser Asn Thr Trp His Gly Thr Phe
    2030                2035                2040
Pro Ile Asn Ala His Thr Thr Gly Pro Cys Thr Pro Ser Pro Ala
    2045                2050                2055
Pro Asn Tyr Ser Lys Ala Leu Trp Arg Val Ala Ala Glu Glu Tyr
    2060                2065                2070
Val Glu Val Thr Arg Val Gly Asp Phe His Tyr Val Thr Gly Met
    2075                2080                2085
Thr Thr Asp Asn Val Lys Cys Pro Cys Gln Val Pro Ala Pro Glu
    2090                2095                2100
Phe Phe Thr Glu Val Asp Gly Val Arg Leu His Arg Tyr Ala Pro
    2105                2110                2115
Ala Cys Lys Pro Leu Leu Arg Asp Glu Val Thr Phe Gln Val Gly
    2120                2125                2130
Leu Asn Gln Phe Pro Val Gly Ser Gln Leu Pro Cys Glu Pro Glu
    2135                2140                2145
Pro Asp Val Ser Val Leu Thr Ser Met Leu Thr Asp Pro Ser His
    2150                2155                2160
Ile Thr Ala Glu Thr Ala Lys Arg Arg Leu Ala Arg Gly Ser Ser
    2165                2170                2175
Pro Ser Leu Ala Ser Ser Ser Ala Ser Gln Leu Ser Ala Pro Ser
    2180                2185                2190
Leu Lys Ala Thr Cys Thr Thr His His Asp Ser Pro Asp Ala Asp
    2195                2200                2205
Leu Ile Glu Ala Asn Leu Leu Trp Arg Gln Glu Met Gly Gly Asn
    2210                2215                2220
Ile Thr Arg Val Glu Ser Glu Asn Lys Val Val Ile Leu Asp Ser
    2225                2230                2235
Phe Asp Pro Leu Arg Ala Glu Glu Asp Glu Arg Glu Val Ser Val
    2240                2245                2250
Ala Ala Glu Ile Leu Arg Lys Thr Arg Lys Phe Pro Pro Ala Met
    2255                2260                2265
Pro Ile Trp Ala Arg Pro Asp Tyr Asn Pro Pro Leu Leu Glu Thr
    2270                2275                2280
Trp Lys Asp Pro Asp Tyr Val Pro Pro Val Val His Gly Cys Pro
    2285                2290                2295
Leu Pro Pro Thr Lys Thr Pro Pro Ile Pro Pro Pro Arg Arg Lys
    2300                2305                2310
Lys Thr Val Val Leu Thr Glu Ser Thr Val Ser Ser Ala Leu Ala
    2315                2320                2325
Glu Leu Ala Thr Lys Thr Phe Gly Ser Ser Gly Ser Ser Ala Val
    2330                2335                2340
Asp Ser Gly Thr Ala Thr Ala Pro Pro Asn Gln Leu Ser Asp Glu
```

|  |  |  | 2345 |  |  |  | 2350 |  |  |  | 2355 |  |  |
|---|---|---|---|---|---|---|---|---|---|---|---|---|---|
| Val | Asp | Thr | Gly | Ser | Asp | Val | Glu | Ser | Tyr | Ser | Ser | Met | Pro | Pro |
|  |  | 2360 |  |  |  |  | 2365 |  |  |  |  | 2370 |  |  |
| Leu | Glu | Gly | Glu | Pro | Gly | Asp | Pro | Asp | Leu | Ser | Asp | Gly | Ser | Trp |
|  |  | 2375 |  |  |  |  | 2380 |  |  |  |  | 2385 |  |  |
| Ser | Thr | Val | Ser | Glu | Glu | Ala | Gly | Glu | Asp | Val | Val | Cys | Cys | Ser |
|  |  | 2390 |  |  |  |  | 2395 |  |  |  |  | 2400 |  |  |
| Met | Ser | Tyr | Thr | Trp | Thr | Gly | Ala | Leu | Ile | Thr | Pro | Cys | Ala | Ala |
|  |  | 2405 |  |  |  |  | 2410 |  |  |  |  | 2415 |  |  |
| Glu | Glu | Ser | Lys | Leu | Pro | Ile | Asn | Ala | Leu | Ser | Asn | Ser | Leu | Leu |
|  |  | 2420 |  |  |  |  | 2425 |  |  |  |  | 2430 |  |  |
| Arg | His | His | Asn | Met | Val | Tyr | Ala | Thr | Thr | Ser | Arg | Ser | Ala | Ser |
|  |  | 2435 |  |  |  |  | 2440 |  |  |  |  | 2445 |  |  |
| Gln | Arg | Gln | Lys | Lys | Val | Thr | Phe | Asp | Arg | Leu | Gln | Val | Leu | Asp |
|  |  | 2450 |  |  |  |  | 2455 |  |  |  |  | 2460 |  |  |
| Asp | His | Tyr | Arg | Asp | Val | Leu | Lys | Glu | Met | Lys | Ala | Lys | Ala | Ser |
|  |  | 2465 |  |  |  |  | 2470 |  |  |  |  | 2475 |  |  |
| Thr | Val | Lys | Ala | Lys | Leu | Leu | Ser | Val | Glu | Glu | Ala | Cys | Lys | Leu |
|  |  | 2480 |  |  |  |  | 2485 |  |  |  |  | 2490 |  |  |
| Thr | Pro | Pro | His | Ser | Ala | Arg | Ser | Lys | Phe | Gly | Tyr | Gly | Ala | Lys |
|  |  | 2495 |  |  |  |  | 2500 |  |  |  |  | 2505 |  |  |
| Asp | Val | Arg | Asn | Leu | Ser | Ser | Lys | Ala | Val | Asn | His | Ile | Asn | Ser |
|  |  | 2510 |  |  |  |  | 2515 |  |  |  |  | 2520 |  |  |
| Val | Trp | Lys | Asp | Leu | Leu | Glu | Asp | Thr | Glu | Thr | Pro | Ile | Asp | Thr |
|  |  | 2525 |  |  |  |  | 2530 |  |  |  |  | 2535 |  |  |
| Thr | Ile | Met | Ala | Lys | Asn | Glu | Val | Phe | Cys | Val | Gln | Pro | Glu | Lys |
|  |  | 2540 |  |  |  |  | 2545 |  |  |  |  | 2550 |  |  |
| Gly | Gly | Arg | Lys | Pro | Ala | Arg | Leu | Ile | Val | Tyr | Pro | Asp | Leu | Gly |
|  |  | 2555 |  |  |  |  | 2560 |  |  |  |  | 2565 |  |  |
| Val | Arg | Val | Cys | Glu | Lys | Met | Ala | Leu | Tyr | Asp | Val | Val | Ser | Thr |
|  |  | 2570 |  |  |  |  | 2575 |  |  |  |  | 2580 |  |  |
| Leu | Pro | Gln | Ala | Val | Met | Gly | Ser | Ser | Tyr | Gly | Phe | Gln | Tyr | Ser |
|  |  | 2585 |  |  |  |  | 2590 |  |  |  |  | 2595 |  |  |
| Pro | Gly | Gln | Arg | Val | Glu | Phe | Leu | Val | Asn | Ala | Trp | Lys | Ser | Lys |
|  |  | 2600 |  |  |  |  | 2605 |  |  |  |  | 2610 |  |  |
| Lys | Asn | Pro | Met | Gly | Phe | Ala | Tyr | Asp | Thr | Arg | Cys | Phe | Asp | Ser |
|  |  | 2615 |  |  |  |  | 2620 |  |  |  |  | 2625 |  |  |
| Thr | Val | Thr | Glu | Asn | Asp | Ile | Arg | Val | Glu | Glu | Ser | Ile | Tyr | Gln |
|  |  | 2630 |  |  |  |  | 2635 |  |  |  |  | 2640 |  |  |
| Cys | Cys | Asp | Leu | Ala | Pro | Glu | Ala | Arg | Gln | Val | Ile | Arg | Ser | Leu |
|  |  | 2645 |  |  |  |  | 2650 |  |  |  |  | 2655 |  |  |
| Thr | Glu | Arg | Leu | Tyr | Val | Gly | Gly | Pro | Leu | Thr | Asn | Ser | Lys | Gly |
|  |  | 2660 |  |  |  |  | 2665 |  |  |  |  | 2670 |  |  |
| Gln | Asn | Cys | Gly | Tyr | Arg | Arg | Cys | Arg | Ala | Ser | Gly | Val | Leu | Thr |
|  |  | 2675 |  |  |  |  | 2680 |  |  |  |  | 2685 |  |  |
| Thr | Ser | Cys | Gly | Asn | Thr | Leu | Thr | Cys | Tyr | Leu | Lys | Ala | Ser | Ala |
|  |  | 2690 |  |  |  |  | 2695 |  |  |  |  | 2700 |  |  |
| Ala | Cys | Arg | Ala | Ala | Lys | Leu | Gln | Asp | Cys | Thr | Met | Leu | Val | Cys |
|  |  | 2705 |  |  |  |  | 2710 |  |  |  |  | 2715 |  |  |
| Gly | Asp | Asp | Leu | Val | Val | Ile | Cys | Glu | Ser | Ala | Gly | Thr | Gln | Glu |
|  |  | 2720 |  |  |  |  | 2725 |  |  |  |  | 2730 |  |  |
| Asp | Ala | Ala | Ser | Leu | Arg | Val | Phe | Thr | Glu | Ala | Met | Thr | Arg | Tyr |
|  |  | 2735 |  |  |  |  | 2740 |  |  |  |  | 2745 |  |  |

```
Ser Ala  Pro Pro Gly Asp Pro  Pro Arg Pro Glu Tyr  Asp Leu Glu
    2750                 2755                 2760

Leu Ile  Thr Ser Cys Ser Ser  Asn Val Ser Val Ala  His Asp Ala
    2765                 2770                 2775

Ser Gly  Lys Arg Val Tyr Tyr  Leu Thr Arg Asp Pro  Thr Thr Pro
    2780                 2785                 2790

Leu Ala  Arg Ala Ala Trp Glu  Thr Ala Lys His Thr  Pro Val Asn
    2795                 2800                 2805

Ser Trp  Leu Gly Asn Ile Ile  Met Tyr Ala Pro Thr  Leu Trp Ala
    2810                 2815                 2820

Arg Met  Ile Leu Met Thr His  Phe Phe Ser Ile Leu  Leu Ala Gln
    2825                 2830                 2835

Glu Gln  Leu Glu Lys Ala Leu  Asp Cys Gln Ile Tyr  Gly Ala Thr
    2840                 2845                 2850

Tyr Ser  Ile Glu Pro Leu Asp  Leu Pro Gln Ile Ile  Gln Arg Leu
    2855                 2860                 2865

His Gly  Leu Ser Ala Phe Ser  Leu His Ser Tyr Ser  Pro Gly Glu
    2870                 2875                 2880

Ile Asn  Arg Val Ala Ser Cys  Leu Arg Lys Leu Gly  Val Pro Pro
    2885                 2890                 2895

Leu Arg  Val Trp Arg His Arg  Ala Arg Ser Val Arg  Ala Lys Leu
    2900                 2905                 2910

Leu Ser  Gln Gly Gly Arg Ala  Ala Thr Cys Gly Lys  Tyr Leu Phe
    2915                 2920                 2925

Asn Trp  Ala Val Arg Thr Lys  Leu Lys Leu Thr Pro  Ile Pro Ala
    2930                 2935                 2940

Ala Ser  Gln Leu Asp Leu Ser  Gly Trp Phe Ile Ala  Gly Tyr Ser
    2945                 2950                 2955

Gly Gly  Asp Ile Tyr His Ser  Leu Ser Arg Ala Arg  Pro Arg Trp
    2960                 2965                 2970

Phe Met  Leu Cys Leu Leu Leu  Leu Ser Val Gly Val  Gly Ile Tyr
    2975                 2980                 2985

Leu Leu  Pro Asn Arg
    2990
```

```
<210> SEQ ID NO 97
<211> LENGTH: 9363
<212> TYPE: RNA
<213> ORGANISM: Artificial Sequence
<220> FEATURE:
<223> OTHER INFORMATION: Chimeric virus of Hepatitis C virus and GBV-B
<220> FEATURE:
<221> NAME/KEY: CDS
<222> LOCATION: (342)..(9140)

<400> SEQUENCE: 97
gccagccccc ugaugggggc gacacuccac cauagaucac uccccuguga ggaacuacug      60
ucuucacgca gaaagcgucu agccauggcg uuaguaugag ugucgugcag ccuccaggac     120
ccccccuccc gggagagcca uagugggucug cggaaccggu gaguacaccg gaauugccag    180
gacgaccggg uccuuucuug gaucaacccg cucaaugccu ggagauuugg gcgugccccc     240
gcgagacugc uagccgagua guguuggguc gcgaaaggcc uugugguacu gccugauagg     300
gugcuugcga gugccccggg aggucucgua gaccgugcau c aug ccu guu auu ucu    356
                                              Met Pro Val Ile Ser
                                              1               5 acu caa aca agu ccu gua ccu gcg ccc aga acg cgc aag aac aag cag     404
Thr Gln Thr Ser Pro Val Pro Ala Pro Arg Thr Arg Lys Asn Lys Gln
```

```
                       10                  15                  20
acg cag gcu uca uau ccu gug ucc auu aaa aca ucu guu gaa agg gga        452
Thr Gln Ala Ser Tyr Pro Val Ser Ile Lys Thr Ser Val Glu Arg Gly
             25                  30                  35 caa cga gca aag cgc aaa guc cag cgc gau gcu cgg ccu cgu aau uac        500
Gln Arg Ala Lys Arg Lys Val Gln Arg Asp Ala Arg Pro Arg Asn Tyr
         40                  45                  50 aaa auu gcu ggu auc cau gau ggc uug cag aca uug gcu cag gcu gcu        548
Lys Ile Ala Gly Ile His Asp Gly Leu Gln Thr Leu Ala Gln Ala Ala
     55                  60                  65 uug cca gcu cau ggu ugg gga cgc caa gac ccu cgc cau aag ucu cgc        596
Leu Pro Ala His Gly Trp Gly Arg Gln Asp Pro Arg His Lys Ser Arg
70                  75                  80                  85 aau cuu gga auc cuu cug gau uac ccu uug ggg ugg auu ggu gau guu        644
Asn Leu Gly Ile Leu Leu Asp Tyr Pro Leu Gly Trp Ile Gly Asp Val
                 90                  95                 100 aca acu cac aca ccu cua gua ggc ccg cug gug gca gga gcg guc guu        692
Thr Thr His Thr Pro Leu Val Gly Pro Leu Val Ala Gly Ala Val Val
             105                 110                 115 cga cca guc ugc cag aua gua cgc uug cug gag gau gga guc aac ugg        740
Arg Pro Val Cys Gln Ile Val Arg Leu Leu Glu Asp Gly Val Asn Trp
         120                 125                 130 gcu acu ggu ugg uuc ggu guc cac cuu uuu gug gua ugu cug cua ucu        788
Ala Thr Gly Trp Phe Gly Val His Leu Phe Val Val Cys Leu Leu Ser
     135                 140                 145 uug gcc ugu ccc ugu agu ggg gcg cgg guc acu gac cca gac aca aau        836
Leu Ala Cys Pro Cys Ser Gly Ala Arg Val Thr Asp Pro Asp Thr Asn
150                 155                 160                 165 acc aca auc cug acc aau ugc ugc cag cgu aau cag guu auc uau ugu        884
Thr Thr Ile Leu Thr Asn Cys Cys Gln Arg Asn Gln Val Ile Tyr Cys
                 170                 175                 180 ucu ccu ucc acu ugc cua cac gag ccu ggu ugu gug auc ugu gcg gac        932
Ser Pro Ser Thr Cys Leu His Glu Pro Gly Cys Val Ile Cys Ala Asp
             185                 190                 195 gag ugc ugg guu ccc gcc aau ccg uac auc uca cac ccu ucc aau ugg        980
Glu Cys Trp Val Pro Ala Asn Pro Tyr Ile Ser His Pro Ser Asn Trp
         200                 205                 210 acu ggc acg gac ucc uuc uug gcu gac cac auu gau uuu guu aug ggc       1028
Thr Gly Thr Asp Ser Phe Leu Ala Asp His Ile Asp Phe Val Met Gly
     215                 220                 225 gcu cuu gug acc ugu gac gcc cuu gac auu ggu gag uug ugu ggu gcg       1076
Ala Leu Val Thr Cys Asp Ala Leu Asp Ile Gly Glu Leu Cys Gly Ala
230                 235                 240                 245 ugu gua uua guc ggu gac ugg cuu guc agg cac ugg cuu auu cac aua       1124
Cys Val Leu Val Gly Asp Trp Leu Val Arg His Trp Leu Ile His Ile
                 250                 255                 260 gac cuc aau gaa acu ggu acu ugu uac cug gaa gug ccc acu gga aua       1172
Asp Leu Asn Glu Thr Gly Thr Cys Tyr Leu Glu Val Pro Thr Gly Ile
             265                 270                 275 gau ccu ggg uuc cua ggg uuu auc ggg ugg aug gcc ggc aag guc gag       1220
Asp Pro Gly Phe Leu Gly Phe Ile Gly Trp Met Ala Gly Lys Val Glu
         280                 285                 290 gcu guc auc uuc uug acc aaa cug gcu uca caa gua cca uac gcu auu       1268
Ala Val Ile Phe Leu Thr Lys Leu Ala Ser Gln Val Pro Tyr Ala Ile
     295                 300                 305 gcg acu aug uuu agc agu gua cac uac cug gcg guu ggc gcu cug auc       1316
Ala Thr Met Phe Ser Ser Val His Tyr Leu Ala Val Gly Ala Leu Ile
310                 315                 320                 325 uac uau gcc ucu cgg ggc aag ugg uau cag uug cuc cua gcg cuu aug       1364
Tyr Tyr Ala Ser Arg Gly Lys Trp Tyr Gln Leu Leu Leu Ala Leu Met
```

```
              330                 335                 340
cuu uac aua gaa gcg acc ucu gga aac ccc auc agg gug ccc acu gga    1412
Leu Tyr Ile Glu Ala Thr Ser Gly Asn Pro Ile Arg Val Pro Thr Gly
            345                 350                 355 ugc uca aua gcu gag uuu ugc ucg ccu uug aug aua cca ugu ccu ugc    1460
Cys Ser Ile Ala Glu Phe Cys Ser Pro Leu Met Ile Pro Cys Pro Cys
        360                 365                 370 cac ucu uau uug agu gag aau gug uca gaa guc auu ugu uac agu cca    1508
His Ser Tyr Leu Ser Glu Asn Val Ser Glu Val Ile Cys Tyr Ser Pro
    375                 380                 385 aag ugg acc agg ccu auc acu cua gag uau aac aac ucc aua ucu ugg    1556
Lys Trp Thr Arg Pro Ile Thr Leu Glu Tyr Asn Asn Ser Ile Ser Trp
390                 395                 400                 405 uac ccc uau aca auc ccu ggu gcg agg gga ugu aug guu aaa uuc aaa    1604
Tyr Pro Tyr Thr Ile Pro Gly Ala Arg Gly Cys Met Val Lys Phe Lys
                410                 415                 420 aau aac aca ugg ggu ugc ugc cgu auu cgc aau gug cca ucg uac ugc    1652
Asn Asn Thr Trp Gly Cys Cys Arg Ile Arg Asn Val Pro Ser Tyr Cys
            425                 430                 435 acu aug ggc acu gau gca gug ugg aac gac acu cgc aac acu uac gaa    1700
Thr Met Gly Thr Asp Ala Val Trp Asn Asp Thr Arg Asn Thr Tyr Glu
        440                 445                 450 gca ugc ggu gua aca cca ugg cua aca acc gca ugg cac aac ggc uca    1748
Ala Cys Gly Val Thr Pro Trp Leu Thr Thr Ala Trp His Asn Gly Ser
    455                 460                 465 gcc cug aaa uug gcu aua uua caa uac ccu ggg ucu aaa gaa aug uuu    1796
Ala Leu Lys Leu Ala Ile Leu Gln Tyr Pro Gly Ser Lys Glu Met Phe
470                 475                 480                 485 aaa ccu cau aau ugg aug uca ggc cau uug uau uuu gag gga uca gau    1844
Lys Pro His Asn Trp Met Ser Gly His Leu Tyr Phe Glu Gly Ser Asp
                490                 495                 500 acc cuu aua guu uac uuu uau gac ccu gug aau ucc acu cuc cua cca    1892
Thr Pro Ile Val Tyr Phe Tyr Asp Pro Val Asn Ser Thr Leu Leu Pro
            505                 510                 515 ccg gag agg ugg gcu agg uug ccc ggu acc cca ccu gug gua cgu ggu    1940
Pro Glu Arg Trp Ala Arg Leu Pro Gly Thr Pro Pro Val Val Arg Gly
        520                 525                 530 ucu ugg uua cag guu ccg caa ggg uuu uac agu gau gug aaa gac cua    1988
Ser Trp Leu Gln Val Pro Gln Gly Phe Tyr Ser Asp Val Lys Asp Leu
    535                 540                 545 gcc aca gga uug auc acc aaa gac aaa gcc ugg aaa aau uau cag guc    2036
Ala Thr Gly Leu Ile Thr Lys Asp Lys Ala Trp Lys Asn Tyr Gln Val
550                 555                 560                 565 uua uau ucc gcc acg ggu gcu uug ucu cuu acg gga guu acc acc aag    2084
Leu Tyr Ser Ala Thr Gly Ala Leu Ser Leu Thr Gly Val Thr Thr Lys
                570                 575                 580 gcc gug gug cua auu cug uug ggg uug ugu ggc agc aag uau cuu auu    2132
Ala Val Val Leu Ile Leu Leu Gly Leu Cys Gly Ser Lys Tyr Leu Ile
            585                 590                 595 uua gcc uac cuc ugu uac uug ucc cuu ugu uuu ggg cgc gcu ucu ggu    2180
Leu Ala Tyr Leu Cys Tyr Leu Ser Leu Cys Phe Gly Arg Ala Ser Gly
        600                 605                 610 uac ccu uug cgu ccu gug cuc cca ucc cag ucg uau cuc caa gcu ggc    2228
Tyr Pro Leu Arg Pro Val Leu Pro Ser Gln Ser Tyr Leu Gln Ala Gly
    615                 620                 625 ugg gau guu uug ucu aaa gcu caa gua gcc ccu uuu gcu uug auu uuc    2276
Trp Asp Val Leu Ser Lys Ala Gln Val Ala Pro Phe Ala Leu Ile Phe
630                 635                 640                 645 uuc auc ugu ugc uau cuc cgc ugc agg cua cgu uau gcu gcc cuu uua    2324
Phe Ile Cys Cys Tyr Leu Arg Cys Arg Leu Arg Tyr Ala Ala Leu Leu
```

-continued

|  |  |  |  |  |  |  |  |  |  |  |  |  |  |  |  |
|---|---|---|---|---|---|---|---|---|---|---|---|---|---|---|---|
|  |  |  |  | 650 |  |  |  | 655 |  |  |  | 660 |  |  |  |
| ggg | uuu | gug | ccc | aug | gcu | gag | gcc | gcc | uua | gag | aac | cug | gug | auc | cuc | 2372 |
| Gly | Phe | Val | Pro | Met | Ala | Glu | Ala | Ala | Leu | Glu | Asn | Leu | Val | Ile | Leu |
|  |  |  |  | 665 |  |  |  | 670 |  |  |  | 675 |  |  |  |
| aau | gcg | gcg | ucu | gug | gcc | gga | gcg | cau | ggc | guu | cuc | ucu | uuc | cuu | gug | 2420 |
| Asn | Ala | Ala | Ser | Val | Ala | Gly | Ala | His | Gly | Val | Leu | Ser | Phe | Leu | Val |
|  |  | 680 |  |  |  |  | 685 |  |  |  |  | 690 |  |  |  |
| uuc | uuc | ugc | gcu | gcc | ugg | uac | auc | aag | ggc | aag | cug | guc | ccc | ggg | gcg | 2468 |
| Phe | Phe | Cys | Ala | Ala | Trp | Tyr | Ile | Lys | Gly | Lys | Leu | Val | Pro | Gly | Ala |
|  | 695 |  |  |  |  | 700 |  |  |  |  | 705 |  |  |  |  |
| gca | uau | gcc | uuc | uau | ggu | gua | ugg | ccg | cug | cuc | cug | cuu | cug | cug | uca | 2516 |
| Ala | Tyr | Ala | Phe | Tyr | Gly | Val | Trp | Pro | Leu | Leu | Leu | Leu | Leu | Leu | Ser |
| 710 |  |  |  |  | 715 |  |  |  |  | 720 |  |  |  |  | 725 |
| uua | cca | cca | cga | gca | uac | gcc | uug | gac | cgg | gag | aug | gcu | gca | ucg | ugc | 2564 |
| Leu | Pro | Pro | Arg | Ala | Tyr | Ala | Leu | Asp | Arg | Glu | Met | Ala | Ala | Ser | Cys |
|  |  |  |  | 730 |  |  |  |  | 735 |  |  |  |  | 740 |  |
| gga | ggc | gcg | guu | uuc | gua | ggu | cug | aug | cuc | cug | acc | uug | uca | cca | cac | 2612 |
| Gly | Gly | Ala | Val | Phe | Val | Gly | Leu | Met | Leu | Leu | Thr | Leu | Ser | Pro | His |
|  |  |  | 745 |  |  |  |  | 750 |  |  |  |  | 755 |  |  |
| uac | aag | gug | uuu | cuc | gcu | agg | cuc | aua | ugg | ugg | uua | cag | uau | uuu | auc | 2660 |
| Tyr | Lys | Val | Phe | Leu | Ala | Arg | Leu | Ile | Trp | Trp | Leu | Gln | Tyr | Phe | Ile |
|  |  | 760 |  |  |  |  | 765 |  |  |  |  | 770 |  |  |  |
| acc | agg | gcc | gag | gcg | cac | uug | cag | gug | ugg | guc | ccc | ccc | cuc | aac | guu | 2708 |
| Thr | Arg | Ala | Glu | Ala | His | Leu | Gln | Val | Trp | Val | Pro | Pro | Leu | Asn | Val |
|  | 775 |  |  |  |  | 780 |  |  |  |  | 785 |  |  |  |  |
| cgg | ggg | ggc | cgc | gau | gcc | auc | auc | cuc | cuc | acg | ugu | gug | guc | cac | cca | 2756 |
| Arg | Gly | Gly | Arg | Asp | Ala | Ile | Ile | Leu | Leu | Thr | Cys | Val | Val | His | Pro |
| 790 |  |  |  |  | 795 |  |  |  |  | 800 |  |  |  |  | 805 |
| gag | cua | auu | uuu | gac | auc | acc | aaa | auc | uug | cuc | gcc | aug | cuc | ggu | ccg | 2804 |
| Glu | Leu | Ile | Phe | Asp | Ile | Thr | Lys | Ile | Leu | Leu | Ala | Met | Leu | Gly | Pro |
|  |  |  |  | 810 |  |  |  |  | 815 |  |  |  |  | 820 |  |
| cuc | aug | gug | cuc | cag | gcu | ggc | cua | acu | aga | gug | ccg | uac | uuc | gua | cgc | 2852 |
| Leu | Met | Val | Leu | Gln | Ala | Gly | Leu | Thr | Arg | Val | Pro | Tyr | Phe | Val | Arg |
|  |  |  | 825 |  |  |  |  | 830 |  |  |  |  | 835 |  |  |
| gcu | caa | ggg | cuc | auc | cgu | gca | ugc | aug | uua | gug | cgg | aaa | guc | gcu | ggg | 2900 |
| Ala | Gln | Gly | Leu | Ile | Arg | Ala | Cys | Met | Leu | Val | Arg | Lys | Val | Ala | Gly |
|  |  | 840 |  |  |  |  | 845 |  |  |  |  | 850 |  |  |  |
| ggc | cac | uau | guc | caa | aug | gcc | cuc | aug | aaa | cug | gcc | gca | cug | acg | ggu | 2948 |
| Gly | His | Tyr | Val | Gln | Met | Ala | Leu | Met | Lys | Leu | Ala | Ala | Leu | Thr | Gly |
|  | 855 |  |  |  |  | 860 |  |  |  |  | 865 |  |  |  |  |
| acg | uac | guu | uau | gac | cau | cuu | acu | ccg | cug | cag | gac | ugg | gcc | cac | gcg | 2996 |
| Thr | Tyr | Val | Tyr | Asp | His | Leu | Thr | Pro | Leu | Gln | Asp | Trp | Ala | His | Ala |
| 870 |  |  |  |  | 875 |  |  |  |  | 880 |  |  |  |  | 885 |
| ggc | uug | cga | gac | cuu | gca | gug | gca | guu | gag | ccc | guc | guc | uuc | ucu | gac | 3044 |
| Gly | Leu | Arg | Asp | Leu | Ala | Val | Ala | Val | Glu | Pro | Val | Val | Phe | Ser | Asp |
|  |  |  |  | 890 |  |  |  |  | 895 |  |  |  |  | 900 |  |
| aug | gag | acu | aag | guc | auc | acc | ugg | ggg | gca | gac | acc | gca | gcg | ugu | ggg | 3092 |
| Met | Glu | Thr | Lys | Val | Ile | Thr | Trp | Gly | Ala | Asp | Thr | Ala | Ala | Cys | Gly |
|  |  |  | 905 |  |  |  |  | 910 |  |  |  |  | 915 |  |  |
| gac | auc | auc | ucg | ggc | cua | ccc | guc | ucc | gcc | cga | agg | ggg | agg | gag | aua | 3140 |
| Asp | Ile | Ile | Ser | Gly | Leu | Pro | Val | Ser | Ala | Arg | Arg | Gly | Arg | Glu | Ile |
|  |  | 920 |  |  |  |  | 925 |  |  |  |  | 930 |  |  |  |
| cuu | cug | ggc | ccc | gcc | gac | agg | uuu | gga | gag | cag | ggg | ugg | cga | cuc | cuc | 3188 |
| Leu | Leu | Gly | Pro | Ala | Asp | Arg | Phe | Gly | Glu | Gln | Gly | Trp | Arg | Leu | Leu |
|  | 935 |  |  |  |  | 940 |  |  |  |  | 945 |  |  |  |  |
| gcg | ccu | auc | acg | gcu | uac | gcu | caa | cag | acg | cgg | ggc | cua | cuu | ggc | ugu | 3236 |
| Ala | Pro | Ile | Thr | Ala | Tyr | Ala | Gln | Gln | Thr | Arg | Gly | Leu | Leu | Gly | Cys |
| 950 |  |  |  |  | 955 |  |  |  |  | 960 |  |  |  |  | 965 |
| auc | auc | acc | agc | cuc | aca | ggc | cgg | gac | aag | aac | cag | guc | gag | ggg | gag | 3284 |
| Ile | Ile | Thr | Ser | Leu | Thr | Gly | Arg | Asp | Lys | Asn | Gln | Val | Glu | Gly | Glu |

-continued

```
              970                 975                 980
guu cag gug guu ucc acc gca acg caa ucu uuc cug gcg acc ugc guc       3332
Val Gln Val Val Ser Thr Ala Thr Gln Ser Phe Leu Ala Thr Cys Val
            985                 990                 995 aac ggc gug ugu ugg acu guc uac cau ggu gcc ggc ucg aag acc           3377
Asn Gly Val Cys Trp Thr Val Tyr His Gly Ala Gly Ser Lys Thr
           1000                1005                1010 cug gcc ggc ccg aag ggc cca auc acc caa aug uac acc aau gug           3422
Leu Ala Gly Pro Lys Gly Pro Ile Thr Gln Met Tyr Thr Asn Val
           1015                1020                1025 gac caa gac cuc guc ggc ugg ccg gcg ccc ccc ggg gcg cgc ucc           3467
Asp Gln Asp Leu Val Gly Trp Pro Ala Pro Pro Gly Ala Arg Ser
           1030                1035                1040 cug aca ccg ugc acc ugc ggc agc ucg gac cuc uac cug guc acg           3512
Leu Thr Pro Cys Thr Cys Gly Ser Ser Asp Leu Tyr Leu Val Thr
           1045                1050                1055 agg cau gcu gau guc auu ccg gug cgc cgg cgg ggc gac agc agg           3557
Arg His Ala Asp Val Ile Pro Val Arg Arg Arg Gly Asp Ser Arg
           1060                1065                1070 ggg agu cua cuc ucu ccc agg ccc auc ucc uac uua aag ggc ucc           3602
Gly Ser Leu Leu Ser Pro Arg Pro Ile Ser Tyr Leu Lys Gly Ser
           1075                1080                1085 uca ggu ggu cca cug cuu ugc ccc cug ggg cac gcu gug ggc auc           3647
Ser Gly Gly Pro Leu Leu Cys Pro Leu Gly His Ala Val Gly Ile
           1090                1095                1100 uuc cgg gcc gcu gug ugc acc cgg ggg guu gca aag gcg gug gau           3692
Phe Arg Ala Ala Val Cys Thr Arg Gly Val Ala Lys Ala Val Asp
           1105                1110                1115 uuu gua ccu guu gag ucu aug gaa acc acc aug cgg ucu ccg guc           3737
Phe Val Pro Val Glu Ser Met Glu Thr Thr Met Arg Ser Pro Val
           1120                1125                1130 uuu acg gau aau uca ucu ccc ccg gcc gua ccg cag aca uuc caa           3782
Phe Thr Asp Asn Ser Ser Pro Pro Ala Val Pro Gln Thr Phe Gln
           1135                1140                1145 gug gcc cau cua cac gcu ccc acu ggc agu ggc aag agc acu aag           3827
Val Ala His Leu His Ala Pro Thr Gly Ser Gly Lys Ser Thr Lys
           1150                1155                1160 gug ccg gcu gcg uac gca gcc caa ggg uac aag gua cuc guc uug           3872
Val Pro Ala Ala Tyr Ala Ala Gln Gly Tyr Lys Val Leu Val Leu
           1165                1170                1175 aac cca ucc guu gcc gcu acc uua ggg uuu ggg gcg uac aug ucu           3917
Asn Pro Ser Val Ala Ala Thr Leu Gly Phe Gly Ala Tyr Met Ser
           1180                1185                1190 aaa gca cau ggu guu gag ccu aac auc aga acu ggg gua agg acc           3962
Lys Ala His Gly Val Glu Pro Asn Ile Arg Thr Gly Val Arg Thr
           1195                1200                1205 auc acc acg ggc gcu ucc auc acg uau ucc acc uac ggu aag uuc           4007
Ile Thr Thr Gly Ala Ser Ile Thr Tyr Ser Thr Tyr Gly Lys Phe
           1210                1215                1220 cuu gcc gac ggu ggu ugc ucu ggg ggc gcc uau gac auc aua aua           4052
Leu Ala Asp Gly Gly Cys Ser Gly Gly Ala Tyr Asp Ile Ile Ile
           1225                1230                1235 ugu gau gag ugc cac uca acu gac ucg acu ucc auc uug ggc auu           4097
Cys Asp Glu Cys His Ser Thr Asp Ser Thr Ser Ile Leu Gly Ile
           1240                1245                1250 ggc aca guc cug gac caa gcg gag acg gcu gga gcg cgg cuc guc           4142
Gly Thr Val Leu Asp Gln Ala Glu Thr Ala Gly Ala Arg Leu Val
           1255                1260                1265 gug cuc gcc acc gcu acg ccu ccg gga ucg guc acc gug cca cau           4187
Val Leu Ala Thr Ala Thr Pro Pro Gly Ser Val Thr Val Pro His
```

-continued

| | | | | | | | | | | | | |
|---|---|---|---|---|---|---|---|---|---|---|---|---|
| | | | | 1270 | | | | 1275 | | | 1280 | |
| ccc | aau | auc | gag | gag | gug | gcc | uug | ccc | agc | acc | gga | gaa | auu | ccc | 4232 |
| Pro | Asn | Ile | Glu | Glu | Val | Ala | Leu | Pro | Ser | Thr | Gly | Glu | Ile | Pro | |
| | | 1285 | | | | 1290 | | | | 1295 | | | | | |
| uuc | uac | ggc | aaa | gcc | auc | ccc | auu | gag | acc | auc | aag | ggg | ggg | agg | 4277 |
| Phe | Tyr | Gly | Lys | Ala | Ile | Pro | Ile | Glu | Thr | Ile | Lys | Gly | Gly | Arg | |
| | | 1300 | | | | 1305 | | | | 1310 | | | | | |
| cac | cuc | auc | uuc | ugc | cac | ucc | aag | aag | aaa | ugu | gac | gag | cuc | gcu | 4322 |
| His | Leu | Ile | Phe | Cys | His | Ser | Lys | Lys | Lys | Cys | Asp | Glu | Leu | Ala | |
| | | 1315 | | | | 1320 | | | | 1325 | | | | | |
| gca | aag | cug | gug | ggc | cuc | gga | guu | aac | gcu | guu | gcg | uac | uac | cgg | 4367 |
| Ala | Lys | Leu | Val | Gly | Leu | Gly | Val | Asn | Ala | Val | Ala | Tyr | Tyr | Arg | |
| | | 1330 | | | | 1335 | | | | 1340 | | | | | |
| ggu | cuu | gau | gug | ucc | guc | aua | cca | aca | agc | gga | gau | guc | guu | guc | 4412 |
| Gly | Leu | Asp | Val | Ser | Val | Ile | Pro | Thr | Ser | Gly | Asp | Val | Val | Val | |
| | | 1345 | | | | 1350 | | | | 1355 | | | | | |
| gug | gca | aca | gac | gcu | cua | aug | acg | ggc | uuc | acc | ggc | gac | uuu | gac | 4457 |
| Val | Ala | Thr | Asp | Ala | Leu | Met | Thr | Gly | Phe | Thr | Gly | Asp | Phe | Asp | |
| | | 1360 | | | | 1365 | | | | 1370 | | | | | |
| uca | gug | auc | gac | ugu | aau | acu | ugu | guc | acc | cag | aca | guu | gau | uuc | 4502 |
| Ser | Val | Ile | Asp | Cys | Asn | Thr | Cys | Val | Thr | Gln | Thr | Val | Asp | Phe | |
| | | 1375 | | | | 1380 | | | | 1385 | | | | | |
| agc | uug | gac | ccu | acc | uuc | acc | auu | gag | acg | aca | acc | gug | ccc | caa | 4547 |
| Ser | Leu | Asp | Pro | Thr | Phe | Thr | Ile | Glu | Thr | Thr | Thr | Val | Pro | Gln | |
| | | 1390 | | | | 1395 | | | | 1400 | | | | | |
| gac | gcg | gug | ucg | cgu | ucg | cag | cga | cga | ggc | agg | acu | ggc | agg | ggc | 4592 |
| Asp | Ala | Val | Ser | Arg | Ser | Gln | Arg | Arg | Gly | Arg | Thr | Gly | Arg | Gly | |
| | | 1405 | | | | 1410 | | | | 1415 | | | | | |
| agg | aug | ggc | aua | uac | agg | uuu | gug | gcu | cca | ggg | gaa | cgg | ccc | ucg | 4637 |
| Arg | Met | Gly | Ile | Tyr | Arg | Phe | Val | Ala | Pro | Gly | Glu | Arg | Pro | Ser | |
| | | 1420 | | | | 1425 | | | | 1430 | | | | | |
| ggc | aug | uuc | gau | ucu | ucg | guc | cug | ugu | gag | ugu | uau | gac | gcg | ggc | 4682 |
| Gly | Met | Phe | Asp | Ser | Ser | Val | Leu | Cys | Glu | Cys | Tyr | Asp | Ala | Gly | |
| | | 1435 | | | | 1440 | | | | 1445 | | | | | |
| ugu | gcu | ugg | uau | gag | cuc | acg | ccc | gcc | gag | acc | uca | guc | agg | uug | 4727 |
| Cys | Ala | Trp | Tyr | Glu | Leu | Thr | Pro | Ala | Glu | Thr | Ser | Val | Arg | Leu | |
| | | 1450 | | | | 1455 | | | | 1460 | | | | | |
| cgg | gcu | uac | cua | aau | aca | cca | ggg | cug | ccc | guc | ugc | cag | gac | cac | 4772 |
| Arg | Ala | Tyr | Leu | Asn | Thr | Pro | Gly | Leu | Pro | Val | Cys | Gln | Asp | His | |
| | | 1465 | | | | 1470 | | | | 1475 | | | | | |
| cug | gag | uuu | ugg | gag | ggg | guc | uuc | aca | ggc | cuc | acc | cac | aua | gau | 4817 |
| Leu | Glu | Phe | Trp | Glu | Gly | Val | Phe | Thr | Gly | Leu | Thr | His | Ile | Asp | |
| | | 1480 | | | | 1485 | | | | 1490 | | | | | |
| gcc | cau | uuc | uug | ucc | cag | acu | aag | cag | gca | gga | gau | aac | uuc | ccc | 4862 |
| Ala | His | Phe | Leu | Ser | Gln | Thr | Lys | Gln | Ala | Gly | Asp | Asn | Phe | Pro | |
| | | 1495 | | | | 1500 | | | | 1505 | | | | | |
| uac | cug | gua | gca | uac | cag | gcu | acg | gug | ugc | gcc | agg | gcc | cag | gcu | 4907 |
| Tyr | Leu | Val | Ala | Tyr | Gln | Ala | Thr | Val | Cys | Ala | Arg | Ala | Gln | Ala | |
| | | 1510 | | | | 1515 | | | | 1520 | | | | | |
| ccc | ccu | cca | ucg | ugg | gau | caa | aug | ugg | aag | ugu | cuc | aua | cgg | cug | 4952 |
| Pro | Pro | Pro | Ser | Trp | Asp | Gln | Met | Trp | Lys | Cys | Leu | Ile | Arg | Leu | |
| | | 1525 | | | | 1530 | | | | 1535 | | | | | |
| aag | ccu | aca | cua | cac | ggg | cca | acg | ccc | cug | uug | uau | agg | cua | gga | 4997 |
| Lys | Pro | Thr | Leu | His | Gly | Pro | Thr | Pro | Leu | Leu | Tyr | Arg | Leu | Gly | |
| | | 1540 | | | | 1545 | | | | 1550 | | | | | |
| gcc | guc | cag | aau | gag | guc | auc | cuc | aca | cau | ccc | aua | acc | aaa | uac | 5042 |
| Ala | Val | Gln | Asn | Glu | Val | Ile | Leu | Thr | His | Pro | Ile | Thr | Lys | Tyr | |
| | | 1555 | | | | 1560 | | | | 1565 | | | | | |
| auc | aug | gca | ugc | aug | ucg | gcu | gac | cua | gag | guc | guc | acu | agc | acc | 5087 |
| Ile | Met | Ala | Cys | Met | Ser | Ala | Asp | Leu | Glu | Val | Val | Thr | Ser | Thr | |

-continued

|     |     |     |     |     |     |     |     |     |     |     |     |     |     |     |      |
|-----|-----|-----|-----|-----|-----|-----|-----|-----|-----|-----|-----|-----|-----|-----|------|
|     |     |     | 1570|     |     |     | 1575|     |     |     | 1580|     |     |     |      |
| ugg | gug | cug | guc | ggc | ggg | guc | cuu | gca | gcu | cug | gcc | gcg | uac | ugc | 5132 |
| Trp | Val | Leu | Val | Gly | Gly | Val | Leu | Ala | Ala | Leu | Ala | Ala | Tyr | Cys |      |
|     |     | 1585|     |     |     |     | 1590|     |     |     |     | 1595|     |     |      |
| cug | acg | acg | ggc | agc | gug | guc | auu | gug | ggc | agg | auc | auc | uug | ucc | 5177 |
| Leu | Thr | Thr | Gly | Ser | Val | Val | Ile | Val | Gly | Arg | Ile | Ile | Leu | Ser |      |
|     |     | 1600|     |     |     |     | 1605|     |     |     |     | 1610|     |     |      |
| ggg | aag | ccg | gcu | auu | ccu | gac | agg | gaa | guc | cuc | uac | cgg | gag | 5222 |     |
| Gly | Lys | Pro | Ala | Ile | Ile | Pro | Asp | Arg | Glu | Val | Leu | Tyr | Arg | Glu |      |
|     |     | 1615|     |     |     |     | 1620|     |     |     |     | 1625|     |     |      |
| uuc | gau | gaa | aug | gaa | gag | ugu | gcc | uca | cac | cuc | ccc | uac | auc | gaa | 5267 |
| Phe | Asp | Glu | Met | Glu | Glu | Cys | Ala | Ser | His | Leu | Pro | Tyr | Ile | Glu |      |
|     |     | 1630|     |     |     |     | 1635|     |     |     |     | 1640|     |     |      |
| cag | gga | aug | cag | cuc | gcc | gaa | caa | uuc | aag | cag | aag | gcg | cuc | ggg | 5312 |
| Gln | Gly | Met | Gln | Leu | Ala | Glu | Gln | Phe | Lys | Gln | Lys | Ala | Leu | Gly |      |
|     |     | 1645|     |     |     |     | 1650|     |     |     |     | 1655|     |     |      |
| uug | cug | cag | aca | gcc | acc | aag | caa | gcg | gaa | gcc | gcu | gcu | ccu | gug | 5357 |
| Leu | Leu | Gln | Thr | Ala | Thr | Lys | Gln | Ala | Glu | Ala | Ala | Ala | Pro | Val |      |
|     |     | 1660|     |     |     |     | 1665|     |     |     |     | 1670|     |     |      |
| gug | gag | ucc | aag | ugg | cga | gcc | cuu | gag | gcc | uuc | ugg | gcg | aag | cac | 5402 |
| Val | Glu | Ser | Lys | Trp | Arg | Ala | Leu | Glu | Ala | Phe | Trp | Ala | Lys | His |      |
|     |     | 1675|     |     |     |     | 1680|     |     |     |     | 1685|     |     |      |
| aug | ugg | aau | uuc | auc | agc | ggg | aua | cag | uac | uua | gca | ggc | uug | ucc | 5447 |
| Met | Trp | Asn | Phe | Ile | Ser | Gly | Ile | Gln | Tyr | Leu | Ala | Gly | Leu | Ser |      |
|     |     | 1690|     |     |     |     | 1695|     |     |     |     | 1700|     |     |      |
| acu | cug | ccu | ggg | aac | ccc | gcg | aua | gca | uca | cug | aug | gca | uuc | aca | 5492 |
| Thr | Leu | Pro | Gly | Asn | Pro | Ala | Ile | Ala | Ser | Leu | Met | Ala | Phe | Thr |      |
|     |     | 1705|     |     |     |     | 1710|     |     |     |     | 1715|     |     |      |
| gcc | ucu | auc | acc | agc | ccg | cuu | acc | acc | cua | cac | acc | cuc | cug | uuu | 5537 |
| Ala | Ser | Ile | Thr | Ser | Pro | Leu | Thr | Thr | Leu | His | Thr | Leu | Leu | Phe |      |
|     |     | 1720|     |     |     |     | 1725|     |     |     |     | 1730|     |     |      |
| aac | auc | uug | gga | gga | ugg | gug | gcc | gcc | caa | cuu | gcc | ccc | ccc | ggu | 5582 |
| Asn | Ile | Leu | Gly | Gly | Trp | Val | Ala | Ala | Gln | Leu | Ala | Pro | Pro | Gly |      |
|     |     | 1735|     |     |     |     | 1740|     |     |     |     | 1745|     |     |      |
| gcu | gcc | ucg | gcu | uuc | gug | ggc | gcc | ggc | auu | gcu | ggc | gca | gcu | guu | 5627 |
| Ala | Ala | Ser | Ala | Phe | Val | Gly | Ala | Gly | Ile | Ala | Gly | Ala | Ala | Val |      |
|     |     | 1750|     |     |     |     | 1755|     |     |     |     | 1760|     |     |      |
| ggc | agc | aua | ggc | cuu | ggg | aag | gug | cuu | gug | gac | auc | cug | gcg | ggu | 5672 |
| Gly | Ser | Ile | Gly | Leu | Gly | Lys | Val | Leu | Val | Asp | Ile | Leu | Ala | Gly |      |
|     |     | 1765|     |     |     |     | 1770|     |     |     |     | 1775|     |     |      |
| uau | gga | gca | ggg | gug | gca | ggc | gcg | cuc | gug | gcc | uuc | aag | guc | aug | 5717 |
| Tyr | Gly | Ala | Gly | Val | Ala | Gly | Ala | Leu | Val | Ala | Phe | Lys | Val | Met |      |
|     |     | 1780|     |     |     |     | 1785|     |     |     |     | 1790|     |     |      |
| agc | ggc | gag | aug | ccc | ucc | acc | gag | gac | cug | guc | aac | uua | cuc | ccu | 5762 |
| Ser | Gly | Glu | Met | Pro | Ser | Thr | Glu | Asp | Leu | Val | Asn | Leu | Leu | Pro |      |
|     |     | 1795|     |     |     |     | 1800|     |     |     |     | 1805|     |     |      |
| gcc | auc | cuc | ucu | ccu | ggu | gcc | cuu | guc | guc | ggg | guc | gug | ugc | gca | 5807 |
| Ala | Ile | Leu | Ser | Pro | Gly | Ala | Leu | Val | Val | Gly | Val | Val | Cys | Ala |      |
|     |     | 1810|     |     |     |     | 1815|     |     |     |     | 1820|     |     |      |
| gca | aua | cug | cgu | cgg | cau | gug | ggc | ccg | ggg | gag | ggg | gcu | gug | caa | 5852 |
| Ala | Ile | Leu | Arg | Arg | His | Val | Gly | Pro | Gly | Glu | Gly | Ala | Val | Gln |      |
|     |     | 1825|     |     |     |     | 1830|     |     |     |     | 1835|     |     |      |
| ugg | aug | aac | cgg | cug | aua | gcg | uuc | gcc | ucg | cgg | ggu | aac | cac | guc | 5897 |
| Trp | Met | Asn | Arg | Leu | Ile | Ala | Phe | Ala | Ser | Arg | Gly | Asn | His | Val |      |
|     |     | 1840|     |     |     |     | 1845|     |     |     |     | 1850|     |     |      |
| ucc | ccc | acg | cac | uau | gug | ccu | gag | agc | gac | gcu | gca | gcg | cgu | guc | 5942 |
| Ser | Pro | Thr | His | Tyr | Val | Pro | Glu | Ser | Asp | Ala | Ala | Ala | Arg | Val |      |
|     |     | 1855|     |     |     |     | 1860|     |     |     |     | 1865|     |     |      |
| aca | cag | auc | cuc | ucu | agc | cuc | acc | auc | acu | cag | cua | cug | aag | agg | 5987 |
| Thr | Gln | Ile | Leu | Ser | Ser | Leu | Thr | Ile | Thr | Gln | Leu | Leu | Lys | Arg |      |

-continued

```
              1870                1875                1880
cuc cac cag  ugg auu aau aag  gac ugc ucc aca  cca ugc ucc ggc       6032
Leu His Gln  Trp Ile Asn Lys  Asp Cys Ser Thr  Pro Cys Ser Gly
              1885                1890                1895 ucg ugg cuu  agg gac guu ugg  gac ugg aua ugc  acg guu uug agu       6077
Ser Trp Leu  Arg Asp Val Trp  Asp Trp Ile Cys  Thr Val Leu Ser
              1900                1905                1910 gac uuc aag  acc ugg cuc cag  ucc aag cuc cug  cca cgg uua ccg       6122
Asp Phe Lys  Thr Trp Leu Gln  Ser Lys Leu Leu  Pro Arg Leu Pro
              1915                1920                1925 gga guu cca  uuc cuu uca ugc  caa cgu ggg uau  aag ggg guc ugg       6167
Gly Val Pro  Phe Leu Ser Cys  Gln Arg Gly Tyr  Lys Gly Val Trp
              1930                1935                1940 cgg gga gau  ggc auc aug cag  acc ucc ugc cca  ugu gga gca caa       6212
Arg Gly Asp  Gly Ile Met Gln  Thr Ser Cys Pro  Cys Gly Ala Gln
              1945                1950                1955 auc gcc gga  cau guc aag aac  ggu ucc aug agg  auc guu ggg ccu       6257
Ile Ala Gly  His Val Lys Asn  Gly Ser Met Arg  Ile Val Gly Pro
              1960                1965                1970 aaa acc ugu  agc aac acg ugg  cac gga aca uuc  ccc auu aac gcg       6302
Lys Thr Cys  Ser Asn Thr Trp  His Gly Thr Phe  Pro Ile Asn Ala
              1975                1980                1985 cac acc acg  ggc ccc ugc aca  ccc ucc cca gcg  ccg aac uac ucu       6347
His Thr Thr  Gly Pro Cys Thr  Pro Ser Pro Ala  Pro Asn Tyr Ser
              1990                1995                2000 aag gcg uug  ugg cgg gug gcu  gcu gag gag uac  gug gaa guc acg       6392
Lys Ala Leu  Trp Arg Val Ala  Ala Glu Glu Tyr  Val Glu Val Thr
              2005                2010                2015 cgg gug ggg  gau uuc cau uac  gug acg ggc aug  acc acu gac aac       6437
Arg Val Gly  Asp Phe His Tyr  Val Thr Gly Met  Thr Thr Asp Asn
              2020                2025                2030 gua aaa ugc  cca ugc cag guu  ccg gcc ccc gaa  uuc uuc aca gag       6482
Val Lys Cys  Pro Cys Gln Val  Pro Ala Pro Glu  Phe Phe Thr Glu
              2035                2040                2045 gug gau ggg  gua cgg cug cac  agg uac gcu ccg  gcg ugc aaa ccu       6527
Val Asp Gly  Val Arg Leu His  Arg Tyr Ala Pro  Ala Cys Lys Pro
              2050                2055                2060 cuc cua cgg  gau gag guc aca  uuc cag guc ggg  cuc aac cag uuc       6572
Leu Leu Arg  Asp Glu Val Thr  Phe Gln Val Gly  Leu Asn Gln Phe
              2065                2070                2075 ccg guu ggg  uca cag cuc cca  ugc gag ccc gaa  ccg gau gua uca       6617
Pro Val Gly  Ser Gln Leu Pro  Cys Glu Pro Glu  Pro Asp Val Ser
              2080                2085                2090 gug cuc acu  ucc aug cuu acc  gac ccu ucc cac  auc aca gca gag       6662
Val Leu Thr  Ser Met Leu Thr  Asp Pro Ser His  Ile Thr Ala Glu
              2095                2100                2105 acg gcu aag  cgu agg cug gcc  aga ggg ucu ucc  ccu ucu uug gcc       6707
Thr Ala Lys  Arg Arg Leu Ala  Arg Gly Ser Ser  Pro Ser Leu Ala
              2110                2115                2120 agc ucu uca  gcu agu cag uug  ucu gcg ccc uca  uug aag gcg aca       6752
Ser Ser Ser  Ala Ser Gln Leu  Ser Ala Pro Ser  Leu Lys Ala Thr
              2125                2130                2135 ugc acc acc  cau cau gac ucc  cca gac gcu gac  cuc auu gag gcc       6797
Cys Thr Thr  His His Asp Ser  Pro Asp Ala Asp  Leu Ile Glu Ala
              2140                2145                2150 aac cuc cug  ugg cgg cag gag  aug gga ggg aac  auc acc cgu gug       6842
Asn Leu Leu  Trp Arg Gln Glu  Met Gly Gly Asn  Ile Thr Arg Val
              2155                2160                2165 gag uca gag  aac aag gug gua  auc cug gac ucu  uuu gac ccg cuu       6887
Glu Ser Glu  Asn Lys Val Val  Ile Leu Asp Ser  Phe Asp Pro Leu
```

```
                      2170                   2175                   2180
cga  gcg  gag  gag  gac  gag  agg  gag  gug  ucu  guu  gcg  gcg  gag  auc         6932
Arg  Ala  Glu  Glu  Asp  Glu  Arg  Glu  Val  Ser  Val  Ala  Ala  Glu  Ile
               2185                   2190                   2195 cug  cgg  aaa  acc  agg  aag  uuc  ccc  cca  gcg  aug  ccc  aua  ugg  gca         6977
Leu  Arg  Lys  Thr  Arg  Lys  Phe  Pro  Pro  Ala  Met  Pro  Ile  Trp  Ala
          2200                   2205                   2210 cgc  ccg  gac  uac  aac  cca  ccg  cug  cua  gag  acu  ugg  aag  gac  ccg         7022
Arg  Pro  Asp  Tyr  Asn  Pro  Pro  Leu  Leu  Glu  Thr  Trp  Lys  Asp  Pro
          2215                   2220                   2225 gac  uac  guc  ccu  cca  gug  gug  cac  ggg  ugc  cca  uug  cca  ccu  acc         7067
Asp  Tyr  Val  Pro  Pro  Val  Val  His  Gly  Cys  Pro  Leu  Pro  Pro  Thr
          2230                   2235                   2240 aag  acc  ccu  cca  aua  cca  ccu  ccg  cgg  agg  aaa  aag  aca  guu  guc         7112
Lys  Thr  Pro  Pro  Ile  Pro  Pro  Arg  Arg  Lys  Lys  Thr  Val  Val
          2245                   2250                   2255 cug  aca  gag  ucc  acc  gug  ucu  ucu  gcc  cug  gcg  gag  cuu  gcc  aca         7157
Leu  Thr  Glu  Ser  Thr  Val  Ser  Ser  Ala  Leu  Ala  Glu  Leu  Ala  Thr
          2260                   2265                   2270 aag  acc  uuu  ggc  agc  ucc  gga  ucg  ucg  gcc  guc  gac  agc  ggc  aca         7202
Lys  Thr  Phe  Gly  Ser  Ser  Gly  Ser  Ser  Ala  Val  Asp  Ser  Gly  Thr
          2275                   2280                   2285 gcg  acc  gcc  ccc  ccu  aac  cag  cuc  ucc  gac  gaa  gug  gau  aca  gga         7247
Ala  Thr  Ala  Pro  Pro  Asn  Gln  Leu  Ser  Asp  Glu  Val  Asp  Thr  Gly
          2290                   2295                   2300 ucc  gac  guu  gag  ucg  uac  ucc  ucc  aug  ccc  ccc  cuu  gag  gga  gag         7292
Ser  Asp  Val  Glu  Ser  Tyr  Ser  Ser  Met  Pro  Pro  Leu  Glu  Gly  Glu
          2305                   2310                   2315 ccg  ggg  gac  ccc  gau  cuc  agc  gac  ggg  ucu  ugg  ucu  acu  gua  agu         7337
Pro  Gly  Asp  Pro  Asp  Leu  Ser  Asp  Gly  Ser  Trp  Ser  Thr  Val  Ser
          2320                   2325                   2330 gag  gag  gcu  ggu  gag  gac  guc  guc  ugc  ugc  ucg  aug  ucc  uac  aca         7382
Glu  Glu  Ala  Gly  Glu  Asp  Val  Val  Cys  Cys  Ser  Met  Ser  Tyr  Thr
          2335                   2340                   2345 ugg  aca  ggc  gcc  uug  auc  acg  ccg  ugc  gcc  gcg  gag  gag  agc  aag         7427
Trp  Thr  Gly  Ala  Leu  Ile  Thr  Pro  Cys  Ala  Ala  Glu  Glu  Ser  Lys
          2350                   2355                   2360 cug  ccc  auc  aau  gcg  cug  agc  aac  ucu  uug  cug  cgc  cac  cac  aac         7472
Leu  Pro  Ile  Asn  Ala  Leu  Ser  Asn  Ser  Leu  Leu  Arg  His  His  Asn
          2365                   2370                   2375 aug  guc  uau  gcc  aca  aca  ucc  cgc  agc  gca  agc  caa  cgg  cag  aaa         7517
Met  Val  Tyr  Ala  Thr  Thr  Ser  Arg  Ser  Ala  Ser  Gln  Arg  Gln  Lys
          2380                   2385                   2390 aag  guc  acc  uuu  gac  aga  cug  caa  guc  cug  gac  gac  cau  uac  cgg         7562
Lys  Val  Thr  Phe  Asp  Arg  Leu  Gln  Val  Leu  Asp  Asp  His  Tyr  Arg
          2395                   2400                   2405 gac  gug  cuc  aag  gag  aug  aag  gcg  aag  gcg  ucc  aca  guu  aag  gcu         7607
Asp  Val  Leu  Lys  Glu  Met  Lys  Ala  Lys  Ala  Ser  Thr  Val  Lys  Ala
          2410                   2415                   2420 aaa  cuu  cua  ucc  gua  gaa  gag  gcc  ugc  aag  cug  acg  ccc  cca  cac         7652
Lys  Leu  Leu  Ser  Val  Glu  Glu  Ala  Cys  Lys  Leu  Thr  Pro  Pro  His
          2425                   2430                   2435 uca  gcc  agg  ucc  aaa  uuu  ggc  uau  ggg  gcg  aag  gac  guc  cgg  aac         7697
Ser  Ala  Arg  Ser  Lys  Phe  Gly  Tyr  Gly  Ala  Lys  Asp  Val  Arg  Asn
          2440                   2445                   2450 cua  ucc  agc  aag  gcc  guu  aac  cac  auc  aac  ucc  gug  ugg  aag  gac         7742
Leu  Ser  Ser  Lys  Ala  Val  Asn  His  Ile  Asn  Ser  Val  Trp  Lys  Asp
          2455                   2460                   2465 uug  cug  gaa  gac  acu  gag  aca  cca  auu  gac  acc  acc  auc  aug  gca         7787
Leu  Leu  Glu  Asp  Thr  Glu  Thr  Pro  Ile  Asp  Thr  Thr  Ile  Met  Ala
```

-continued

```
              2470              2475              2480
aaa aau gag guc uuc ugu guu caa cca gag aag gga ggc cgc aag    7832
Lys Asn Glu Val Phe Cys Val Gln Pro Glu Lys Gly Gly Arg Lys
         2485              2490              2495 cca gcu cgc cuu auc gua uac cca gac uug ggg gug cgu gug ugc    7877
Pro Ala Arg Leu Ile Val Tyr Pro Asp Leu Gly Val Arg Val Cys
         2500              2505              2510 gag aaa aug gcc cuu uac gac gug guc ucc acu cuu ccu cag gcc    7922
Glu Lys Met Ala Leu Tyr Asp Val Val Ser Thr Leu Pro Gln Ala
         2515              2520              2525 gug aug ggc ucc uca uac gga uuc cag uac ucu ccu ggg cag cgg    7967
Val Met Gly Ser Ser Tyr Gly Phe Gln Tyr Ser Pro Gly Gln Arg
         2530              2535              2540 guc gag uuc cug gug aau gcc ugg aaa uca aag aag aac ccu aug    8012
Val Glu Phe Leu Val Asn Ala Trp Lys Ser Lys Lys Asn Pro Met
         2545              2550              2555 ggc uuc gca uau gac acc cgc ugu uuu gac uca acg guc acc gag    8057
Gly Phe Ala Tyr Asp Thr Arg Cys Phe Asp Ser Thr Val Thr Glu
         2560              2565              2570 aac gac auc cgu guu gag gag uca auu uac caa ugu ugu gac uug    8102
Asn Asp Ile Arg Val Glu Glu Ser Ile Tyr Gln Cys Cys Asp Leu
         2575              2580              2585 gcc ccc gag gcc aga cag gug aua agg ucg cuc aca gag cgg cuu    8147
Ala Pro Glu Ala Arg Gln Val Ile Arg Ser Leu Thr Glu Arg Leu
         2590              2595              2600 uau guc ggg ggc ccc cug acu aau uca aaa ggg cag aac ugc ggu    8192
Tyr Val Gly Gly Pro Leu Thr Asn Ser Lys Gly Gln Asn Cys Gly
         2605              2610              2615 uau cgc cgg ugc cgc gcc agc ggc gug cug acg acu agc ugc ggu    8237
Tyr Arg Arg Cys Arg Ala Ser Gly Val Leu Thr Thr Ser Cys Gly
         2620              2625              2630 aau acc cuc aca ugu uac uug aag gcc ucu gca gcc ugu cga gcu    8282
Asn Thr Leu Thr Cys Tyr Leu Lys Ala Ser Ala Ala Cys Arg Ala
         2635              2640              2645 gca aag cuc cag gac ugc acg aug cuc gug ugc ggg gac gac cuu    8327
Ala Lys Leu Gln Asp Cys Thr Met Leu Val Cys Gly Asp Asp Leu
         2650              2655              2660 guc guu auc ugu gaa agc gcg ggg acc cag gag gac gcg gcg agc    8372
Val Val Ile Cys Glu Ser Ala Gly Thr Gln Glu Asp Ala Ala Ser
         2665              2670              2675 cua cga guc uuc acg gag gcu aug acu agg uac ucc gcc ccc ccc    8417
Leu Arg Val Phe Thr Glu Ala Met Thr Arg Tyr Ser Ala Pro Pro
         2680              2685              2690 ggg gac ccg ccc cga ccg gaa uac gac uug gag uug aua aca uca    8462
Gly Asp Pro Pro Arg Pro Glu Tyr Asp Leu Glu Leu Ile Thr Ser
         2695              2700              2705 ugc ucc ucc aac gug ucg guc gcg cac gau gca ucu ggc aaa cgg    8507
Cys Ser Ser Asn Val Ser Val Ala His Asp Ala Ser Gly Lys Arg
         2710              2715              2720 gug uau uac cuc acc cgu gac ccc acc acc ccc cuu gcg cgg gcu    8552
Val Tyr Tyr Leu Thr Arg Asp Pro Thr Thr Pro Leu Ala Arg Ala
         2725              2730              2735 gcg ugg gag aca gcu aaa cac acu cca guc aac ucc ugg cua ggc    8597
Ala Trp Glu Thr Ala Lys His Thr Pro Val Asn Ser Trp Leu Gly
         2740              2745              2750 aac auc auc aug uau gcg ccc acc cuc ugg gca agg aug auu cug    8642
Asn Ile Ile Met Tyr Ala Pro Thr Leu Trp Ala Arg Met Ile Leu
         2755              2760              2765 aug acu cac uuc uuc ucc auc cuu cua gcu cag gag cag cuu gaa    8687
Met Thr His Phe Phe Ser Ile Leu Leu Ala Gln Glu Gln Leu Glu
```

-continued

```
              2770                2775                2780
aaa gcc cug gau ugu cag auc uac ggg gcc acu uac ucc auu gaa       8732
Lys Ala Leu Asp Cys Gln Ile Tyr Gly Ala Thr Tyr Ser Ile Glu
        2785                2790                2795 cca cuu gac cua ccu cag auc auu caa cga cuc cau ggu cuu agc       8777
Pro Leu Asp Leu Pro Gln Ile Ile Gln Arg Leu His Gly Leu Ser
        2800                2805                2810 gca uuc uca cuc cau agu uac ucu cca ggu gaa auc aau agg gug       8822
Ala Phe Ser Leu His Ser Tyr Ser Pro Gly Glu Ile Asn Arg Val
        2815                2820                2825 gcu uca ugc cuc agg aaa cuu ggg gua ccg ccc uug cga guc ugg       8867
Ala Ser Cys Leu Arg Lys Leu Gly Val Pro Pro Leu Arg Val Trp
        2830                2835                2840 aga cau cgg gcc aga agu guc cgc gcu aag cua cug ucc cag ggg       8912
Arg His Arg Ala Arg Ser Val Arg Ala Lys Leu Leu Ser Gln Gly
        2845                2850                2855 ggg agg gcu gcc acu ugu ggc aag uac cuc uuc aac ugg gca gua       8957
Gly Arg Ala Ala Thr Cys Gly Lys Tyr Leu Phe Asn Trp Ala Val
        2860                2865                2870 agg acc aag cuc aaa cuc acu cca auc ccg gcu gcg ucc cag uug       9002
Arg Thr Lys Leu Lys Leu Thr Pro Ile Pro Ala Ala Ser Gln Leu
        2875                2880                2885 gac uug ucc ggc ugg uuc auu gcu ggu uac agc ggg gga gac aua       9047
Asp Leu Ser Gly Trp Phe Ile Ala Gly Tyr Ser Gly Gly Asp Ile
        2890                2895                2900 uau cac agc cug ucu cgu gcc cga ccc cgc ugg uuu aug uug ugc       9092
Tyr His Ser Leu Ser Arg Ala Arg Pro Arg Trp Phe Met Leu Cys
        2905                2910                2915 cua cuc cua cuu ucu gug ggg gua ggc auc uac cug cuc ccc aau       9137
Leu Leu Leu Leu Ser Val Gly Val Gly Ile Tyr Leu Leu Pro Asn
        2920                2925                2930 cga ugaacggggg gcuaaacacu ccaggccauu aggccauucu guuuuuuuu         9190
Arg uuuuuuuuuu uuuuuuuuuu uuuuuuuuuu uuuuuuuuuu uuuuuccuuu uuuuuuuuuu 9250
uuuucccuuu cuuuuggugg cuccaucuua gcccuaguca cggcuagcug ugaaaggucc 9310
gugagccgca ugacugcaga gagugcugau acuggccucu cugcagauca ugc        9363

<210> SEQ ID NO 98
<211> LENGTH: 2933
<212> TYPE: PRT
<213> ORGANISM: Artificial Sequence
<220> FEATURE:
<223> OTHER INFORMATION: Chimeric virus of Hepatitis C virus and GBV-B

<400> SEQUENCE: 98

Met Pro Val Ile Ser Thr Gln Thr Ser Pro Val Pro Ala Pro Arg Thr
1               5                   10                  15

Arg Lys Asn Lys Gln Thr Gln Ala Ser Tyr Pro Val Ser Ile Lys Thr
            20                  25                  30

Ser Val Glu Arg Gly Gln Arg Ala Lys Arg Lys Val Gln Arg Asp Ala
        35                  40                  45

Arg Pro Arg Asn Tyr Lys Ile Ala Gly Ile His Asp Gly Leu Gln Thr
    50                  55                  60

Leu Ala Gln Ala Ala Leu Pro Ala His Gly Trp Gly Arg Gln Asp Pro
65                  70                  75                  80

Arg His Lys Ser Arg Asn Leu Gly Ile Leu Leu Asp Tyr Pro Leu Gly
                85                  90                  95

Trp Ile Gly Asp Val Thr Thr His Thr Pro Leu Val Gly Pro Leu Val
```

-continued

```
                100             105                 110
Ala Gly Ala Val Val Arg Pro Val Cys Gln Ile Val Arg Leu Leu Glu
        115                 120                 125

Asp Gly Val Asn Trp Ala Thr Gly Trp Phe Gly Val His Leu Phe Val
        130                 135                 140

Val Cys Leu Leu Ser Leu Ala Cys Pro Cys Ser Gly Ala Arg Val Thr
145                 150                 155                 160

Asp Pro Asp Thr Asn Thr Thr Ile Leu Thr Asn Cys Cys Gln Arg Asn
                165                 170                 175

Gln Val Ile Tyr Cys Ser Pro Ser Thr Cys Leu His Glu Pro Gly Cys
            180                 185                 190

Val Ile Cys Ala Asp Glu Cys Trp Val Pro Ala Asn Pro Tyr Ile Ser
        195                 200                 205

His Pro Ser Asn Trp Thr Gly Thr Asp Ser Phe Leu Ala Asp His Ile
        210                 215                 220

Asp Phe Val Met Gly Ala Leu Val Thr Cys Asp Ala Leu Asp Ile Gly
225                 230                 235                 240

Glu Leu Cys Gly Ala Cys Val Leu Val Gly Asp Trp Leu Val Arg His
                245                 250                 255

Trp Leu Ile His Ile Asp Leu Asn Glu Thr Gly Thr Cys Tyr Leu Glu
                260                 265                 270

Val Pro Thr Gly Ile Asp Pro Gly Phe Leu Gly Phe Ile Gly Trp Met
            275                 280                 285

Ala Gly Lys Val Glu Ala Val Ile Phe Leu Thr Lys Leu Ala Ser Gln
        290                 295                 300

Val Pro Tyr Ala Ile Ala Thr Met Phe Ser Ser Val His Tyr Leu Ala
305                 310                 315                 320

Val Gly Ala Leu Ile Tyr Tyr Ala Ser Arg Gly Lys Trp Tyr Gln Leu
                325                 330                 335

Leu Leu Ala Leu Met Leu Tyr Ile Glu Ala Thr Ser Gly Asn Pro Ile
                340                 345                 350

Arg Val Pro Thr Gly Cys Ser Ile Ala Glu Phe Cys Ser Pro Leu Met
            355                 360                 365

Ile Pro Cys Pro Cys His Ser Tyr Leu Ser Glu Asn Val Ser Glu Val
        370                 375                 380

Ile Cys Tyr Ser Pro Lys Trp Thr Arg Pro Ile Thr Leu Glu Tyr Asn
385                 390                 395                 400

Asn Ser Ile Ser Trp Tyr Pro Tyr Thr Ile Pro Gly Ala Arg Gly Cys
                405                 410                 415

Met Val Lys Phe Lys Asn Asn Thr Trp Gly Cys Cys Arg Ile Arg Asn
                420                 425                 430

Val Pro Ser Tyr Cys Thr Met Gly Thr Asp Ala Val Trp Asn Asp Thr
        435                 440                 445

Arg Asn Thr Tyr Glu Ala Cys Gly Val Thr Pro Trp Leu Thr Thr Ala
        450                 455                 460

Trp His Asn Gly Ser Ala Leu Lys Leu Ala Ile Leu Gln Tyr Pro Gly
465                 470                 475                 480

Ser Lys Glu Met Phe Lys Pro His Asn Trp Met Ser Gly His Leu Tyr
                485                 490                 495

Phe Glu Gly Ser Asp Thr Pro Ile Val Tyr Phe Tyr Asp Pro Val Asn
            500                 505                 510

Ser Thr Leu Leu Pro Pro Glu Arg Trp Ala Arg Leu Pro Gly Thr Pro
        515                 520                 525
```

-continued

```
Pro Val Val Arg Gly Ser Trp Leu Gln Val Pro Gln Gly Phe Tyr Ser
530                 535                 540

Asp Val Lys Asp Leu Ala Thr Gly Leu Ile Thr Lys Asp Lys Ala Trp
545                 550                 555                 560

Lys Asn Tyr Gln Val Leu Tyr Ser Ala Thr Gly Ala Leu Ser Leu Thr
                565                 570                 575

Gly Val Thr Thr Lys Ala Val Val Leu Ile Leu Leu Gly Leu Cys Gly
            580                 585                 590

Ser Lys Tyr Leu Ile Leu Ala Tyr Leu Cys Tyr Leu Ser Leu Cys Phe
        595                 600                 605

Gly Arg Ala Ser Gly Tyr Pro Leu Arg Pro Val Leu Pro Ser Gln Ser
610                 615                 620

Tyr Leu Gln Ala Gly Trp Asp Val Leu Ser Lys Ala Gln Val Ala Pro
625                 630                 635                 640

Phe Ala Leu Ile Phe Phe Ile Cys Cys Tyr Leu Arg Cys Arg Leu Arg
                645                 650                 655

Tyr Ala Ala Leu Leu Gly Phe Val Pro Met Ala Glu Ala Ala Leu Glu
            660                 665                 670

Asn Leu Val Ile Leu Asn Ala Ala Ser Val Ala Gly Ala His Gly Val
        675                 680                 685

Leu Ser Phe Leu Val Phe Phe Cys Ala Ala Trp Tyr Ile Lys Gly Lys
690                 695                 700

Leu Val Pro Gly Ala Ala Tyr Ala Phe Tyr Gly Val Trp Pro Leu Leu
705                 710                 715                 720

Leu Leu Leu Leu Ser Leu Pro Pro Arg Ala Tyr Ala Leu Asp Arg Glu
                725                 730                 735

Met Ala Ala Ser Cys Gly Gly Ala Val Phe Val Gly Leu Met Leu Leu
            740                 745                 750

Thr Leu Ser Pro His Tyr Lys Val Phe Leu Ala Arg Leu Ile Trp Trp
        755                 760                 765

Leu Gln Tyr Phe Ile Thr Arg Ala Glu Ala His Leu Gln Val Trp Val
770                 775                 780

Pro Pro Leu Asn Val Arg Gly Gly Arg Asp Ala Ile Ile Leu Leu Thr
785                 790                 795                 800

Cys Val His Pro Glu Leu Ile Phe Asp Ile Thr Lys Ile Leu Leu
                805                 810                 815

Ala Met Leu Gly Pro Leu Met Val Leu Gln Ala Gly Leu Thr Arg Val
            820                 825                 830

Pro Tyr Phe Val Arg Ala Gln Gly Leu Ile Arg Ala Cys Met Leu Val
        835                 840                 845

Arg Lys Val Ala Gly Gly His Tyr Val Gln Met Ala Leu Met Lys Leu
850                 855                 860

Ala Ala Leu Thr Gly Thr Tyr Val Tyr Asp His Leu Thr Pro Leu Gln
865                 870                 875                 880

Asp Trp Ala His Ala Gly Leu Arg Asp Leu Ala Val Ala Val Glu Pro
                885                 890                 895

Val Val Phe Ser Asp Met Glu Thr Lys Val Ile Thr Trp Gly Ala Asp
            900                 905                 910

Thr Ala Ala Cys Gly Asp Ile Ile Ser Gly Leu Pro Val Ser Ala Arg
        915                 920                 925

Arg Gly Arg Glu Ile Leu Leu Gly Pro Ala Asp Arg Phe Gly Glu Gln
930                 935                 940

Gly Trp Arg Leu Leu Ala Pro Ile Thr Ala Tyr Ala Gln Gln Thr Arg
945                 950                 955                 960
```

```
Gly Leu Leu Gly Cys Ile Ile Thr Ser Leu Thr Gly Arg Asp Lys Asn
            965                 970                 975
Gln Val Glu Gly Glu Val Gln Val Val Ser Thr Ala Thr Gln Ser Phe
            980                 985                 990
Leu Ala Thr Cys Val Asn Gly Val  Cys Trp Thr Val Tyr  His Gly Ala
            995                  1000                 1005
Gly Ser Lys Thr Leu Ala Gly  Pro Lys Gly Pro Ile  Thr Gln Met
        1010                 1015                 1020
Tyr Thr Asn Val Asp Gln Asp  Leu Val Gly Trp Pro  Ala Pro Pro
        1025                 1030                 1035
Gly Ala Arg Ser Leu Thr Pro  Cys Thr Cys Gly Ser  Ser Asp Leu
        1040                 1045                 1050
Tyr Leu Val Thr Arg His Ala  Asp Val Ile Pro Val  Arg Arg Arg
        1055                 1060                 1065
Gly Asp Ser Arg Gly Ser Leu  Leu Ser Pro Arg Pro  Ile Ser Tyr
        1070                 1075                 1080
Leu Lys Gly Ser Ser Gly Gly  Pro Leu Leu Cys Pro  Leu Gly His
        1085                 1090                 1095
Ala Val Gly Ile Phe Arg Ala  Ala Val Cys Thr Arg  Gly Val Ala
        1100                 1105                 1110
Lys Ala Val Asp Phe Val Pro  Val Glu Ser Met Glu  Thr Thr Met
        1115                 1120                 1125
Arg Ser Pro Val Phe Thr Asp  Asn Ser Ser Pro Pro  Ala Val Pro
        1130                 1135                 1140
Gln Thr Phe Gln Val Ala His  Leu His Ala Pro Thr  Gly Ser Gly
        1145                 1150                 1155
Lys Ser Thr Lys Val Pro Ala  Ala Tyr Ala Ala Gln  Gly Tyr Lys
        1160                 1165                 1170
Val Leu Val Leu Asn Pro Ser  Val Ala Ala Thr Leu  Gly Phe Gly
        1175                 1180                 1185
Ala Tyr Met Ser Lys Ala His  Gly Val Glu Pro Asn  Ile Arg Thr
        1190                 1195                 1200
Gly Val Arg Thr Ile Thr Thr  Gly Ala Ser Ile Thr  Tyr Ser Thr
        1205                 1210                 1215
Tyr Gly Lys Phe Leu Ala Asp  Gly Gly Cys Ser Gly  Gly Ala Tyr
        1220                 1225                 1230
Asp Ile Ile Ile Cys Asp Glu  Cys His Ser Thr Asp  Ser Thr Ser
        1235                 1240                 1245
Ile Leu Gly Ile Gly Thr Val  Leu Asp Gln Ala Glu  Thr Ala Gly
        1250                 1255                 1260
Ala Arg Leu Val Val Leu Ala  Thr Ala Thr Pro Pro  Gly Ser Val
        1265                 1270                 1275
Thr Val Pro His Pro Asn Ile  Glu Glu Val Ala Leu  Pro Ser Thr
        1280                 1285                 1290
Gly Glu Ile Pro Phe Tyr Gly  Lys Ala Ile Pro Ile  Glu Thr Ile
        1295                 1300                 1305
Lys Gly Gly Arg His Leu Ile  Phe Cys His Ser Lys  Lys Lys Cys
        1310                 1315                 1320
Asp Glu Leu Ala Ala Lys Leu  Val Gly Leu Gly Val  Asn Ala Val
        1325                 1330                 1335
Ala Tyr Tyr Arg Gly Leu Asp  Val Ser Val Ile Pro  Thr Ser Gly
        1340                 1345                 1350
Asp Val Val Val Val Ala Thr  Asp Ala Leu Met Thr  Gly Phe Thr
```

```
                    1355                1360                1365

Gly Asp Phe Asp Ser Val Ile Asp Cys Asn Thr Cys Val Thr Gln
    1370                1375                1380

Thr Val Asp Phe Ser Leu Asp Pro Thr Phe Thr Ile Glu Thr Thr
    1385                1390                1395

Thr Val Pro Gln Asp Ala Val Ser Arg Ser Gln Arg Arg Gly Arg
    1400                1405                1410

Thr Gly Arg Gly Arg Met Gly Ile Tyr Arg Phe Val Ala Pro Gly
    1415                1420                1425

Glu Arg Pro Ser Gly Met Phe Asp Ser Ser Val Leu Cys Glu Cys
    1430                1435                1440

Tyr Asp Ala Gly Cys Ala Trp Tyr Glu Leu Thr Pro Ala Glu Thr
    1445                1450                1455

Ser Val Arg Leu Arg Ala Tyr Leu Asn Thr Pro Gly Leu Pro Val
    1460                1465                1470

Cys Gln Asp His Leu Glu Phe Trp Glu Gly Val Phe Thr Gly Leu
    1475                1480                1485

Thr His Ile Asp Ala His Phe Leu Ser Gln Thr Lys Gln Ala Gly
    1490                1495                1500

Asp Asn Phe Pro Tyr Leu Val Ala Tyr Gln Ala Thr Val Cys Ala
    1505                1510                1515

Arg Ala Gln Ala Pro Pro Ser Trp Asp Gln Met Trp Lys Cys
    1520                1525                1530

Leu Ile Arg Leu Lys Pro Thr Leu His Gly Pro Thr Pro Leu Leu
    1535                1540                1545

Tyr Arg Leu Gly Ala Val Gln Asn Glu Val Ile Leu Thr His Pro
    1550                1555                1560

Ile Thr Lys Tyr Ile Met Ala Cys Met Ser Ala Asp Leu Glu Val
    1565                1570                1575

Val Thr Ser Thr Trp Val Leu Val Gly Gly Val Leu Ala Ala Leu
    1580                1585                1590

Ala Ala Tyr Cys Leu Thr Thr Gly Ser Val Val Ile Val Gly Arg
    1595                1600                1605

Ile Ile Leu Ser Gly Lys Pro Ala Ile Ile Pro Asp Arg Glu Val
    1610                1615                1620

Leu Tyr Arg Glu Phe Asp Glu Met Glu Glu Cys Ala Ser His Leu
    1625                1630                1635

Pro Tyr Ile Glu Gln Gly Met Gln Leu Ala Glu Gln Phe Lys Gln
    1640                1645                1650

Lys Ala Leu Gly Leu Leu Gln Thr Ala Thr Lys Gln Ala Glu Ala
    1655                1660                1665

Ala Ala Pro Val Val Glu Ser Lys Trp Arg Ala Leu Glu Ala Phe
    1670                1675                1680

Trp Ala Lys His Met Trp Asn Phe Ile Ser Gly Ile Gln Tyr Leu
    1685                1690                1695

Ala Gly Leu Ser Thr Leu Pro Gly Asn Pro Ala Ile Ala Ser Leu
    1700                1705                1710

Met Ala Phe Thr Ala Ser Ile Thr Ser Pro Leu Thr Thr Leu His
    1715                1720                1725

Thr Leu Leu Phe Asn Ile Leu Gly Gly Trp Val Ala Ala Gln Leu
    1730                1735                1740

Ala Pro Pro Gly Ala Ala Ser Ala Phe Val Gly Ala Gly Ile Ala
    1745                1750                1755
```

```
Gly Ala Ala Val Gly Ser Ile Gly Leu Gly Lys Val Leu Val Asp
    1760            1765                1770

Ile Leu Ala Gly Tyr Gly Ala Gly Val Ala Gly Ala Leu Val Ala
    1775            1780                1785

Phe Lys Val Met Ser Gly Glu Met Pro Ser Thr Glu Asp Leu Val
    1790            1795                1800

Asn Leu Leu Pro Ala Ile Leu Ser Pro Gly Ala Leu Val Val Gly
    1805            1810                1815

Val Val Cys Ala Ala Ile Leu Arg Arg His Val Gly Pro Gly Glu
    1820            1825                1830

Gly Ala Val Gln Trp Met Asn Arg Leu Ile Ala Phe Ala Ser Arg
    1835            1840                1845

Gly Asn His Val Ser Pro Thr His Tyr Val Pro Glu Ser Asp Ala
    1850            1855                1860

Ala Ala Arg Val Thr Gln Ile Leu Ser Ser Leu Thr Ile Thr Gln
    1865            1870                1875

Leu Leu Lys Arg Leu His Gln Trp Ile Asn Lys Asp Cys Ser Thr
    1880            1885                1890

Pro Cys Ser Gly Ser Trp Leu Arg Asp Val Trp Asp Trp Ile Cys
    1895            1900                1905

Thr Val Leu Ser Asp Phe Lys Thr Trp Leu Gln Ser Lys Leu Leu
    1910            1915                1920

Pro Arg Leu Pro Gly Val Pro Phe Leu Ser Cys Gln Arg Gly Tyr
    1925            1930                1935

Lys Gly Val Trp Arg Gly Asp Gly Ile Met Gln Thr Ser Cys Pro
    1940            1945                1950

Cys Gly Ala Gln Ile Ala Gly His Val Lys Asn Gly Ser Met Arg
    1955            1960                1965

Ile Val Gly Pro Lys Thr Cys Ser Asn Thr Trp His Gly Thr Phe
    1970            1975                1980

Pro Ile Asn Ala His Thr Thr Gly Pro Cys Thr Pro Ser Pro Ala
    1985            1990                1995

Pro Asn Tyr Ser Lys Ala Leu Trp Arg Val Ala Ala Glu Glu Tyr
    2000            2005                2010

Val Glu Val Thr Arg Val Gly Asp Phe His Tyr Val Thr Gly Met
    2015            2020                2025

Thr Thr Asp Asn Val Lys Cys Pro Cys Gln Val Pro Ala Pro Glu
    2030            2035                2040

Phe Phe Thr Glu Val Asp Gly Val Arg Leu His Arg Tyr Ala Pro
    2045            2050                2055

Ala Cys Lys Pro Leu Leu Arg Asp Glu Val Thr Phe Gln Val Gly
    2060            2065                2070

Leu Asn Gln Phe Pro Val Gly Ser Gln Leu Pro Cys Glu Pro Glu
    2075            2080                2085

Pro Asp Val Ser Val Leu Thr Ser Met Leu Thr Asp Pro Ser His
    2090            2095                2100

Ile Thr Ala Glu Thr Ala Lys Arg Arg Leu Ala Arg Gly Ser Ser
    2105            2110                2115

Pro Ser Leu Ala Ser Ser Ser Ala Ser Gln Leu Ser Ala Pro Ser
    2120            2125                2130

Leu Lys Ala Thr Cys Thr Thr His His Asp Ser Pro Asp Ala Asp
    2135            2140                2145

Leu Ile Glu Ala Asn Leu Leu Trp Arg Gln Glu Met Gly Gly Asn
    2150            2155                2160
```

```
Ile Thr Arg Val Glu Ser Glu Asn Lys Val Val Ile Leu Asp Ser
2165                2170                2175

Phe Asp Pro Leu Arg Ala Glu Glu Asp Glu Arg Glu Val Ser Val
2180                2185                2190

Ala Ala Glu Ile Leu Arg Lys Thr Arg Lys Phe Pro Pro Ala Met
2195                2200                2205

Pro Ile Trp Ala Arg Pro Asp Tyr Asn Pro Pro Leu Leu Glu Thr
2210                2215                2220

Trp Lys Asp Pro Asp Tyr Val Pro Pro Val Val His Gly Cys Pro
2225                2230                2235

Leu Pro Pro Thr Lys Thr Pro Pro Ile Pro Pro Pro Arg Arg Lys
2240                2245                2250

Lys Thr Val Val Leu Thr Glu Ser Thr Val Ser Ser Ala Leu Ala
2255                2260                2265

Glu Leu Ala Thr Lys Thr Phe Gly Ser Ser Gly Ser Ser Ala Val
2270                2275                2280

Asp Ser Gly Thr Ala Thr Ala Pro Pro Asn Gln Leu Ser Asp Glu
2285                2290                2295

Val Asp Thr Gly Ser Asp Val Glu Ser Tyr Ser Ser Met Pro Pro
2300                2305                2310

Leu Glu Gly Glu Pro Gly Asp Pro Asp Leu Ser Asp Gly Ser Trp
2315                2320                2325

Ser Thr Val Ser Glu Glu Ala Gly Glu Asp Val Val Cys Cys Ser
2330                2335                2340

Met Ser Tyr Thr Trp Thr Gly Ala Leu Ile Thr Pro Cys Ala Ala
2345                2350                2355

Glu Glu Ser Lys Leu Pro Ile Asn Ala Leu Ser Asn Ser Leu Leu
2360                2365                2370

Arg His His Asn Met Val Tyr Ala Thr Thr Ser Arg Ser Ala Ser
2375                2380                2385

Gln Arg Gln Lys Lys Val Thr Phe Asp Arg Leu Gln Val Leu Asp
2390                2395                2400

Asp His Tyr Arg Asp Val Leu Lys Glu Met Lys Ala Lys Ala Ser
2405                2410                2415

Thr Val Lys Ala Lys Leu Leu Ser Val Glu Glu Ala Cys Lys Leu
2420                2425                2430

Thr Pro Pro His Ser Ala Arg Ser Lys Phe Gly Tyr Gly Ala Lys
2435                2440                2445

Asp Val Arg Asn Leu Ser Ser Lys Ala Val Asn His Ile Asn Ser
2450                2455                2460

Val Trp Lys Asp Leu Leu Glu Asp Thr Glu Thr Pro Ile Asp Thr
2465                2470                2475

Thr Ile Met Ala Lys Asn Glu Val Phe Cys Val Gln Pro Glu Lys
2480                2485                2490

Gly Gly Arg Lys Pro Ala Arg Leu Ile Val Tyr Pro Asp Leu Gly
2495                2500                2505

Val Arg Val Cys Glu Lys Met Ala Leu Tyr Asp Val Val Ser Thr
2510                2515                2520

Leu Pro Gln Ala Val Met Gly Ser Ser Tyr Gly Phe Gln Tyr Ser
2525                2530                2535

Pro Gly Gln Arg Val Glu Phe Leu Val Asn Ala Trp Lys Ser Lys
2540                2545                2550

Lys Asn Pro Met Gly Phe Ala Tyr Asp Thr Arg Cys Phe Asp Ser
```

2555                2560                2565

Thr Val Thr Glu Asn Asp Ile Arg Val Glu Glu Ser Ile Tyr Gln
    2570                2575                2580

Cys Cys Asp Leu Ala Pro Glu Ala Arg Gln Val Ile Arg Ser Leu
    2585                2590                2595

Thr Glu Arg Leu Tyr Val Gly Gly Pro Leu Thr Asn Ser Lys Gly
    2600                2605                2610

Gln Asn Cys Gly Tyr Arg Arg Cys Arg Ala Ser Gly Val Leu Thr
    2615                2620                2625

Thr Ser Cys Gly Asn Thr Leu Thr Cys Tyr Leu Lys Ala Ser Ala
    2630                2635                2640

Ala Cys Arg Ala Ala Lys Leu Gln Asp Cys Thr Met Leu Val Cys
    2645                2650                2655

Gly Asp Asp Leu Val Val Ile Cys Glu Ser Ala Gly Thr Gln Glu
    2660                2665                2670

Asp Ala Ala Ser Leu Arg Val Phe Thr Glu Ala Met Thr Arg Tyr
    2675                2680                2685

Ser Ala Pro Pro Gly Asp Pro Pro Arg Pro Glu Tyr Asp Leu Glu
    2690                2695                2700

Leu Ile Thr Ser Cys Ser Ser Asn Val Ser Val Ala His Asp Ala
    2705                2710                2715

Ser Gly Lys Arg Val Tyr Tyr Leu Thr Arg Asp Pro Thr Thr Pro
    2720                2725                2730

Leu Ala Arg Ala Ala Trp Glu Thr Ala Lys His Thr Pro Val Asn
    2735                2740                2745

Ser Trp Leu Gly Asn Ile Ile Met Tyr Ala Pro Thr Leu Trp Ala
    2750                2755                2760

Arg Met Ile Leu Met Thr His Phe Phe Ser Ile Leu Leu Ala Gln
    2765                2770                2775

Glu Gln Leu Glu Lys Ala Leu Asp Cys Gln Ile Tyr Gly Ala Thr
    2780                2785                2790

Tyr Ser Ile Glu Pro Leu Asp Leu Pro Gln Ile Ile Gln Arg Leu
    2795                2800                2805

His Gly Leu Ser Ala Phe Ser Leu His Ser Tyr Ser Pro Gly Glu
    2810                2815                2820

Ile Asn Arg Val Ala Ser Cys Leu Arg Lys Leu Gly Val Pro Pro
    2825                2830                2835

Leu Arg Val Trp Arg His Arg Ala Arg Ser Val Arg Ala Lys Leu
    2840                2845                2850

Leu Ser Gln Gly Gly Arg Ala Ala Thr Cys Gly Lys Tyr Leu Phe
    2855                2860                2865

Asn Trp Ala Val Arg Thr Lys Leu Lys Leu Thr Pro Ile Pro Ala
    2870                2875                2880

Ala Ser Gln Leu Asp Leu Ser Gly Trp Phe Ile Ala Gly Tyr Ser
    2885                2890                2895

Gly Gly Asp Ile Tyr His Ser Leu Ser Arg Ala Arg Pro Arg Trp
    2900                2905                2910

Phe Met Leu Cys Leu Leu Leu Leu Ser Val Gly Val Gly Ile Tyr
    2915                2920                2925

Leu Leu Pro Asn Arg
    2930

<210> SEQ ID NO 99
<211> LENGTH: 9399

```
<212> TYPE: RNA
<213> ORGANISM: GB virus B
<220> FEATURE:
<221> NAME/KEY: CDS
<222> LOCATION: (446)..(9037)

<400> SEQUENCE: 99
accacaaaca cuccaguuug uuacacuccg cuaggaaugc uccuggagca ccccccuag      60 cagggcgugg gggauuuccc cugcccgucu gcagaagggu ggagccaacc accuuaguau   120
guaggcggcg ggacucauga cgcucgcgug augacaagcg ccaagcuuga cuuggauggc   180
ccugaugggc guucauggu ucggguggug uggcgcuuua ggcagccucc acgcccacca    240
ccucccagau agagcggcgg cacuguaggg aagaccgggg accggucacu accaaggacg   300
cagaccucuu uuugaguauc acgccuccgg aaguaguugg gcaagcccac cuauaugugu   360 ugggauggu ggggguuagcc auccauaccg uacugccuga uagggucccuu gcgaggggau    420 cugggagucu cguagaccgu agcac aug ccu guu auu ucu acu caa aca agu     472
                              Met Pro Val Ile Ser Thr Gln Thr Ser
                                1               5 ccu gua ccu gcg ccc aga acg cgc aag aac aag cag acg cag gcu uca     520
Pro Val Pro Ala Pro Arg Thr Arg Lys Asn Lys Gln Thr Gln Ala Ser
 10              15                  20                  25 uau ccu gug ucc auu aaa aca ucu guu gaa agg gga caa cga gca aag     568
Tyr Pro Val Ser Ile Lys Thr Ser Val Glu Arg Gly Gln Arg Ala Lys
             30                  35                  40 cgc aaa guc cag cgc gau gcu cgg ccu cgu aau uac aaa auu gcu ggu     616
Arg Lys Val Gln Arg Asp Ala Arg Pro Arg Asn Tyr Lys Ile Ala Gly
         45                  50                  55 auc cau gau ggc uug cag aca uug gcu cag gcu gcu uug cca gcu cau     664
Ile His Asp Gly Leu Gln Thr Leu Ala Gln Ala Ala Leu Pro Ala His
     60                  65                  70 ggu gga cgc caa gac ccu cgc cau aag ucu cgc aau cuu gga auc         712
Gly Trp Gly Arg Gln Asp Pro Arg His Lys Ser Arg Asn Leu Gly Ile
 75                  80                  85 cuu cug gau uac ccu uug ggg ugg auu ggu gau guu aca acu cac aca     760
Leu Leu Asp Tyr Pro Leu Gly Trp Ile Gly Asp Val Thr Thr His Thr
 90                  95                 100                 105 ccu cua gua ggc ccg cug gug gca gga gcg guc guu cga cca guc ugc     808
Pro Leu Val Gly Pro Leu Val Ala Gly Ala Val Val Arg Pro Val Cys
             110                 115                 120 cag aua gua cgc uug cug gag gau gga guc aac ugg gcu acu ggu ugg     856
Gln Ile Val Arg Leu Leu Glu Asp Gly Val Asn Trp Ala Thr Gly Trp
         125                 130                 135 uuc ggu guc cac cuu uuu gug gua ugu cug cua ucu uug gcc ugu ccc     904
Phe Gly Val His Leu Phe Val Val Cys Leu Leu Ser Leu Ala Cys Pro
     140                 145                 150 ugu agu ggg gcg cgg guc acu gac cca gac aca aau acc aca auc cug     952
Cys Ser Gly Ala Arg Val Thr Asp Pro Asp Thr Asn Thr Thr Ile Leu
 155                 160                 165 acc aau ugc ugc cag cgu aau cag guu auc uau ugu ucu ccu ucc acu    1000
Thr Asn Cys Cys Gln Arg Asn Gln Val Ile Tyr Cys Ser Pro Ser Thr
 170                 175                 180                 185 ugc cua cac gag ccu ggu ugu gug auc ugu gcg gac gag ugc ugg guu    1048
Cys Leu His Glu Pro Gly Cys Val Ile Cys Ala Asp Glu Cys Trp Val
             190                 195                 200 ccc gcc aau ccg uac auc uca cac ccu ucc aau ugg acu ggc acg gac    1096
Pro Ala Asn Pro Tyr Ile Ser His Pro Ser Asn Trp Thr Gly Thr Asp
         205                 210                 215 ucc uuc uug gcu gac cac auu gau uuu guu aug ggc gcu cuu gug acc    1144
Ser Phe Leu Ala Asp His Ile Asp Phe Val Met Gly Ala Leu Val Thr
```

```
             220                 225                 230
ugu gac gcc cuu gac auu ggu gag uug ugu ggu gcg ugu gua uua guc    1192
Cys Asp Ala Leu Asp Ile Gly Glu Leu Cys Gly Ala Cys Val Leu Val
            235                 240                 245 ggu gac ugg cuu guc agg cac ugg cuu auu cac aua gac cuc aau gaa    1240
Gly Asp Trp Leu Val Arg His Trp Leu Ile His Ile Asp Leu Asn Glu
250                 255                 260                 265 acu ggu acu ugu uac cug gaa gug ccc acu gga aua gau ccu ggg uuc    1288
Thr Gly Thr Cys Tyr Leu Glu Val Pro Thr Gly Ile Asp Pro Gly Phe
                270                 275                 280 cua ggg uuu auc ggg ugg aug gcc ggc aag guc gag gcu guc auc uuc    1336
Leu Gly Phe Ile Gly Trp Met Ala Gly Lys Val Glu Ala Val Ile Phe
            285                 290                 295 uug acc aaa cug gcu uca caa gua cca uac gcu auu gcg acu aug uuu    1384
Leu Thr Lys Leu Ala Ser Gln Val Pro Tyr Ala Ile Ala Thr Met Phe
        300                 305                 310 agc agu gua cac uac cug gcg guu ggc gcu cug auc uac uau gcc ucu    1432
Ser Ser Val His Tyr Leu Ala Val Gly Ala Leu Ile Tyr Tyr Ala Ser
    315                 320                 325 cgg ggc aag ugg uau cag uug cuc cua gcg cuu aug cuu uac aua gaa    1480
Arg Gly Lys Trp Tyr Gln Leu Leu Leu Ala Leu Met Leu Tyr Ile Glu
330                 335                 340                 345 gcg acc ucu gga aac ccc auc agg gug ccc acu gga ugc uca aua gcu    1528
Ala Thr Ser Gly Asn Pro Ile Arg Val Pro Thr Gly Cys Ser Ile Ala
                350                 355                 360 gag uuu ugc ucg ccu uug aug aua cca ugu ccu ugc cac ucu uau uug    1576
Glu Phe Cys Ser Pro Leu Met Ile Pro Cys Pro Cys His Ser Tyr Leu
            365                 370                 375 agu gag aau gug uca gaa guc auu ugu uac agu cca aag ugg acc agg    1624
Ser Glu Asn Val Ser Glu Val Ile Cys Tyr Ser Pro Lys Trp Thr Arg
        380                 385                 390 ccu auc acu cua gag uau aac aac ucc aua ucu ugg uac ccc uau aca    1672
Pro Ile Thr Leu Glu Tyr Asn Asn Ser Ile Ser Trp Tyr Pro Tyr Thr
    395                 400                 405 auc ccu ggu gcg agg gga ugu aug guu aaa uuc aaa aau aac aca ugg    1720
Ile Pro Gly Ala Arg Gly Cys Met Val Lys Phe Lys Asn Asn Thr Trp
410                 415                 420                 425 ggu ugc ugc cgu auu cgc aau gug cca ucg uac ugc acu aug ggc acu    1768
Gly Cys Cys Arg Ile Arg Asn Val Pro Ser Tyr Cys Thr Met Gly Thr
                430                 435                 440 gau gca gug ugg aac gac acu cgc aac acu uac gaa gca ugc ggu gua    1816
Asp Ala Val Trp Asn Asp Thr Arg Asn Thr Tyr Glu Ala Cys Gly Val
            445                 450                 455 aca cca ugg cua aca acc gca ugg cac aac ggc uca gcc cug aaa uug    1864
Thr Pro Trp Leu Thr Thr Ala Trp His Asn Gly Ser Ala Leu Lys Leu
        460                 465                 470 gcu aua uua caa uac ccu ggg ucu aaa gaa aug uuu aaa ccu cau aau    1912
Ala Ile Leu Gln Tyr Pro Gly Ser Lys Glu Met Phe Lys Pro His Asn
    475                 480                 485 ugg aug uca ggc cau uug uau uuu gag gga uca gau acc ccu aua guu    1960
Trp Met Ser Gly His Leu Tyr Phe Glu Gly Ser Asp Thr Pro Ile Val
490                 495                 500                 505 uac uuu uau gac ccu gug aau ucc acu cuc cua cca ccg gag agg ugg    2008
Tyr Phe Tyr Asp Pro Val Asn Ser Thr Leu Leu Pro Pro Glu Arg Trp
                510                 515                 520 gcu agg uug ccc ggu acc cca ccu gug gua cgu ggu ucu ugg uua cag    2056
Ala Arg Leu Pro Gly Thr Pro Pro Val Val Arg Gly Ser Trp Leu Gln
            525                 530                 535 guu ccg caa ggg uuu uac agu gau gug aaa gac cua gcc aca gga uug    2104
Val Pro Gln Gly Phe Tyr Ser Asp Val Lys Asp Leu Ala Thr Gly Leu
```

-continued

```
              540                 545                 550
auc acc aaa gac aaa gcc ugg aaa aau uau cag guc uua uau ucc gcc    2152
Ile Thr Lys Asp Lys Ala Trp Lys Asn Tyr Gln Val Leu Tyr Ser Ala
    555                 560                 565 acg ggu gcu uug ucu cuu acg gga guu acc acc aag gcc gug gug cua    2200
Thr Gly Ala Leu Ser Leu Thr Gly Val Thr Thr Lys Ala Val Val Leu
570                 575                 580                 585 auu cug uug ggg uug ugu ggc agc aag uau cuu auu uua gcc uac cuc    2248
Ile Leu Leu Gly Leu Cys Gly Ser Lys Tyr Leu Ile Leu Ala Tyr Leu
                590                 595                 600 ugu uac uug ucc cuu ugu uuu ggg cgc gcu ucu ggu uac ccu uug cgu    2296
Cys Tyr Leu Ser Leu Cys Phe Gly Arg Ala Ser Gly Tyr Pro Leu Arg
            605                 610                 615 ccu gug cuc cca ucc cag ucg uau cuc caa gcu ggc ugg gau guu uug    2344
Pro Val Leu Pro Ser Gln Ser Tyr Leu Gln Ala Gly Trp Asp Val Leu
        620                 625                 630 ucu aaa gcu caa gua gcu ccu uuu gcu uug auu uuc uuc auc ugu ugc    2392
Ser Lys Ala Gln Val Ala Pro Phe Ala Leu Ile Phe Phe Ile Cys Cys
    635                 640                 645 uau cuc cgc ugc agg cua cgu uau gcu gcc cuu uua ggg uuu gug ccc    2440
Tyr Leu Arg Cys Arg Leu Arg Tyr Ala Ala Leu Leu Gly Phe Val Pro
650                 655                 660                 665 aug gcu gcg ggc uug ccc cua acu uuc uuu guu gca gca gcu gcu gcc    2488
Met Ala Ala Gly Leu Pro Leu Thr Phe Phe Val Ala Ala Ala Ala Ala
                670                 675                 680 caa cca gau uau gac ugg ugg gug cga cug cua gug gca ggg uua guu    2536
Gln Pro Asp Tyr Asp Trp Trp Val Arg Leu Leu Val Ala Gly Leu Val
            685                 690                 695 uug ugg gcc ggc cgu aac cgu ggu cac cgc aua gcu cug cuu gua ggu    2584
Leu Trp Ala Gly Arg Asn Arg Gly His Arg Ile Ala Leu Leu Val Gly
        700                 705                 710 ccu ugg ccu cug gua gcg cuu uua acc cuc uug cau uug guu acg ccu    2632
Pro Trp Pro Leu Val Ala Leu Leu Thr Leu Leu His Leu Val Thr Pro
    715                 720                 725 gcu uca gcu uuu gau acc gag aua auu gga ggg cug aca aua cca ccu    2680
Ala Ser Ala Phe Asp Thr Glu Ile Ile Gly Gly Leu Thr Ile Pro Pro
730                 735                 740                 745 gua gua gca uua guu guc aug ucu cgu uuu ggc uuc uuu gcu cac uug    2728
Val Val Ala Leu Val Val Met Ser Arg Phe Gly Phe Phe Ala His Leu
                750                 755                 760 uua ccu cgc ugu gcu uua guu aac ucc uau cuu ugg caa cgu ugg gag    2776
Leu Pro Arg Cys Ala Leu Val Asn Ser Tyr Leu Trp Gln Arg Trp Glu
            765                 770                 775 aau ugg uuu ugg aac guu aca cua aga ccg gag agg uuu uuc cuu gug    2824
Asn Trp Phe Trp Asn Val Thr Leu Arg Pro Glu Arg Phe Phe Leu Val
        780                 785                 790 cug guu ugu uuc ccc ggu gcg aca uau gac gcg cug gug acu uuc ugu    2872
Leu Val Cys Phe Pro Gly Ala Thr Tyr Asp Ala Leu Val Thr Phe Cys
    795                 800                 805 gug ugu cac gua gcu cuu cua ugu uua aca ucc agu gca gca ucg uuc    2920
Val Cys His Val Ala Leu Leu Cys Leu Thr Ser Ser Ala Ala Ser Phe
810                 815                 820                 825 uuu ggg acu gac ucu agg guu agg gcc cau aga aug uug gug cgu cuc    2968
Phe Gly Thr Asp Ser Arg Val Arg Ala His Arg Met Leu Val Arg Leu
                830                 835                 840 gga aag ugu cau gcu ugg uau ucu cau uau guu cuu aag uuu uuc cuc    3016
Gly Lys Cys His Ala Trp Tyr Ser His Tyr Val Leu Lys Phe Phe Leu
            845                 850                 855 uua gug uuu ggu gag aau ggu gug uuc uau aag cac uug cau ggu        3064
Leu Val Phe Gly Glu Asn Gly Val Phe Tyr Lys His Leu His Gly
```

-continued

```
              860                 865                 870
gau guc uug ccu aau gau uuu gcc ucg aaa cua cca uug caa gag cca      3112
Asp Val Leu Pro Asn Asp Phe Ala Ser Lys Leu Pro Leu Gln Glu Pro
    875                 880                 885 uuu uuc ccu uuu gaa ggc aag gca agg guc uau agg aau gaa gga aga      3160
Phe Phe Pro Phe Glu Gly Lys Ala Arg Val Tyr Arg Asn Glu Gly Arg
890                 895                 900                 905 cgc uug gcg ugu ggg gac acg guu gau ggu uug ccc guu guu gcg cgu      3208
Arg Leu Ala Cys Gly Asp Thr Val Asp Gly Leu Pro Val Val Ala Arg
                910                 915                 920 cuc ggc gac cuu guu uuc gca ggg uug gcu aug ccg cca gau ggg ugg      3256
Leu Gly Asp Leu Val Phe Ala Gly Leu Ala Met Pro Pro Asp Gly Trp
            925                 930                 935 gcc auu acc gca ccu uuu acg cug cag ugu cuc ucu gaa cgu ggc acg      3304
Ala Ile Thr Ala Pro Phe Thr Leu Gln Cys Leu Ser Glu Arg Gly Thr
        940                 945                 950 cug uca gcg aug gca gug guc aug acu ggu aua gac ccc cga acu ugg      3352
Leu Ser Ala Met Ala Val Val Met Thr Gly Ile Asp Pro Arg Thr Trp
    955                 960                 965 acu gga acu auc uuc aga uua gga ucu cug gcc acu agc uac aug gga      3400
Thr Gly Thr Ile Phe Arg Leu Gly Ser Leu Ala Thr Ser Tyr Met Gly
970                 975                 980                 985 uuu guu ugu gac aac gug uug uau acu gcu cac cau ggc agc aag  ggg     3448
Phe Val Cys Asp Asn Val Leu Tyr Thr Ala His His Gly Ser Lys  Gly
                990                 995                 1000 cgc cgg uug gcu  cau ccc aca ggc ucu  aua cac cca aua acc  guu       3493
Arg Arg Leu Ala  His Pro Thr Gly Ser  Ile His Pro Ile Thr  Val
                1005                 1010                 1015 gac gcg gcu aau  gac cag gac auc uau  caa cca cca ugu gga  gcu       3538
Asp Ala Ala Asn  Asp Gln Asp Ile Tyr  Gln Pro Pro Cys Gly  Ala
                1020                 1025                 1030 ggg ucc cuu acu  cgg ugc ucu ugc ggg  gag acc aag ggg uau  cug       3583
Gly Ser Leu Thr  Arg Cys Ser Cys Gly  Glu Thr Lys Gly Tyr  Leu
                1035                 1040                 1045 gua aca cga cug  ggg uca uug guu gag  guc aac aaa ucc gau  gac       3628
Val Thr Arg Leu  Gly Ser Leu Val Glu  Val Asn Lys Ser Asp  Asp
                1050                 1055                 1060 ccu uau ugg ugu  gug ugc ggg gcc cuu  ccc aug gcu guu gcc  aag       3673
Pro Tyr Trp Cys  Val Cys Gly Ala Leu  Pro Met Ala Val Ala  Lys
                1065                 1070                 1075 ggu ucu uca ggu  gcc ccg auu cug ugc  ucc ucc ggg cau guu  auu       3718
Gly Ser Ser Gly  Ala Pro Ile Leu Cys  Ser Ser Gly His Val  Ile
                1080                 1085                 1090 ggg aug uuc acc  gcu gcu aga aau ucu  ggc ggu uca guc agu  cag       3763
Gly Met Phe Thr  Ala Ala Arg Asn Ser  Gly Gly Ser Val Ser  Gln
                1095                 1100                 1105 auu agg guu agg  ccg uug gug ugu gcu  gga uac cau ccc cag  uac       3808
Ile Arg Val Arg  Pro Leu Val Cys Ala  Gly Tyr His Pro Gln  Tyr
                1110                 1115                 1120 aca gca cau gcc  acu cuu gau aca aaa  ccu acu gug ccu aac  gag       3853
Thr Ala His Ala  Thr Leu Asp Thr Lys  Pro Thr Val Pro Asn  Glu
                1125                 1130                 1135 uau uca gug caa  auu uua auu gcc ccc  acu ggc agc ggc aag  uca       3898
Tyr Ser Val Gln  Ile Leu Ile Ala Pro  Thr Gly Ser Gly Lys  Ser
                1140                 1145                 1150 acc aaa uua cca  cuu ucu uac aug cag  gag aag uau gag guc  uug       3943
Thr Lys Leu Pro  Leu Ser Tyr Met Gln  Glu Lys Tyr Glu Val  Leu
                1155                 1160                 1165 guc cua aau ccc  agu gug gcu aca aca  gca uca aug cca aag  uac       3988
Val Leu Asn Pro  Ser Val Ala Thr Thr  Ala Ser Met Pro Lys  Tyr
```

```
                  1170              1175              1180
aug cac gcg acg uac ggc gug aau cca aau ugc uau uuu aau ggc       4033
Met His Ala Thr Tyr Gly Val Asn Pro Asn Cys Tyr Phe Asn Gly
                  1185              1190              1195 aaa ugu acc aac aca ggg gcu uca cuu acg uac agc aca uau ggc       4078
Lys Cys Thr Asn Thr Gly Ala Ser Leu Thr Tyr Ser Thr Tyr Gly
                  1200              1205              1210 aug uac cug acc gga gca ugu ucc cgg aac uau gau gua auc auu       4123
Met Tyr Leu Thr Gly Ala Cys Ser Arg Asn Tyr Asp Val Ile Ile
                  1215              1220              1225 ugu gac gaa ugc cau gcu acc gau gca acc acc gug uug ggc auu       4168
Cys Asp Glu Cys His Ala Thr Asp Ala Thr Thr Val Leu Gly Ile
                  1230              1235              1240 gga aag guc cua acc gaa gcu cca ucc aaa aau guu agg cua gug       4213
Gly Lys Val Leu Thr Glu Ala Pro Ser Lys Asn Val Arg Leu Val
                  1245              1250              1255 guu cuu gcc acg gcu acc ccc ccu gga gua auc ccu aca cca cau       4258
Val Leu Ala Thr Ala Thr Pro Pro Gly Val Ile Pro Thr Pro His
                  1260              1265              1270 gcc aac aua acu gag auu caa uua acc gau gaa ggc acu auc ccc       4303
Ala Asn Ile Thr Glu Ile Gln Leu Thr Asp Glu Gly Thr Ile Pro
                  1275              1280              1285 uuu cau gga aaa aag auu aag gag gaa aau cug aag aaa ggg aga       4348
Phe His Gly Lys Lys Ile Lys Glu Glu Asn Leu Lys Lys Gly Arg
                  1290              1295              1300 cac cuu auc uuu gag gcu acc aaa aaa cac ugu gau gag cuu gcu       4393
His Leu Ile Phe Glu Ala Thr Lys Lys His Cys Asp Glu Leu Ala
                  1305              1310              1315 aac gag uua gcu cga aag gga aua aca gcu guc ucu uac uau agg       4438
Asn Glu Leu Ala Arg Lys Gly Ile Thr Ala Val Ser Tyr Tyr Arg
                  1320              1325              1330 gga ugu gac auc uca aaa auc ccu gag ggc gac ugu gua gua guu       4483
Gly Cys Asp Ile Ser Lys Ile Pro Glu Gly Asp Cys Val Val Val
                  1335              1340              1345 gcc acu gau gcc uug ugu aca ggg uac acu ggu gac uuu gau ucc       4528
Ala Thr Asp Ala Leu Cys Thr Gly Tyr Thr Gly Asp Phe Asp Ser
                  1350              1355              1360 gug uau gac ugc agc cuc aug gua gaa ggc aca ugc cau guu gac       4573
Val Tyr Asp Cys Ser Leu Met Val Glu Gly Thr Cys His Val Asp
                  1365              1370              1375 cuu gac ccu acu uuc acc aug ggu guu cgu gug ugc ggg guu uca       4618
Leu Asp Pro Thr Phe Thr Met Gly Val Arg Val Cys Gly Val Ser
                  1380              1385              1390 gca aua guu aaa ggc cag cgu agg ggc cgc aca ggc cgu ggg aga       4663
Ala Ile Val Lys Gly Gln Arg Arg Gly Arg Thr Gly Arg Gly Arg
                  1395              1400              1405 gcu ggc aua uac uac uau gua gac ggg agu ugu acc ccu ucg ggu       4708
Ala Gly Ile Tyr Tyr Tyr Val Asp Gly Ser Cys Thr Pro Ser Gly
                  1410              1415              1420 aug guu ccu gaa ugc aac auu guu gaa gcc uuc gac gca gcc aag       4753
Met Val Pro Glu Cys Asn Ile Val Glu Ala Phe Asp Ala Ala Lys
                  1425              1430              1435 gca ugg uau ggu uug uca uca aca gaa gcu caa acu auu cug gac       4798
Ala Trp Tyr Gly Leu Ser Ser Thr Glu Ala Gln Thr Ile Leu Asp
                  1440              1445              1450 acc uau cgc acc caa ccu ggg uua ccu gcg aua gga gca aau uug       4843
Thr Tyr Arg Thr Gln Pro Gly Leu Pro Ala Ile Gly Ala Asn Leu
                  1455              1460              1465 gac gag ugg gcu gau cuc uuu ucu aug guc aac ccc gaa ccu uca       4888
Asp Glu Trp Ala Asp Leu Phe Ser Met Val Asn Pro Glu Pro Ser
```

-continued

|  |  |  |  |  |  |  |  |  |  |  |  |  |
|---|---|---|---|---|---|---|---|---|---|---|---|---|
|  |  | 1470 |  |  | 1475 |  |  | 1480 |  |  |  |  |
| uuu | guc | aau | acu | gca | aaa | aga | acu | gcu | gac | aau | uau | guu | uug | uug | 4933 |
| Phe | Val | Asn | Thr | Ala | Lys | Arg | Thr | Ala | Asp | Asn | Tyr | Val | Leu | Leu |  |
|  |  | 1485 |  |  | 1490 |  |  | 1495 |  |  |  |  |
| acu | gca | gcc | caa | cua | caa | cug | ugu | cau | cag | uau | ggc | uau | gcu | gcu | 4978 |
| Thr | Ala | Ala | Gln | Leu | Gln | Leu | Cys | His | Gln | Tyr | Gly | Tyr | Ala | Ala |  |
|  |  | 1500 |  |  | 1505 |  |  | 1510 |  |  |  |  |
| ccc | aau | gac | gca | cca | cgg | ugg | cag | gga | gcc | cgg | cuu | ggg | aaa | aaa | 5023 |
| Pro | Asn | Asp | Ala | Pro | Arg | Trp | Gln | Gly | Ala | Arg | Leu | Gly | Lys | Lys |  |
|  |  | 1515 |  |  | 1520 |  |  | 1525 |  |  |  |  |
| ccu | ugu | ggg | guu | cug | ugg | cgc | uug | gac | ggc | gcu | gac | gcc | ugu | ccu | 5068 |
| Pro | Cys | Gly | Val | Leu | Trp | Arg | Leu | Asp | Gly | Ala | Asp | Ala | Cys | Pro |  |
|  |  | 1530 |  |  | 1535 |  |  | 1540 |  |  |  |  |
| ggc | cca | gag | ccc | agc | gag | gug | acc | aga | uac | caa | aug | ugc | uuc | acu | 5113 |
| Gly | Pro | Glu | Pro | Ser | Glu | Val | Thr | Arg | Tyr | Gln | Met | Cys | Phe | Thr |  |
|  |  | 1545 |  |  | 1550 |  |  | 1555 |  |  |  |  |
| gaa | guc | aau | acu | ucu | ggg | aca | gcc | gca | cuc | gcu | guu | ggc | guu | gga | 5158 |
| Glu | Val | Asn | Thr | Ser | Gly | Thr | Ala | Ala | Leu | Ala | Val | Gly | Val | Gly |  |
|  |  | 1560 |  |  | 1565 |  |  | 1570 |  |  |  |  |
| gug | gcu | aug | gcu | uau | cua | gcc | auu | gac | acu | uuu | ggc | gcc | acu | ugu | 5203 |
| Val | Ala | Met | Ala | Tyr | Leu | Ala | Ile | Asp | Thr | Phe | Gly | Ala | Thr | Cys |  |
|  |  | 1575 |  |  | 1580 |  |  | 1585 |  |  |  |  |
| gug | cgg | cgu | ugc | ugg | ucu | auu | aca | uca | guc | ccu | acc | ggu | gcu | acu | 5248 |
| Val | Arg | Arg | Cys | Trp | Ser | Ile | Thr | Ser | Val | Pro | Thr | Gly | Ala | Thr |  |
|  |  | 1590 |  |  | 1595 |  |  | 1600 |  |  |  |  |
| guc | gcc | cca | gug | guu | gac | gaa | gaa | gaa | auc | gug | gag | gag | ugu | gca | 5293 |
| Val | Ala | Pro | Val | Val | Asp | Glu | Glu | Glu | Ile | Val | Glu | Glu | Cys | Ala |  |
|  |  | 1605 |  |  | 1610 |  |  | 1615 |  |  |  |  |
| uca | uuc | auu | ccc | uug | gag | gcc | aug | guu | gcu | gca | auu | gac | aag | cug | 5338 |
| Ser | Phe | Ile | Pro | Leu | Glu | Ala | Met | Val | Ala | Ala | Ile | Asp | Lys | Leu |  |
|  |  | 1620 |  |  | 1625 |  |  | 1630 |  |  |  |  |
| aag | agu | aca | auc | acc | aca | acu | agu | ccu | uuc | aca | uug | gaa | acc | gcc | 5383 |
| Lys | Ser | Thr | Ile | Thr | Thr | Thr | Ser | Pro | Phe | Thr | Leu | Glu | Thr | Ala |  |
|  |  | 1635 |  |  | 1640 |  |  | 1645 |  |  |  |  |
| cuu | gaa | aaa | cuu | aac | acc | uuu | cuu | ggg | ccu | cau | gca | gcu | aca | auc | 5428 |
| Leu | Glu | Lys | Leu | Asn | Thr | Phe | Leu | Gly | Pro | His | Ala | Ala | Thr | Ile |  |
|  |  | 1650 |  |  | 1655 |  |  | 1660 |  |  |  |  |
| cuu | gcu | auc | aua | gag | uau | ugc | ugu | ggu | uua | guc | acu | uua | ccu | gac | 5473 |
| Leu | Ala | Ile | Ile | Glu | Tyr | Cys | Cys | Gly | Leu | Val | Thr | Leu | Pro | Asp |  |
|  |  | 1665 |  |  | 1670 |  |  | 1675 |  |  |  |  |
| aau | ccc | uuu | gca | uca | ugc | gug | uuu | gcu | uuc | auu | gcg | ggu | auu | acu | 5518 |
| Asn | Pro | Phe | Ala | Ser | Cys | Val | Phe | Ala | Phe | Ile | Ala | Gly | Ile | Thr |  |
|  |  | 1680 |  |  | 1685 |  |  | 1690 |  |  |  |  |
| acc | cca | cua | ccu | cac | aag | auc | aaa | aug | uuc | cug | uca | uua | uuu | gga | 5563 |
| Thr | Pro | Leu | Pro | His | Lys | Ile | Lys | Met | Phe | Leu | Ser | Leu | Phe | Gly |  |
|  |  | 1695 |  |  | 1700 |  |  | 1705 |  |  |  |  |
| ggc | gca | auu | gcg | ucc | aag | cuu | aca | gac | gcu | aga | ggc | gca | cug | gcg | 5608 |
| Gly | Ala | Ile | Ala | Ser | Lys | Leu | Thr | Asp | Ala | Arg | Gly | Ala | Leu | Ala |  |
|  |  | 1710 |  |  | 1715 |  |  | 1720 |  |  |  |  |
| uuc | aug | aug | gcc | ggg | gcu | gcg | gga | aca | gcu | cuu | ggu | aca | ugg | aca | 5653 |
| Phe | Met | Met | Ala | Gly | Ala | Ala | Gly | Thr | Ala | Leu | Gly | Thr | Trp | Thr |  |
|  |  | 1725 |  |  | 1730 |  |  | 1735 |  |  |  |  |
| ucg | gug | ggu | uuu | guc | uuu | gac | aug | cua | ggc | ggc | uau | gcu | gcc | gcc | 5698 |
| Ser | Val | Gly | Phe | Val | Phe | Asp | Met | Leu | Gly | Gly | Tyr | Ala | Ala | Ala |  |
|  |  | 1740 |  |  | 1745 |  |  | 1750 |  |  |  |  |
| uca | ucc | acu | gcu | ugc | uug | aca | uuu | aaa | ugc | uug | aug | ggu | gag | ugg | 5743 |
| Ser | Ser | Thr | Ala | Cys | Leu | Thr | Phe | Lys | Cys | Leu | Met | Gly | Glu | Trp |  |
|  |  | 1755 |  |  | 1760 |  |  | 1765 |  |  |  |  |
| ccc | acu | aug | gau | cag | cuu | gcu | ggu | uua | guc | uac | ucc | gcg | uuc | aau | 5788 |
| Pro | Thr | Met | Asp | Gln | Leu | Ala | Gly | Leu | Val | Tyr | Ser | Ala | Phe | Asn |  |

-continued

```
                 1770                      1775                      1780
ccg gcc gca gga guu gug ggc guc uug uca gcu ugu gca aug uuu          5833
Pro Ala Ala Gly Val Val Gly Val Leu Ser Ala Cys Ala Met Phe
                 1785                      1790                      1795
gcu uug aca aca gca ggg cca gau cac ugg ccc aac aga cuu cuu          5878
Ala Leu Thr Thr Ala Gly Pro Asp His Trp Pro Asn Arg Leu Leu
                 1800                      1805                      1810
acu aug cuu gcu agg agc aac acu gua ugu aau gag uac uuu auu          5923
Thr Met Leu Ala Arg Ser Asn Thr Val Cys Asn Glu Tyr Phe Ile
                 1815                      1820                      1825
gcc acu cgu gac auc cgc agg aag aua cug ggc auu cug gag gca          5968
Ala Thr Arg Asp Ile Arg Arg Lys Ile Leu Gly Ile Leu Glu Ala
                 1830                      1835                      1840
ucu acc ccc ugg agu guc aua uca gcu ugc auc cgu ugg cuc cac          6013
Ser Thr Pro Trp Ser Val Ile Ser Ala Cys Ile Arg Trp Leu His
                 1845                      1850                      1855
acc ccg acg gag gau gau ugc ggc cuc auu gcu ugg ggu cua gag          6058
Thr Pro Thr Glu Asp Asp Cys Gly Leu Ile Ala Trp Gly Leu Glu
                 1860                      1865                      1870
auu ugg cag uau gug ugc aau uuc uuu gug auu ugc uuu aau guc          6103
Ile Trp Gln Tyr Val Cys Asn Phe Phe Val Ile Cys Phe Asn Val
                 1875                      1880                      1885
cuu aaa gcu gga guu cag agc aug guu aac auu ccu ggu ugu ccu          6148
Leu Lys Ala Gly Val Gln Ser Met Val Asn Ile Pro Gly Cys Pro
                 1890                      1895                      1900
uuc uac agc ugc cag aag ggg uac aag ggc ccc ugg auu gga uca          6193
Phe Tyr Ser Cys Gln Lys Gly Tyr Lys Gly Pro Trp Ile Gly Ser
                 1905                      1910                      1915
ggu aug cuc caa gca cgc ugu cca ugc ggu gcu gaa cuc auc uuu          6238
Gly Met Leu Gln Ala Arg Cys Pro Cys Gly Ala Glu Leu Ile Phe
                 1920                      1925                      1930
ucu guu gag aau ggu uuu gca aaa cuu uac aaa gga ccc aga acu          6283
Ser Val Glu Asn Gly Phe Ala Lys Leu Tyr Lys Gly Pro Arg Thr
                 1935                      1940                      1945
ugu uca aau uac ugg aga ggg gcu guu cca guc aac gcu agg cug          6328
Cys Ser Asn Tyr Trp Arg Gly Ala Val Pro Val Asn Ala Arg Leu
                 1950                      1955                      1960
ugu ggg ucg gcu aga ccg gac cca acu gau ugg acu agu cuu guc          6373
Cys Gly Ser Ala Arg Pro Asp Pro Thr Asp Trp Thr Ser Leu Val
                 1965                      1970                      1975
guc aau uau ggc guu agg gac uac ugu aaa uau gag aaa aug gga          6418
Val Asn Tyr Gly Val Arg Asp Tyr Cys Lys Tyr Glu Lys Met Gly
                 1980                      1985                      1990
gau cac auu uuu guu aca gca gua ucc ucu cca aau guc ugu uuc          6463
Asp His Ile Phe Val Thr Ala Val Ser Ser Pro Asn Val Cys Phe
                 1995                      2000                      2005
acc cag gug ccc cca acc uug aga gcu gca gug gcc gug gac ggc          6508
Thr Gln Val Pro Pro Thr Leu Arg Ala Ala Val Ala Val Asp Gly
                 2010                      2015                      2020
gua cag guu cag ugu uau cua ggu gag ccc aaa acu ccu ugg acg          6553
Val Gln Val Gln Cys Tyr Leu Gly Glu Pro Lys Thr Pro Trp Thr
                 2025                      2030                      2035
aca ucu gcu ugc ugu uac ggu ccu gac ggu aag ggu aaa acu guu          6598
Thr Ser Ala Cys Cys Tyr Gly Pro Asp Gly Lys Gly Lys Thr Val
                 2040                      2045                      2050
aag cuu ccc uuc cgc guu gac ggu cac aca ccu ggu gug cgc aug          6643
Lys Leu Pro Phe Arg Val Asp Gly His Thr Pro Gly Val Arg Met
                 2055                      2060                      2065
caa cuu aau uug cgu gau gca cuu gag aca aau gac ugu aau ucc          6688
Gln Leu Asn Leu Arg Asp Ala Leu Glu Thr Asn Asp Cys Asn Ser
```

-continued

|  | 2070 | | | | | 2075 | | | | | 2080 | | | |
|---|---|---|---|---|---|---|---|---|---|---|---|---|---|---|
| aca<br>Thr | aac<br>Asn | aac<br>Asn<br>2085 | acu<br>Thr | ccu<br>Pro | agu<br>Ser | gau<br>Asp<br>2090 | gaa<br>Glu | gcc<br>Ala | gca<br>Ala | gug<br>Val<br>2095 | ucc<br>Ser | gcu<br>Ala | cuu<br>Leu | guu<br>Val | 6733 |
| uuc<br>Phe | aaa<br>Lys | cag<br>Gln<br>2100 | gag<br>Glu | uug<br>Leu | cgg<br>Arg | cgu<br>Arg<br>2105 | aca<br>Thr | aac<br>Asn | caa<br>Gln | uug<br>Leu<br>2110 | cuu<br>Leu | gag<br>Glu | gca<br>Ala | auu<br>Ile | 6778 |
| uca<br>Ser | gcu<br>Ala | ggc<br>Gly<br>2115 | guu<br>Val | gac<br>Asp | acc<br>Thr | acc<br>Thr<br>2120 | aaa<br>Lys | cug<br>Leu | cca<br>Pro | gcc<br>Ala<br>2125 | ccc<br>Pro | ucc<br>Ser | auc<br>Ile | gaa<br>Glu | 6823 |
| gag<br>Glu | gua<br>Val | gug<br>Val<br>2130 | gua<br>Val | aga<br>Arg | aag<br>Lys | cgc<br>Arg<br>2135 | cag<br>Gln | uuc<br>Phe | cgg<br>Arg | gca<br>Ala<br>2140 | aga<br>Arg | acu<br>Thr | ggu<br>Gly | ucg<br>Ser | 6868 |
| cuu<br>Leu | acc<br>Thr | uug<br>Leu<br>2145 | ccu<br>Pro | ccc<br>Pro | ccu<br>Pro | ccg<br>Pro<br>2150 | aga<br>Arg | ucc<br>Ser | guc<br>Val | cca<br>Pro<br>2155 | gga<br>Gly | gug<br>Val | uca<br>Ser | ugu<br>Cys | 6913 |
| ccu<br>Pro | gaa<br>Glu | agc<br>Ser<br>2160 | cug<br>Leu | caa<br>Gln | cga<br>Arg | agu<br>Ser<br>2165 | gac<br>Asp | ccg<br>Pro | uua<br>Leu | gaa<br>Glu<br>2170 | ggu<br>Gly | ccu<br>Pro | uca<br>Ser | aac<br>Asn | 6958 |
| cuc<br>Leu | ccu<br>Pro | ccu<br>Pro<br>2175 | uca<br>Ser | cca<br>Pro | ccu<br>Pro | guu<br>Val<br>2180 | cua<br>Leu | cag<br>Gln | uug<br>Leu | gcc<br>Ala<br>2185 | aug<br>Met | ccg<br>Pro | aug<br>Met | ccc<br>Pro | 7003 |
| cug<br>Leu | uug<br>Leu | gga<br>Gly<br>2190 | gcg<br>Ala | ggu<br>Gly | gag<br>Glu | ugu<br>Cys<br>2195 | aac<br>Asn | ccu<br>Pro | uuc<br>Phe | acu<br>Thr<br>2200 | gca<br>Ala | auu<br>Ile | gga<br>Gly | ugu<br>Cys | 7048 |
| gca<br>Ala | aug<br>Met | acc<br>Thr<br>2205 | gaa<br>Glu | aca<br>Thr | ggc<br>Gly | gga<br>Gly<br>2210 | ggc<br>Gly | ccu<br>Pro | gau<br>Asp | gau<br>Asp<br>2215 | uua<br>Leu | ccc<br>Pro | agu<br>Ser | uac<br>Tyr | 7093 |
| ccu<br>Pro | ccc<br>Pro | aaa<br>Lys<br>2220 | aag<br>Lys | gag<br>Glu | guc<br>Val | ucu<br>Ser<br>2225 | gaa<br>Glu | ugg<br>Trp | uca<br>Ser | gac<br>Asp<br>2230 | gaa<br>Glu | agu<br>Ser | ugg<br>Trp | ucg<br>Ser | 7138 |
| acg<br>Thr | gcu<br>Ala | aca<br>Thr<br>2235 | acc<br>Thr | gcu<br>Ala | ucc<br>Ser | agc<br>Ser<br>2240 | uac<br>Tyr | guu<br>Val | acu<br>Thr | ggc<br>Gly<br>2245 | ccc<br>Pro | ccg<br>Pro | uac<br>Tyr | ccu<br>Pro | 7183 |
| aag<br>Lys | aua<br>Ile | cgg<br>Arg<br>2250 | gga<br>Gly | aag<br>Lys | gau<br>Asp | ucc<br>Ser<br>2255 | acu<br>Thr | cag<br>Gln | uca<br>Ser | gcc<br>Ala<br>2260 | ccc<br>Pro | gcc<br>Ala | aaa<br>Lys | cgg<br>Arg | 7228 |
| ccu<br>Pro | aca<br>Thr | aaa<br>Lys<br>2265 | aag<br>Lys | aag<br>Lys | uug<br>Leu | gga<br>Gly<br>2270 | aag<br>Lys | agu<br>Ser | gag<br>Glu | uuu<br>Phe<br>2275 | ucg<br>Ser | ugc<br>Cys | agc<br>Ser | aug<br>Met | 7273 |
| agc<br>Ser | uac<br>Tyr | acc<br>Thr<br>2280 | ugg<br>Trp | acc<br>Thr | gac<br>Asp | gug<br>Val<br>2285 | auu<br>Ile | agc<br>Ser | uuc<br>Phe | aaa<br>Lys<br>2290 | acu<br>Thr | gcu<br>Ala | ucu<br>Ser | aaa<br>Lys | 7318 |
| guu<br>Val | cug<br>Leu | ucu<br>Ser<br>2295 | gca<br>Ala | acu<br>Thr | cgg<br>Arg | gcc<br>Ala<br>2300 | auc<br>Ile | acu<br>Thr | agu<br>Ser | ggu<br>Gly<br>2305 | uuc<br>Phe | cuc<br>Leu | aaa<br>Lys | caa<br>Gln | 7363 |
| aga<br>Arg | uca<br>Ser | uug<br>Leu<br>2310 | gug<br>Val | uau<br>Tyr | gug<br>Val | acu<br>Thr<br>2315 | gag<br>Glu | ccg<br>Pro | cgg<br>Arg | gau<br>Asp<br>2320 | gcg<br>Ala | gag<br>Glu | cuu<br>Leu | aga<br>Arg | 7408 |
| aaa<br>Lys | caa<br>Gln | aaa<br>Lys<br>2325 | guc<br>Val | acu<br>Thr | auu<br>Ile | aau<br>Asn<br>2330 | aga<br>Arg | caa<br>Gln | ccu<br>Pro | cug<br>Leu<br>2335 | uuc<br>Phe | ccc<br>Pro | cca<br>Pro | uca<br>Ser | 7453 |
| uac<br>Tyr | cac<br>His | aag<br>Lys<br>2340 | caa<br>Gln | gug<br>Val | aga<br>Arg | uug<br>Leu<br>2345 | gcu<br>Ala | aag<br>Lys | gaa<br>Glu | aaa<br>Lys<br>2350 | gcu<br>Ala | uca<br>Ser | aaa<br>Lys | guu<br>Val | 7498 |
| guc<br>Val | ggu<br>Gly | guc<br>Val<br>2355 | aug<br>Met | ugg<br>Trp | gac<br>Asp | uau<br>Tyr<br>2360 | gau<br>Asp | gaa<br>Glu | gua<br>Val | gca<br>Ala<br>2365 | gcu<br>Ala | cac<br>His | acg<br>Thr | ccc<br>Pro | 7543 |
| ucu<br>Ser | aag<br>Lys | ucu<br>Ser | gcu<br>Ala | aag<br>Lys | ucc<br>Ser | cac<br>His | auc<br>Ile | acu<br>Thr | ggc<br>Gly | cuu<br>Leu | cgg<br>Arg | ggc<br>Gly | acu<br>Thr | gau<br>Asp | 7588 |

-continued

|  |  |  |  |  |  |  |  |  |  |  |  |  |
|---|---|---|---|---|---|---|---|---|---|---|---|---|
|  |  | 2370 |  |  |  | 2375 |  |  |  | 2380 |  |  |
| guu | cgu | ucu | gga | gca | gcc | cgc | aag | gcu | guu | cug | gac | uug | cag | aag | 7633 |
| Val | Arg | Ser | Gly | Ala | Ala | Arg | Lys | Ala | Val | Leu | Asp | Leu | Gln | Lys |  |
|  |  | 2385 |  |  |  | 2390 |  |  |  | 2395 |  |  |
| ugu | guc | gag | gca | ggu | gag | aua | ccg | agu | cau | uau | cgg | caa | acu | gug | 7678 |
| Cys | Val | Glu | Ala | Gly | Glu | Ile | Pro | Ser | His | Tyr | Arg | Gln | Thr | Val |  |
|  |  | 2400 |  |  |  | 2405 |  |  |  | 2410 |  |  |
| aua | guu | cca | aag | gag | gag | guc | uuc | gug | aag | acc | ccc | cag | aaa | cca | 7723 |
| Ile | Val | Pro | Lys | Glu | Glu | Val | Phe | Val | Lys | Thr | Pro | Gln | Lys | Pro |  |
|  |  | 2415 |  |  |  | 2420 |  |  |  | 2425 |  |  |
| aca | aag | aaa | ccc | cca | agg | cuu | auc | ucg | uac | ccc | cac | cuu | gaa | aug | 7768 |
| Thr | Lys | Lys | Pro | Pro | Arg | Leu | Ile | Ser | Tyr | Pro | His | Leu | Glu | Met |  |
|  |  | 2430 |  |  |  | 2435 |  |  |  | 2440 |  |  |
| aga | ugu | guu | gag | aag | aug | uac | uac | ggu | cag | guu | gcu | ccu | gac | gua | 7813 |
| Arg | Cys | Val | Glu | Lys | Met | Tyr | Tyr | Gly | Gln | Val | Ala | Pro | Asp | Val |  |
|  |  | 2445 |  |  |  | 2450 |  |  |  | 2455 |  |  |
| guu | aaa | gcu | guc | aug | gga | gau | gcg | uac | ggg | uuu | gua | gau | cca | cgu | 7858 |
| Val | Lys | Ala | Val | Met | Gly | Asp | Ala | Tyr | Gly | Phe | Val | Asp | Pro | Arg |  |
|  |  | 2460 |  |  |  | 2465 |  |  |  | 2470 |  |  |
| acc | cgu | guc | aag | cgu | cug | uug | ucg | aug | ugg | uca | ccc | gau | gca | guc | 7903 |
| Thr | Arg | Val | Lys | Arg | Leu | Leu | Ser | Met | Trp | Ser | Pro | Asp | Ala | Val |  |
|  |  | 2475 |  |  |  | 2480 |  |  |  | 2485 |  |  |
| gga | gcc | aca | ugc | gau | aca | gug | ugu | uuu | gac | agu | acc | auc | aca | ccc | 7948 |
| Gly | Ala | Thr | Cys | Asp | Thr | Val | Cys | Phe | Asp | Ser | Thr | Ile | Thr | Pro |  |
|  |  | 2490 |  |  |  | 2495 |  |  |  | 2500 |  |  |
| gag | gau | auc | aug | gug | gag | aca | gac | auc | uac | uca | gca | gcu | aaa | cuc | 7993 |
| Glu | Asp | Ile | Met | Val | Glu | Thr | Asp | Ile | Tyr | Ser | Ala | Ala | Lys | Leu |  |
|  |  | 2505 |  |  |  | 2510 |  |  |  | 2515 |  |  |
| agu | gac | caa | cac | cga | gcu | ggc | auu | cac | acc | auu | gcg | agg | cag | uua | 8038 |
| Ser | Asp | Gln | His | Arg | Ala | Gly | Ile | His | Thr | Ile | Ala | Arg | Gln | Leu |  |
|  |  | 2520 |  |  |  | 2525 |  |  |  | 2530 |  |  |
| uac | gcu | gga | gga | ccg | aug | auc | gcu | uau | gau | ggc | cga | gag | auc | gga | 8083 |
| Tyr | Ala | Gly | Gly | Pro | Met | Ile | Ala | Tyr | Asp | Gly | Arg | Glu | Ile | Gly |  |
|  |  | 2535 |  |  |  | 2540 |  |  |  | 2545 |  |  |
| uau | cgu | agg | ugu | agg | ucu | ucc | ggc | guc | uau | acu | acc | uca | agu | ucc | 8128 |
| Tyr | Arg | Arg | Cys | Arg | Ser | Ser | Gly | Val | Tyr | Thr | Thr | Ser | Ser | Ser |  |
|  |  | 2550 |  |  |  | 2555 |  |  |  | 2560 |  |  |
| aac | agu | uug | acc | ugc | ugg | cug | aag | gua | aau | gcu | gca | gcc | gaa | cag | 8173 |
| Asn | Ser | Leu | Thr | Cys | Trp | Leu | Lys | Val | Asn | Ala | Ala | Ala | Glu | Gln |  |
|  |  | 2565 |  |  |  | 2570 |  |  |  | 2575 |  |  |
| gcu | ggc | aug | aag | aac | ccu | cgc | uuc | cuu | auu | ugc | ggc | gau | gau | ugc | 8218 |
| Ala | Gly | Met | Lys | Asn | Pro | Arg | Phe | Leu | Ile | Cys | Gly | Asp | Asp | Cys |  |
|  |  | 2580 |  |  |  | 2585 |  |  |  | 2590 |  |  |
| acc | gua | auu | ugg | aag | agc | gcc | gga | gca | gau | gca | gac | aaa | caa | gca | 8263 |
| Thr | Val | Ile | Trp | Lys | Ser | Ala | Gly | Ala | Asp | Ala | Asp | Lys | Gln | Ala |  |
|  |  | 2595 |  |  |  | 2600 |  |  |  | 2605 |  |  |
| aug | cgu | guc | uuu | gcu | agc | ugg | aug | aag | gug | aug | ggu | gca | cca | caa | 8308 |
| Met | Arg | Val | Phe | Ala | Ser | Trp | Met | Lys | Val | Met | Gly | Ala | Pro | Gln |  |
|  |  | 2610 |  |  |  | 2615 |  |  |  | 2620 |  |  |
| gau | ugu | gug | ccu | caa | ccc | aaa | uac | agu | uug | gaa | gaa | uua | aca | uca | 8353 |
| Asp | Cys | Val | Pro | Gln | Pro | Lys | Tyr | Ser | Leu | Glu | Glu | Leu | Thr | Ser |  |
|  |  | 2625 |  |  |  | 2630 |  |  |  | 2635 |  |  |
| ugc | uca | uca | aau | guu | acc | ucu | gga | auu | acc | aaa | agu | ggc | aag | ccu | 8398 |
| Cys | Ser | Ser | Asn | Val | Thr | Ser | Gly | Ile | Thr | Lys | Ser | Gly | Lys | Pro |  |
|  |  | 2640 |  |  |  | 2645 |  |  |  | 2650 |  |  |
| uac | uac | uuu | cuu | aca | aga | gau | ccu | cgu | auc | ccc | cuu | ggc | agg | ugc | 8443 |
| Tyr | Tyr | Phe | Leu | Thr | Arg | Asp | Pro | Arg | Ile | Pro | Leu | Gly | Arg | Cys |  |
|  |  | 2655 |  |  |  | 2660 |  |  |  | 2665 |  |  |
| ucu | gcc | gag | ggu | cug | gga | uac | aac | ccc | agu | gcu | gcg | ugg | auu | ggg | 8488 |
| Ser | Ala | Glu | Gly | Leu | Gly | Tyr | Asn | Pro | Ser | Ala | Ala | Trp | Ile | Gly |  |

|     |     |     |     |     |     |     |     |     |     |     |     |     |     |      |
|-----|-----|-----|-----|-----|-----|-----|-----|-----|-----|-----|-----|-----|-----|------|
| uau | cua | aua | cau | cac | uac | cca | ugu | uug | ugg | guu | agc | cgu | gug | uug | 8533 |
| Tyr | Leu | Ile | His | His | Tyr | Pro | Cys | Leu | Trp | Val | Ser | Arg | Val | Leu |     |
|     |     |     | 2685 |     |     |     | 2690 |     |     |     |     | 2695 |     |     |     |

```
                2670                    2675                    2680 uau cua aua cau cac uac cca ugu uug ugg guu agc cgu gug uug       8533
Tyr Leu Ile His His Tyr Pro Cys Leu Trp Val Ser Arg Val Leu
            2685                2690                2695 gcu guc cau uuc aug gag cag aug cuc uuu gag gac aaa cuu ccc       8578
Ala Val His Phe Met Glu Gln Met Leu Phe Glu Asp Lys Leu Pro
            2700                2705                2710 gag acu gug acc uuu gac ugg uau ggg aaa aau uau acg gug ccu       8623
Glu Thr Val Thr Phe Asp Trp Tyr Gly Lys Asn Tyr Thr Val Pro
            2715                2720                2725 gua gaa gau cug ccc agc auc auu gcu ggu gug cac ggu auu gag       8668
Val Glu Asp Leu Pro Ser Ile Ile Ala Gly Val His Gly Ile Glu
            2730                2735                2740 gcu uuc ucg gug gug cgc uac acc aac gcu gag auc cuc aga guu       8713
Ala Phe Ser Val Val Arg Tyr Thr Asn Ala Glu Ile Leu Arg Val
            2745                2750                2755 ucc caa uca cua aca gac aug acc aug ccc ccc cug cga gcc ugg       8758
Ser Gln Ser Leu Thr Asp Met Thr Met Pro Pro Leu Arg Ala Trp
            2760                2765                2770 cga aag aaa gcc agg gcg guc cuc gcc agc gcc aag agg cgu ggc       8803
Arg Lys Lys Ala Arg Ala Val Leu Ala Ser Ala Lys Arg Arg Gly
            2775                2780                2785 gga gca cac gca aaa uug gcu cgc uuc cuu uuc ugg cau gcu aca       8848
Gly Ala His Ala Lys Leu Ala Arg Phe Leu Leu Trp His Ala Thr
            2790                2795                2800 ucu aga ccu cua cca gau uug gau aag acg agc gug gcu cgg uac       8893
Ser Arg Pro Leu Pro Asp Leu Asp Lys Thr Ser Val Ala Arg Tyr
            2805                2810                2815 acc acu uuc aau uau ugu gau guu uac ucc ccg gag ggg gau gug       8938
Thr Thr Phe Asn Tyr Cys Asp Val Tyr Ser Pro Glu Gly Asp Val
            2820                2825                2830 uuu auu aca cca cag aga aga uug cag aag uuc cuu gug aag uau       8983
Phe Ile Thr Pro Gln Arg Arg Leu Gln Lys Phe Leu Val Lys Tyr
            2835                2840                2845 uug gcu guc auu guu uuu gcc cua ggg cuc auu gcu guu gga uua       9028
Leu Ala Val Ile Val Phe Ala Leu Gly Leu Ile Ala Val Gly Leu
            2850                2855                2860 gcc auc agc ugaccccca aaucaaaaau uaacuaacag uuuuuuuuuu            9077
Ala Ile Ser uuuuuuuuuu uuuagggcag cggcaacagg ggagaccccg ggcuuaacga ccccgccgau  9137
gugaguuugg cgaccauggu ggaucagaac cguuucgggu gaagccaugg ucugaagggg  9197 augacgucc uucuggcuca uccacaaaaa ccgucucggg ugggugagga guccuggcug   9257
ugugggaagc agucaguaua auucccgucg uguguggga cgccacgacga cguauuuguc  9317 cgcugugcag agcguaguac caagggcugc accccgguuu uuguuccaag cggagggcaa  9377 ccccgcuug gaauuaaaaa cu                                            9399

<210> SEQ ID NO 100
<211> LENGTH: 2864
<212> TYPE: PRT
<213> ORGANISM: GB virus B

<400> SEQUENCE: 100

Met Pro Val Ile Ser Thr Gln Thr Ser Pro Val Pro Ala Pro Arg Thr
1               5                   10                  15

Arg Lys Asn Lys Gln Thr Gln Ala Ser Tyr Pro Val Ser Ile Lys Thr
            20                  25                  30

Ser Val Glu Arg Gly Gln Arg Ala Lys Arg Lys Val Gln Arg Asp Ala
```

-continued

```
                35                  40                  45
Arg Pro Arg Asn Tyr Lys Ile Ala Gly Ile His Asp Gly Leu Gln Thr
 50                  55                  60
Leu Ala Gln Ala Ala Leu Pro Ala His Gly Trp Gly Arg Gln Asp Pro
 65                  70                  75                  80
Arg His Lys Ser Arg Asn Leu Gly Ile Leu Leu Asp Tyr Pro Leu Gly
                 85                  90                  95
Trp Ile Gly Asp Val Thr Thr His Thr Pro Leu Val Gly Pro Leu Val
                100                 105                 110
Ala Gly Ala Val Val Arg Pro Val Cys Gln Ile Val Arg Leu Leu Glu
                115                 120                 125
Asp Gly Val Asn Trp Ala Thr Gly Trp Phe Gly Val His Leu Phe Val
130                 135                 140
Val Cys Leu Leu Ser Leu Ala Cys Pro Cys Ser Gly Ala Arg Val Thr
145                 150                 155                 160
Asp Pro Asp Thr Asn Thr Thr Ile Leu Thr Asn Cys Cys Gln Arg Asn
                165                 170                 175
Gln Val Ile Tyr Cys Ser Pro Ser Thr Cys Leu His Glu Pro Gly Cys
                180                 185                 190
Val Ile Cys Ala Asp Glu Cys Trp Val Pro Ala Asn Pro Tyr Ile Ser
                195                 200                 205
His Pro Ser Asn Trp Thr Gly Thr Asp Ser Phe Leu Ala Asp His Ile
                210                 215                 220
Asp Phe Val Met Gly Ala Leu Val Thr Cys Asp Ala Leu Asp Ile Gly
225                 230                 235                 240
Glu Leu Cys Gly Ala Cys Val Leu Val Gly Asp Trp Leu Val Arg His
                245                 250                 255
Trp Leu Ile His Ile Asp Leu Asn Glu Thr Gly Thr Cys Tyr Leu Glu
                260                 265                 270
Val Pro Thr Gly Ile Asp Pro Gly Phe Leu Gly Phe Ile Gly Trp Met
                275                 280                 285
Ala Gly Lys Val Glu Ala Val Ile Phe Leu Thr Lys Leu Ala Ser Gln
                290                 295                 300
Val Pro Tyr Ala Ile Ala Thr Met Phe Ser Ser Val His Tyr Leu Ala
305                 310                 315                 320
Val Gly Ala Leu Ile Tyr Tyr Ala Ser Arg Gly Lys Trp Tyr Gln Leu
                325                 330                 335
Leu Leu Ala Leu Met Leu Tyr Ile Glu Ala Thr Ser Gly Asn Pro Ile
                340                 345                 350
Arg Val Pro Thr Gly Cys Ser Ile Ala Glu Phe Cys Ser Pro Leu Met
                355                 360                 365
Ile Pro Cys Pro Cys His Ser Tyr Leu Ser Glu Asn Val Ser Glu Val
370                 375                 380
Ile Cys Tyr Ser Pro Lys Trp Thr Arg Pro Ile Thr Leu Glu Tyr Asn
385                 390                 395                 400
Asn Ser Ile Ser Trp Tyr Pro Tyr Thr Ile Pro Gly Ala Arg Gly Cys
                405                 410                 415
Met Val Lys Phe Lys Asn Asn Thr Trp Gly Cys Cys Arg Ile Arg Asn
                420                 425                 430
Val Pro Ser Tyr Cys Thr Met Gly Thr Asp Ala Val Trp Asn Asp Thr
                435                 440                 445
Arg Asn Thr Tyr Glu Ala Cys Gly Val Thr Pro Trp Leu Thr Thr Ala
450                 455                 460
```

```
Trp His Asn Gly Ser Ala Leu Lys Leu Ala Ile Leu Gln Tyr Pro Gly
465                 470                 475                 480

Ser Lys Glu Met Phe Lys Pro His Asn Trp Met Ser Gly His Leu Tyr
            485                 490                 495

Phe Glu Gly Ser Asp Thr Pro Ile Val Tyr Phe Tyr Asp Pro Val Asn
        500                 505                 510

Ser Thr Leu Leu Pro Pro Glu Arg Trp Ala Arg Leu Pro Gly Thr Pro
    515                 520                 525

Pro Val Val Arg Gly Ser Trp Leu Gln Val Pro Gln Gly Phe Tyr Ser
530                 535                 540

Asp Val Lys Asp Leu Ala Thr Gly Leu Ile Thr Lys Asp Lys Ala Trp
545                 550                 555                 560

Lys Asn Tyr Gln Val Leu Tyr Ser Ala Thr Gly Ala Leu Ser Leu Thr
                565                 570                 575

Gly Val Thr Thr Lys Ala Val Val Leu Ile Leu Leu Gly Leu Cys Gly
            580                 585                 590

Ser Lys Tyr Leu Ile Leu Ala Tyr Leu Cys Tyr Leu Ser Leu Cys Phe
        595                 600                 605

Gly Arg Ala Ser Gly Tyr Pro Leu Arg Pro Val Leu Pro Ser Gln Ser
610                 615                 620

Tyr Leu Gln Ala Gly Trp Asp Val Leu Ser Lys Ala Gln Val Ala Pro
625                 630                 635                 640

Phe Ala Leu Ile Phe Phe Ile Cys Cys Tyr Leu Arg Cys Arg Leu Arg
                645                 650                 655

Tyr Ala Ala Leu Leu Gly Phe Val Pro Met Ala Ala Gly Leu Pro Leu
            660                 665                 670

Thr Phe Phe Val Ala Ala Ala Ala Gln Pro Asp Tyr Asp Trp Trp
        675                 680                 685

Val Arg Leu Leu Val Ala Gly Leu Val Leu Trp Ala Gly Arg Asn Arg
690                 695                 700

Gly His Arg Ile Ala Leu Leu Val Gly Pro Trp Pro Leu Val Ala Leu
705                 710                 715                 720

Leu Thr Leu Leu His Leu Val Thr Pro Ala Ser Ala Phe Asp Thr Glu
                725                 730                 735

Ile Ile Gly Gly Leu Thr Ile Pro Pro Val Val Ala Leu Val Val Met
            740                 745                 750

Ser Arg Phe Gly Phe Phe Ala His Leu Leu Pro Arg Cys Ala Leu Val
        755                 760                 765

Asn Ser Tyr Leu Trp Gln Arg Trp Glu Asn Trp Phe Trp Asn Val Thr
770                 775                 780

Leu Arg Pro Glu Arg Phe Phe Leu Val Leu Cys Phe Pro Gly Ala
785                 790                 795                 800

Thr Tyr Asp Ala Leu Val Thr Phe Cys Val Cys His Val Ala Leu Leu
                805                 810                 815

Cys Leu Thr Ser Ser Ala Ala Ser Phe Phe Gly Thr Asp Ser Arg Val
            820                 825                 830

Arg Ala His Arg Met Leu Val Arg Leu Gly Lys Cys His Ala Trp Tyr
        835                 840                 845

Ser His Tyr Val Leu Lys Phe Phe Leu Val Phe Gly Glu Asn Gly
850                 855                 860

Val Phe Phe Tyr Lys His Leu His Gly Asp Val Leu Pro Asn Asp Phe
865                 870                 875                 880

Ala Ser Lys Leu Pro Leu Gln Glu Pro Phe Phe Pro Phe Glu Gly Lys
                885                 890                 895
```

-continued

Ala Arg Val Tyr Arg Asn Glu Gly Arg Arg Leu Ala Cys Gly Asp Thr
            900                 905                 910

Val Asp Gly Leu Pro Val Val Ala Arg Leu Gly Asp Leu Val Phe Ala
        915                 920                 925

Gly Leu Ala Met Pro Pro Asp Gly Trp Ala Ile Thr Ala Pro Phe Thr
930                 935                 940

Leu Gln Cys Leu Ser Glu Arg Gly Thr Leu Ser Ala Met Ala Val Val
945                 950                 955                 960

Met Thr Gly Ile Asp Pro Arg Thr Trp Thr Gly Thr Ile Phe Arg Leu
            965                 970                 975

Gly Ser Leu Ala Thr Ser Tyr Met Gly Phe Val Cys Asn Val Leu
            980                 985                 990

Tyr Thr Ala His His Gly Ser Lys Gly Arg Arg Leu Ala His Pro Thr
        995                 1000                1005

Gly Ser Ile His Pro Ile Thr Val Asp Ala Ala Asn Asp Gln Asp
    1010                1015                1020

Ile Tyr Gln Pro Pro Cys Gly Ala Gly Ser Leu Thr Arg Cys Ser
    1025                1030                1035

Cys Gly Glu Thr Lys Gly Tyr Leu Val Thr Arg Leu Gly Ser Leu
    1040                1045                1050

Val Glu Val Asn Lys Ser Asp Asp Pro Tyr Trp Cys Val Cys Gly
    1055                1060                1065

Ala Leu Pro Met Ala Val Ala Lys Gly Ser Ser Gly Ala Pro Ile
    1070                1075                1080

Leu Cys Ser Ser Gly His Val Ile Gly Met Phe Thr Ala Ala Arg
    1085                1090                1095

Asn Ser Gly Gly Ser Val Ser Gln Ile Arg Val Arg Pro Leu Val
    1100                1105                1110

Cys Ala Gly Tyr His Pro Gln Tyr Thr Ala His Ala Thr Leu Asp
    1115                1120                1125

Thr Lys Pro Thr Val Pro Asn Glu Tyr Ser Val Gln Ile Leu Ile
    1130                1135                1140

Ala Pro Thr Gly Ser Gly Lys Ser Thr Lys Leu Pro Leu Ser Tyr
    1145                1150                1155

Met Gln Glu Lys Tyr Glu Val Leu Val Leu Asn Pro Ser Val Ala
    1160                1165                1170

Thr Thr Ala Ser Met Pro Lys Tyr Met His Ala Thr Tyr Gly Val
    1175                1180                1185

Asn Pro Asn Cys Tyr Phe Asn Gly Lys Cys Thr Asn Thr Gly Ala
    1190                1195                1200

Ser Leu Thr Tyr Ser Thr Tyr Gly Met Tyr Leu Thr Gly Ala Cys
    1205                1210                1215

Ser Arg Asn Tyr Asp Val Ile Ile Cys Asp Glu Cys His Ala Thr
    1220                1225                1230

Asp Ala Thr Thr Val Leu Gly Ile Gly Lys Val Leu Thr Glu Ala
    1235                1240                1245

Pro Ser Lys Asn Val Arg Leu Val Val Leu Ala Thr Ala Thr Pro
    1250                1255                1260

Pro Gly Val Ile Pro Thr Pro His Ala Asn Ile Thr Glu Ile Gln
    1265                1270                1275

Leu Thr Asp Glu Gly Thr Ile Pro Phe His Gly Lys Lys Ile Lys
    1280                1285                1290

Glu Glu Asn Leu Lys Lys Gly Arg His Leu Ile Phe Glu Ala Thr
    1295                1300                1305

-continued

```
Lys Lys His Cys Asp Glu Leu Ala Asn Glu Leu Ala Arg Lys Gly
1310                1315                1320

Ile Thr Ala Val Ser Tyr Tyr Arg Gly Cys Asp Ile Ser Lys Ile
1325                1330                1335

Pro Glu Gly Asp Cys Val Val Val Ala Thr Asp Ala Leu Cys Thr
1340                1345                1350

Gly Tyr Thr Gly Asp Phe Asp Ser Val Tyr Asp Cys Ser Leu Met
1355                1360                1365

Val Glu Gly Thr Cys His Val Asp Leu Asp Pro Thr Phe Thr Met
1370                1375                1380

Gly Val Arg Val Cys Gly Val Ser Ala Ile Val Lys Gly Gln Arg
1385                1390                1395

Arg Gly Arg Thr Gly Arg Gly Arg Ala Gly Ile Tyr Tyr Tyr Val
1400                1405                1410

Asp Gly Ser Cys Thr Pro Ser Gly Met Val Pro Glu Cys Asn Ile
1415                1420                1425

Val Glu Ala Phe Asp Ala Ala Lys Ala Trp Tyr Gly Leu Ser Ser
1430                1435                1440

Thr Glu Ala Gln Thr Ile Leu Asp Thr Tyr Arg Thr Gln Pro Gly
1445                1450                1455

Leu Pro Ala Ile Gly Ala Asn Leu Asp Glu Trp Ala Asp Leu Phe
1460                1465                1470

Ser Met Val Asn Pro Glu Pro Ser Phe Val Asn Thr Ala Lys Arg
1475                1480                1485

Thr Ala Asp Asn Tyr Val Leu Leu Thr Ala Ala Gln Leu Gln Leu
1490                1495                1500

Cys His Gln Tyr Gly Tyr Ala Ala Pro Asn Asp Ala Pro Arg Trp
1505                1510                1515

Gln Gly Ala Arg Leu Gly Lys Lys Pro Cys Gly Val Leu Trp Arg
1520                1525                1530

Leu Asp Gly Ala Asp Ala Cys Pro Gly Pro Glu Pro Ser Glu Val
1535                1540                1545

Thr Arg Tyr Gln Met Cys Phe Thr Glu Val Asn Thr Ser Gly Thr
1550                1555                1560

Ala Ala Leu Ala Val Gly Val Gly Val Ala Met Ala Tyr Leu Ala
1565                1570                1575

Ile Asp Thr Phe Gly Ala Thr Cys Val Arg Arg Cys Trp Ser Ile
1580                1585                1590

Thr Ser Val Pro Thr Gly Ala Thr Val Ala Pro Val Val Asp Glu
1595                1600                1605

Glu Glu Ile Val Glu Glu Cys Ala Ser Phe Ile Pro Leu Glu Ala
1610                1615                1620

Met Val Ala Ala Ile Asp Lys Leu Lys Ser Thr Ile Thr Thr Thr
1625                1630                1635

Ser Pro Phe Thr Leu Glu Thr Ala Leu Glu Lys Leu Asn Thr Phe
1640                1645                1650

Leu Gly Pro His Ala Ala Thr Ile Leu Ala Ile Ile Glu Tyr Cys
1655                1660                1665

Cys Gly Leu Val Thr Leu Pro Asp Asn Pro Phe Ala Ser Cys Val
1670                1675                1680

Phe Ala Phe Ile Ala Gly Ile Thr Thr Pro Leu Pro His Lys Ile
1685                1690                1695

Lys Met Phe Leu Ser Leu Phe Gly Gly Ala Ile Ala Ser Lys Leu
1700                1705                1710
```

-continued

```
Thr Asp Ala Arg Gly Ala Leu Ala Phe Met Met Ala Gly Ala Ala
    1715                1720                1725

Gly Thr Ala Leu Gly Thr Trp Thr Ser Val Gly Phe Val Phe Asp
    1730                1735                1740

Met Leu Gly Gly Tyr Ala Ala Ala Ser Ser Thr Ala Cys Leu Thr
    1745                1750                1755

Phe Lys Cys Leu Met Gly Glu Trp Pro Thr Met Asp Gln Leu Ala
    1760                1765                1770

Gly Leu Val Tyr Ser Ala Phe Asn Pro Ala Ala Gly Val Val Gly
    1775                1780                1785

Val Leu Ser Ala Cys Ala Met Phe Ala Leu Thr Thr Ala Gly Pro
    1790                1795                1800

Asp His Trp Pro Asn Arg Leu Leu Thr Met Leu Ala Arg Ser Asn
    1805                1810                1815

Thr Val Cys Asn Glu Tyr Phe Ile Ala Thr Arg Asp Ile Arg Arg
    1820                1825                1830

Lys Ile Leu Gly Ile Leu Glu Ala Ser Thr Pro Trp Ser Val Ile
    1835                1840                1845

Ser Ala Cys Ile Arg Trp Leu His Thr Pro Thr Glu Asp Asp Cys
    1850                1855                1860

Gly Leu Ile Ala Trp Gly Leu Glu Ile Trp Gln Tyr Val Cys Asn
    1865                1870                1875

Phe Phe Val Ile Cys Phe Asn Val Leu Lys Ala Gly Val Gln Ser
    1880                1885                1890

Met Val Asn Ile Pro Gly Cys Pro Phe Tyr Ser Cys Gln Lys Gly
    1895                1900                1905

Tyr Lys Gly Pro Trp Ile Gly Ser Gly Met Leu Gln Ala Arg Cys
    1910                1915                1920

Pro Cys Gly Ala Glu Leu Ile Phe Ser Val Glu Asn Gly Phe Ala
    1925                1930                1935

Lys Leu Tyr Lys Gly Pro Arg Thr Cys Ser Asn Tyr Trp Arg Gly
    1940                1945                1950

Ala Val Pro Val Asn Ala Arg Leu Cys Gly Ser Ala Arg Pro Asp
    1955                1960                1965

Pro Thr Asp Trp Thr Ser Leu Val Val Asn Tyr Gly Val Arg Asp
    1970                1975                1980

Tyr Cys Lys Tyr Glu Lys Met Gly Asp His Ile Phe Val Thr Ala
    1985                1990                1995

Val Ser Ser Pro Asn Val Cys Phe Thr Gln Val Pro Pro Thr Leu
    2000                2005                2010

Arg Ala Ala Val Ala Val Asp Gly Val Gln Val Gln Cys Tyr Leu
    2015                2020                2025

Gly Glu Pro Lys Thr Pro Trp Thr Thr Ser Ala Cys Cys Tyr Gly
    2030                2035                2040

Pro Asp Gly Lys Gly Lys Thr Val Lys Leu Pro Phe Arg Val Asp
    2045                2050                2055

Gly His Thr Pro Gly Val Arg Met Gln Leu Asn Leu Arg Asp Ala
    2060                2065                2070

Leu Glu Thr Asn Asp Cys Asn Ser Thr Asn Asn Thr Pro Ser Asp
    2075                2080                2085

Glu Ala Ala Val Ser Ala Leu Val Phe Lys Gln Glu Leu Arg Arg
    2090                2095                2100

Thr Asn Gln Leu Leu Glu Ala Ile Ser Ala Gly Val Asp Thr Thr
    2105                2110                2115
```

-continued

Lys Leu Pro Ala Pro Ser Ile Glu Val Val Arg Lys Arg
    2120            2125            2130

Gln Phe Arg Ala Arg Thr Gly Ser Leu Thr Leu Pro Pro Pro
    2135            2140            2145

Arg Ser Val Pro Gly Val Ser Cys Pro Glu Ser Leu Gln Arg Ser
    2150            2155            2160

Asp Pro Leu Glu Gly Pro Ser Asn Leu Pro Pro Ser Pro Pro Val
    2165            2170            2175

Leu Gln Leu Ala Met Pro Met Pro Leu Leu Gly Ala Gly Glu Cys
    2180            2185            2190

Asn Pro Phe Thr Ala Ile Gly Cys Ala Met Thr Glu Thr Gly Gly
    2195            2200            2205

Gly Pro Asp Asp Leu Pro Ser Tyr Pro Pro Lys Lys Glu Val Ser
    2210            2215            2220

Glu Trp Ser Asp Glu Ser Trp Ser Thr Ala Thr Ala Ser Ser
    2225            2230            2235

Tyr Val Thr Gly Pro Pro Tyr Pro Lys Ile Arg Gly Lys Asp Ser
    2240            2245            2250

Thr Gln Ser Ala Pro Ala Lys Arg Pro Thr Lys Lys Lys Leu Gly
    2255            2260            2265

Lys Ser Glu Phe Ser Cys Ser Met Ser Tyr Thr Trp Thr Asp Val
    2270            2275            2280

Ile Ser Phe Lys Thr Ala Ser Lys Val Leu Ser Ala Thr Arg Ala
    2285            2290            2295

Ile Thr Ser Gly Phe Leu Lys Gln Arg Ser Leu Val Tyr Val Thr
    2300            2305            2310

Glu Pro Arg Asp Ala Glu Leu Arg Lys Gln Lys Val Thr Ile Asn
    2315            2320            2325

Arg Gln Pro Leu Phe Pro Pro Ser Tyr His Lys Gln Val Arg Leu
    2330            2335            2340

Ala Lys Glu Lys Ala Ser Lys Val Val Gly Val Met Trp Asp Tyr
    2345            2350            2355

Asp Glu Val Ala Ala His Thr Pro Ser Lys Ser Ala Lys Ser His
    2360            2365            2370

Ile Thr Gly Leu Arg Gly Thr Asp Val Arg Ser Gly Ala Ala Arg
    2375            2380            2385

Lys Ala Val Leu Asp Leu Gln Lys Cys Val Glu Ala Gly Glu Ile
    2390            2395            2400

Pro Ser His Tyr Arg Gln Thr Val Ile Val Pro Lys Glu Glu Val
    2405            2410            2415

Phe Val Lys Thr Pro Gln Lys Pro Thr Lys Lys Pro Pro Arg Leu
    2420            2425            2430

Ile Ser Tyr Pro His Leu Glu Met Arg Cys Val Glu Lys Met Tyr
    2435            2440            2445

Tyr Gly Gln Val Ala Pro Asp Val Val Lys Ala Val Met Gly Asp
    2450            2455            2460

Ala Tyr Gly Phe Val Asp Pro Arg Thr Arg Val Lys Arg Leu Leu
    2465            2470            2475

Ser Met Trp Ser Pro Asp Ala Val Gly Ala Thr Cys Asp Thr Val
    2480            2485            2490

Cys Phe Asp Ser Thr Ile Thr Pro Glu Asp Ile Met Val Glu Thr
    2495            2500            2505

Asp Ile Tyr Ser Ala Ala Lys Leu Ser Asp Gln His Arg Ala Gly
    2510            2515            2520

| | | | | | | | | | |
|---|---|---|---|---|---|---|---|---|---|
| Ile | His | Thr | Ile | Ala | Arg | Gln | Leu | Tyr | Ala | Gly | Gly | Pro | Met | Ile |
| | 2525 | | | | 2530 | | | | 2535 | | | | | |

Ile His Thr Ile Ala Arg Gln Leu Tyr Ala Gly Gly Pro Met Ile
    2525                2530              2535

Ala Tyr Asp Gly Arg Glu Ile Gly Tyr Arg Arg Cys Arg Ser Ser
    2540                2545              2550

Gly Val Tyr Thr Thr Ser Ser Ser Asn Ser Leu Thr Cys Trp Leu
    2555                2560              2565

Lys Val Asn Ala Ala Ala Glu Gln Ala Gly Met Lys Asn Pro Arg
    2570                2575              2580

Phe Leu Ile Cys Gly Asp Asp Cys Thr Val Ile Trp Lys Ser Ala
    2585                2590              2595

Gly Ala Asp Ala Asp Lys Gln Ala Met Arg Val Phe Ala Ser Trp
    2600                2605              2610

Met Lys Val Met Gly Ala Pro Gln Asp Cys Val Pro Gln Pro Lys
    2615                2620              2625

Tyr Ser Leu Glu Glu Leu Thr Ser Cys Ser Ser Asn Val Thr Ser
    2630                2635              2640

Gly Ile Thr Lys Ser Gly Lys Pro Tyr Tyr Phe Leu Thr Arg Asp
    2645                2650              2655

Pro Arg Ile Pro Leu Gly Arg Cys Ser Ala Glu Gly Leu Gly Tyr
    2660                2665              2670

Asn Pro Ser Ala Ala Trp Ile Gly Tyr Leu Ile His His Tyr Pro
    2675                2680              2685

Cys Leu Trp Val Ser Arg Val Leu Ala Val His Phe Met Glu Gln
    2690                2695              2700

Met Leu Phe Glu Asp Lys Leu Pro Glu Thr Val Thr Phe Asp Trp
    2705                2710              2715

Tyr Gly Lys Asn Tyr Thr Val Pro Val Glu Asp Leu Pro Ser Ile
    2720                2725              2730

Ile Ala Gly Val His Gly Ile Glu Ala Phe Ser Val Val Arg Tyr
    2735                2740              2745

Thr Asn Ala Glu Ile Leu Arg Val Ser Gln Ser Leu Thr Asp Met
    2750                2755              2760

Thr Met Pro Pro Leu Arg Ala Trp Arg Lys Lys Ala Arg Ala Val
    2765                2770              2775

Leu Ala Ser Ala Lys Arg Arg Gly Gly Ala His Ala Lys Leu Ala
    2780                2785              2790

Arg Phe Leu Leu Trp His Ala Thr Ser Arg Pro Leu Pro Asp Leu
    2795                2800              2805

Asp Lys Thr Ser Val Ala Arg Tyr Thr Thr Phe Asn Tyr Cys Asp
    2810                2815              2820

Val Tyr Ser Pro Glu Gly Asp Val Phe Ile Thr Pro Gln Arg Arg
    2825                2830              2835

Leu Gln Lys Phe Leu Val Lys Tyr Leu Ala Val Ile Val Phe Ala
    2840                2845              2850

Leu Gly Leu Ile Ala Val Gly Leu Ala Ile Ser
    2855                2860

<210> SEQ ID NO 101
<211> LENGTH: 30
<212> TYPE: DNA
<213> ORGANISM: Artificial Sequence
<220> FEATURE:
<223> OTHER INFORMATION: Synthetic PCR primer

<400> SEQUENCE: 101
ggaaccggtg agtacaccgg aattgccagg                                      30

```
<210> SEQ ID NO 102
<211> LENGTH: 31
<212> TYPE: DNA
<213> ORGANISM: Artificial Sequence
<220> FEATURE:
<223> OTHER INFORMATION: Synthetic PCR primer

<400> SEQUENCE: 102
acccgtacgc catgcgccag ggccctggca g                           31

<210> SEQ ID NO 103
<211> LENGTH: 30
<212> TYPE: DNA
<213> ORGANISM: Artificial Sequence
<220> FEATURE:
<223> OTHER INFORMATION: Synthetic PCR primer

<400> SEQUENCE: 103
gatatcgtac agcccggata cgttgcgcac                             30

<210> SEQ ID NO 104
<211> LENGTH: 30
<212> TYPE: DNA
<213> ORGANISM: Artificial Sequence
<220> FEATURE:
<223> OTHER INFORMATION: Synthetic PCR primer

<400> SEQUENCE: 104
tacgtaactg acccagacac aaataccaca                             30

<210> SEQ ID NO 105
<211> LENGTH: 30
<212> TYPE: DNA
<213> ORGANISM: Artificial Sequence
<220> FEATURE:
<223> OTHER INFORMATION: Synthetic PCR primer

<400> SEQUENCE: 105
cctcagccat gggcacaaac cctaaaaggg                             30

<210> SEQ ID NO 106
<211> LENGTH: 30
<212> TYPE: DNA
<213> ORGANISM: Artificial Sequence
<220> FEATURE:
<223> OTHER INFORMATION: Synthetic PCR primer

<400> SEQUENCE: 106
gatatccgct gcctcataca caatgcttga                             30

<210> SEQ ID NO 107
<211> LENGTH: 783
<212> TYPE: RNA
<213> ORGANISM: Hepatitis C virus

<400> SEQUENCE: 107
gccucacacc uccccuacau cgaacaggga augcagcucg ccgaacaauu caagcagaag      60
gcgcucgggu ugcugcagac agccaccaag caagcggaag ccgcugcucc ugugguggag     120
uccaaguggc gagccuuga ggccuucugg gcgaagcaca uggaauuu caucagcggg        180 auacaguacu uagcaggcuu guccacucug ccugggaacc ccgcgauagc aucacugaug     240
gcauucacag ccucuaucac cagcccgcuu accacccaac acacccuccu guuuaacauc     300
uugggaggau ggguggccgc ccaacuugcc cccccggug cugccucggc uuucguggc      360 gccggcauug cuggcgcagc uguuggcagc auaggccuug ggaaggugcu ugggacauc     420
```

```
cuggcggguu auggagcagg gguggcaggc gcgcucgugg ccuucaaggu caugagcggc    480
gagaugcccu ccaccgagga ccuggucaac uuacucccug ccauccucuc uccuggugcc    540
cuugucgucg gggucgugug cgcagcaaua cugcgucggc augugggccc ggggagggg    600 gcugugcaau ggaugaaccg gcugauagcg uucgccucgc ggguaacca cgucuccccc    660 acgcacuaug ugccugagag cgacgcugca gcgcguguca cacagauccu ucuagccuc    720 accaucacuc agcuacugaa gaggcuccac caguggauua augaggacug ucccacacca   780
ugc                                                                 783
```

<210> SEQ ID NO 108
<211> LENGTH: 261
<212> TYPE: PRT
<213> ORGANISM: Hepatitis C virus

<400> SEQUENCE: 108

```
Ala Ser His Leu Pro Tyr Ile Glu Gln Gly Met Gln Leu Ala Glu Gln
1               5                   10                  15

Phe Lys Gln Lys Ala Leu Gly Leu Leu Gln Thr Ala Thr Lys Gln Ala
            20                  25                  30

Glu Ala Ala Pro Val Val Glu Ser Lys Trp Arg Ala Leu Glu Ala
        35                  40                  45

Phe Trp Ala Lys His Met Trp Asn Phe Ile Ser Gly Ile Gln Tyr Leu
    50                  55                  60

Ala Gly Leu Ser Thr Leu Pro Gly Asn Pro Ala Ile Ala Ser Leu Met
65                  70                  75                  80

Ala Phe Thr Ala Ser Ile Thr Ser Pro Leu Thr Thr Gln His Thr Leu
                85                  90                  95

Leu Phe Asn Ile Leu Gly Gly Trp Val Ala Ala Gln Leu Ala Pro Pro
            100                 105                 110

Gly Ala Ala Ser Ala Phe Val Gly Ala Gly Ile Ala Gly Ala Ala Val
        115                 120                 125

Gly Ser Ile Gly Leu Gly Lys Val Leu Val Asp Ile Leu Ala Gly Tyr
    130                 135                 140

Gly Ala Gly Val Ala Gly Ala Leu Val Ala Phe Lys Val Met Ser Gly
145                 150                 155                 160

Glu Met Pro Ser Thr Glu Asp Leu Val Asn Leu Leu Pro Ala Ile Leu
                165                 170                 175

Ser Pro Gly Ala Leu Val Val Gly Val Val Cys Ala Ala Ile Leu Arg
            180                 185                 190

Arg His Val Gly Pro Gly Glu Gly Ala Val Gln Trp Met Asn Arg Leu
        195                 200                 205

Ile Ala Phe Ala Ser Arg Gly Asn His Val Ser Pro Thr His Tyr Val
    210                 215                 220

Pro Glu Ser Asp Ala Ala Ala Arg Val Thr Gln Ile Leu Ser Ser Leu
225                 230                 235                 240

Thr Ile Thr Gln Leu Leu Lys Arg Leu His Gln Trp Ile Asn Glu Asp
                245                 250                 255

Cys Ser Thr Pro Cys
            260
```

HCV/GBV-B CHIMERIC VIRUS

TECHNICAL FIELD

The present invention relates to a chimeric RNA derived from RNAs of hepatitis C virus (this may be hereinafter referred to as "HCV") and GB virus B (this may be hereinafter referred to as "GBV-B"), and a chimeric virus having the chimeric RNA.

BACKGROUND ART

HCV is the causative factor of chronic hepatitis C and, according to statistics by WHO, it is assumed that 170 million people are infected therewith. HCV is a virus classified to the genus *Flavivirus* in the family Flaviviridae, and it is considered that its infection is caused via blood or a blood component, followed by its growth in the liver. In an infected patient, a relatively mild symptom is observed at the initial stage of infection, but it frequently becomes chronic and leads to development of chronic hepatitis after a certain length of asymptomatic period. As the period of infection becomes longer, the condition of the disease becomes worse to cause liver cirrhosis, leading to liver cancer at high frequency. In 95% of liver cancer, hepatitis viruses are involved, and 80% of such cases are considered to be due to infection with HCV.

HCV has a plus-strand RNA of about 9600 bases as the genome, and it is assumed, based on analysis of the gene sequence, there are at least 6 types of genotypes. The genome of about 9600 bases works as mRNA in a host cell, and a continuous polyprotein having a length of about 3000 amino acids is synthesized, which is cleaved by signal peptidases and signal peptidyl peptidases of the host and proteases encoded by the HCV genome. As a result, 10 types of proteins, that is, the core, E1, E2, p7, NS2, NS3, NS4A, NS4B, NS5A and NS5B are produced. In addition to this translational frame (open reading frame), there exist the untranslated regions (UTRs) in the 5'-end and the 3'-end, which are responsible for the functions of translational regulation and regulation of replication of the genome.

Among these, the core, E1 and E2 are structural proteins constituting the virus. The virus genome is considered to be packaged by the core protein to form a capsid, and surrounded by the E1 and E2 envelope proteins anchored to the lipid bilayer membrane, thereby forming a virus particle (virion). The function of p7 is not clear, but it is reported to be indispensable for growth of the virus. NS2 is a metal protease and necessary for cleavage of itself, but other functions are not known. NS3 to NS5B are considered to form a complex which works as an RNA replication apparatus together with host proteins, thereby replicating the genomic RNA.

For therapy of chronic hepatitis C, interferon is widely used. In recent years, by virtue of improvements in the formulation of interferon and improvements in the administration method such as a combination therapy with interferon and ribavirin, the rate of successful elimination of HCV from the body, leading to complete response is gradually increasing. However, the rate of complete response by administration of interferon is still about five tenth, and there are many cases where serious side effects are caused by administration of interferon and where administration of interferon cannot be applied to an elderly patient, so that development of a therapeutic method and an agent effective for HCV is demanded.

Infection with HCV occurs via blood or a blood component in human, and, in terms of non-human organisms, anthropoids (chimpanzee) are infected with HCV and the infection causes hepatitis, leading to chronic hepatitis in some cases. However, none of small experimental animals which can be easily kept is known to be infected with HCV at a high rate.

On the other hand, it was revealed that inoculation of serum, which was collected from a surgeon who developed acute hepatitis, to a small primate tamarin causes hepatitis therein. By analyzing blood of the monkey suffering from post-transfusion hepatitis with unknown etiology by molecular biological techniques, two types of viruses, GBV-A and GBV-B, were identified (Non-patent Document 1). Among these, GBV-B was revealed to be most closely related to HCV in view of the molecular structure and to infect New World monkeys such as tamarin and marmoset, inducing hepatitis (Non-patent Document 2). Since HCV has a narrow range of host species and there is no suitable animal model for HCV, the animal model of GBV-B and tamarin is considered to be useful as an alternative model for infection and growth of HCV. However, although the structural similarity between GBV-B and HCV has been confirmed, GBV-B has an amino acid homology of as small as about 28% with HCV. Therefore, even if the animal model of GBV-B and tamarin is used as it is as a development and evaluation system for drugs which specifically act on HCV, it is impossible to carry out screening of drugs which specifically act on HCV.

In order to construct an animal model for HCV using GBV-B, attempts are being made to prepare an HCV/GBV-B chimeric virus by, using the genes of GBV-B as the basis, replacing a part of the genes of GBV-B with the corresponding genes of HCV, or inserting a part of the genes of HCV into the genes of GBV-B. Rijnbrand et al. showed that GBV-B in which a part of its 5'-UTR was replaced with the corresponding 5'-UTR of HCV can infect tamarin (Non-patent Document 3). Further, Haqshenas et al. prepared a chimeric virus by inserting the hyper variable region 1 (HVR1) of HCV into HVR1 in the envelope protein E2 of GBV-B, and infection of marmoset by the chimeric virus was confirmed (Non-patent Document 4). However, the genes in these chimeric viruses are mostly genes from GBV-B, and the chimeric viruses do not have the replication function as HCV. Therefore, these chimeric viruses cannot be said to be useful for development of therapeutic agents for HCV.

[Patent Document 1] WO 2008/136470 A1

[Non-patent Document 1] "Journal of Virology" (USA) 1995, vol. 69, pp. 5621-5630.

[Non-patent Document 2] "Virology" (USA) 1999, vol. 262, pp. 470-478.

[Non-patent Document 3] "Hepatology" (USA) 2005, vol. 41, pp. 986-994.

[Non-patent Document 4] Journal of General Virology (UK) 2007, vol. 88, pp. 895-902.

DISCLOSURE OF THE INVENTION

Problems to be Solved by the Invention

Since no animal model other than chimpanzee exists which is infected with HCV and allows growth of HCV, it has been difficult to efficiently develop the drugs. Further, use of chimpanzee in animal experiments is prohibited by application of the animal protection law. From such reasons, the methods of interferon therapy which are widely used at present have been developed and improved directly using patients as subjects, which have been a heavy burden to the patients. Therefore, in development and evaluation of the drugs, use of small animal models in their preclinical tests is important. GBV-B which infects a small primate tamarin is similar to HCV in terms of the gene structure and induces hepatitis symptoms, so that it is expected to be useful as an animal model for HCV. The present invention aims to provide an HCV/GBV-B chimeric virus which can infect tamarin or marmoset and maintain the replication function of HCV, in order to construct an HCV animal model which can be used as a development or evaluation system for HCV drugs.

Means for Solving the Problems

The present inventors intensively studied on an HCV/GBV-B chimeric virus which can be used for development of drugs which specifically and effectively act on HCV, to prepare an HCV/GBV-B chimeric RNA by linking an RNA of HCV comprising an RNA encoding the NS4B protein having leucine at the 1804th position and lysine at the 1966th position in the amino acid sequence of the polyprotein of HCV to an RNA of GBV-B, which HCV/GBV-B chimeric RNA maintains the replication function as HCV and is capable of persistently infecting tamarin or marmoset and increasing therein.

The replication efficiency of this HCV/GBV-B chimeric RNA in a human liver cancer-derived cell line was higher than that of HCV which is the parent strain. That is, the present inventors discovered that the obtained HCV/GBV-B chimeric RNA sufficiently maintains the replication function of HCV.

Further, when this HCV/GBV-B chimeric RNA was introduced to primary hepatocytes of marmoset, the HCV/GBV-B chimeric RNA increased autonomously in the cells, while persistently releasing the core protein in the cell supernatant. That is, the present inventors discovered that transfection of an HCV/GBV-B chimeric RNA into primary hepatocytes of marmoset enables production of an HCV/GBV-B chimeric virus which is capable of reinfection.

The present invention is based on such discoveries.

Thus, the present invention relates to an HCV/GBV-B chimeric RNA comprising an RNA of HCV and an RNA of GB virus-B, the RNA of HCV comprising an RNA encoding the NS4B protein having leucine at the 1804th position and lysine at the 1966th position in the amino acid sequence of the polyprotein of HCV.

A preferred embodiment of the HCV/GBV-B chimeric RNA of the present invention comprises:

(A) an HCV 5'-side RNA comprising an RNA of the 5'-UTR of HCV;

(B) a GBV-B RNA comprising an RNA encoding the E1 protein and the E2 protein of GBV-B; and (C) an HCV 3'-side RNA comprising an RNA encoding the NS3 protein, NS4A protein, NS4B protein, NS5A protein and NS5B protein, and an RNA of the 3'-UTR, of HCV;

the GBV-B RNA (B) being inserted between the HCV 5'-side RNA (A) and the HCV 3'-side RNA (C).

In another preferred embodiment of the HCV/GBV-B chimeric RNA of the present invention, the HCV 5'-side RNA (A) comprises an RNA of the 5'-UTR and an RNA encoding a part or all of the core protein;

the GBV-B RNA (B) comprises an RNA encoding a part of the core protein, and the E1 protein, E2 protein and p6 protein; and the HCV 3'-side RNA (C) comprises an RNA encoding the p7 protein, NS2 protein, NS3 protein, NS4A protein, NS4B protein, NS5A protein and NS5B protein, and an RNA of the 3'-UTR;

which HCV/GBV-B chimeric RNA is preferably an RNA having the base sequence shown in SEQ ID NO:55.

The present invention also relates to an HCV/GBV-B minus-strand chimeric RNA which is complementary to the HCV/GBV-B chimeric RNA.

The present invention also relates to an HCV/GBV-B chimeric virus comprising the HCV/GBV-B chimeric RNA.

The present invention also relates to an HCV/GBV-B chimeric DNA encoding the HCV/GBV-B chimeric RNA.

The present invention also relates to the HCV/GBV-B chimeric protein translated from the RNA, or from the DNA according to claim 7.

The present invention also relates to an HCV/GBV-B chimeric RNA—replicating cell comprising the HCV/GBV-B chimeric RNA.

The present invention also relates to a non-human animal to which the HCV/GBV-B chimeric RNA, or the HCV/GBV-B chimeric virus according to claim 6 was inoculated.

In the present specification, "HCV/GBV-B chimeric gene" means both an HCV/GBV-B chimeric RNA and an HCV/GBV-B chimeric DNA.

Effect of the Invention

By the HCV/GBV-B chimeric RNA of the present invention, it is possible to provide a replicon RNA which can replicate in a human liver-derived cell in vitro at high efficiency. Further, HCV/GBV-B chimeric virus particles can be produced which can autonomously replicate and is capable of persistent infection and reinfection in primary hepatocytes of marmoset.

By using the HCV/GBV-B chimeric virus of the present invention, an HCV animal model using a small primate such as tamarin or marmoset can be constructed. By using this animal model, it is possible to carry out not only basic research of HCV, but also development and evaluation of drugs to suppress or inhibit aggravation of hepatitis, thereby enabling development and evaluation of more effective prophylactic agents and therapeutic agents for the infection.

The present invention also provides cells in which this HCV/GBV-B chimeric gene can replicate. Using the HCV/GBV-B chimeric replication system of the cells in which this HCV/GBV-B chimeric gene replicates, drugs to suppress growth of HCV can be screened. Further, the animal model is also effective as a method to evaluate the effect of the drugs screened. In this case, it is important to carry out evaluation of the drugs using this method, and, if the method is indispensable for control of the drugs, it can also be used as a method to produce the drugs.

BEST MODE FOR CARRYING OUT THE INVENTION

Figure 1:
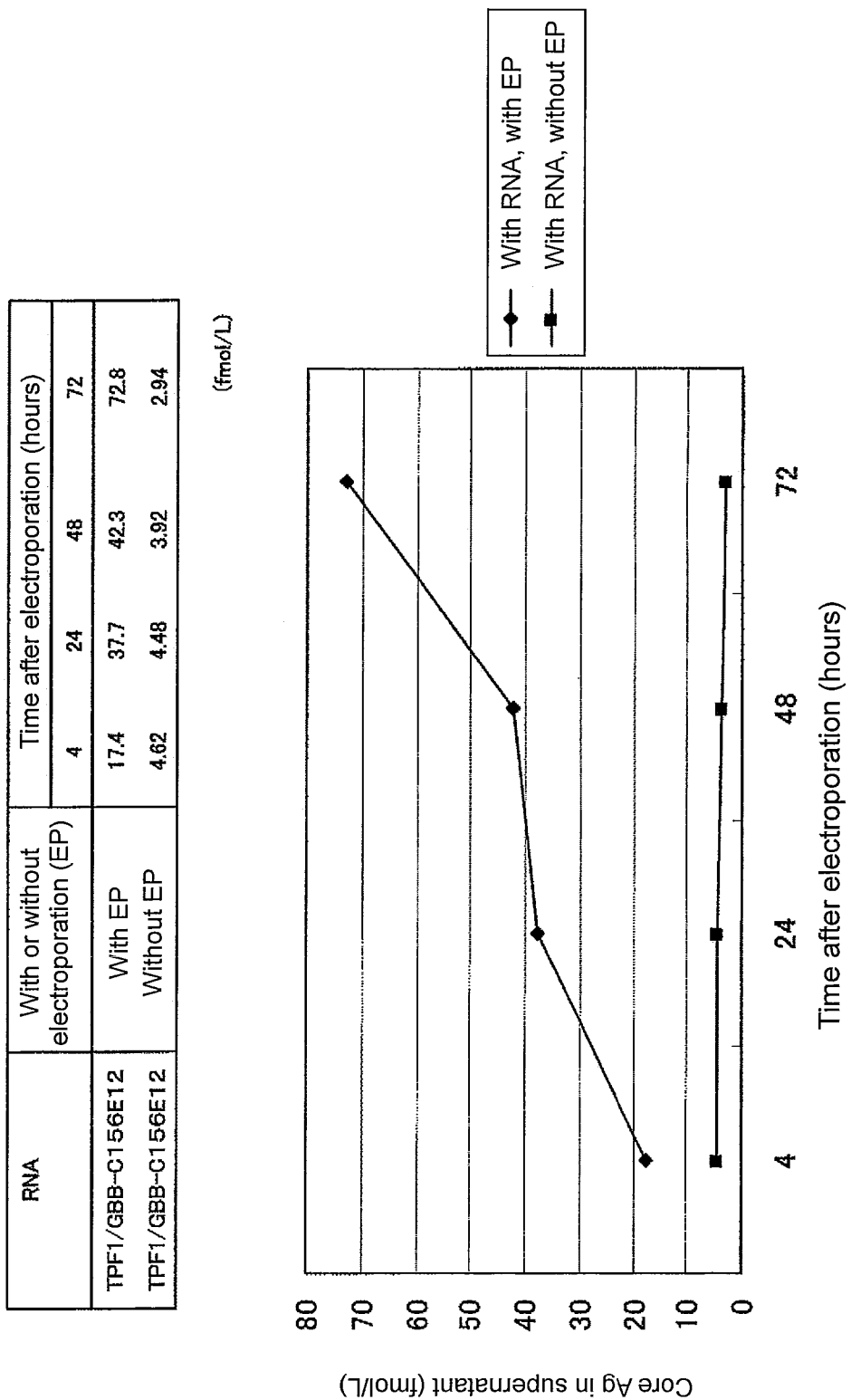
FIG. 1 is a diagram showing the concentration of the core protein of HCV in the supernatant measured 4 hours, 24 hours, 48 hours and 72 hours after transfection of the HCV/GBV-B chimeric RNA of the present invention to Huh-7 cells.

The HCV/GBV-B chimeric RNA of the present invention is constituted by an RNA of HCV and an RNA of GBV-B linked to each other, and comprises an RNA encoding the NS4B protein having leucine at the 1804th position and lysine at the 1966th position in the amino acid sequence of the polyprotein of HCV. The HCV/GBV-B chimeric RNA of the present invention encodes a virus particle that can grow in a hepatocyte of a primate mammal such as tamarin or marmoset.

In the term "leucine at the 1804th position and lysine at the 1966th position", each of the numbers indicates the amino acid No. in the full length polyprotein of HCV having 3010 amino acids. The leucine at the 1804th position and the lysine at the 1966th position are amino acids contained in the NS4B protein. The present inventors previously reported an RNA of HCV which has a base sequence encoding these amino acids (Patent Document 1), and an NS4B protein containing these amino acids had not been reported until then. Therefore, an HCV polyprotein containing these amino acids, and an RNA replicon containing a polynucleotide encoding these amino acids had not been reported, too.

The polyprotein of HCV comprises, for example, in HCV of genotype 1b having 3010 amino acids, a core protein having the sequence of the 1st to 191st amino acids, E1 protein having the sequence of the 192nd to 383rd amino acids, E2 protein having the sequence of the 384th to 746th amino acids, p7 protein having the sequence of the 747th to 809th amino acids, NS2 protein having the sequence of the 810th to 1026th amino acids, NS3 protein having the sequence of the 1027th to 1657th amino acids, NS4A protein having the sequence of the 1658th to 1711st amino acids, NS4B protein having the sequence of the 1712nd to 1972nd amino acids, NS5A protein having the sequence of the 1973rd to 2419th amino acids, or NS5B protein having the sequence of the 2420th to 3010th amino acids. In the present specification, the polyprotein of HCV means a continuous protein translated from the RNA of HCV, and, for example, in HCV of genotype 1b, it is a protein having 3010 amino acids.

Since the HCV/GBV-B chimeric RNA of the present invention comprises leucine at the 1804th position and lysine at the 1966th position in the full length polyprotein of HCV having 3010 amino acids, it can replicate in a cell derived from human liver, and can autonomously replicate in a primary hepatocyte of marmoset to produce an HCV/GBV-B chimeric virus particle capable of reinfection.

The HCV/GBV-B chimeric RNA may further contain an RNA that does not substantially inhibit replication of, and infection with, the chimeric RNA. For example, it may contain a selection marker gene, a reporter gene or an IRES sequence.

The HCV/GBV-B chimeric RNA of the present invention is not restricted as long as it contains the polynucleotide encoding leucine at the 1804th position and lysine at the 1966th position, and it preferably comprises a 5'-side RNA of HCV, a GBV-B RNA, and a 3'-side RNA of HCV. It is more preferably a chimeric RNA having the nucleotide sequence shown in SEQ ID NO:55.

(A) 5'-Side RNA of HCV

The 5'-side RNA of HCV comprises at least an RNA of the 5'-UTR of HCV. It may further comprise an RNA encoding a part or all of the core protein of HCV.

In terms of the gene of HCV, for example, the HCV gene of a common genotype 1b is composed of an RNA of the 5'-UTR (1st to 341st positions); followed by an RNA encoding the core protein (342nd to 914th positions), RNA encoding the E1 protein (915th to 1490th positions) and RNA encoding the E2 protein (1941st to 2579th positions), which are structural proteins of the virus, and an RNA encoding the p7 protein (2580th to 2768th positions), RNA encoding the NS2 protein (2769th to 3419th positions), RNA encoding the NS3 protein (3420th to 5312nd positions), RNA encoding the NS4A protein (5313rd to 5474th positions), RNA encoding the NS4B protein (5475th to 6257th positions), RNA encoding the NS5A protein (6258th to 7598th positions) and RNA encoding the NS5B protein (7599th to 9371st positions), which are nonstructural proteins; and further, an RNA of the 3'-UTR (the 9372nd and following positions).

The 5'-UTR is usually composed of 341 nucleotides in the HCV gene of genotype 1b, and the RNA in the 5'-side of HCV preferably comprises the total length of its nucleotide sequence.

Further, the RNA encoding the core protein is composed of the 573 nucleotides at the 342nd to 914th positions, and the RNA in the 5'-side of HCV may comprise all or a part of the nucleotides.

The nucleotide sequence of the RNA in the 5'-side of HCV is not restricted and has a homology of preferably not less than 90%, more preferably not less than 93%, most preferably not less than 95% to the nucleotide sequence of the corresponding region in SEQ ID NO:55. Since the HCV/GBV-B chimeric RNA comprises the 5'-side RNA of HCV, drugs which inhibit the function of the RNA in the 5'-UTR or the RNA encoding the core protein can be screened.

(B) GBV-B RNA

The GBV-B RNA preferably comprises at least an RNA encoding the E1 protein and an RNA encoding the E2 protein. It may further comprise a part or all of the RNA encoding the core protein and/or a part or all of the RNA encoding the p6 protein.

The gene of GBV-B is composed of an RNA of the 5'-UTR (1st to 445th positions); followed by an RNA encoding the core protein (446th to 913rd positions), RNA encoding the E1 protein (914th to 1489th positions) and RNA encoding the E2 protein (1490th to 2284th positions), which are structural proteins of the virus, and an RNA encoding the p6 protein (2285th to 2452nd positions), RNA encoding the p7 protein (2453rd to 2641st positions), an RNA encoding the NS2 protein (2642nd to 3265th positions), RNA encoding the NS3 protein (3266th to 5125th positions), RNA encoding the NS4A protein (5126th to 5290th positions), RNA encoding the NS4B protein (5291st to 6034th positions), RNA encoding the NS5A protein (6035th to 7267th positions) and RNA encoding the NS5B protein (7268th to 9037th positions), which are nonstructural proteins; and further, an RNA of the 3'-UTR (the 9038th and following positions). It is structurally different from the gene of HCV that GBV-B has the region encoding the p6 protein.

The RNA encoding the E1 protein of GBV-B is preferably composed of the 576 nucleotides at the 914th to 1489th positions and comprises the full-length sequence of the nucleotides. The RNA encoding the E2 protein is preferably composed of the 795 nucleotides at the 1490th to 2284th positions and comprises the full-length sequence of the nucleotides.

Since the HCV/GBV-B chimeric RNA comprises an RNA encoding the E1 protein and an RNA encoding the E2 protein, it can infect experimental animals such as tamarin and marmoset, or cells derived from these animals.

Further, the RNA encoding the core protein is composed of the 468 nucleotides at the 446th to 913rd positions, and the GBV-B RNA may comprise all or a part of the nucleotides.

Further, the p6 protein is composed of the 168 nucleotides at the 2285th to 2452nd positions, and the GBV-B RNA may comprise all or a part of the nucleotides.

Further, the nucleotide sequence of the GBV-B RNA is not restricted as long as it has the function as the translated protein of GBV-B, that is, as long as the produced chimeric virus has infectivity to experimental animals such as tamarin and marmoset.

(C) 3'-Side RNA of HCV

The 3'-side RNA of HCV comprises at least an RNA encoding the NS3 protein, RNA encoding the NS4A protein, RNA encoding the NS4B protein, RNA encoding the NS5A protein and RNA encoding the NS5B protein; and an RNA of the 3'-UTR. It may further comprise an RNA encoding the p7 protein of HCV and an RNA encoding the NS2 protein of HCV.

The RNA encoding the p7 protein is composed of the 189 nucleotides at the 2580th to 2768th positions, and may comprise all or a part of the nucleotides. The RNA encoding the NS2 protein is composed of the 651 nucleotides at the 2769th to 3419th positions, and may comprise the total length of the nucleotides.

The RNA encoding the NS3 protein is composed of the 1893 nucleotides at the 3420th to 5312nd positions, and preferably comprises the total length of the nucleotides.

The RNA encoding the NS4A protein is composed of the 162 nucleotides at the 5313rd to 5474th positions, and preferably comprises the total length of the nucleotides.

The RNA encoding the NS4B protein is composed of the 783 nucleotides at the 5475th to 6257th positions, and preferably comprises the total length of the nucleotides.

The RNA encoding the NS5A protein is composed of the 1341 nucleotides at the 6258th to 7598th positions, and preferably comprises the total length of the nucleotides.

The RNA encoding the NS5B protein is composed of the 1773 nucleotides at the 7599th to 9371st positions, and preferably comprises the total length of the nucleotides.

The RNA of the 3'-UTR is the RNA of the 9372nd and following positions, and its length varies depending on the virus strain. It is usually composed of a variable region of 41 nucleotides, a poly-U region whose length varies depending on the strain, and a 3' X region of 98 nucleotides. The 3'-side RNA of HCV preferably comprises the total length of its 3'-UTR.

The HCV/GBV-B chimeric RNA may comprise, as the RNA encoding the core, an RNA encoding the core of HCV, an RNA encoding the core of GBV-B, or an RNA encoding a chimeric core of HCV and GBV-B. These core proteins translated from the HCV/GBV-B chimeric RNA may be contained in the HCV/GBV-B chimeric virus particle.

The HCV/GBV-B chimeric RNA may comprise all or a part of the RNA encoding the p6 protein of GBV-B, all or a part of the RNA encoding the p7 protein of HCV, and/or all or a part of the RNA encoding the NS2 protein of HCV.

The 3'-side RNA of HCV comprises an RNA encoding leucine at the 1804th position and lysine at the 1966th position in the amino acid sequence of the polyprotein of HCV. These amino acids are contained in the NS4B protein, and it is thought that, by inclusion of an RNA encoding the two amino acid sequences, more preferably, by inclusion of an RNA encoding the NS4B protein having the two amino acid sequences, the HCV/GBV-B chimeric RNA of the present invention can replicate the RNA and produce a chimeric virus in a primary hepatocyte of marmoset.

The nucleotide sequence of the 3'-side RNA of HCV is not restricted, and has a homology of preferably not less than 80%, more preferably not less than 90%, most preferably not less than 95% to the nucleotide sequence of the corresponding region in SEQ ID NO:55.

Further, since the HCV/GBV-B chimeric RNA comprises the 3'-side RNA of HCV, it can be used for screening or evaluation of drugs that inhibit the functions of the nonstructural proteins and of the RNA in the 3'-UTR.

In the HCV/GBV-B chimeric RNA of the present invention, the 5'-side RNA of HCV (A), the GBV-B-RNA (B) and the 3'-side RNA of HCV (C) are preferably linked together in that order. That is, the GBV-B-RNA (B) is preferably inserted between the 5'-side RNA of HCV (A) and the 3'-side RNA of HCV (C).

In the present invention, the genotype of the HCV RNA is not restricted, and preferably genotype 1b of HCV. The HCV gene can be grouped into at least 6 kinds of genotypes based on its nucleotide sequence, and genotype 1b is a subtype belonging to genotype 1. Identification of HCV of genotype 1b is based on the nucleotide sequence of its RNA, and, for example, an HCV with a polynucleotide having a nucleotide sequence showing a homology of not less than 90% to the base sequence of SEQ ID NO:57 is included therein.

The HCV/GBV-B chimeric RNA of the present invention can replicate in a cell, for example, human hepatocyte, tamarin hepatocyte or marmoset hepatocyte. That is, it can also function as a replicon RNA. In cases where it functions as a replicon RNA, the HCV/GBV-B chimeric RNA of the present invention functions as a plus-strand RNA which works as the template for a protein, that is, mRNA. A minus-strand RNA is synthesized from this plus-strand RNA, and, using the minus-strand RNA as a template, a plus-strand RNA can be synthesized. The HCV/GBV-B minus-strand chimeric RNA of the present invention is also useful since it works as a template for an HCV/GBV-B chimeric RNA which is a plus strand.

The HCV/GBV-B chimeric virus of the present invention comprises the HCV/GBV-B chimeric RNA, and may comprise several proteins constituting the virus translated from the HCV/GBV-B chimeric RNA. The proteins constituting the virus are not restricted, and examples thereof include the core protein of HCV; a chimeric core protein composed of a part of the core protein of HCV and a part of the core protein of GBV-B; and the E1 protein and the E2 protein of GBV-B.

The HCV/GBV-B chimeric DNA of the present invention is not restricted as long as it is a DNA corresponding to the HCV/GBV-B chimeric RNA. Examples thereof include a single-stranded cDNA synthesized from the HCV/GBV-B chimeric RNA by reverse transcriptase, a double-stranded DNA composed of the single-stranded cDNA and a complementary strand thereof, and a double-stranded DNA incorporated into a plasmid.

The vector of the present invention is a vector comprising the HCV/GBV-B chimeric DNA. Examples thereof include, but are not limited to, plasmid vectors; linear double-stranded DNA vectors; and virus vectors such as adenovirus vectors, adeno-associated virus vectors, retrovirus vectors and lentivirus vectors; and the vector is preferably a plasmid vector.

The HCV/GBV-B chimeric protein of the present invention is a protein translated from the HCV/GBV-B chimeric RNA, and examples thereof include a single chimeric polyprotein (SEQ ID NO:56) translated from the region in the RNA encoding the protein, or a chimeric core protein composed of a part of the core protein of HCV and a part of the core protein of GBV-B.

The HCV/GBV-B chimeric RNA of the present invention can be prepared using arbitrary genetic engineering techniques. The chimeric RNA can be prepared by, for example, the following method, although the method is not restricted.

A DNA encoding the HCV/GBV-B chimeric RNA is inserted into a cloning vector by a conventional method, to prepare a DNA clone. The obtained DNA is inserted into the downstream of an RNA promoter, to prepare a DNA clone which can produce a replicon RNA. More particularly, for example, a gene is constructed from TPF1 clone (Patent Document 1), which was isolated from a patient suffering from fulminant hepatitis C, by deleting the region from the 156th position in the core protein to the E2 protein. A gene of GBV-B composed of the region from the 124th position in the core protein to the p6 protein is chemically synthesized, and, by inserting and linking the synthesized gene to the portion deleted in HCV, an HCV/GBV-B chimeric gene can be constructed. The RNA promoter is preferably included in the plasmid clone. The RNA promoter is not restricted, and examples thereof include the T7 RNA promoter, SP6 RNA promoter and SP3 RNA promoter, among which the T7 RNA promoter is especially preferred.

Another preferred mode of the present invention is as follows.

That is, in this mode (this may be hereinafter referred to as "E1 fusion type" for convenience), the HCV/GBV-B chimeric RNA comprises:

(A) an HCV 5'-side RNA comprising an RNA of the 5'-UTR of HCV and an RNA encoding the core protein and a part of the E1 protein of HCV;

(B) a GBV-B-RNA comprising an RNA encoding a part of the E1 protein and an RNA encoding the E2 protein of GBV-B; and (C) an HCV 3'-side RNA comprising an RNA encoding the NS3 protein, NS4A protein, NS4B protein, NS5A protein and NS5B protein of HCV, and an RNA of the 3'-UTR of HCV; preferably an RNA encoding the p7 protein, NS2 protein, NS3 protein, NS4A protein, NS4B protein, NS5A protein and NS5B protein of HCV, and an RNA of the 3'-UTR of HCV. The GBV-B RNA (B) is inserted between the HCV 5'-side RNA (A) and the HCV 3'-side RNA (C); the part of the E1 protein encoded by the HCV 5'-side RNA (A) is a part of the N-terminus side of the E1 protein, the part of the E1 protein encoded by the GBV-B RNA (B) is a part of the C-terminus side of the E1 protein; and these both parts are fused together to cover the total length of the E1 protein.

In the E1 fusion type, the RNA of the 5'-UTR and the core protein in the HCV 5'-side RNA (A) are as described above, and these preferably have the nucleotide sequences of the corresponding regions in the nucleotide sequence shown in SEQ ID NO:57 (i.e., the RNA of the 5'-UTR corresponds to the 1st to 341st positions in the nucleotide sequence shown in SEQ ID NO:57, and the coding region of the core protein corresponds to the 342nd to 914th positions in the nucleotide sequence shown in SEQ ID NO:57) or nucleotide sequences having homologies of not less than 90%, more preferably not less than 93%, still more preferably not less than 95%, still more preferably not less than 99% to these nucleotide sequences. The sequences are preferably those with which a virus particle that can grow in a primate hepatocyte can be constructed. The term "homology" of nucleotide sequences means a value calculated by aligning two nucleotide sequences to be compared such that the number of matched bases is the maximum, and dividing the number of the matched bases by the total number of bases, which value is represented in percentage. Upon the above-described alignment, a gap(s) is/are inserted as required into one or both of the two sequences to be compared. Such alignment of sequences can be carried out using a well-known program such as BLAST, FASTA or CLUSTAL W. In cases where a gap(s) is/are inserted, the above-described total number of bases is counted regarding one gap as one base. In cases where the thus counted total number of bases is different between the two sequences to be compared, the homology (%) is calculated by dividing the number of matched bases by the total number of bases in the longer sequence.

In the E1 fusion type, the HCV 5'-side RNA (A) also comprises the region encoding a part of the N-terminus side of the E1 protein. Since the E1 protein of HCV corresponds to the region from the 915th to 1490th positions in the nucleotide sequence shown in SEQ ID NO:57 as described above, the HCV 5'-side RNA (A) preferably has a sequence of a partial region in the 5'-side of this sequence, or a nucleotide sequence having a homology of not less than 90%, more preferably not less than 93%, still more preferably not less than 95%, still more preferably not less than 99% thereto, and can preferably construct a virus particle that can grow in a hepatocyte of primate such as tamarin or marmoset. Here, the region encoding a part of the N-terminus side of the E1 protein is preferably a region of not more than 30 amino acids from the N-terminus of the E1 protein in view of the ability of the virus particle to grow in a primate hepatocyte. In the following Examples, v11-E12 chimeric RNA, which encodes the 11 amino acids from the N-terminus of the E1 protein, and v27-E12 chimeric RNA, which encodes the 27 amino acids from the N-terminus of the E1 protein, were constructed, and both of these were confirmed to have excellent abilities to increase in a primary hepatocyte of marmoset.

The following RNA of GBV-B (GBV-B RNA) (B) encodes a part of the C-terminus side of the E1 protein, and the E2 protein. Here, the term "a part of the C-terminus side" means that the part is located closer to the C-terminus than the partial region of the E1 protein encoded by the HCV 5'-side RNA (A) and, in a preferred mode, the most part of the E1 protein is encoded by the GBV-B RNA (B). The nucleotide sequence of the total length of the GBV-B RNA is shown in SEQ ID NO:99, and the amino acid sequence encoded thereby is shown in SEQ ID NO:100. In the nucleotide sequence shown in SEQ ID NO:99, the E1 protein-coding region corresponds to the 914th to 1489th positions, and the E2 protein-coding region corresponds to the 1490th to 2284th positions. The GBV-B RNA (B) further preferably encodes the p6 protein. In the nucleotide sequence shown in SEQ ID NO:99, the p6 protein-coding region corresponds to the 2285th to 2452nd positions. The GBV-B RNA (B) preferably has the nucleotide sequence of the corresponding region shown in SEQ ID NO:99, or a nucleotide sequence having a homology of not less than 90%, more preferably not less than 93%, still more preferably not less than 95%, still more preferably not less than 99% thereto, and can preferably construct a virus particle that can grow in a primate hepatocyte.

In the E1 fusion type, the E1 protein is encoded by both of the HCV 5'-side RNA (A) and the GBV-B-RNA (B), and the total length of the E1 protein is covered by fusion of the both portions. The region encoded by the both may be partially overlapped with each other. In such a case, the size of the overlapping region is preferably 1 to 24 amino acids. For example, in the v11 chimeric gene prepared in Examples below, the HCV 5'-side RNA (A) encodes the 11 amino acids from the N-terminus of the E1 protein, and, on the other hand, the GBV-B RNA (B) encodes the 3rd and following amino acids from the N-terminus of the E1 protein, so that 8 amino acids are overlapping. Similarly, in v27, the HCV 5'-side RNA (A) encodes the 27 amino acids from the N-terminus of the E1 protein, and, on the other hand, the GBV-B RNA (B) encodes the 3rd and following amino acids from the N-terminus of the E1 protein, so that 24 amino acids are overlapping.

The following HCV 3'-side RNA (C) is the same as described above, and comprises an RNA encoding the NS3 protein, NS4A protein, NS4B protein, NS5A protein and NS5B protein, and an RNA of the 3'-UTR; preferably an RNA encoding the p7 protein, NS2 protein, NS3 protein, NS4A protein, NS4B protein, NS5A protein and NS5B protein, and an RNA of the 3'-UTR. As described above, in the nucleotide sequence shown in SEQ ID NO:57, the coding region of the p7 protein is from the 2580th position to the 2768th position; the coding region of the NS2 protein is from the 2769th position to the 3419th position; the coding region of the NS3 protein is from the 3420th position to the 5312nd position; the coding region of the NS4A protein is from the 5313rd position to the 5474th position; the coding region of the NS4B protein is from the 5475th position to the 6257th position; the coding region of the NS5A protein is from the 6258th position to the 7598th position; the coding region of the NS5B protein is from the 7599th position to the 9371st position; and the RNA of the 3'-UTR corresponds to the 9372nd and following positions. The HCV 3'-side RNA (C) preferably has the nucleotide sequences of these regions in the sequence shown in SEQ ID NO:57, or nucleotide sequences having homologies of not less than 90%, more preferably not less than 93%, still more preferably not less than 95%, still more preferably not less than 99% thereto, and can preferably construct a virus particle that can grow in a primate hepatocyte.

Needless to say, the above-described (A), (B) and (C) are linked together such that a continuous reading frame is attained, and the protein encoded thereby encodes a virus particle that can grow in a hepatocyte of primate such as tamarin or marmoset. Preferred examples of the E1 fusion type include the v11-E12 chimeric RNA (SEQ ID NO:93) and the v27-E12 chimeric RNA (SEQ ID NO:95) constructed in the Examples below, and RNAs having homologies of not less than 90%, more preferably not less than 95%, still more preferably not less than 99% thereto, which encode a virus particle that can grow in a primate hepatocyte.

Another preferred mode is an RNA wherein the entire core protein is encoded by the GBV-B RNA (this may be hereinafter referred to as "core GB type" for convenience). That is, the core GB type comprises:
(A) an HCV 5'-side RNA comprising an RNA of the 5'-UTR of HCV;
(B) a GBV-B RNA comprising an RNA encoding the core protein, E1 protein and E2 protein of GBV-B; and
(C) an HCV 3'-side RNA comprising an RNA encoding the NS3 protein, NS4A protein, NS4B protein, NS5A protein and NS5B protein of HCV, and an RNA of the 3'-UTR of HCV; preferably an RNA encoding the p7 protein, NS2 protein, NS3 protein, NS4A protein, NS4B protein, NS5A protein and NS5B protein of HCV, and an RNA of the 3'-UTR of HCV.

In the core GB type, the RNA of the 5'-UTR in the HCV 5'-side RNA (A) is the same as the RNA in the 5'-UTR of the above-described E1 fusion type, and preferred examples thereof are also the same as those in the E1 fusion type.

In the core GB type, the following core protein is encoded by the GBV-B RNA (B). The core protein-coding region in the GBV-B RNA corresponds to the 446th to 913rd positions in the nucleotide sequence shown in SEQ ID NO:99, and the core protein-coding region of the core GB type has the nucleotide sequence of this region in SEQ ID NO:99, or has a homology of preferably not less than 90%, more preferably not less than 95%, still more preferably not less than 99% to the nucleotide sequence, and preferably encodes a virus particle that can grow in a primate hepatocyte.

The total length of the following E1 protein-coding region is also encoded by the GBV-B RNA (B). As described above, in the nucleotide sequence shown in SEQ ID NO:99, the E1 protein-coding region corresponds to the 914th to 1489th positions; and the E2 protein-coding region corresponds to the 1490th to 2284th positions. The GBV-B RNA (B) further preferably encodes the p6 protein. In the nucleotide sequence shown in SEQ ID NO:99, the p6 protein-coding region corresponds to the 2285th to 2452nd positions. The GBV-B RNA (B) preferably has the nucleotide sequence of the corresponding region in SEQ ID NO:99, or a sequence having a homology of not less than 90%, more preferably not less than 93%, still more preferably not less than 95%, still more preferably not less than 99% thereto, and can preferably construct a virus particle that can grow in a primate hepatocyte.

The structure of the downstream of the E1 protein-coding region (including the HCV 3'-side RNA (C)) is the same as that of the E1 fusion type described above, and the explanations on these regions in the E1 fusion type equally apply as they are.

Needless to say, the above-described regions (A), (B) and (C) are linked together such that a continuous reading frame is attained, and the protein encoded thereby encodes a virus particle that can grow in a hepatocyte of primate such as tamarin or marmoset. Preferred examples of the core GB type include the C6 chimeric RNA (SEQ ID NO:97) constructed in the Examples below, and RNAs having homologies of not less than 90%, more preferably not less than 95%, still more preferably not less than 99% thereto, which encode a virus particle that can grow in a primate hepatocyte.

In the same manner as described above, the E1 fusion type and the core GB type can also be prepared using arbitrary genetic engineering techniques. The chimeric RNA can be prepared by, for example, the following method, although the method is not restricted.

A DNA encoding the HCV/GBV-B chimeric RNA is inserted into a cloning vector by a conventional method, to prepare a DNA clone. The obtained DNA is inserted into the downstream of an RNA promoter, to prepare a DNA clone which can produce a replicon RNA. More particularly, for example, in pTPF1/4B (Patent Document 1, SEQ ID NO:57), which was prepared by mutating the amino acid sequence encoded by TPF1 clone isolated from a patient suffering from fulminant hepatitis C such that the 1804th position is leucine and the 1966th position is lysine, the region encoded by the above-described GBV-B RNA (B) is deleted to construct a DNA. On the other hand, the DNA of the above-described GBV-B RNA (B) is chemically synthesized, and, by inserting and linking the synthesized DNA to the portion deleted in HCV, the HCV/GBV-B chimeric gene can be constructed. The RNA promoter is preferably included in the plasmid clone. The RNA promoter is not restricted, and examples thereof include the T7 RNA promoter, SP6 RNA promoter and SP3 RNA promoter, among which the T7 RNA promoter is especially preferred. Particular methods for construction of preferred examples of the E1 fusion type and the core GB type are described in detail in the Examples below.

The HCV/GBV-B chimeric RNA of the present invention can be prepared from a vector to which the above-described DNA was inserted. Using the DNA clone as a template, the RNA is synthesized by RNA polymerase. The RNA synthesis can be initiated from the 5'-UTR by a conventional method. In cases where the template DNA is a plasmid clone, it is also possible to excise the DNA region linked to the downstream of an RNA promoter from the plasmid clone with a restriction enzyme, followed by synthesizing the RNA using the DNA fragment as a template. The 3'-end of the synthesized RNA is preferably coincident with the 3'-UTR of the virus genomic RNA, with neither addition of another sequence nor deletion. For example, in a preferred mode of the HCV/GBV-B chimeric RNA of the present invention, the template DNA is inserted into a vector which has a T7 RNA promoter at a position corresponding to the upstream of the 5'-UTR of HCV, and an XhoI restriction site at a position corresponding to the end of the 3'-UTR of HCV. After digestion with XhoI, the HCV genomic RNA can be synthesized by T7 RNA polymerase.

The replication cell of the present invention can be prepared by introducing the HCV/GBV-B chimeric RNA into an arbitrary cell. The cell to which the HCV/GBV-B chimeric RNA is introduced is not restricted, and it is preferably a monkey liver-derived cell or a human liver-derived cell. Examples of the monkey liver-derived cell include a marmoset primary hepatocyte and a tamarin primary hepatocyte. Examples of the cell derived from human liver cancer include Huh7 cell, HepG2 cell and Hep3B cell, and IMY-N9 cell, and examples of the other cancer cells include HeLa cell, CHO cell, COS cell, Vero cell and 293 cell.

Transfection of the HCV/GBV-B chimeric RNA into the cell can be carried out by an arbitrary transfection method. Examples of such a method of transfection include electroporation, the particle gun method and the lipofection method. For example, in cases where the transfection is carried out to a Huh7 cell, which is a human liver cancer-derived cell line, electroporation is especially preferred. In cases where the transfection is carried out to a monkey liver-derived cell, the lipofection method is preferred.

By using the replication cell, substances that control infection with HCV can be screened. The term "control infection with hepatitis C virus" means control (e.g., promotion or suppression) of replication of the RNA of HCV or control (e.g., promotion or suppression) of translation of the RNA into proteins.

More particularly, screening of a test substance can be carried out by bringing the test substance into contact with the replication cell and analyzing the level of increase in the HCV/GBV-B chimeric RNA. The term "level of increase in the HCV/GBV-B chimeric RNA" means a change in the rate or the amount of replication of the replicon RNA. More particularly, the amount of the HCV/GBV-B chimeric RNA in the replication cell is detected or measured, followed by comparing it with the amount of the HCV/GBV-B chimeric RNA in a control, that is, a replication cell that was not brought into contact with the test substance, thereby allowing screening of the test substance. Further, screening of the test substance can be carried out also by detecting or measuring the amount of a protein of HCV, a protein of GBV-B, or an HCV/GBV-B chimeric protein in the cell or the supernatant, followed by comparing it with that of a replication cell that was not brought into contact with the test substance. The protein of HCV which can be detected or measured by the screening is not restricted, and it is preferably the core protein, which can be measured also by using a commercially available kit. Further, by automating the screening method, the method can be applied to a high throughput screening method.

The replication cell of the present invention can produce an HCV/GBV-B chimeric RNA, HCV/GBV-B chimeric protein and HCV/GBV-B chimeric virus. Further, the replication of an HCV/GBV-B chimeric RNA in the replication cell of the present invention may be either transient replication or persistent replication. Further, in cases where an HCV/GBV-B chimeric virus is produced, cells can be reinfected with the produced virus.

By inoculating the HCV/GBV-B chimeric RNA or the HCV/GBV-B chimeric virus of the present invention to an experimental animal, a model animal for HCV infection can be prepared.

The non-human experimental animal is not restricted as long as it allows replication of the HCV/GBV-B chimeric virus or it can be infected with the virus, and the non-human experimental animal is preferably a small primate, more preferably marmoset or tamarin.

The method for administration of the HCV/GBV-B chimeric RNA to an experimental animal is not restricted, and examples thereof include intraperitoneal, intramuscular, intraspinal, intracranial, intravenous, intrarespiratory, oral, and intrahepatic administration, and the method for administration is preferably direct intrahepatic administration. The method for administration of the HCV/GBV-B chimeric virus to an experimental animal is also not restricted, and examples thereof include intraperitoneal, intramuscular, intraspinal, intracranial, intravenous, intrarespiratory, oral, and intrahepatic administration, and the method for administration is preferably intravenous administration.

By using an experimental animal wherein replication or infection of the HCV/GBV-B chimeric RNA or the HCV/GBV-B chimeric virus occurred, it is possible to screen or evaluate substances that control infection with HCV.

For example, screening or evaluation of a test substance can be carried out by administering the test substance to an experimental animal and analyzing the level of increase in the HCV/GBV-B chimeric virus, development of hepatitis and/or the like.

<Actions>

The RNA of HCV used for the HCV/GBV-B chimeric RNA of the present invention comprises the RNA encoding the NS4B protein having leucine at the 1804th position and lysine at the 1966th position in the amino acid sequence of the polyprotein of HCV. In a common HCV, the amino acid at the 1804th position is glutamine, and the amino acid at the 1966th position is glutamic acid, but, by their replacement with leucine at the 1804th position and lysine at the 1966th position, the replication efficiency of the RNA surprisingly increases. Therefore, a chimeric virus comprising the above-described RNA is considered to show highly efficient replication and growth in a cell or the living body of tamarin, or in a cell or the living body of marmoset. It is thought that, although the above-described RNA of HCV can replicate in cells of tamarin and marmoset even in cases it is not a chimeric virus, employment of a chimeric virus prepared with an RNA of GBV-B can achieve higher replication efficiency or infection efficiency. Since an RNA of genotype 1b of HCV comprising leucine at the 1804th position and lysine at the 1966th position especially increases replication efficiency, the genotype of the RNA of HCV to be used in the chimeric RNA is preferably 1b. Further, since the HCV/GBV-B chimeric RNA or the HCV/GBV-B chimeric virus of the present invention has the replication function in a Huh-7 cell, they are considered to maintain the replication function as HCV. Therefore, the non-human animal of the present invention is useful for development of prophylactic agents and therapeutic agents for HCV.

EXAMPLES

The present invention will now be described concretely by way of Examples, but the scope of the present invention is not restricted by these.

REFERENCE EXAMPLES

Construction of Highly Infective HCV (pTPF1/4B)

Patent Document:1, SEQ ID NO:57

Reference Example 1

Isolation and Analysis of Full-Length Gene of Fulminant Hepatitis C Virus (A) Extraction of RNA from Serum From 250 μL of serum collected from a fulminant hepatitis patient in the acute stage, RNA was purified using High Pure Viral Nucleic Acid Kit (Roche diagnostics corporation) according to the method recommended by the manufacturer.

(B) Synthesis of cDNA and Amplification of cDNA by PCR

A primer XR58R was added to the purified RNA, and reverse transcription was carried out with SuperSucript II reverse transcriptase (Invitrogen) according to the method recommended by the manufacturer at 42° C. for 1 hour, to obtain cDNA. RNase H (Invitrogen) was added to the obtained reaction solution, and the reaction was allowed to proceed at 37° C. for 30 minutes, to degrade the RNA. The resulting reaction solution was subjected to polymerase chain reaction (PCR) using the HC-LongA1 primer and the 1b9405R primer, and Takara LA Taq DNA polymerase (Takara Shuzo Co., Ltd.), by the thermal cycle reaction of 30 cycles of 94° C. for 20 seconds and 68° C. for 9 minutes, to amplify cDNA. Further, a part of the obtained reaction solution was subjected to PCR using the HC85F and HC9302R primers to amplify the HCV cDNA.

(C) Cloning of cDNA

The amplified DNA fragment was separated by electrophoresis using 0.7% agarose gel, and the DNA fragment was recovered using QIAquick gel purification kit (QIAGEN) according to the method recommended by the manufacturer. The recovered DNA fragment was subjected to a ligation reaction with pGEM-T easy vector (Promega), and the DH5α strain was transformed with the resulting plasmid. An ampicillin-resistant transformant was selected and cultured using 2YT medium. From the cultured bacterial cells, the plasmid was purified using Wizard Plus SV Miniprep DNA Purification System.

(D) Determination of Nucleotide Sequence

The nucleotide sequence of the HCV cDNA was determined using a primer designed based on the nucleotide sequence of genotype 1b of HCV. The reaction was carried out using CEQ DTCS Quick Start Kit (Beckman Coulter) according to the method recommended by the manufacturer, followed by analysis using CEQ2000 XL DNA analysis system (Software version 4.0.0, Beckman Coulter). The obtained data were analyzed using Sequencher (Version 4.1.2, Gene Codes Corporation). The obtained HCV clone was designated pTPF1-0193.

(E) Obtaining cDNA of 5'-UTR and Determining its Base Sequence

Further, from the RNA obtained in the above-described step (A), a cDNA of the end of the 5'-UTR was obtained by the 5'-RACE method. The reaction was carried out using 5' RACE System for Rapid Amplification of cDNA Ends, Version2.0 (Invitrogen), according to the instructions attached to the kit.

As the antisense primer for the synthesis of cDNA, Chiba-as was used. cDNA was synthesized using SuperScript II Reverse Transcriptase (Invitrogen) and purified with an S.N.A.P column, followed by TdT-tailing reaction to add dCTP to the cDNA. Using the 5' RACE Abridged Anchor primer and the KY78 primer attached to the kit, and Takara LA Taq DNA polymerase (Takara Shuzo Co., Ltd.), the 1st PCR was carried out. Using a part of the PCR product, as a template, and the UTP primer and the KM2 primer attached to the kit, the 2nd PCR was carried out using Takara LA Taq DNA polymerase (Takara Shuzo Co., Ltd.), to obtain a PCR product. This PCR product was cloned into pGEM-T easy vector, and the nucleotide sequence of the product was determined according to the above-described step (D). The HCV cDNA clone containing the 1st to 709th positions in the obtained sequence was designated pTPF1-0007.

(F) Obtaining cDNA of 3'-UTR and Determining its Nucleotide Sequence

From the RNA obtained in the above-described step (A), a cDNA of the end of the 3'-UTR was obtained by the 3'-RACE method. First, Poly(A) was added to RNA of a patient using Poly(A) Tailing Kit (Ambion) according to the instructions attached to the kit. The above-described steps (B) to (D) were carried out in the same manner except that the dT-Adp primer was used instead of the XR58R primer; the 3UTR-1F primer and the Adp primer were used as the primers for the 1st PCR; and the XR58F primer and the Adp primer were used as the primers for the 2nd PCR. The obtained HCV cDNA clone was designated pTPF1-8994.

The obtained HCV strain was designated the TPF1 strain. The TPF1 strain was an HCV having a total length of 9594 bases. The polynucleotide of the TPF1 strain obtained had a coding region encoding continuous 3010 amino acids between the 342nd position and the 9374th position thereof.

Reference Example 2

Preparation of Subgenomic RNA Replicon

The total length of the polynucleotide of the HCV TPF1 strain was inserted into the downstream of the T7 promoter sequence of pBluescript II SK(+) (the resulting plasmid is hereinafter referred to as pTPF1).

Subsequently, a part of the region encoding structural proteins and nonstructural proteins of pTPF1 was replaced with a neomycin resistance gene (neomycin phosphotransferase, NPT-II) and EMCV-IRES (the internal ribosomal entry site of encephalomyocarditis virus), to construct a plasmid DNA pRepTPF1. This construction was carried out according to a reported process (Lohmann et al., Science, (1999) 285, p. 110-113).

More particularly, pTPF1 was cleaved with restriction enzymes AgeI and BsrGI, and, to the cleaved site, a fragment prepared by PCR amplification of the sequence of the region from the 5'-UTR to the core region derived from pTPF1 and the neomycin resistance gene derived from pcDNA3.1(+), followed by cleavage thereof with restriction enzymes AgeI and PmeI; and a fragment prepared by PCR amplification of the sequence of the region from EMCV-IRES to the NS3 region, followed by cleavage thereof with restriction enzymes PmeI and BsrGI; were inserted by ligation. This plasmid DNA pRepTPF1 was digested with XbaI and used as a template for synthesis of RNA using Megascript T7 kit (Ambion). The RNA was purified by the method recommended by the manufacture.

Human liver cancer cells (Huh7, JCRB0403) were cultured under 5% carbon dioxide at 37° C. in culture medium prepared by adding fetal bovine serum (FBS) to 10%, and penicillin and streptomycin to 50 U/mL and 50 μg/mL, respectively, to Dulbecco's modified Eagle medium (D-MEM, IWAKI). The cells before confluence were peeled off from the culture dish by trypsin/EDTA treatment, and trypsin was then inactivated by resuspending the cells in serum-containing medium. After washing the cells twice with PBS, they were resuspended in Cytomix (120 mM potassium chloride, 10 mM potassium phosphate, 5 mM magnesium chloride, 25 mM HEPES, 0.15 mM calcium chloride, 2 mM EGTA, pH7.6) supplemented with 1.25% DMSO and transferred to an electroporation cuvette with a gap of 0.4 cm.

After adding an appropriate amount of the RNA to the cells, the cells were sufficiently cooled on ice for 5 minutes. Using an electroporator (Bio-Rad), the cells were pulsed at 960 uF, 250V. The cells were immediately resuspended in 8 mL of medium, and an aliquot thereof was plated. After a given period of culture, G418 (neomycin) was added to the culture plate to a concentration of 1 mg/mL. Thereafter, culture was continued while replacing the culture medium at 4-day intervals. About 20 days after the plating, colonies of live cells were cloned from the culture plate, and culture was continued. By such cloning of colonies, cells wherein the pRepTPF1 replicon RNA is autonomously replicating could be established. Whether or not replication of the replicon RNA occurred was determined by analyzing the copy number of replicated replicon RNA contained in cellular RNA by quantitative RT-PCR.

Method of Quantification of Minus Strand

Whether or not autonomous replication of the replicon RNA was occurring was assayed whether or not the minus strand of the 5'-UTR region of the HCV RNA could be detected in the cells. Specific quantification of the minus strand was carried out in the same manner as in the method of specific detection of minus strand RNA described in Japanese Patent Application No. 8-187097.

In the cells to which the RNA synthesized in vitro using pRepTPF-1 as a template was introduced by electroporation, a significant amount of minus strands could be detected, and therefore autonomous replication of the replicon RNA in the cells was confirmed.

Reference Example 3

Analysis of Adaptive Mutations

From the replicon RNA-replicating cell line established according to Reference Example 2 by synthesizing RNA in vitro using pRepTPF1 as a template and transfecting it to Huh7 cells, intracellular RNA was extracted using ISOGEN (Nippon Gene Co., Ltd.) under conditions recommended by the manufacturer.

From this intracellular RNA, DNA corresponding to almost the entire region of the replicon RNA was amplified in the same manner as in the case of obtaining the gene from TPF1 in Reference Example 1. More particularly, using the extracted intracellular RNA as a template and SuperSucript II reverse transcriptase (Invitrogen) and the XR58R primer, cDNA corresponding to the replicon RNA was synthesized.

A part of this cDNA was amplified by PCR and cloned into the pGEM-T easy vector, and the sequence of the clone was determined. As a result, substitution of A to T at the 5752nd nucleotide position and G to A at the 6237th nucleotide position were found. These resulted in mutation of Q (glutamine) to L (leucine) at the 1804th amino acid position and E (glutamic acid) to K (lysine) at the 1966th amino acid position, respectively.

Subsequently, the influence of the amino acid substitutions on replication of the replicon RNA was studied. First, to the HCV RNA replicon pRepTPF1 prepared in Reference Example 2, the adaptive mutations at the 1804th amino acid position (Q to L) and the 1906th amino acid position (E to K) were introduced using Quick Mutagenesis Kit (Stratagene) according to the method recommended by the manufacturer. This replicon RNA in which the amino acid substitutions were introduced was designated pRep4B.

Plasmid DNAs of pRepTPF1, which does not have the nucleotide sequence that cause the mutations, and pRep4B, which has the amino acid mutations, were digested with XbaI, and RNAs were synthesized using these DNAs as templates and Megascript T7 kit (Ambion). The RNAs were purified by the method recommended by the manufacturer. Each of the purified RNAs was transfected to Huh7 cells, and the cells were cultured in the presence of G418 for about 20 days, and then the live cells were stained with crystal violet. The numbers of colonies stained were counted, and the number of colonies per 1 µg of the transfected replicon RNA was calculated.

When 1 µg of RepTPF1 RNA was transfected, a single G418-resistant colony was selected, and when 1 µg of Rep4B RNA was transfected, $10^4$ colonies were selected. That is, the nucleotide mutations that cause the amino acid mutations in the replicon RNA were considered to be adaptive mutations that increase the replication efficiency of the replicon RNA in Huh7 cells.

Reference Example 4

Effect of Adaptive Mutation on Replication of HCV RNA

The full-length HCV DNA pTPF1 prepared in Reference Example 2 was digested with a restriction enzyme SfiI, and, to the cleaved site, a fragment prepared by digesting pRep4B with the restriction enzyme SfiI was inserted by ligation, thereby preparing a full-length HCV DNA pTPF1/4B to which the adaptive mutations were inserted. Its nucleotide sequence (described as RNA) is shown in SEQ ID NO:57, and the amino acid sequence encoded thereby is shown in SEQ ID NO:58.

Example 1

Construction of HCV/GBV-B Chimeric Gene (1) C156 Chimeric Gene (SEQ ID NO:55)

The above-described pTPF1/4B comprising the gene of HCV whose growth in a human liver cancer cell line had been confirmed was subjected to polymerase chain reaction (PCR) in the presence of the AgeI primer 5'-GGAACCGGTGAG-TACACCGGAATTGCCAGG-3' (SEQ ID NO:101) and the SpII primer 5'-ACCCGTACGCCATGCGCCAGGGC-CCTGGCAG-3' (SEQ ID NO:102) using Takara EX Taq DNA polymerase (Takara Shuzo Co., Ltd.), by the thermal cycle reaction of 20 cycles of 94° C. for 20 seconds and 68° C. for 30 seconds, to amplify the region from the 5'-UTR to the 156th position in the core protein in the TPF1 genome.

The amplified fragment was separated by 0.7% agarose gel electrophoresis, and the DNA fragment was recovered using QIAquick gel purification kit (QIAGEN) according to the method recommended by the manufacturer. The recovered TPF1 fragment was subjected to a ligation reaction with pGEM-T easy vector (Promega) according to the method recommended by the manufacturer, and the DH5α strain was transformed with the resulting plasmid. A transformant which was resistant to ampicillin and formed a white colony by plate culture on agar medium was selected, and cultured using 2YT medium to which ampicillin was added to 100

μg/mL From the cultured bacterial cells, the plasmid was purified using Wizard Plus SV Miniprep DNA Purification System.

The sequence reaction of the TPF1 fragment incorporated in the purified plasmid was carried out using primers suitable for the vector and the HCV sequence and CEQ DTCS Quick Start Kit (Beckman Coulter) according to the method -continued GBBP6-as1 (SEQ ID NO: 28):
5'-
GCCCGCAGCCATGGGCACAAACCCTAAAAGGGCAGCATAACGTAGCCTG-
3'

GBBP6-as2 (SEQ ID NO: 29):
5'-
CAGCGGAGATAGCAACAGATGAAGAAAATCAAAGCAAAAGGAGCTACTT
GAGCTTTAGAC-3'

GBBP6-as3 (SEQ ID NO: 30):
5'-
AAAACATCCCAGCCAGCTTGGAGATACGACTGGGATGGGAGCACAGGAC
GCAAAGGGTAA-3'

GBBE2-as4 (SEQ ID NO: 31):
5'-
CCAGAAGCGCGCCCAAAACAAAGGGACAAGTAACAGAGGTAGGCTAAA
ATAAGATACTTG-3'

GBBE2-as5 (SEQ ID NO: 32):
5'-
CTGCCACACAACCCCAACAGAATTAGCACCACGGCCTTGGTGGTAACTCC
CGTAAGAGAC-3'

GBBE2-as6 (SEQ ID NO: 33):
5'-
AAAGCACCCGTGGCGGAATATAAGACCTGATAATTTTTCCAGGCTTTGTC
TTTGGTGATC-3'

GBBE2-as7 (SEQ ID NO: 34):
5'-
AATCCTGTGGCTAGGTCTTTCACATCACTGTAAAACCCTTGCGGAACCTG
TAACCAAGAA-3'

GBBE2-as8 (SEQ ID NO: 35):
5'-
CCACGTACCACAGGTGGGGTACCGGGCAACCTAGCCCACCTCTCCGGTG
GTAGGAGAGTG-3'

GBBE2-as9 (SEQ ID NO: 36):
5'-
GAATTCACAGGGTCATAAAAGTAAACTATAGGGGTATCTGATCCCTCAAA
ATACAAATGG-3'

GBBE2-as10 (SEQ ID NO: 37):
5'-
CCTGACATCCAATTATGAGGTTTAAACATTTCTTTAGACCCAGGGTATTG
TAATATAGCC-3'

GBBE2-as11 (SEQ ID NO: 38):
5'-
AATTTCAGGGCTGAGCCGTTGTGCCATGCGGTTGTTAGCCATGGTGTTAC
ACCGCATGCT-3'

GBBE2-as12 (SEQ ID NO: 39):
5'-
TCGTAAGTGTTGCGAGTGTCGTTCCACACTGCATCAGTGCCCATAGTGCA
GTACGATGGC-3'

GBBE2-as13 (SEQ ID NO: 40):
5'-
ACATTGCGAATACGGCAGCAACCCCATGTGTTATTTTTGAATTTAACCAT
ACATCCCCTC-3'

GBBE2-as14 (SEQ ID NO: 41):
5'-
GCACCAGGGATTGTATAGGGGTACCAAGATATGGAGTTGTTATACTCTAG
AGTGATAGGC-3'

GBBE2-as15 (SEQ ID NO: 42):
5'-
CTGGTCCACTTTGGACTGTAACAAATGACTTCTGACACATTCTCACTCAA
ATAAGAGTGG-3'

GBBE2-as16 (SEQ ID NO: 43):
5'-
CAAGGACATGGTATCATCAAAGGCGAGCAAAACTCAGCTATTGAGCATC
CAGTGGGCACC-3'

-continued

GBBE21-as17 (SEQ ID NO: 44):
5'-
CTGATGGGGTTTCCAGAGGTCGCTTCTATGTAAAGCATAAGCGCTAGGAG
CAACTGATAC-3'

GBBE1-as18 (SEQ ID NO: 45):
5'-
CACTTGCCCCGAGAGGCATAGTAGATCAGAGCGCCAACCGCCAGGTAGT
GTACACTGCTA-3'

GBBE1-as19 (SEQ ID NO: 46):
5'-
AACATAGTCGCAATAGCGTATGGTACTTGTGAAGCCAGTTTGGTCAAGAA
GATGACAGCC-3'

GBBE1-as20 (SEQ ID NO: 47):
5'-
TCGACCTTGCCGGCCATCCACCCGATAAACCCTAGGAACCCAGGATCTAT
TCCAGTGGGC-3'

GBBE1-as21 (SEQ ID NO: 48):
5'-
ACTTCCAGGTAACAAGTACCAGTTTCATTGAGGTCTATGTGAATAAGCCA
GTGCCTGACA-3'

GBBE1-as22 (SEQ ID NO: 49):
5'-
AGCCAGTCACCGACTAATACACACGCACCACACAACTCACCAATGTCAA
GGGCGTCACAG-3'

GBBE1-as23 (SEQ ID NO: 50):
5'-
GTCACAAGAGCGCCCATAACAAAATCAATGTGGTCAGCCAAGAAGGAGT
CCGTGCCAGTC-3'

GBBE1-as24 (SEQ ID NO: 51):
5'-
CAATTGGAAGGGTGTGAGATGTACGGATTGGCGGGAACCCAGCACTCGT
CCGCACAGATC-3'

GBBE1-as25 (SEQ ID NO: 52):
5'-
ACACAACCAGGCTCGTGTAGGCAAGTGGAAGGAGAACAATAGATAACCT
GATTACGCTGG-3'

GBBE1C-as26 (SEQ ID NO: 53):
5'-
CAGCAATTGGTCAGGATTGTGGTATTTGTGTCTGGGTCAGTGACCCGCGC
CCCACTACAG-3'

GBBC-as27 (SEQ ID NO: 54):
5'-
GGACAGGCCAAAGATAGCAGACATACCACAAAAAGGTGGACACCGAAC
CAACCAGTAGCCCA-3'

For phosphorylation of the 5'-end of each synthetic gene, the phosphorylation reaction was carried out using T4 Polynucleotide Kinase (Takara Shuzo Co., Ltd.). These phosphorylation products were mixed together and slowly cooled from 95° C. to room temperature, thereby allowing annealing of the respective synthetic genes, followed by carrying out ligation reaction using Takara Ligation Kit (Takara Shuzo Co., Ltd.). This ligation product was subjected to blunting of the ends of the double-stranded DNA using Klenow Fragment (Takara Shuzo Co., Ltd.). This double-stranded DNA was cloned into the pGEM-T easy vector, and its nucleotide sequence was determined, thereby confirming that the DNA is the desired GBV-B gene.

In order to convert the XbaI site in pTPF1/4B to an XhoI site, a gene mutation was introduced to pTPF1/4B such that T at the 9594th nucleotide position was mutated to C using Quick Mutagenesis Kit (Stratagene) according to the method recommended by the manufacturer. The plasmid to which this mutation was introduced was designated pTPF1/4B-Xho.

By ligating the AgeI-SplI fragment prepared by cloning from pTPF1/4B by PCR and digestion with the restriction enzymes; the BbvCI-RsrII fragment prepared from pTPF1/

4B by digestion with the restriction enzymes; and the SpII-BbvCI fragment prepared from the GBV-B gene by digestion with the restriction enzymes; into the vector prepared by digestion of pTPF1/4B-Xho with AgeI-RsrII, an HCV/GBV-B chimeric plasmid p -continued GBBC-s42 (SEQ ID NO: 73):
5'-
CTTCTTGGCTGACCACATTGATTTTGTTATGGGCGCTCTTGTGACCTGTG
ACGCCCTTGA-3'

GBBC-s43 (SEQ ID NO: 74):
5'-
CATTGGTGAGTTGTGTGGTGCGTGTGTATTAGTCGGTGACTGGCTTGTCA
GGCACTGGCT-3'

GBBC-s44 (SEQ ID NO: 75):
5'-
TATTCACATAGACCTCAATGAAACTGGTACTTGTTACCTGGAAGTGCCCA
CTGGAATAGA-3'

GBBC-as28 (SEQ ID NO: 76):
5'-
CCTAGGAACCCAGGATCTATTCCAGTGGGCACTTCCAGGTAACAAGTACC
AGTTTCATTG-3'

GBBC-as29 (SEQ ID NO: 77):
5'-
AGGTCTATGTGAATAAGCCAGTGCCTGACAAGCCAGTCACCGACTAATAC
ACACGCACCA-3'

GBBC-as30 (SEQ ID NO: 78):
5'-
CACAACTCACCAATGTCAAGGGCGTCACAGGTCACAAGAGCGCCCATAA
CAAAATCAATG-3'

GBBC-as31 (SEQ ID NO: 79):
5'-
TGGTCAGCCAAGAAGGAGTCCGTGCCAGTCCAATTGGAAGGGTGTGAGA
TGTACGATTG-3'

GBBC-as32 (SEQ ID NO: 80):
5'-
GCGGGAACCCAGCACTCGTCCGCACAGATCACACAACCAGGCTCGTGTA
GGCAAGTGGAA-3'

GBBC-as33 (SEQ ID NO: 81):
5'-
GGAGAACAATAGATAACCTGATTACGCTGGCAGCAATTGGTCAGGATTG
TGGTATTTGTG-3'

GBBC-as34 (SEQ ID NO: 82):
5'-
TCTGGGTCAGTGACCCGCGCCCCACTACAGGGACAGGCCAAAGATAGCA
GACATACCACA-3'

GBBC-as35 (SEQ ID NO: 83):
5'-
AAAAGGTGGACACCGAACCAACCAGTAGCCCAGTTGACTCCATCCTCCA
GCAAGCGTACT-3'

GBBC-as36 (SEQ ID NO: 84):
5'-
ATCTGGCAGACTGGTCGAACGACCGCTCCTGCCACCAGCGGGCCTACTAG
AGGTGTGTGA-3'

GBBC-as37 (SEQ ID NO: 85):
5'-
GTTGTAACATCACCAATCCACCCCAAAGGGTAATCCAGAAGGATTCCAA
GATTGCGAGAC-3'

GBBC-as38 (SEQ ID NO: 86):
5'-
TTATGGCGAGGGTCTTGGCGTCCCCAACCATGAGCTGGCAAAGCAGCCTG
AGCCAATGTC-3'

GBBC-as39 (SEQ ID NO: 87):
5'-
TGCAAGCCATCATGGATACCAGCAATTTTGTAATTACGAGGCCGAGCATC
GCGCTGGACT-3'

GBBC-as40 (SEQ ID NO: 88):
5'-
TTGCGCTTTGCTCGTTGTCCCCTTTCAACAGATGTTTAATGGACACAGG
ATATGAAGCC-3'

GBBC-as41 (SEQ ID NO: 89):
5'-
TGCGTCTGCTTGTTCTTGCGCGTTCTGGGCGCAGGTACAGGACTTGTTTG
AGTAGAAATA-3'

GBBC-as42 (SEQ ID NO: 90):
5'-
ACAGGCATGATGCACGGTCTACGAGACCTCCCGGGGCACTCGCAAGCAC
CCTATCAGGCA-3'

GBBC-as43 (SEQ ID NO: 91):
5'-
GTACCACAAGGCCTTTCGCGACCCAACACTACTCGGCTAGCAGTCTCGCG
GGGGCACGCC-3'

GBBC-as44 (SEQ ID NO: 92):
5'-
CAAATCTCCAGGCATTGAGCGGGTTGATCCAAGAAAGGACCCGGTCGTC
CTGGCAATTCC-3'

For phosphorylation of the 5'-end of each synthetic gene, phosphorylation reaction was carried out using T4 Polynucleotide Kinase (Takara Shuzo Co., Ltd.). These phosphorylation products were mixed together and slowly cooled from 95° C. to room temperature, thereby allowing annealing of the respective synthetic genes, followed by carrying out ligation reaction using Takara Ligation Kit (Takara Shuzo Co., Ltd.). This ligation product was subjected to blunting of the ends of the double-stranded DNA using Klenow Fragment (Takara Shuzo Co., Ltd.). This double-stranded DNA was cloned into the pGEM-T easy vector, and its nucleotide sequence was determined, thereby confirming that the DNA is composed of the 5'-UTR of TPF1 and the genes in the region from the core protein to the 125th position in E1 protein of GBV-B.

The gene fragment prepared by digestion of the above synthesized TPF1 5'-UTR and the genes in the region from the core protein to the 125th position in E1 protein of GBV-B was ligated into the vector prepared by digestion of the HCV/GBV-B chimeric plasmid pTPF/GBB-C156E12 with restriction enzymes AgeI-AvrII, thereby constructing an HCV/GBV-B chimeric plasmid pTPF/GBB-C6, which has the region from the core protein to the p6 protein of GBV-B.

Example 2

Increase of HCV/GBV-B Chimeric Gene in Huh7 Cell pTPF/GBB-C156E12 constructed in Example 1 was digested with XhoI, and, using the resulting digestion product as a template, RNA was synthesized using Megascript T7 kit (Ambion) or AmpliScribe T7-Flash transcription kit (Epicentre). The RNA was purified according to the method recommended by the manufacturer.

Human liver cancer cells (Huh7, JCRB0403) were cultured under 5% carbon dioxide at 37° C. in culture medium prepared by adding fetal bovine serum (FBS) to 10%, and penicillin and streptomycin to 50 U/mL and 50 μg/mL, respectively, to Dulbecco's modified Eagle medium (D-MEM, IWAKI). The cells before confluence were peeled off from the culture dish by trypsin/EDTA treatment, and trypsin was then inactivated by resuspending the cells in serum-containing medium. After washing the cells twice with PBS, they were resuspended in Cytomix (120 mM potassium chloride, 10 mM potassium phosphate, 5 mM magnesium chloride, 25 mM HEPES, 0.15 mM calcium chloride, 2 mM EGTA, pH7.6) supplemented with 1.25% DMSO and transferred to an electroporation cuvette with a gap of 0.4 cm.

After adding 10 μg of the RNA to the cells, the cells were sufficiently cooled on ice for 5 minutes. Using an electroporator (Bio-Rad), the cells were pulsed at 960 μF, 250V. The cells after transfection were immediately resuspended in 10 mL of medium, and 1 mL each thereof was plated on a 12-well plate (22.1 mm diameter), and then the culture was begun. The culture supernatant was collected 4 hours, 24 hours, 48 hours and 72 hours after the beginning of the culture. The collected culture supernatant was centrifuged at 2 k rpm for 10 minutes, and the resulting supernatant was collected. The measurement was carried out with 100 μl of the supernatant using a kit for the HCV core antigen (FUJIREBIO INC., Lumipulse).

As shown in FIG. 1, the measurement of the core antigen in the experimental group wherein the RNA was transfected to the cells using an electroporator (with electroporation) began to increase at 24 hours, and was still increasing at 72 hours. On the other hand, in the control group (without electroporation), it was confirmed that the measurement of the core antigen in the supernatant was below the detection limit These results indicate that the HCV/GBV-B chimeric gene of the present invention replicates in the cells and that the core protein is secreted into the supernatant. Thus, it was shown that the HCV/GBV-B chimeric gene can replicate in vitro.

Example 3

Increase of HCV/GBV-B Chimeric Gene in Primary Hepatocytes of Marmoset

An attempt was made in order to evaluate whether or not the HCV/GBV-B chimeric genotype, which could replicate in Huh7 cells in Example 2, can replicate in primary hepatocytes of marmoset. RNA of pTPF/GBB-C156E12 was synthesized in the same manner as in Example 2.

Primary hepatocytes of marmoset (BIOPREDIC INTERNATIONAL) were cultured according to the method recommended by the manufacturer. More particularly, frozen primary hepatocytes of marmoset were melt in a water bath at 37° C., and suspended in 30 mL of Leibovitz's L-15 medium (Invitrogen) supplemented with 1% GlutaMAX-I Supplement (Invitrogen), which had been prewarmed to 37° C. The cell suspension was centrifuged at 1 k rpm (160×g) for 1 minute and the supernatant was removed, and the resulting cell pellet was resuspended in William's medium E (Invitrogen) supplemented with 1% GlutaMAX-I Supplement (Invitrogen), 4 μg/mL Bovine insulin and 10% fetal bovine serum (FBS) such that a density of about $6 \times 10^5$ cells/mL was attained. The resuspended cells were plated on a collagen type I-coated 24-well plate (15.6 mm diameter) in an amount of 0.5 mL each, followed by culture under 5% carbon dioxide at 37° C.

To the primary hepatocytes of marmoset cultured for 1 day, 2 μg/well of purified TPF/GBB-C156E12 and 4 μL/well of a gene transfection reagent HilyMax (DOJINDO) were added, followed by culture under 5% carbon dioxide at 37° C. for 4 hours. Gene transfection was carried out according to the method recommended by the manufacturer. Thereafter, the cells were washed 3 times with PBS, and cultured in William's medium E (Invitrogen) supplemented with 1% Glutamax-I supplement (Invitrogen), 4 μg/mL bovine insulin and 50 μM hydrocortisone hemisuccinate (growth medium) under 5% carbon dioxide at 37° C. The culture supernatant was collected at 4 hours, 24 hours, 48 hours, 72 hours, 96 hours, 144 hours, 192 hours, 240 hours, 288 hours and 336 hours during the culture. The collected culture supernatant was subjected to centrifugation at 2 k rpm for 10 minutes, and the resulting supernatant was collected. The measurement was carried out with 100 μL of the supernatant using a kit for the HCV core antigen (FUJIREBIO INC., Lumipulse).

Figure 2:
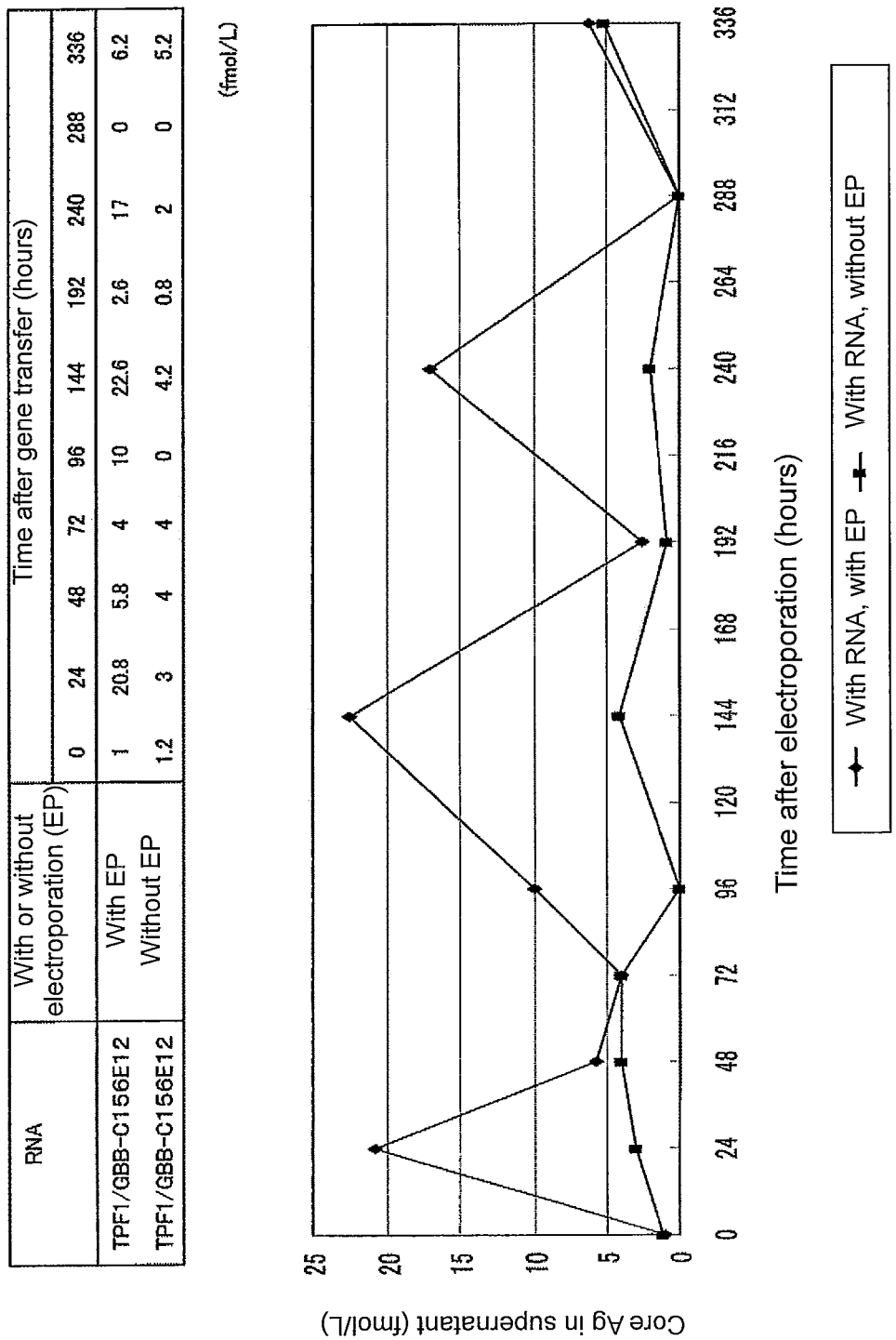
FIG. 2 is a diagram showing the concentration of the core protein of HCV in the supernatant after transfection of the HCV/GBV-B chimeric RNA of the present invention to primary hepatocytes of marmoset.

As shown in FIG. 2, the measurement of the core antigen was higher than that in the control group (without electroporation) at 24 hours, 144 hours and 240 hours. These results indicate that the HCV/GBV-B chimeric gene of the present invention continuously replicates in the primary hepatocytes of marmoset, and that the core protein is sporadically secreted into the supernatant. Thus, it was shown that the HCV/GBV-B chimeric gene can continuously replicate in the living body (liver) of marmoset.

Example 4

Infection of Primary Hepatocytes of Marmoset by HCV/GBV-B Chimeric Virus pTPF/GBB-C156E12, pTPF1/GBB-v11E12, pTPF/GBB-v27E12 and pTPF/GBB-C6 constructed in Example 1 were digested with XhoI, and RNAs were synthesized in the same manner as in Example 2.

The primary hepatocytes of marmoset were cultured by the method described in Example 3. The resuspended cells were plated on a collagen type I-coated 6-well plate (34.6 mm diameter) in an amount of 2 mL each, followed by culture under 5% carbon dioxide at 37° C.

To the primary hepatocytes of marmoset cultured for 1 day, 5 μg/well of the 4 types of purified TPF/GBB chimeric RNAs and 15 μL/well of a gene transfection reagent HilyMax were added, followed by culture under 5% carbon dioxide at 37° C. for 4 hours. Gene transfection was carried out according to the method recommended by the manufacturer. Thereafter, the cells were washed 3 times with PBS, and the growth medium was then added thereto, followed by beginning culture under 5% carbon dioxide at 37° C. The culture supernatant was collected 48 hours later, and the collected culture supernatant was centrifuged at 2 k rpm for 10 minutes, followed by collecting the resulting supernatant. The collected culture supernatant was stored at −80° C. until use for the infection test.

Further, as the cells to be infected, primary hepatocytes of marmoset were newly melt, and cultured in a collagen type I-coated 6-well plate. After 1 day of culture, 500 μL of the culture supernatant (5-fold diluted) collected 48 hours after the gene transfection was added to the cells, and culture was carried out under 5% carbon dioxide at 37° C. for 6 hours. Thereafter, the cells were washed 3 times with PBS, and the growth medium was added thereto, followed by beginning culture under 5% carbon dioxide at 37° C. The culture supernatant was collected at 24 hours, 48 hours, 72 hours, 96 hours, 120 hours, 144 hours, 168 hours, 192 hours and 216 hours. The collected culture supernatant was centrifuged at 2 k rpm for 10 minutes, and the resulting supernatant was collected. Whether or not reinfection with the TPF1/GBB chimera occurred was determined by measuring the number of genome of the chimeric virus contained in the culture supernatant by quantitative RT-PCR.

Figure 3:
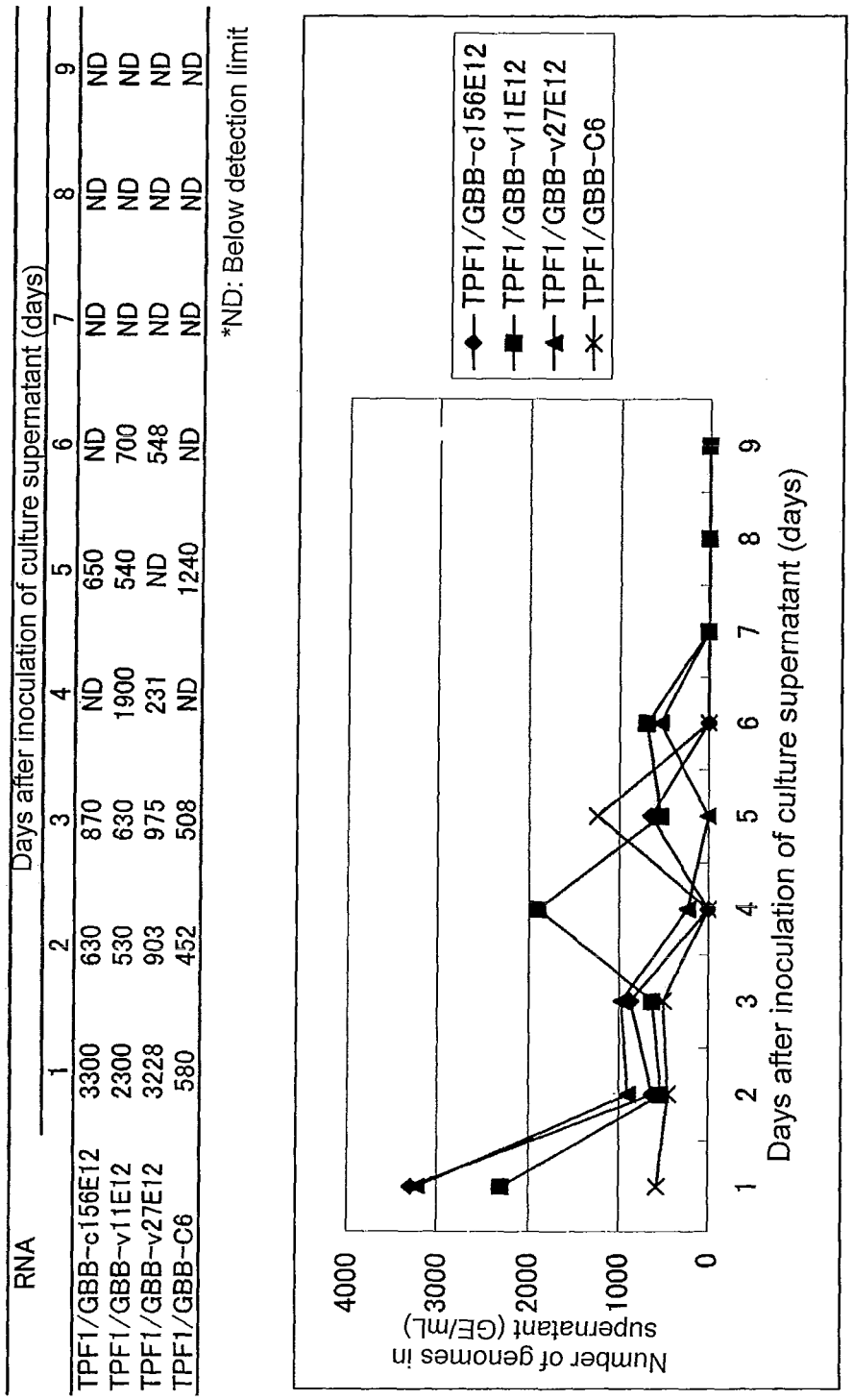
FIG. 3 is a diagram showing the number of the HCV genome in the supernatant after transfection of the HCV/GBV-B chimeric virus of the present invention synthesized in vitro to primary hepatocytes of marmoset.

As shown in FIG. 3, the genome numbers of all the TPF1/GBB chimeric viruses used in the infection test once decreased almost to the detection limit, but increased thereafter. These results indicate that the culture supernatant obtained by gene transfection of the HCV/GBV-B chimeric RNA of the present invention into primary hepatocytes of marmoset contains chimeric virus particles which can reinfect native primary hepatocytes of mannoset. Thus, it was shown that the HCV/GBV-B chimeric virus is capable of reinfection in the living body (liver) of marmoset.

INDUSTRIAL APPLICABILITY

By infecting a small primate such as tamarin or marmoset with the HCV/GBV-B chimeric virus of the present invention, an animal model for HCV can be constructed. By using this animal mode, development and evaluation of drugs to suppress or inhibit aggravation of hepatitis can be carried out, and therefore development and evaluation of more effective prophylactic agents and therapeutic agents for the infection are possible.

The invention claimed is:

1. A hepatitis C virus/GB virus-B (HCV/GBV-B) chimeric RNA comprising an RNA of hepatitis C virus and an RNA of GB virus-B, comprising:

(A) an HCV 5'-side RNA comprising the 5'-untranslated region of hepatitis C virus;

(B) a GBV-B RNA comprising an RNA encoding the E1 protein and the E2 protein of GB virus-B; and (C) an HCV 3'-side RNA comprising an RNA encoding the NS3 protein, the NS4A protein, the NS4B protein wherein leucine is substituted for the amino acid that corresponds to the amino acid at position 93 of SEQ ID NO: 108 and lysine is substituted for the amino acid that corresponds to the amino acid at position 255 of SEQ ID NO: 108, the NS5A protein and the NS5B protein of hepatitis C virus and the 3'-untranslated region of hepatitis C virus;

said GBV-B RNA (B) being inserted between the HCV 5'-side RNA (A) and the HCV 3'-side RNA (C).

2. The HCV/GBV-B chimeric RNA of claim 1, wherein said HCV 5'-side RNA (A) comprises the 5'-untranslated region of hepatitis C virus and an RNA encoding a part or all of the HCV core protein;

said GBV-B RNA (B) comprises an RNA encoding a part of the GBV-B core protein when (A) comprises a part of the HCV core protein, and RNA encoding the E1 protein, the E2 protein and the p6 protein of GB virus-B; and said HCV 3'-side RNA (C) comprises an RNA encoding the p7 protein, the NS2 protein, the NS3 protein, the NS4A protein, the NS4B protein, the NS5A protein and the NS5B protein of hepatitis C virus, and the 3'-untranslated region of hepatitis C virus.

3. The HCV/GBV-B chimeric RNA of any one of claim 1 or 2, wherein each of said HCV 5'-side RNA (A) and said HCV 3'-side RNA (C) has not less than 99% homology to the nucleotide sequence of the corresponding region in the nucleotide sequence as set forth in SEQ ID NO:57, which HCV/GBV-B chimeric RNA encodes a virus particle that can grow in a hepatic cell of a primate.

4. The HCV/GBV-B chimeric RNA of claim 1, wherein said GBV-B RNA (B) comprises an RNA encoding the whole core protein, the E1 protein, the E2 protein and the p6 protein of GB virus-B; and said HCV 3'-side RNA (C) comprises an RNA encoding the NS3 protein, the NS4A protein, the NS4B protein, the NS5A protein and the NS5B protein of hepatitis C virus, and the 3'-untranslated region of hepatitis C virus.

5. A hepatitis C virus/GB virus-B (HCV/GBV-B) chimeric RNA comprising:

(A) an HCV 5'-side RNA comprising the 5'-untranslated region of hepatitis C virus and an RNA encoding the core protein and a part of the E1 protein of hepatitis C virus;

(B) a GBV-B RNA comprising an RNA encoding a part of the E1 protein, and the E2 protein, of GB virus-B; and (C) an HCV 3'-side RNA comprising an RNA encoding the NS3 protein, the NS4A protein, the NS4B protein, the NS5A protein and the NS5B protein of hepatitis C virus and the 3'-untranslated region of hepatitis C virus; wherein leucine is substituted for the amino acid that corresponds to the amino acid at position 93 of SEQ ID NO: 108 and lysine is substituted for the amino acid that corresponds to the amino acid at position 255 of SEQ ID NO: 108, said GBV-B RNA (B) being inserted between the HCV 5'-side RNA (A) and the HCV 3'-side RNA (C), said part of the E1 protein encoded by the HCV 5'-side RNA (A) being a part of the N-terminus side of the E1 protein, said part of the E1 protein encoded by the GBV-B RNA (B) being a part of the C-terminus side of the E1 protein, which both parts are fused together to cover the total length of the E1 protein.

6. The HCV/GBV-B chimeric RNA of claim 5, wherein said part of the E1 protein encoded by the HCV 5'-side RNA (A) is a region of not more than 30 amino acids from the N-terminus of the E1 protein.

7. The HCV/GBV-B chimeric RNA of claim 4 or claim 5, wherein said HCV 3'-side RNA (C) comprises an RNA encoding the p7 protein, the NS2 protein, the NS3 protein, the NS4A protein, the NS4B protein, the NS5A protein and the NS5B protein of hepatitis C virus, and the 3'-untranslated region of hepatitis C virus.

8. The HCV/GBV-B chimeric RNA of claim 4, wherein each of said HCV 5'-side RNA (A) and said HCV 3'-side RNA (C) has not less than 99% homology to the nucleotide sequence of the corresponding region in the nucleotide sequence as set forth in SEQ ID NO:57, and said GBV-B RNA (B) has not less than 99% homology to the nucleotide sequence of the corresponding region in the nucleotide sequence as set forth in SEQ ID NO:99, which HCV/GBV-B chimeric RNA encodes a virus particle that can grow in a hepatic cell of a primate.

9. A hepatitis C virus/GB virus-B (HCV/GBV-B) chimeric RNA comprising the nucleotide sequence as set forth in SEQ ID NO:55.

10. The HCV/GBV-B chimeric RNA of claim 1, having not less than 99% homology to the nucleotide sequence as set forth in SEQ ID NO:93, 95 or 97, which HCV/GBV-B chimeric RNA encodes a virus particle that can grow in a hepatic cell of a primate.

11. An HCV/GBV-B chimeric RNA comprising the nucleotide sequence as set forth in SEQ ID NO:93, 95 or 97.

12. An HCV/GBV-B minus-strand chimeric RNA comprising a nucleotide sequence complementary to the entire HCV/GBV-B chimeric RNA of claim 1 or claim 9.

13. An HCV/GBV-B chimeric virus comprising the HCV/GBV-B chimeric RNA of claim 1 or claim 9.

14. An HCV/GBV-B chimeric DNA encoding the HCV/GBV-B chimeric RNA of claim 1 or claim 9.

15. A vector comprising the DNA of claim 14.

16. An isolated HCV/GBV-B chimeric RNA-replicating cell comprising the HCV/GBV-B chimeric RNA of claim 1 or claim 9.

* * * * *